(12) United States Patent  (10) Patent No.: US 8,829,173 B2
Gruber et al.  (45) Date of Patent: Sep. 9, 2014

(54) RECOMBINANT VECTORS

(75) Inventors: Harry E. Gruber, Rancho Santa Fe, CA (US); Douglas J. Jolly, Encinitas, CA (US); Omar D. Perez, San Diego, CA (US); Christopher R. Logg, South Pasadena, CA (US)

(73) Assignee: Tocagen Inc., San Diego, CA (US)

( * ) Notice: Subject to any disclaimer, the term of this patent is extended or adjusted under 35 U.S.C. 154(b) by 106 days.

(21) Appl. No.: 13/072,704

(22) Filed: Mar. 26, 2011

(65) Prior Publication Data

US 2011/0287020 A1    Nov. 24, 2011

Related U.S. Application Data

(63) Continuation-in-part of application No. PCT/US2009/058512, filed on Sep. 26, 2009.

(60) Provisional application No. 61/100,666, filed on Sep. 26, 2008, provisional application No. 61/120,618, filed on Dec. 8, 2008, provisional application No. 61/186,823, filed on Jun. 13, 2009, provisional application No. 61/318,728, filed on Mar. 29, 2010.

(51) Int. Cl.
*A61K 48/00* (2006.01)
*C07H 21/00* (2006.01)
*C12N 15/867* (2006.01)
*A61K 35/76* (2006.01)
*C12N 15/63* (2006.01)
*C12N 9/78* (2006.01)
*C12N 15/86* (2006.01)
*A61K 38/22* (2006.01)

(52) U.S. Cl.
CPC . *A61K 48/00* (2013.01); *C12N 9/78* (2013.01); *C12N 15/86* (2013.01); *C12N 2740/13043* (2013.01); *A61K 38/2292* (2013.01)
USPC ..... 536/23.2; 536/23.4; 536/24.1; 435/320.1; 435/69.1; 435/325; 435/227; 424/93.6; 424/93.7; 424/94.1

(58) Field of Classification Search
None
See application file for complete search history.

(56) References Cited

U.S. PATENT DOCUMENTS

| | | | |
|---|---|---|---|
| 6,033,905 A | 3/2000 | Eiden et al. | |
| 6,117,681 A | 9/2000 | Salmons et al. | |
| 6,303,380 B1 | 10/2001 | Lin et al. | |
| 6,410,313 B1 | 6/2002 | Kasahara et al. | |
| 6,448,390 B1 | 9/2002 | Albritton et al. | |
| 6,451,304 B1* | 9/2002 | Friedmann et al. | 424/93.2 |
| 6,576,463 B1 | 6/2003 | Kasahara et al. | |
| 6,806,080 B2 | 10/2004 | Kasahara et al. | |
| 6,899,871 B2 | 5/2005 | Kasahara et al. | |
| 6,953,688 B2* | 10/2005 | Ferrick et al. | 435/320.1 |
| 7,056,730 B2 | 6/2006 | Pedersen et al. | |
| 2002/0068362 A1 | 6/2002 | Murray et al. | |
| 2002/0137889 A1 | 9/2002 | Soong et al. | |
| 2003/0003565 A1 | 1/2003 | Dubensky | |
| 2003/0157070 A1 | 8/2003 | Jolly | |
| 2003/0157718 A1 | 8/2003 | Pedersen et al. | |
| 2003/0165466 A1 | 9/2003 | Gromeier et al. | |
| 2003/0219410 A1 | 11/2003 | Calatrava | |
| 2004/0068762 A1* | 4/2004 | Attar et al. | 800/18 |
| 2004/0096972 A1 | 5/2004 | Audit et al. | |
| 2004/0142449 A1 | 7/2004 | Tonjes et al. | |
| 2004/0146489 A1 | 7/2004 | Yu et al. | |
| 2004/0197308 A1 | 10/2004 | Takahashi et al. | |
| 2004/0248827 A1 | 12/2004 | Zheng et al. | |
| 2005/0002903 A1* | 1/2005 | Kasahara et al. | 424/93.2 |
| 2005/0059004 A1 | 3/2005 | Atabekov et al. | |
| 2007/0003522 A1 | 1/2007 | Albritton | |
| 2007/0254357 A1 | 11/2007 | Gregory et al. | |
| 2008/0008685 A1* | 1/2008 | Kasahara | 424/93.2 |
| 2008/0227736 A1 | 9/2008 | Chen et al. | |
| 2009/0169580 A1* | 7/2009 | Whelan et al. | 424/199.1 |

FOREIGN PATENT DOCUMENTS

| | | |
|---|---|---|
| WO | 9920742 A2 | 4/1999 |
| WO | 9936561 A1 | 7/1999 |
| WO | 2007095201 A2 | 8/2007 |
| WO | 2007107156 A2 | 9/2007 |
| WO | 2008151633 A2 | 12/2008 |
| WO | 2010002937 A1 | 1/2010 |
| WO | 2010036986 A2 | 4/2010 |
| WO | 2010045002 A2 | 4/2010 |

OTHER PUBLICATIONS

Three different Score results to Kasahara et al (2008).*
Score result to Ferrick et al.*
Score result to Friedmann et al.*
Score result to Attar et al.*
Aagaard et al., "Fv1-like restriction of N-tropic replication-competent murine leukaemia viruses in mCAT-1-expressing human cells," Journal of General Virology 83:439-442 (2002).
Addison et al., "Comparison of the human versus murine cytomegalovirus immediate early gene promoters for transgene expression by adenoviral vectors," J. Gen. Virol. 78:1653-1661 (1997).
Akbulut et al., "Cytotoxic effect of replication-competent adenoviral vectors carrying L-plastin promoter regulated E1A and cytosine deaminase genes in cancers of the breast, ovary, and colon," Cancer Gene Therapy 10:388-395 (2003).
Akbulut et al., "Vector targeting makes 5-fluorouracil chemotherapy less toxic and more effective in animal models of epithelial neoplasms," 10(22):7738-46 (2004).
Ambrose et al., "In vitro characterization of a simian immunodeficiency virus human immunodeficiency virus (HIV) chimera expressing HIV type 1 reverse transcriptase to study antiviral resistance in pigtail macaques," J. Virol. 78:13553-13561 (2004).

(Continued)

*Primary Examiner* — Catherine Hibbert
(74) *Attorney, Agent, or Firm* — Joseph R. Baker, Jr.; Gavrilovich, Dodd & Lindsey LLP

(57) ABSTRACT

This disclosure provides recombinant replication competent retroviral vectors having increased stability. The disclosure further relates compositions and uses of such vectors in the treatment of disease and disorders.

33 Claims, 89 Drawing Sheets

(56) References Cited

OTHER PUBLICATIONS

Anello et al., "Adenovirus Mediated Cytosine Deaminase Gene Transduction and 5-fluorocytosine Therapy Sensitizes Mouse Prostate Cancer to Irradiation," The Journal of Urology 164(6):2173-2177 (2005).
Arrigo et al., "Regulation of Rous sarcoma virus RNA splicing and stability," Mol. Cell Biol. 8:4858-4867 (1988).
Bachrach et al., "Efficient Gene Transfer into Spleen Cells of Newborn Mice by a Replication-Competent Retroviral Vector," 293(2):328-334 (2002).
Bachrach et al., "In Vivo Infection of Mice by Replication-Competent MLV-Based Retrovirus Vectors," Methods in Molecular Medicine 76:343-352 (2003).
Baranick et al., "Splicing mediates the activity of four putative cellular internal ribosome entry sites," PNAS 105 (12):4733-4738 (2008).
Barsov et al., "Adaptation of chimeric retroviruses in vitro and in vivo: isolation of avian retroviral vectors with extended host range," J. Virol. 75:4973-4983 (2001).
Beijer, Gijsbertus. International Preliminary Report on Patentability. International Application No. PCT/US2009/058510. Date of mailing: Apr. 7, 2011.
Beijer, Gijsbertus. International Preliminary Report on Patentability. International Application No. PCT/US2009/058512. Date of Mailing: Apr. 7, 2011.
Blackburn et al., "Adenovrial transduction of a cytosine deaminase/thymidine kinase fusion gene into prostate carcinoma cells enhances prodrug and radiation sensitivity," International Journal of Cancer 82(2):293-297 (1999).
Bourbeau et al., "Suicide gene therapy with an adenovirus expressing the fusion gene CD::UPRT in human glioblastomas: different sensitivities correlate with p53 status," The Journal of Gene Medicine 6:1320-1332 (2004).
Bourbeau et al., "Improvement of antitumor activity by gene amplification with a replicating but nondisseminating adenovirus," 67(7):3387-95 (2007).
Bunnell et al., "Transplantation of transduced nonhuman primate CD34+ cells using a gibbon ape leukemia virus vector: restricted expression of the gibbon ape leukemia virus receptor to a subset of CD34+ cells," Gene Ther. 6:48-56 (1999).
Chang et al., "A Replication-Competent Feline Leukemia Virus, Subgroup A (FELV-A), Tagged with Green Fluorescent Protein Reporter Exhibits in Vitro Biological Properties Similar to Those of the Parental FeIV-A," Journal of Virology 75(18):8837-8841 (2001).
Cherry et al., "Retroviral Expression in Embryonic Stem Cells and Hematopoietic Stem Cells," Molecular and Cellular Biology 20(20):7419-7426 (2000).
Chio, Jun Ho. International Search Report and Written Opinion. International Application No. PCT/US2009/058510. Date of mailing of the International Search Report Jul. 6, 2010.
Cho, Jeong Han. International Search Report and Written Opinion. International Application No. PCT/US2009/058512. Date of mailing of the Report: May 11, 2011.
Coulombe et al., "A replication-competent promoter-trap retrovirus," J. Virol. 70:6810-6815 (1996).
Cupelli et al., "Transcriptional initiation and postinitiation effects of murine leukemia virus long terminal repeat R-region sequences," J. Virol. 65:6961-6968 (1991).
Cupelli et al., "The secondary structure of the R region of a murine leukemia virus is important for stimulation of long terminal repeat-driven gene expression," J. Virol. 72:7807-7814 (1998).
Delassus et al., "Genetic organization of gibbon ape leukemia virus," Virology 173:205-213 (1989).
Delviks, Krista Anda., "Development of murine leukemia virus-based vectors for more effective gene therapy: genetic analysis of direct repeat deletions," Dissertation, West Virginia (1999).
Dias et al., "Targeted chemotherapy for head and neck cancer with a chimeric oncolytic adenovirus coding for bifunctional suicide protein FCU1," Clin. Cancer Res. 16(9):2540-9; Epub Apr. 13, 2010.
Diaz et al., "Exchange of viral promoter/enhancer elements with heterologous regulatory sequences generates targeted hybrid long terminal repeat vectors for gene therapy of melanoma," J. Virol. 72:789-795 (1998).
Dillon et al., "Construction of a replication competent murine retrovirus vector expressing the human immunodeficiency virus type 1 Tat transactivator protein," J. Virol. 65:4490-4493 (1991).
Donahue et al., "Helper virus induced T cell lymphoma in nonhuman primates after retroviral mediated gene transfer," J. Expt. Med. 176:1125-1135 (1992).
Duch et al., "Transgene stability for three replication-competent murine leukemia virus vectors," Gene 329:61-69 (2004).
Edelstein et al., "Gene therapy clinical trials worldwide 1989-2004—an overview," J. Gene Med. 6:597-602 (2004).
Erbs et al., "In Vivo Cancer Gene Therapy by Adenovirus-mediated Transfer of a Bifunctional Yeast Cystosine Deaminase/Uracil Phosphoribosyltransferase Fusion Gene," Cancer Research 60(14):3813-3822 (2000).
Erbs et al. "Modified vaccinia virus Ankara as a vector for suicide gene therapy," Cancer Gene Ther. 15(1):18-28 (2008); Epub Nov. 9, 2007.
Erlwein et al., "The proline-rich region of the ecotropic Moloney murine leukaemia virus envelope protein tolerates the insertion of the green fluorescent protein and allows the generation of replication-competent virus," J. Gen. Virol. 84:369-373 (2003).
Ernst et al., "A structured retroviral RNA element that mediates nucleocytoplasmic export of intron containing RNA," Mol. Cell Biol. 17:135-144. (1997).
Evans et al., "A neutralizable epitope common to the envelope glycoproteins of ecotropic, polytropic, and amphotropic murine leukemia viruses," J. Virol. 64: 6176-6183 (1990).
Finger et al., "Replicating retroviral vectors mediating continuous production and secretion of therapeutic gene products from cancer cells," Cancer Gene Ther. 12:464-474 (2005).
Fischer et al., "Mechanisms of thymidine kinase/ganciclovir and cytosine deaminase/5-fluorocytosine suicide gene therapy-induced cell death in glioma cells," Oncogene 24:1231-1243 (2005).
Foloppe et al., "Targeted delivery of a suicide gene to human colorectal tumors by a conditionally replicating vaccinia virus," Gene Ther. 15(20):1361-71 (2008); Epub May 15, 2008.
Freytag et al., "Phase I Study of Replication-competent Adenovirus-mediated Double Suicide Gene Therapy for the Treatment of Locally Recurrent Prostate Cancer," Cancer Res. 62:4968 (2002).
Garton et al., "Efficient Expression of Exogenous Genes in Primary Vascular Cells Using IRES-Based Retroviral Vectors," Biotechniques 32:830-843 (2002).
Giffo-Schmitt, Beate. International Preliminary Report on Patentability. International Application No. PCT/US2009/049322. Date of Issuance of Report: Jan. 5, 2011.
Guffey et al., "Engineered herpes simplex virus expressing bacterial cytosine deaminase for experimental therapy for brain tumors," Cancer Gene Therapy 14(1):45-56 (2007); Epub Sep. 22, 2006.
Hacein-Bey-Abina et al., "LMO2-associated clonal T cell proliferation intwo patients after gene therapy for SCID-X1," Science 302:415-419 (2003).
Hiavaty et al., "Effects of sequences of prokaryotic origin on titer and transgene expression in retroviral vectors," Virology 330:351-360 (2004).
Hiraoka et al., "Tumor-Selective Gene Expression in a Hepatic Metastasis Model after Locoregional Delivery of a Replication-Competent Retrovirus Vector," Clin. Cancer Res. 12(23):7108-7116 (2006).
Hiraoka et al., "Therapeutic Efficacy of Replication-Competent Retrovirus Vector-Mediated Suicide Gene Therapy in a Multifocal Colorectal Cancer Metastasis Model," Cancer Research 67(11):5345-5353 (2007).
Hirschowitz et al., "In vivo adenovirus-mediated gene transfer of the *Escherichia coli* cytosine deaminase gene to human colon carcinoma-derived tumors induces chemosensitivity to 5-fluorocytosine," Hum. Gene Ther. 6(8):1055-63 (1995).
Horn et al., "Highly efficient gene transfer into baboon marrow repopulating cells using GALV-pseudotype oncoretroviral vectors produced by human packaging cells," Blood 100:3960-3967 (2002).

(56) References Cited

OTHER PUBLICATIONS

Huber et al., "Metabolism of 5-fluorocytosine to 5-fluorouracil in human colorectal tumor cells transduced with the cytosine deaminase gene: significant antitumor effects when only a small percentage of tumor cells express cytosine deaminase," PNAS 91(17):8302-8306 (1994).

Hughes, Stephen H., "The RCAS Vector System," Folia Biologica (Praha) 50(3-4):107019 (2004).

Jespersen et al., "Epression of hterologous genes from an IRES translational cassette in replication competent murine leukemia virus vectors," Gene 239(2):227-235 (1999).

Johann et al., "Definition of a domain of GLVR1 which is necessary for infection by gibbon ape leukemia virus and which is highly polymorphic between species," J. Virol. 67:6733-6736 (1993).

Kaliberov et al., "Mutation of *Escherichia coli* cytosine deaminase significantly enhances molecular chemotherapy of human glioma," Gene Ther. 14(14):1111-9; Epub May 10, 2007.

Kaliberova et al., "Molecular chemotherapy of pancreatic cancer using novel mutant bacterial cytosine deaminase gene," 7(9):2845-54 (2008).

Kawasaki et al., "Replication-competent retrovirus vector-mediated prodrug activator gene therapy in experimental models of human malignant mesothelioma," Cancer Gene Therapy 18:571-578 (2011).

Kikuchi et al., "Highly Efficient Gene Delivery for Bladder Cancers by Intravesically Administered Replication-Competent Retroviral Vectors," Clin. Cancer Res. 13:4511-4518 (2007).

Klein et al., "Rapid identification of viable retrovirus-transduced cells using the green fluorescent protein as a marker," Gene Ther. 4:1256-1260 (1997).

Kornblihtt et al., "Multiple links between transcription and splicing," RNA 10:1489-1498 (2004).

Kurozumi et al., "Apotosis Induction With 5-Fluorocytosine/ Cytosine Deaminase gene therapy for Human Malignant Glioma Cells Mediated by Adenovirus," Journal of Neuro-Oncology 66(1-2):117-127 (2004).

Lazo et al., "Splice acceptor site for the env message of Moloney murine leukemia virus," J. Virol. 61:2038-2041 (1987).

Lipinski et al., "Optimization of a synthetic beta-catenin-dependent promoter for tumor-specific cancer gene therapy," Mol. Ther. 10:150-161 (2004).

Liu et al., "Tumor-specific therapeutic effect induced by an oncolytic adenoviral vector containing heat shock protein 70 and prodrug activation genes," 13(16):1235-43; Epub Apr. 13, 2006.

Liu et al. "Engineering conditionally replication-competent adenoviral vectors carrying the cytosine deaminase gene increase the infectivity and therapeutic effect for breast cancer gene therapy," 13(4):346-56 (2006).

Liu et al., "The receptors for gibbon ape leukemia virus and amphotropic murine leukemia virus are not downregulated in productively infected cells," Retrovirology 8:53 (2011).

Logg et al., "A Uniquely Stable Replication-Competent Retrovirus Vector Achieves Efficient Gene Delivery in Vitro and in Solid Tumors," Human Gene Therapy 12:921-932 (2001).

Logg et al., "Genomic Stability of Murine Leukemia Viruses Containing Insertions at the Env-3' Untranslated Region Boundary," Journal of Virology 75(15):6989-6998 (2001).

Logg et al., "Tissue-Specific Transcriptional Targeting of a Replication-Competent Retroviral Vector," Journal of Virology 76(24):12783-12791 (2002).

Logg et al., "Retrovirus-Mediated Gene Transfer to Tumors," Methods in Molecular Biology 246:499-525 (2004).

Lu et al., "Highly efficient gene transfer to solid tumors in vivo by tumor-selective replicating retrovirus vectors," Int. J. Mol. Med. 25(5):769-75 (2010).

Maguire, Simon. Examination Report. New Zealand Application No. 592070. Date of Report: May 24, 2011.

Malim et al., "The HIV-1 rev trans-activator acts through a structured target sequence to activate nuclear export of unspliced viral mRNA," Nature 338:254-257 (1989).

Marzio et al., "In vitro evolution of highly replicating, doxycycline-dependent HIV for applications in vaccine studies," Proc. Natl Acad. Sci. USA 98:6342-6347 (2001).

Metzl et al., "Tissue- and Tumor-Specific Targeting of Murine Leukemia Virus-Based Replication-Competent Retroviral Vectors," Journal of Virology 80(14):7070-7078 (2006).

Mild et al., "Frequent intrapatient recombination between human immunodeficiency virus type 1 R5 and X4 envelopes: implications for coreceptor switch," J. Virol. 81:3369-3376 (2007).

Tai et al., "Antibody-Mediated Targeting of Replication-Competent Retroviral Vectors," Human Gene Therapy 14:789-802 (2003).

Tai et al., "Single-Shot, Multicycle Suicide Gene Therapy by Replication-Competent Retrovirus Vectors Achieves Long-Term Survival Benefit in Experimental Glioma," Molecular Therapy 12(5):842-851 (2005).

Tai et al., "Replication-competent retrovirus vectors for cancer gene therapy," Frontiers in Bioscience 13:3083-95 (2008).

Takeuchi et al., "Type C retrovirus inactivation by human complement is determined by both the viral genome and the producer cell," J. Virol. 68: 8001-8007 (1994).

Trubetskoy et al., "R region sequences in the long terminal repeat of a murine retrovirus specifically increase expression of unspliced RNAs," J. Virol. 73:3477-3483 (1999).

Valsamakis et al., The human immunodeficiency virus type 1 polyadenylylation signal: a 3' long terminal repeat element upstream of the AAUAAA necessary for efficient polyadenylylation, Proc. Natl. Acad. Sci. USA 88:2108-2112 (1991).

Van Santen et al., "mRNA precursor splicing in vivo: sequence requirements determined by deletion analysis of an intervening sequence," Proc. Natl Acad. Sci. USA 82:2885-2889 (1985).

Wang et al., "Highly Efficient and Tumor-Restricted Gene Transfer to Malignant Gliomas by Replication-Competant Retroviral Vectors," Human Gene Therapy 14:117-127 (2003).

Wang et al., "A murine leukemia virus with Cre-LoxP excisible coding sequences allowing superinfection, transgene delivery, and generation of host genomic deletions," Retrovirology 1(5) (2004).

Warmann et al., "Adenovirus-mediated cytosine deaminase/5-fluorocytosine suicide gene therapy of human hepatoblastoma in vitro," Pediatric Blood & Cancer, 53: 145-151 (2009).

Xie et al., "Adenovirus-mediated tissue-targeted expression of a caspase-9-based artificial death switch for the treatment of prostate cancer," Cancer Res. 61:6795-6804 (2001).

Xie et al., "Enhanced Retinal Ganglion Cell Differentiation by ath5 and NSCL1 Coexpression," IOVS 45(9):2922-2928 (2004).

Yamashita et al., "The cell cycle independence of HIV infections is not determined by known karyophilic viral elements," PLoS Pathog. 1:e18 (2005).

Yap et al., "Trim5alpha protein restricts both HIV-1 and murine leukemia virus," Proc. Natl. Acad. Sci. USA 101:10786-10791 (2004).

Yi, et al., "Retroviral gene therapy: safety issues and possible solutions," Curr. Gene Ther. 5:25-35 (2005).

Young et al., "Chimeric Retroviral Helper Virus and Picornavirus IRES Sequence to Eliminate DNA Methylation for Improved Retroviral Packaging Cells," J. Virol. 74(11):5242-5249 (2000).

Young, Lee W. International Search Report and Written Opinion. International Application No. PCT/US2009/049322. Date of mailing: Sep. 2, 2009.

Miller et al., "Gene transfer by retrovirus vectors occurs only in cells that are actively replicating at the time of infection," Mol. Cell. Biol. 10:4239-4242 (1990).

Miller et al., "Construction and properties of retrovirus packaging cells based on gibbon ape leukemia virus," J.Virol. 65:2220-2224 (1991).

Miller et al., "Intratumurol 5-Fluorouracil Produced by Cytosine Deaminase/5-Fluorocytosine Gene Therapy Is Effective for Experimental Human Glioblastomas," Cancer Res. 62:773 (2002).

Morgan et al., "Retroviral vectors containing putative internal ribosome entry sites: development of a polycistronic gene transfer system and applications to human gene therapy," Nucleic Acids Research 20(6):1293-1299 (1992).

(56) References Cited

OTHER PUBLICATIONS

Mullen et al., "Transfer of the bacterial gene for cytosine deaminase to mammalian cells confers lethal sensitivity to 5-fluorocytosine: a negative selection system," PNAS 89(1):33-37 (1992).
Mukesh et al., "High and Selective Expression of Yeast Cytosine Deaminase Under a Carcinoembryonic Antigen Promoter-Enhancer," Cancer Res. 62:2337-2342 (2002).
Murakami et al., "High-level expression of exogenous genes by replication-competent retrovirus vectors with an internal ribosomal entry site," Gene 202:23-29 (1997).
Nack et al., "Replacement of the murine leukemia virus (MLV) envelope gene with a truncated HIV envelope gene in MLV generates a virus with impaired replication capacity," Virology 315:209-216 (2003).
Nakamura et al., "Multimodality Therapy with a Replication-conditional Herpes Simplex Virus 1 Mutant that Expresses Yeast Cytosine Deaminase for intratumoral Conversion of 5-Fluorocytosine to 5-Fluorouracil," Cancer Res. 61:5447-5452 (2001); Epub Jul. 1, 2001.
Naldini et al., "Efficient transfer, integration, and sustained long-term expression of the transgene in adult rat brains injected with a lentiviral vector," Proc. Natl. Acad. Sci. USA 93:11382-11388 (1996).
Negroni et al., "Treatment of colon cancer cells using the cytosine deaminase/5-fluorocytosine suicide system induces apotosis, modulation of the proteome, and Hsp90B phsophorylation," Molecular Cancer Therapeutics 6:2747-2756 (2007).
Nogues et al., "Transcriptional activators differ in their abilities to control alternative splicing," J. Biol. Chem. 277:43110-43114 (2002).
O'Reilly et al., "Second-site changes affect viability of amphotropic/ecotropic chimeric enveloped murine leukemia viruses," J. Virol. 74:899-913 (2000).
Roscigno et al., "A mutational analysis of the polypyrimidine tract of introns. Effects of sequence differences in pyrimidine tracts on splicing," J. Biol. Chem. 268:11222-11229 (1993).
Overbaugh et al., "Receptors and entry cofactors for retroviruses include single and multiple transmembrane-spanning proteins as well as newly described glycophosphatidylinositol-anchored and secreted proteins," Microbiol. Mol. Biol. Rev. 65:371-389 (2001).
Owens et al., "Human and simian immunodeficiency virus capsid proteins are major viral determinants of early, postentry replication blocks in simian cells," J. Virol. 77:726-731 (2003).
Paar et al., "Effects of Viral Strain, Transgene Position, and Target Cell Type on Replication Kinetics, Genomic Stability and Transgene Expression of Replication-Competent Murine Leukemia Virus-Based Vectors," Journal of Virology 81(13):6973-6983 (2007).
Paar et al., "Influence of vector design and host cell on the mechanism of recombination and emergence of mutant subpopulations of replicating retroviral vectors," BMC Molecular Biology 10(8) (2009).
Paola et al., "Suicide Gene Therapy With the Yeast Fusion Gene Cytosine Deaminase/Uracil Phosphoribosyltransferase is Not Enough For Pancreatic Cancer," Pancreas 35(3):224-231 (2007).
Poon et al. "Nucleocapsid and matrix protein contributions to selective human immunodeficiency virus type 1 genomic RNA packaging," J. Virol. 72:1983-1993 (1998).
Qiao et al. "VSV-G pseudotyped, MuLV-based, semi-replication-competent retrovirus for cancer treatment. Gene Ther," 13:1457-1470 (2006).
Rainov et al., "Clinical trials with retrovirus mediated gene therapy—what have we learned?," J. Neurooncol. 65:227-236 (2003).

Reik et al., Replication-competent Moloney murine leukemia virus carrying a bacterial suppressor tRNA gene: selective cloning of proviral and flanking host sequences. Proc. Natl. Acad. Sci. USA 82:1141-1145 (1985).
Robson et al., "Selection of optimal polypurine tract region sequences during Moloney murine leukemia virus replication," J. Virol. 74:10293-10303 (2000).
Saavedra et al., "The simian retrovirus-1 constitutive transport element, unlike the HIV-1 RRE, uses factors required for cellular mRNA export," Curr. Biol. 7:619-628 (1997).
Sanders, D. A. "No false start for novel pseudotyped vectors," Curr. Opin. Biotechnol. 13, 437-442 (2002).
Segall et al., "Characterization and Detection of Artificial Replication-Competent Lentivirus of Altered Host Range," Molecular Therapy 8:118-129 (2003).
Shikova-Lekova et al. "Replication-competent hybrids between murine leukemia virus and foamy virus," J. Virol. 77, 7677-7681 (2003).
Shin et al., "Replication of lengthened Moloney murine leukemia virus genomes is impaired at multiple stages," J. Virol. 74:2694-2702 (2000).
Short et al., "Correlation of leukemogenic potential of murine retroviruses with transcriptional tissue preference of the viral long terminal repeats," J. Virol. 61:1067-1072 (1987).
Sliva et al., "Stable integration of a functional shRNA expression cassette into the murine leukemia virus genome," Virology 351(1):218-225 (2006).
Sodroski et al., "Repetitive structure in the long-terminal-repeat element of a type II human T-cell leukemia virus," Proc. Natl. Acad. Sci. USA 81:4617-4621. 1984.
Soifer et al., "A Novel, Helper-Dependent, Adenovirus-Retrovirus Hybrid Vector: Stable Transduction by a Two-Stage Mechanism," Molecular Therapy 5(5):599-608 (2002).
Solly et al., "Replicative retroviral vectors for cancer gene therapy," Cancer Gene Ther. 10:30-39 (2003).
Staffa et al., Identification of positive and negative splicing regulatory elements within the terminal tat-rev exon of human immunodeficiency virus type 1. Mol. Cell Biol. 15:4597-4605 (1995).
Stuhlmann et al., "Construction and properties of replication-competent murine retroviral vectors encoding methotrexate resistance," Mol. Cell. Biol. 9:100-108 (1989).
Subramanian et al., "Temperature-sensitive replication-competent adenovirus shRNA vectors to study cellular genes in virus-induced apoptosis," Methods in Molecular Medicine 130:125-134 (2007).
Sun et al., "Chronic gene delivery of interferon-inducible protein 10 through replication competent retrovirus vectors suppresses tumor growth," Cancer Gene Ther. 12:900-912 (2005).
Svarovskaia et al., Retroviral mutation rates and reverse transcriptase fidelity, Front. Biosci. 8:d117-d134 (2003).
Swanstrom et al., "Synthesis, assembly, and processing of viral proteins," In Retroviruses (Coffin, J. M., Hughes, S. H. & Varmus, H., eds), pp. 263-334, (1997). Cold Spring Harbor Laboratory Press, Plainview, NY.
Yin et al., "Insertion of sequences into the 3' untranslated region of a replication-competent spleen necrosis virus vector disrupts env gene expression," Arch Virol (1999) 144:73-87.
Marvich, Maria, Notice of Allowance issued in U.S. Appl. No. 13/072,705, United States Patent and Trademark Office, Feb. 18, 2014.

* cited by examiner

SEQ ID NO:2:   1   MVTGGMASKWDQKGMDIAYEEAALGYKEGGVPIGGCLINNKDGSVLGRGHNMRFQKGSAT
SEQ ID NO:4:   1   MVTGGMASKWDQKGMDIAYEEALLGYKEGGVPIGGCLINNKDGSVLGRGHNMRFQKGSAT

SEQ ID NO:2   61   LHGEISTLENCGRLEGKVYKDTTLYTTLSPCDMCTGAIIMYGIPRCVVGENVNFKSKGEK
SEQ ID NO:4   61   LHGEISTLENCGRLEGKVYKDTTLYTTLSPCDMCTGAIIMYGIPRCVIGENVNFKSKGEK

SEQ ID NO:2:  121  YLQTRGHEVVVVDDERCKKIMKQFIDERPQDWFEDIGE-
SEQ ID NO:4:  121  YLQTRGHEVVVVDDERCKKLMKQFIDERPQDWFEDIGE-

SEQ ID NO: 31
Length: 596 nt
Type: DNA pri-miR-128-1
Organism: human
ACGCGTactggagtcaatgaaagcaaCTATTTCAAAAGATCAGATTACTTACCAGTTTCACTAATAAAGATTTAT
TACTTTAAACCTTTATCATAAAATGTATGCTTTGAATACTGTGAAGTACACTGCATATAAGGAGTGTGGTATAGT
ATAAAGAAACTTTCTGCAGGTAGTAATTATAGTGAAGATTTTAGGTTTACAAAGCCCTAGCTGTTTTCTGTGTAG
CTTTTATTATTCTTATGACTCTTGACAAGTTTGTAGCTTCACCATATACATTTAATATTTTGCAATAATTGGCCT
TGTTCCTGAGCTGTTGGATTCGGGGCCGTAGCACTGTCTGAGAGGTTTACATTTCTCACAGTGAACCGGTCTCTT
TTTCAGCTGCTTCCTGGCTTCTTTTTACTCAGGTTTCCACTGCTTTTTGCTTTTTTAATGCTGTATGAAGGTG
TTAACATTTGTTTATATTTTTCATTAATTGTAATACCTTTAAATCATGCATCATACTCAGAAATAGGGATTAGAA
TTTAAGTGACATCTTTGGCCTAATATAATTTACCTGTTAAAaatttgtgaaagctattgcttaGCGGCCGC SEQ ID No.32
Length: 511 nt
Type: DNA pri-miR-128-2
Organism: human
ACGCGTCCATGTCCGTACCTTTCTAGTTCATACCTTCTTTTAATTTTTTTTTTCTTTTCAATTTGAAGAGAGTGC
TTCCTCTGTTCTTAAGGCTAGGGAACCAAATTAGGTTGTTTCAATATCGTGCTAAAAGATACTGCCTTTAGAAGA
AGGCTATTGACAATCCAGCGTGTCTCGGTGGAACTCTGACTCCATGGTTCACTTTCATGATGGCCACATGCCTCC
TGCCCAGAGCCCGGCAGCCACTGTGCAGTGGGAAGGGGGCCGATACACTGTACGAGAGTGAGTAGCAGGTCTCA
CAGTGAACCGGTCTCTTTCCCTACTGTGTCACACTCCTAATGGAATGCCGTTATCCAAAGAGCAGCACGAACCCG
ACAGGGCTGAGTGGCTTGTGCTAGGGAGAGGTTTGTGTCATTCCTGCTGACCAAACTGCAGGAAAAACTGCTAAT
TGTCATGCTGAAGACTGCCTGACGGGGAGACTCTGCCTTCTGTAAGTAGGTCAGCGGCCGC
SEQ ID NO:33
Length: 203 nt
Type: DNA pre-miR128-1 linked to the human H1 promoter
Organism: human
acgcgtAATTCATATTTGCATGTCGCTATGTGTTCTGGGAAATCACCATAAACGTGAAATGTCTTTGCATTTGGG
AATCTTATAAGTTCTGTATGAGACCACTCGGAtgagctgttggattcggggccgtagcactgtctgagaggttta
catttctcacagtgaaccggtctctttttcagctgcttcTTTTTTgcggccgc SEQ ID NO: 34
Length: 205 nt
Type: DNA pre-miR128-1 linked to the human H1 promoter
Organism: human
gcggccgcAATTCATATTTGCATGTCGCTATGTGTTCTGGGAAATCACCATAAACGTGAAATGTCTTTGGATTTG
GGAATCTTATAAGTTCTGTATGAGACCACTCGGAtgagctgttggattcggggccgtagcactgtctgagaggtt
tacatttctcacagtgaaccggtctctttttcagctgcttcTTTTTTgcggccgc Sequence ID No. 35
Length: 45 bp
Type: DNA target sequence of the miR-142-3p
Organism: N/A
gcggccgcGTCGACTCCATAAAGTAGGAAACACTACAgcggccgc

FIGURE 1A

Sequence ID No. 36
Length: 128 bp
Type: DNA   target sequence four time repeat miR-142-3pT4X
Organism: N/A
gcggccgcGTCGACTCCATAAAGTAGGAAACACTACACGATTCCATAAAGTAGGAAACACTACAaccggtTCCAT
AAAGTAGGAAACACTACATCACTCCATAAAGTAGGAAACACTACAgcggccgc Sequence ID No. 37
Length: 1131 bp
Type: DNA        HSV-TK
Organism: herpes simplex virus-1
ATGGCTTCGTACCCCGGCCATCAGCACGCGTCTGCGTTCGACCAGGCTGCGCGTTCTCGCGGCCATAGCAACCGA
CGTACGGCGTTGCGCCCTCGCCGGCAGCAAGAAGCCACGGAAGTCCGCCCGGAGCAGAAAATGCCCACGCTACTG
CGGGTTTATATAGACGGTCCCCACGGGATGGGGAAAACCACCACCACGCAACTGCTGGTCGCCCTGGGTTCGCGC
GACGATATCGTCTACGTACCCGAGCCGATGACTTACTGGCAGGTGCTGGGGGCTTCGAGACAATCGCGAACATC
TACACCACACAACACCGCCTCGACCAGGGTGAGATATCGGCCGGGGACGGCGGCGGTGGTAATGACAAGCGCCCAG
ATAACAATGGGCATGCCTTATGCCGTGACCGACGCCGTTCTGGCTCCTCATATCGGGGGGAGGCTGGGAGCTCA
CATGCCCCGCCCCCGGCCCTCACCCTCATCTTCGACCGCCATCCCATCGCCGCCCTCCTGTGTTACCCGGCCGCG
CGATACCTTATGGGCAGCATGACCCCCCAGGCCGTGCTGGCGTTCGTGGCCCTCATCCCGCCGACCTTGCCCGGC
ACAAACATCGTGTTGGGGGCCCTTCCGGAGGACAGACACATCGACCGCCTGGCCAAACGCCAGCGCCCCGGCGAG
CGGCTTGACCTGGCTATGCTGGCCGCGATTCGCCGCCTTTACGAGCTGCTTGCCAATACCGTGCGGTATCTGCAG
GGCGGCGGGTCGTGGCGGGAGGATTGGGGACAGCTTTCGGGGACGGCCGTGCCGCCCCAGGGTGCCGAGCCCCAG
AGCAACGCGGGCCCACGACCCCATATCGGGGACACGTTATTTACCCTGTTTCGGGCCCCCGAGTTGCTGGCCCCC
AACGGCGACCTGTATAACGTGTTTGCCTGGGCCTTGGACGTCTTGGCCAAACGCCTCCGTCCCATGCACGTCTTT
ATCCTGGATTACGACCAATCGCCCGCCGGCTACCGGGACGCCCTGCTGCAACTTACCTCCGGGATGGTCCAGACC
CACGTCACCACCCCCGGCTCCATACCGACGATCTGCGACCTGGCGCGCACGTTTGCCCGGGAGATGGGGGAGGCT
AACTAA
Sequence ID No. 38
Length: 501 bp
Type: DNA Gamma IFN
Organism: human
ATGAAATATACAAGTTATATCTTGGCTTTTCAGCTCTGCATCGTTTTGGGTTCTCTTGGCTGTTACTGCCAGGAC
CATATGTAAAAGAAGCAGAAAACCTTAAGAAATATTTTAATGCAGGTCATTCAGATGTAGCGGATAATGGAACTC
TTTTCTTAGGCATTTTGAAGAATTGGAAAGAGGAGAGTGACAGAAAAATAATGCAGAGCCAAATTGTCTCCTTTT
ACTTCAAACTTTTTAAAAACTTTAAAGATGACCAGAGCATCCAAAAGAGTGTGGAGACCATCAAGGAAGACATGA
ATGTAAGTTTTTCAATAGCAACAAAAAGAAACGAGATGACTTCGAAAAGCTGACTAATTATTCGGTAACTGACTT
GAATGTCCAACGCAAAGCAATACATGAACTCATCCAAGTGATGGCTGAACTGTCGCCAGCAGCTAAAACAGGGAA
GCGAAAAAGGAGTCAGATGCTGTTTCGAGGTCGAAGAGCATCCCAGTAA Sequence ID No. 39
Length: 468 bp
Type: DNA Gamma IFN
Organism: mouse
ATGAACGCTACACACTGCATCTTGGCTTTGCAGCTCTTCCTCATGGCTGTTTCTGGCTGTTACTGCCACGGCACA
GTCATTGAAAGCCTAGAAAGTCTGAATAACTATTTTAACTCAAGTGGCATAGATGTGGAAGAAAAGAGTCTCTTC
TTGGATATCTGGAGGAACTGGCAAAAGGATGGTGACATGAAAATCCTGCAGAGCCAGATTATCTCTTTCTACCTC
AGACTCTTTGAAGTCTTGAAAGACAATCAGGCCATCAGCAACAACATAAGCGTCATTGAATCACACCTGATTACT
ACCTTCTTCAGCAACAGCAAGGCGAAAAGGATGCATTCATGAGTATTGCCAAGTTTGAGGTCAACAACCCACAG
GTCCAGCGCCAAGCATTCAATGAGCTCATCCGAGTGGTCCACCAGCTGTTGCCGGAATCCAGCCTCAGGAAGCGG
AAAAGGAGTCGCTGCTGA

FIGURE 1B

```
Sequence ID No. 40
Length: 462 bp
Type: DNA  IL-2
Organism: human

ATGTACAGGATGCAACTCCTGTCTTGCATTGCACTAAGTCTTGCACTTGTCACAAACAGTGCACCTACTTCAAGT
TCTACAAAGAAAACACAGCTACAACTGGAGCATTTACTGCTGGATTTACAGATGATTTTGAATGGAATTAATAAT
TACAAGAATCCCAAACTCACCAGGATGCTCACATTTAAGTTTTACATGCCCAAGAAGGCCACAGAACTGAAACAT
CTTCAGTGTCTAGAAGAAGAACTCAAACCTCTGGAGGAAGTGCTAAATTTAGCTCAAAGCAAAAACTTTCACTTA
AGACCCAGGGACTTAATCAGCAATATCAACGTAATAGTTCTGGAACTAAAGGGATCTGAAACAACATTCATGTGT
GAATATGCTGATGAGACAGCAACCATTGTAGAATTTCTGAACAGATGGATTACCTTTTGTCAAAGCATCATCTCA
ACACTGACTTGA
```

CMV Promoter (1-582)>>>

1    TAGTTATTAATAGTAATCAATTACGGGGTCATTAGTTCATAGCCCATATATGGAGTTCCG 60
     ATCAATAATTATCATTAGTTAATGCCCCAGTAATCAAGTATCGGGTATATACCTCAAGGC

61   CGTTACATAACTTACGGTAAATGGCCCGCCTGGCTGACCGCCCAACGACCCCCGCCCATT 120
     GCAATGTATTGAATGCCATTTACCGGGCGGACGACTGGCGGGTTGCTGGGGGCGGGTAA

121  GACGTCAATAATGACGTATGTTCCCATAGTAACGCCAATAGGGACTTTCCATTGACGTCA 180
     CTGCAGTTATTACTGCATACAAGGGTATCATTGCGGTTATCCCTGAAAGGTAACTGCAGT

181  ATGGGTGGAGTATTTACGGTAAACTGCCCACTTGGCAGTACATCAAGTGTATCATATGCC 240
     TACCCACCTCATAAATGCCATTTGACGGGTGAACCGTCATGTAGTTCACATAGTATACGG

241  AAGTACGCCCCCTATTGACGTCAATGACGGTAAATGGCCCGCCTGGCATTATGCCCAGTA 300
     TTCATGCGGGGATAACTGCAGTTACTGCCATTTACCGGGCGGACCGTAATACGGGTCAT

Ecol05I
                                        |
                                      SnaBI
                                        |
                                      BstSNI
                                        |
301  CATGACCTTATGGGACTTTCCTACTTGGCAGTACATCTACGTATTAGTCATCGCTATTAC 360
     GTACTGGAATACCCTGAAAGGATGAACCGTCATGTAGATGCATAATCAGTAGCGATAATG 361  CATGGTGATGCGGTTTTGGCAGTACATCAATGGGCGTGGATAGCGGTTTGACTCACGGGG 420
     GTACCACTACGCCAAAACCGTCATGTAGTTACCCGCACCTATCGCCAAACTGAGTGCCCC 421  ATTTCCAAGTCTCCACCCCATTGACGTCAATGGGAGTTTGTTTTGGCACCAAAATCAACG 480
     TAAAGGTTCAGAGGTGGGGTAACTGCAGTTACCCTCAAACAAAACCGTGGTTTTAGTTGC 481  GGACTTTCCAAAATGTCGTAACAACTCCGCCCCATTGACGCAAATGGGCGGTAGGCGTGT 540
     CCTGAAAGGTTTTACAGCATTGTTGAGGCGGGGTAACTGCGTTTACCCGCCATCCGCACA R region (583-650)>>>
                                              |
541  ACGGTGGGAGGTCTATATAAGCAGAGCTGGTTTAGTGAACCGGCGCCAGTCCTCCGATTG 600
     TGCCACCCTCCAGATATATTCGTCTCGACCAAATCACTTGGCCGCGGTCAGGAGGCTAAC

FIG. 3D-4

```
                                                      U5 region (651-1202)>>>
                                                      |
601   ACTGAGTCGCCCGGGTACCCGTGTATCAATAAACCCTCTTGCAGTTGCATCCGACTTGT 660
      TGACTCAGCGGGCCCATGGGCACATAGGTTATTTGGGAGAAGTCAAGTAGGCTGAACA 661   GGTCTGCTGTTCCTTGGGAGGGTCTCCTCTGAGTGATTGACTACCCGTCAGCGGGGGTC 720
      CCAGACGACAAGGAACCCTCCCAGAGGAGACTCACTAACTGATGGGCAGTCGCCCCAG 721   TTTCATTTGGGGGCTCGTCCGGGATCGGGAGACCCCTGCCCAGGGACCACCGACCCACCA 780
      AAAGTAAACCCCGAGCAGGCCCTAGCCCTCTGGGGACGGGTCCCTGGTGGCTGGGTGGT 3'SS (788)
             |
781   CCGGGAGGTAAGCTGGCCAGCAACTATCTGTGTCTGTCCGATTGTCTAGTGTCTATGAC 840
      GGCCCTCCATTCGACCGGTCGTTGATAGACACAGACAGGCTAACAGATCACAGATACTG

841   TGATTTATGGGCCTCCGTCGGTACTAGTTAGCTAACTAGCTCTGTATCTGGGGACCCG 900
```

FIG. 3D-4 (Cont'd)

```
           ACTAAAATACGCGGACGCAGCCATGATCAATCGATTGATCGAGACATAGACCGCCTGGGC

901   TGGTGGAACTGACGAGTTCGGAACACCCGGCCGCAACCCTGGGAGACGTCCCAGGGACTT  960
       ACCACCTTGACTGCTCAAGCCTTGTGGGCCGGCGTTGGGACCCTCTGCAGGGTCCCTGAA

961   CGGGGCCGTTTTTGTGGCCCGACCTGAGTCCAAAAATCCCGATCGTTTTGGACTCTTTG  1020
       GCCCCGGCAAAAACACCGGGCTGGACTCAGGTTTTTAGGGCTAGCAAAACCTGAGAAAC

1021   GTGCACCCCCCTTAGAGGAGGGATATGTGGTTCTGGTAGGAGACGAGAACCTAAAACAGT  1080
       CACGTGGGGGGAATCTCCTCCCTATACACCAAGACCATCCTCTGCTCTTGGATTTTGTCA

1081   TCCCGGCCTCCGTCTGAATTTTTGCTTTCGGTTTGGGACCGAAGCCGCGCCGCGCGTCTTG  1140
       AGGGCCGGAGGCAGACTTAAAAACGAAAGCCAAACCCTGGCTTCGGCGCGGCGCGCAGAAC

1141   TCTGCTGCAGCATCGTTCTGTGTTGTCTCTGTCTGACTGTGTTTCTGTATTTGTCTGAGA  1200
       AGACGACGTCGTAGCAAGACACAACAGAGACAGACTGACACAAAGACATAAACAGACTCT gag(1203,2819)>>>
       |
1201   ATATGGGCCAGACTGTTACCACTCCCTTAAGTTTGACCTTAGGTCACTGGAAAGATGTCG  1260
       TATACCCGGTCTGACAATGGTGAGGGAATTCAAACTGGAATCCAGTGACCTTTCTACAGC 1261   AGCGGATCGCTCACAACCAGTCGGTAGATGTCAAGAAGAGACGTTGGGTTACCTTCTGCT  1320
       TCGCCTAGCGAGTGTTGGTCAGCCATCTACAGTTCTTCTCTGCAACCCAATGGAAGACGA 1321   CTGCAGAATGGCCAACCTTTAACGTCGGATGGCCGGCGAGACGGCACCTTTAACCGAGACC  1380
       GACGTCTTACCGGTTGGAAATTGCAGCCTACCGGCCGCTCTGCCGTGGAAATTGGCTCTGG 1381   TCATCACCCAGGTTAAGATCAAGGTCTTTTCACCTGGCCCGCATGGACACCCAGACCAGG  1440
       AGTAGTGGGTCAATTCTAGTTCCAGAAAAGTGGACCGGGCGTACCTGTGGGTCTGGTCC 1441   TCCCCTACATCGTGACCTGGAAGCCTTGGCTTTTGACCCCCTCCCTGGGTCAAGCCCT  1500
       AGGGGATGTAGCACTGGACCCTTCGGAACCGAAAACTGGGGGAGGGACCCAGTTCGGGA 1501   TTGTACACCCTAAGCCTCCGCCTCCTCTTCCTCCATCCGCCCCGTCTCTCCCCCTTGAAC  1560
       AACATGTGGATTCGGAGGCGGAGGAGAAGGAGGTAGGCGGGGCGCAGAGGGGGAACTTG 1561   CTCCTCGGTTCGACCCCGGCCTCGATCCTCCCTTTATCCAGCCCTCACTCCTTCTCTAGGCG  1620
       GAGGAGCCAAGCTGGGCCGGAGCTAGGAGGGAAATAGGTCGGGAGTGAGGAAGAGATCGC 1621   CCAAACCTAAACCTCAAGTTCTTTCTGACAGTGGGGGCCGCTCATCGACCTACTTACAG  1680
       GGTTTGGATTTGGAGTTCAAGAAAGACTGTCACCCCCGGCGAGTAGCTGGATGAATGTC 1681   AAGACCCCCCGCCTTATAGGGACCCAAGACCACCCCCTTCCGACAGGGACGGAAATGGTG  1740
       TTCTGGGGGGCGGAATATCCCTGGGTTCTGGTGGGGAAGGCTGTCCCTGCCTTTACCAC
```

FIG. 3D-5

1741 GAGAAGCGACCCCTGGGGAGAGGCACGGACCCCTCCCAAGGCATCTCGCCTACGTG 1800
     CTCTTCGCTGGGGACCCCTCTCCGTGGCCTGGGGAGGGGTTACCGTAGAGCGGATGCAC

1801 GGAGACGGGAGCCCCCTGTGGCCGACTCCACTACCTCGCAGGCATTCCCCCTCCGCGCAG 1860
     CCTCTGCCCTCGGGGACACCGGCTGAGGTGATGGAGCGTCCGTAAGGGGAGGCGCGTC

1861 GAGGAAACGGACAGCTTCAATACTGGCCGTTCTCCTCTTCTGACCTTTACAACTGGAAAA 1920
     CTCCTTTGCCTGTCGAAGTTATGACCGGCAAGAGGAGAAGACTGGAAATGTTGACCTTTT

1921 ATAATAACCCTTCTTTTTCTGAAGATCCAGGTAAACTGACAGCTCTGATCGAGTCTGTTC 1980
     TATTATTGGGAAGAAAAAGACTTCTAGGTCCATTTGACTGTCGAGACTAGCTCAGACAAG

1981 TCATCACCCATCAGCCCACCTGGGACGACTGTCAGCAGCTGTTGGGACTCTGCTGACCG 2040
     AGTAGTGGGTAGTCGGGTGGACCCTGCTGACAGTCGTCGACAACCCTGAGACGACTGGC

*FIG. 3D-5 (Cont'd)*

3121 ACTTTGAGGGATCAGGAGCCAGGTTATGGGACCAATGGGGCAGCCCCTGCAAGTGTTGA 3180
     TGAAACTCCCTAGTCCTCGGGTCCAATACCCTGGTTACCCCGTCGGGGACGTTCACAACT

3181 CCCTAAATATGAAGATGAGCATCGGCTACATGAGACCTCAAAAGAGCCAGATGTTTCTC 3240
     GGGATTTATATCTTCTACTCGTAGCCGATGTACTCTGGAGTTTTCTCGGTCTACAAAGAG

3241 TAGGGTCCACATGGCTGTCTGATTTTCCTCAGGCCTGGGCGGAAACCGGGGCATGGGAC 3300
     ATCCCAGGTGTACCGACAGACTAAAAGGAGTCCGGACCCGCCTTTGGCCCCGTACCCTG

3'SS (3314)
3301 TGGCAGTTCGCCAGTCCTCTGATCATACCTCTGAAAGCAACCTCTACCCCCGTGTCCA 3360
     ACCGTCAAGCGGTCAGGAGACTAGTATGGAGACTTTCGTTGGAGATGGGGGCACAGGT

3361 TAAAACAATACCCCATGTCACAAGAAGCCAGACTGGGGATCAAGCCCCACATACAGAGAC 3420
     ATTTTGTTATGGGGTACAGTGTTCTTCGGTCTGACCCCTAGTTCGGGGTGTATGTCTCTG

3421 TGTTGGACCAGGGAATACTGGTACCCTGCCAGTCCCCTGGAACACGGCCCTGCTACCCG 3480
     ACAACCTGGTCCCTTATGACCATGGACGGTCAGGGGACCTTGTGCCGGACGATGGGC

3481 TTAAGAAACCAGGGACTAATGATTATAGGCCTGTCCAGGATCTGACAGAAGTCAACAAGC 3540
     AATTCTTTGGTCCCTGATTACTAATATCCGGACAGGTCCTAGACTCTCTTCAGTTGTTCG

3541 GGGTGGAAGACATCCACCCCACCGTGCCCAACCCTTACAACCTCTTGAGCGGGCTCCCAC 3600
     CCCACCTTCTGTAGGTGGGGTGGCACGGGTTGGGAATGTTGGAGAACTCGCCCGAGGGTG

3601 CGTCCCACCAGTGGTACACTGTGCTTGATTTAAAGGATGCCTTTTTCTGCCTGAGACTCC 3660
     GCAGGGTGGTCACCATGTGACACGAACTAAATTTCCTACGGAAAAGACGGACTCTGAGG

PfeI
                                                    |
                                                    TfiI
                                                    |
3661 ACCCCACCAGTCAGCCTCTCTTCGCCTTTGAGTGGAGAGATCCAGAGATGGGAATCTCAG 3720
     TGGGGTGGTCAGTCGGAGAGAAGCGGAAACTCACCTCTCTAGGTCTCTACCCTTAGAGTC

MfeI
     |
     MunI
     |

*FIG. 3D-6*

3721  GACAATTGACCTGGACCAGACTCCCACACGGGTTTCAAAAACAGTCCCACCCTGTTTGATG  3780
      CTGTTAACTGGACCTGGTCTGAGGGTGTCCCAAAGTTTTTGTCAGGGTGGGACAAACTAC

MroI
                              |
                              BseAI
                              |
                              Bsp13I
                              |
                              BspEI
                              |
                              Kpn2I
                              |
                              AccIII
                              |
3781  AGGCACTGCACAGAGACCTAGCAGACTTCCGGATCCAGCACCCAGACTTGATCCTGCTAC  3840
      TCCGTGACGTGTCTCTGGATCGTCTGAAGGCCTAGGTCGTGGGTCTGAACTAGGACGATG

3841  AGTACGTGGATGACTTACTGCTGGCCGGCACTTCTGAGCTAGACTGCCAACAAGTACTC  3900
      TCATGCACCTACTGAATGACGACCGGCCGTGAAGACTCGATCTGACGGTTGTTCATGAG

FIG. 3D-6 (Cont'd)

3121 ACTTTGAGGGATCAGGAGCCCAGGTTATGGGACCAATGGGGCAGCCCCTGCAAGTGTTGA 3180
     TGAAACTCCCTAGTCCTCGGGTCCAATACCCTGGTTACCCCGTCGGGGACGTTCACAACT

3181 CCCTAAATATAGAAGATGAGCATCGGCTACATGAGACCTCAAAAGAGCCAGATGTTTCTC 3240
     GGGATTTATATCTTCTACTCGTAGCCGATGTACTCTGGAGTTTTCTCGGTCTACAAAGAG

3241 TAGGGTCCACATGGCTGTCTGATTTTCCTCAGGCCTGGGCGGAAACCGGGGGCATGGGAC 3300
     ATCCCAGGTGTACCGACAGACTAAAAGGAGTCCGGACCCGCCTTTGGCCCCCGTACCCTG

3'SS (3314)

3301 TGGCAGTCGGCCAGGTCCTCTGATCATACCTCTGAAAGCAACCTCTACCCCGTGTCCA 3360
     ACCGTCAGCCGGTCCAGGAGACTAGTATGGAGACTTTCGTTGGAGATGGGGGCACAGGT

3361 TAAAACAATACCCCATGTCACAAGAAGCCAGACTGGGGATCAAGCCCCACATACAGAGAC 3420
     ATTTTGTTATGGGGTACAGTGTTCTTCGGTCTGACCCCTAGTTCGGGGTGTATGTCTCTG

3421 TGTTGGACCAGGGAATACTGGTACCCTGCCAGTCCCCTGGAACACGGCCCTGCTACCCG 3480
     ACAACCTGGTCCCTTATGACCATGGGACGGTCAGGGGACCTTGTGCGGGACGATGGGC

3481 TTAAGAAACCAGGGACTAATGATTATAGGCCTGTCCAGGATCTGAGAGAAGTCAACAAGC 3540
     AATTCTTTGGTCCCTGATTACTAATATCCGGACAGGTCCTAGACTCTCTTCAGTTGTTCG

3541 GGGTGGAAGACATCCACCCCACCGTGCCCAACCCTTACAACCTCTTGAGCGGGCTCCCAC 3600
     CCCACCTTCTGTAGGTGGGGTGGCACGGGTTGGGAATGTTGGAGAACTCGCCCGAGGGTG

3601 CGTCCCACCAGTGGTACACTGTGCTTGATTTAAAGGATGCCTTTTTCTGCCTGAGACTCC 3660
     GCAGGGTGGTCACCATGTGACACGAACTAAATTTCCTACGGAAAAGACGGACTCTGAGG

FfeI
                                                              |
                                                              TfiI
                                                              |
3661 ACCCCACCAGTCAGCCTCTCTTCGCCTTTGAGTGGAGAGATCCAGAGATGGGAATCTCAG 3720
     TGGGGTGGTCAGTCGGAGAGAAGCGGAAACTCACCTCTCTAGGTCTCTACCCTTAGAGTC

MfeI
     |
     MunI
     |

*FIG. 3D-7*

3721 GACAATTGACCTGGACCAGACTCCCACAGGGTTTCAAAACAGTCCCACCCTGTTGATG 3780
     CTGTTAACTGGACCTGGTCTGAGGGTGTCCCAAAGTTTTGTCAGGGTGGACAAACTAC

MroI
                               |
                              BseAI
                               |
                              Bsp13I
                               |
                              BspEI
                               |
                              Kpn2I
                               |
                              AccIII
                               |
3781 AGGCACTGCACAGAGACCTAGCAGACTTCCGGATCCAGCACCCAGACTTGATCCTGCTAC 3840
     TCCGTGACGTGTCTCTGGATCGTCTGAAGGCCTAGGTCGTGGGTCTGAACTAGGACGATG

3841 AGTACGTGGATGACTTACTGCTGGCCGGCACTTCTGAGCTAGACTGCCAACAAGGTACTC 3900
     TCATGCACCTACTGAATGACGACCGGCCGTGAAGACTCGATCTGACGGTTGTTCCATGAG

FIG. 3D-7 (Cont'd)

```
3901  GGGCCCTGTTACAAACCCTAGGGAACCTCGGGTATCGGGCCTCGGCCAAGAAGCCCAAA  3960
      CCCGGGACAATGTTTGGGATCCCTTGGAGCCCATAGCCCGGAGCCGGTTCTTCGGGTTT

3961  TTTGCCAGAAACAGGTCAAGTATCTGGGGTATCTTCTAAAAGAGGGTCAGAGATGGCTGA  4020
      AAACGGTCTTTGTCCAGTTCATAGACCCCATAGAAGATTTTCTCCCAGTCTCTACCGACT

4021  CTGAGGCCAGAAAAGAGACTGTGATGGGGCAGCCTACTCCGAAGACCCCTGACAACTAA  4080
      GACTCCGGTCTTTTCTCTGACACTACCCCGTCGGATGAGGCTTCTGGGGAGCTGTTGATT

4081  GGGAGTTCCTAGGGACGGCAGGCTTCTGTCGCCTCTGGATCCCTGGGTTTGCAGAAATGG  4140
      CCCTCAAGGATCCCTGCCGTCCGAAGACAGCGGAGACCTAGGGACCCAAAGTCTTTACC

4141  CAGCCCCCTTGTACCCTCTCACCAAAACAGGGACTCTGTTAATTGGGCCAGACCAAC  4200
      GTCGGGGAACATGGGAGAGTGTTTTGCCCTGAGACAATTAACCCGGTCTGGTTG

4201  AAAAGGCCTATCAAGAAATCAAGCAAGCTCTTCTAACTGCCCAGCGCTGGGCTTGCCAG  4260
      TTTCCGGATAGTTCTTTAGTTCGTTCGAGAAGATTGACGGGTCGGACCCAACGGTC

SalI
                                   |
4261  ATTTGACTAAGCCCTTTGAACTCTTTGTCGACGAGAAGCAGGCCTACGCCAAAGTGTCC  4320
      TAAACTGATTCGGGAAACTTGAGAAACAGCTGCTCTTCGTCCGATGCGGTTTCCACAGG

4321  TAACGCAAAAACTGGGACCTTGGCGTCGGCCGGTGGCCTACCTGTCCAAAAAGCTAGACC  4380
      ATTGCGTTTTTGACCCTGGAACCGCAGCCGGCCACCGGATGGACAGGTTTTCGATCTGG

4381  CAGTAGCAGCTGGGTGGCCCCCTTGCCTACGGATGGTAGCAGCCATTGCCGTACTGACAA  4440
      GTCATCGTCGACCCACCGGGGAACGGATGCCTACCATCGTCGGTAACGGCATGACTGTT

4441  AGGATGCAGGCAAGCTAACCATGGACAGCCACTAGTCATTCTGCCCCCCATGCAGTAG  4500
      TCCTACGTCCGTTCGATTGGTACCCTGTCGGTGATCAGTAAGACGGGGGGTACGTCATC

4501  AGGCACTAGTCAAACAACCCCCGACCGCTGGCTTTCCAACGCCCGATGCTCACTATC  4560
      TCCGTGATCAGTTTGTTGGGGGCTGGCGACCGAAAGGTTGCGGGCTACGAGTGATAG

4561  AGGCCTTGCTTTTGGACACGGACCGGGTCAGTTCGGACCGGTGGTAGCCCTGAACCCGG  4620
      TCCGGAACGAAAACCTGTGCCTGGCCCAGGTCAAGCCTGGCACCATCGGGACTTGGGCC

4621  CTACGCTGCTCCCACTGCCTGAGGAAGGGCTGCAACACAACTGCCTTGATATCCTGGCCG  4680
      GATGCGACGAGGGTGACGGACTCCTTCCCGACGTTGTGTTGACGGAACTATAGGACCGGC

4681  AAGCCCAGGGACCCGACCCGACCCTAACGGACCAGCCGCTCCCAGCGGCCGACCACACCT  4740
      TTCGGGTCCCTTGGGCTGGGCTGGATTGCCTGGTCGGCAGGGTCTGCGGCTGGTGTGA

4741  GGTACACGGATGGAAGCAGTCTCTTACAAGAGGGACAGCGTAAGGCGGGAGCTGCGGTGA  4800
      CCATGTGCCTACCTTCGTCAGAGAATGTTCTCCCTGTCGCATTCGGCCCTCGACGCCACT
```

*FIG. 3D-8*

```
                                                          BlpI
                                                          |
                                                          CelII
                                                          |
                                                          Bpu1102I
                                                          |
                                                          Bsp1720I
                                                          |
4801  CCACCGAGACCGAGGTAATCTGGGCTAAAGCCCTGCCAGCCGGGACATCCGCTCAGCGGG  4860
      GGTGGCTCTGGCTCCATTAGACCCGATTTCGGGACGGTCGGCCCTGTAGGCGAGTCGCCC

4861  CTGAACTGATAGCACTCACCCAGGCCCTAAAGATGGCAGAAGGTAAGAAGCTAAATGTTT  4920
      GACTTGACTATCGTGAGTGGGTCCGGGATTTCTACCGTCTTCCATTCTTCGATTTACAAA
```

*FIG. 3D-8 (Cont'd)*

```
4921  ATACTGATAGCCGTTATGCTTTTGCTACTGCCCATATCCATGGAGAAATATACAGAAGGC 4980
      TATGACTATCGGCAATACGAAAACGATGACGGGTATAGGTACCTCTTTATATGTCTTCCG

4981  GTGGGTTGCTCACATCGAAGGCAAAGAGATCAAAATAAGACGAGATCTTGGCCCTAC 5040
      CACCCAACGAGTGTAGTCTTCCGTTTCTCTAGTTTTTATTTCTGCTCTAGAACCGGGATG

5041  TAAAAGCCCTCTTTCTGCCCAAAAGACTTAGCATAATCCATTGTCCAGGACATCAAAAGG 5100
      ATTTTCGGGAGAAAGACGGGTTTTCTGAATCGTATTAGGTAACAGGTCCTGTAGTTTTCC

5101  GACACAGCGCCGAGGCTAGAGGCAACCGGATGGCTGACCAAGCGGCCCGAAAGGCAGCCA 5160
      CTGTGTCGCGGCTCCGATCTCCGTTGGCCTACCGACTGGTTCGCCGGGCTTTCCGTCGGT

5161  TCACAGAGACTCCAGACACCTCTACCCTCCTCATAGAAAATTCATCACCCTACACCTCAG 5220
      AGTGTCTCTGAGGTCTGTGGAGATGGGAGGAGTATCTTTTAAGTAGTGGGATGTGGAGTC

5221  AACATTTTCATTACACAGTGACTGATATAAAGGACCTAACCAAGTTGGGGGCCATTTATG 5280
      TTGTAAAAGTAATGTGTCACTGACTATATTTCCTGGATTGGTTCAACCCCCGGTAAATAC

5281  ATAAAACAAAGAAGTATTGGGTCTACCAAGGAAAACCTGTGATGCCTGACCAGTTTACTT 5340
      TATTTTGTTTCTTCATAACCCAGATGGTTCCTTTTGGACACTACGGACTGGTCAAATGAA

5341  TTGAATTATTAGACTTTCTTCATCAGCTGACTCACCTCAGCTTCTCAAAAATGAAGGCTC 5400
      AACTTAATAATCTGAAGAAGTAGTCGACTGAGTGGAGTCGAAGAGTTTTACTTCCGAG

5401  TCCTAGAGAGAAGCCACAGTCCCTACTACATGCTGAACGGGATCGAACACTCAAAAATA 5460
      AGGATCTCTCTTCGGTGTCAGGGATGATGTACGACTTGCCCTAGCTTGTGAGTTTTTAT

5461  TCACTGAGACCTGCAAAGCTTGTGCACAAGTCAACGCCAGCAAGTCTGGCCGTAAACAGG 5520
      AGTGACTCTGGACGTTTCGAACACGTGTTCAGTTGCGGTCGTTCAGACCGGCAATTTGTCC
```

SacII
|
SgrBI
|
Cfr42I
|
Sfr303I
|
KspI
|

*FIG. 3D-9*

5521 GAACTAGGGTCCGCGGGCATCCGCCGGCACTCATTGGGAGATCGATTTCACCGAGATAA 5580
     CTTGATCCCAGGCGCCCGTAGGCGGGCCGTGAGTAACCCTCTAGCTAAAGTGGCTCTATT

5581 AGCCCGGATTGTATGGCTATAAATATCTTCTAGTTTTTATAGATACCTTTTCTGGCTGGA 5640
     TCGGGCCTAACATACCGATATTTATAGAAGATCAAAAATATCTATGGAAAAGACCGACCT

5641 TAGAAGCCTTCCCAACCAAGAAGAAACCGCCAAGGTCGTAACCAAGAAGCTACTAGAGG 5700
     ATCTTCGGAAGGGTTGGTTCTTCTTTGGCGGTTCCAGCATTGGTTCTTCGATGATCTCC

PaeI
                           |
                          BbuI
                           |
                          SpaHI
                           |
                          SphI
                           |
5701 AGATCTTCCCCAGGTCGGCATGCCTCAGGTATTGGGAACTGACAATGGGCCTGCCTTCG 5760
     TCTAGAAGGGGTCCAGCCGTACGGAGTCCATAACCCTTGACTGTTACCCGGACGGAAGC

FIG. 3D-9 (Cont'd)

6901 CTTCCAAGGGGCTACTCGAGGGGGCAGATGCAACCCTCTAGTCCTAGAATTCACTGATGC 6960
     GAAGGTTCCCCGATGAGCTCCCCCGTCTACGTTGGGAGATCAGGATCTTAAGTGACTACG

6961 AGGAAAAAAGGCTAACTGGGACGGGCCCAAATCGTGGGGACTGAGACTGTACGGGACAGG 7020
     TCCTTTTTTCCGATTGACCCTGCCCGGGTTTAGCACCCCTGACTCTGACATGCCCTGTCC

7021 AACAGATCCTATTACCATGTTCTCCCTGACCCGGCAGGTCCTTAATGTGGGACCCCGAGT 7080
     TTGTCTAGGATAATGGTACAAGAGGGACTGGGCCGTCCAGGAATTACACCCTGGGGCTCA

7081 CCCCATAGGGCCCAACCCAGTATTACCCGACCAAAGACTCCCTTCCTCACCAATAGAGAT 7140
     GGGGTATCCCGGGTTGGGTCATAATGGGCTGGTTTCTGAGGGAAGGAGTGGTTATCTCTA

7141 TGTACCGGCTCCACAGCCACCTAGCCCCCTCAATACCAGTTACCCCCCTTCCACTACCAG 7200
     ACATGGCCGAGGTGTCGGTGGATCGGGGAGTTATGGTCAATGGGGGAAGGTGATGGTC

7201 TACACCCTCAACCTCCCCTACAAGTCCAAGTGTCCGACAGCCACCCCGAGGAACTGGAGA 7260
     ATGTGGGAGTTGGAGGGGATGTTCAGGTTGACAGGGGTGCGGTGGGGGTCCTTGACCTCT

7261 TAGACTACTAGCTCTAGTCAAAGGAGCCTATCAGGCGCTTAACCTCACCAATCCCGACAA 7320
     ATCTGATGATCGAGATCAGTTTCCTCGGATAGTCCGCGAATTGGAGTGGTTAGGGCTGTT

7321 GACCCAAGAATGTTGGCTGTGCTTAGTGTCGGGACCTCCTTATTACGAAGGAGTAGCGGT 7380
     CTGGGTTCTTACAACCGACACGAATCACAGCCCTGGAGGAATAATGCTTCCTCATCGCCA

7381 CGTGGGCCACTTATACCAATCATTCCACCGGCTCCGGCCAACTGTACGGCCACTTCCCAACA 7440
     GCACCCGTGAATATGGTTAGTAAGGTGGCCGAGGCCGGTTGACATGCCGGTGAAGGGTTGT

EcoT22I
                                              |
                                              NsiI
                                              |
                                              Mph1103I
                                              |
                                              Zsp2I
                                              |
                                              BfrBI
                                              | |

FIG. 3D-10

```
7441 TAAGCTTACCCTATCTGAAGTGACAGGACAGGGCTATGCATGGGGGCAGTACCTAAAAC 7500
     ATTCGAATGGGATAGACTTCACTGTCCTGTCCCGGATACGTACCCCGTCATGGATTTTG
                                    NaeI
                                    |
                                    PdiI
                                    |
                                    MroNI
                                    | |
                                    NgoMIV
                                    | |
7501 TCACCAGGCCTTATGTAACACCACCCAAAGCGCCGGCTCAGGATCCTACTACCTTGCAGC 7560
     AGTGGTCCGGAATACATTGTGGTGGGTTTCGCGGCCGAGTCCTAGGATGATGGAACGTCG

AleI
                                                              |
                                                              OliI
                                                              |
7561 ACCCGGCCGAACAATGTGGGCTTGCAGCACTGGATTGACTCCTGCTTGTCCACCACGGT 7620
     TGGGCCGGCTTGTTACACCCGAACGTCGTGACCTAACTGAGGACGAACAGGTGGTGCCA

7621 GCTCAATCTAACCACAGATTATTGTGTATTAGTTGAACTCTGGCCCAGAGTAATTTACCA 7680
     CGAGTTAGATTGGTGTCTAATAACACATAATCAACTTGAGACCGGGTCTCATTAAATGGT
```

*FIG. 3D-10 (Cont'd)*

```
6901  CTTCCAAGGGGCTACTCGAGGGGGCAGATGCAACCCTCTAGTCCTAGAATTCACTGATGC  6960
      GAAGGTTCCCCGATGAGCTCCCCCGTCTACGTTGGGAGATCAGGATCTTAAGTGACTACG

6961  AGGAAAAAAGGCTAACTGGGACGGGCCCAAATCGTGGGGACTGAGACTGTACCGGACAGG  7020
      TCCTTTTTTCCGATTGACCCTGCCCGGGTTTAGCACCCCTGACTCTGACATGGCCTGTCC

7021  AACAGATCCTATTACCATGTTCTCCCTGACCCGGCAGGTCCTTAATGTGGGACCCCGAGT  7080
      TTGTCTAGGATAATGGTACAAGAGGGACTGGGCCGTCCAGGAATTACACCCTGGGGCTCA

7081  CCCGATAGGGCCCAACCCAGTATTACCCGACCAAAGACTCCCTTCCTCACCAATAGAGAT  7140
      GGGCTATCCCGGGTTGGGTCATAATGGGCTGGTTTCTGAGGGAAGGAGTGGTTATCTCTA

7141  TGTACCGGCTCCACAGCCACCTAGCCCCCTCAATACCAGTTACCCCCCTTCCACTACCAG  7200
      ACATGGCCGAGGTGTCGGTGGATCGGGGAGTTATGGTCAATGGGGGAAGGTGATGGTC

7201  TACACCCTCAACCTCCCCTACAAGTCCAAGTGTCCCACAGCCACCCCCAGGAACTGGAGA  7260
      ATGTGGGAGTTGGAGGGGATGTTCAGTTCACAGGGTGTCGGTGGGGTCCTTGACCTCT

7261  TAGACTACTAGCTCTAGTCAAAGGAGGCTATCAGGGGCTTAACCTCACCAATCCCGACAA  7320
      ATCTGATGATCGAGATCAGTTTCCTCCGATAGTCCGCGAATTGGAGTGGTTAGGGCTGTT

7321  GACCCAAGAATGTTGGCTGTGCTTAGTGTCGGGACCTCCTTATTACGAAGGAGTAGCGGT  7380
      CTGGGTTCTTACAACCGACACGAATCACAGCCCTGGAGGAATAATGCTTCCTCATCGCCA

7381  CGTGGGCACTTATACCAATCATTCCACCGCTCCGGCCAACTGTACGGCCACTTCCCAACA  7440
      GCACCCGTGAATATGGTTAGTAAGGTGGCGAGGCCGGTTGACATGCCGGTGAAGGGTTGT
```

EcoT22I  
        |  
        NsiI  
        |  
       Mph1103I  
        |  
        Zsp2I  
        |  
       BfrBI  
       | |

*FIG. 3D-11*

```
7441  TAAGCTTACCCTATCTGAAGTGACAGGACAGGGCCTATGCATGGGGGCAGTACCTAAAAC  7500
      ATTCGAATGGGATAGACTTCACTGTCCTGTCCCGGATACGTACCCCCGTCATGGATTTTG
                                    NaeI
                                     |
                                    PdiI
                                     |
                                    MroNI
                                     | |
                                    NgoMIV
                                     | |
7501  TCACCAGGCCTTATGTAACACCACCCAAAGCGCCGGCTCAGGATCCTACTACCTTGCAGC  7560
      AGTGGTCCGGAATACATTGTGGTGGGTTTCGCGGCCGAGTCCTAGGATGATGGAACGTCG
                                                          AleI
                                                           |
                                                          OliI
                                                           |
7561  ACCCGGCCGGAACAATGTGGGCTTGCAGCACTGGATTGACTCCCTGCTTGTCCACCACGGT  7620
      TGGGCCGGCCTTGTTACACCCGAACGTCGTGACCTAACTGAGGGACGAACAGGTGGTGCCA

7621  GCTCAATCTAACCACAGATTATTGTGTATTAGTTGAACTCTGGCCCAGAGTAATTTACCA  7680
      CGAGTTAGATTGGTGTCTAATAACACATAATCAACTTGAGACCGGGTCTCATTAAATGGT
```

FIG. 3D-11 (Cont'd)

```
7681  CTCCCCCGATTATATGTATGGTCAGCTTGAACAGCGTACCAAATATAAAAGAGAGCCAGT 7740
      GAGGGGGCTAATATACATACCAGTCGAACTTGTCGCATGGTTTATATTTTCTCTCGGTCA

7741  ATCATTGACCCTGGCCCTTCTACTAGGAGGATTAACCATGGGAGGGATTCAGCTGGAAT 7800
      TAGTAACTGGGACCGGGAAGATGATCCTCCTAATTGGTACCCTCCCTAACGTCGACCTTA

7801  AGGGACGGGGACCACTGCCTTAATTAAAACCCAGCAGTTTGAGCAGCTTCATGCCGCTAT 7860
      TCCCTGCCCCTGGTGACGGAATTAATTTTGGGTCGTCAAACTCGTCGAAGTACGGCGATA

7861  CCAGACAGACCTCAACGAAGTCGAAAAGTCAATTACCAACCTRGAAAAGTCACTGACCTC 7920
      GGTCTGTCTGGAGTTGCTTCAGCTTTTCAGTTAATGGTTGGATCTTTTCAGTGACTGGAG

7921  GTTGTCTGAAGTAGTCCTACAGAACCGCAGAGGCCTAGATTTGCTATTCCTAAAGGAGGG 7980
      CAACAGACTTCATCAGGATGTCTTGGCGTCTCCGGATCTAAACGATAAGGATTTCCTCCC

7981  AGGTCTCTGGCGCAGCCCTAAAAGAAGAATGTTGTTTTTATGGAGACCACACGGGGCTAGT 8040
      TCCAGAGACCGCGTCGGGATTTTCTTCTTACAACAAAAATACGTCTGGTGTGCCCCGATCA

8041  GAGAGACAGCATGGCCAAATTAAGAGAAAGGCTTAATCAGAGACAAAAACTATTTGAGAC 8100
      CTCTCTGTCGTACCGGTTTAATTCTCTTTCCGAATTAGTCTCTGTTTTTGATAAACTCTG
```

```
                NspV
                |
                BstBI
                |
                Bsp119I
                |
                AsuII
                |
                Csp45I
                |
                SfuI
                |
                Bpu14I
                |
                BspT104I
                |
```

```
8101  AGGCCAAGGATGGTTCGAAGGGCTGTTTAATAGATCCCCTGTTTACCACCTTAATCTC 8160
      TCCGGTTCCTACCAAGCTTCCCGACAAATTATCTAGGGGACCAAATGGTGGAATTAGAG

8161  CACCATCATGGGACCTCTAATAGTACTCTTACTGATCTTACTCTTTGGACCTTGCATTCT 8220
      GTGGTAGTACCCTGGAGATTATCATGAGAATGACTAGAATGAGAAACCTGGAACGTAAGA

8221  CAATCGATTGGTCCAATTTGTTAAAGACAGGATCTCAGTGGTCCAGGCTCTGTTTTGAC 8280
      GTTAGCTAACCAGGTTAAACAATTTCTGTCCTAGAGTCACCAGGTCCGAGACAAAACTG
```

*FIG. 3D-12*

```
                                                        IRES reg(8327,8876)>>>
                                                        |
                                                      MluI(8325)
                                                        | |
8281  TCAGCAATATCACCAGCTAAAACCCATAGAGTACGAGCCATGAACGCGTTACTGGCCGAA  8340
      AGTCGTTATAGTGGTCGATTTTGGGTATCTCATGCTCGGTACTTGCGCAATGACCGGCTT ires_emcv reg(8378,8876)>>>
                                                        |
8341  GCCGCTTGGAATAAGGCCGGTGTGCGTTTGTCTATATGTTATTTTCCACCATATTGCCGT  8400
      CGGCGAACCTTATTCCGGCCACACGCAAACAGATATACAATAAAAGGTGGTATAACGGCA 8401  CTTTTGGCAATGTGAGGGCCCGGAAACCTGGCCCTGTCTTCTTGACGAGCATTCCTAGGG  8460
      GAAAACCGTTACACTCCCGGGCCTTTGGACCGGGACAGAAGAACTGCTCGTAAGGATCCC
```

*FIG. 3D-12 (Cont'd)*

```
8461  GTCTTTCCCCTCTCGCCAAAGGAATGCAAGGTCTGTTGAATGTCGTGAAGGAAGCAGTTC  8520
      CAGAAAGGGGAGAGCGGTTTCCTTACGTTCCAGACAACTTACAGCACTTCCTTCGTCAAG

8521  CTCTGGAAGCTTCTTGAAGACAAACAACGTCTGTAGGGACCCTTTGCAGGCAGCGGAACC  8580
      GAGACCTTCGAAGAACTTCTGTTTGTTGCAGACATCGCTGGGAAACGTCCGTCGCCTTGG

8581  CCCCACCTGGCGACAGGTGCCTCTGCGGCCAAAAGCCACGTGTATAAGATACACCTGCAA  8640
      GGGGTGGACCGCTGTCCACGGAGACGCCGGTTTTCGGTGCACATATTCTATGTGGACGTT

8641  AGGCGGCACAACCCAGTGCCACGTTGTGAGTTGGATAGTTGTGGAAAGAGTCAAATGGC  8700
      TCCGCCGTGTTGGGGTCACGGTGCAACACTCAACCTATCAACACCTTTCTCAGTTTACCG

8701  TCTCCTCAAGCGTATTCAACAAGGGGCTGAAGGATGCCCAGAAGGTACCCCATTGTATGG  8760
      AGAGGAGTTCGCATAAGTTGTTCCCCGACTTCCTACGGGTCTTCCATGGGGTAACATACC

8761  GATCTGATCTGGGGCCTCGGTGCACATGCTTTACATGTGTTTAGTCGAGGTTAAAAAAAC  8820
      CTAGACTAGACCCCGGAGCCACGTGTACGAAATGTACACAAATCAGCTCCAATTTTTTTG yCD2 (8877,9353)>>>
                                                  |
                                                  PsiI(8874)
                                                  | |
8821  GTCTAGGCCCCCCGAACCACGGGGACGTGGTTTTCCTTTGAAAAACACGATTATATATCC  8880
      CAGATCCGGGGGGCTTGGTGCCCCTGCACCAAAAGGAAACTTTTTGTGCTAATATATAGG

8881  TGACCGGGGCATGCCTCCAAGTGGGATCAAAAGGGCATGGATATCGCTTACGAGGAGG   8940
      ACTGGCCCCGTACGGAGGTTCACCCTAGTTTTCCCGTACCTATAGCGAATGCTCCTCC

8941  CCTTGCTGGCTACAAGGAGGGCGGCGTGCCTATCGGCGGCTGTCTGATCAACAACAAGC  9000
      GGAACGACCGATGTTCCTCCCGCCGCACGGATAGCCGCCGACGACTAGTTGTTGTTCG

9001  ACGGCAGTGTCTGGCAGGGCCACAACATGAGGTTCCAGAAGGCTCGCCACCCTGG     9060
      TGCCGTCACAGACCGTCCCGGTGTTGTACTCCAAGGTCTTCCGAGCGGTGGGACC

9061  ACGGCGAGATCTCCACCCTGGAGAACTGTGCCAGGCTGGAGGGCAAGGTGTACAAGGACA  9120
      TGCCGCTCTAGAGGTGGGACCTCTTGACACGGTCCGACCTCCCGTTCCACATGTTCCTGT

9121  CCACCCTGTACACCACCCTGTCCCCTTGTGACATGTGTACCGGCGCTATCATCATGTACG  9180
      GGTGGGACATGTGGTGGGACAGGGGAACACTGTACACATGGCCGCGATAGTAGTACATGC
```

*FIG. 3D-13*

9181 GCATCCTAGGTGTGTGATCTGCGAGAACGTGAACTTCAAGTCCAAGGGCCAGAAGTACC 9240
     CGTAGGATCCACACACTAGACGCTCTTGCACTTGAAGTTCAGGTTCCCGGTCTTCATGG

9241 TGCAAACCAGGGGCCACGAGGTGGTGGTTGTTGACGATGAGAGGTGTAAGAACTGATGA 9300
     ACGTTTGGTCCCCGGTGCTCCACCACCAACAACTGCTACTCTCCACATTCTTGACTACT

NotI(9356)
                                              |
                                              CciNI
                                              |
9301 AGCAGTTCATCGACGAGAGGCCTCAGGACTGGTTCGAGGATATCGGCAGTAAGCGGCCG 9360
     TCGTCAAGTAGCTGCTCTCCGGAGTCCTGACCAAGCTCCTATAGCCGTCATTCGCCGGC

U3 Region(9405,9854)>>>
                                              |
9361 CGATAAAATAAAAGATTTTATTTAGTCTCCAGAAAAAGGGGGGAATGAAAGACCCCACC 9420
     GCTATTTTATTTTCTAAAATAAATCAGAGGTCTTTTTCCCCCCTTACTTTCTGGGGTGG

*FIG. 3D-13 (Cont'd)*

```
                          BsrI
                           |
                     NheI  |
                      |    |
                   AsuNHI  |  5_LTR2 other(9447,9998)>>>>
                      | |  |  |
      9421 TGTAGTTTGGCAAGCTAGCTTAAGTAACGCCATTTTGCAAGGCATGGAAAAATACATAA 9480
           ACATCAAACCGTTCGATCGAATTCATTGCGGTAAAACGTTCCGTACCTTTTTATGTATT 9481 CTGAGAATAGAGAAGTTCAGATCAAGGTCAGGAACAGATGGAACAGCTGAATATGGGCCA 9540
           GACTCTTATCTCTTCAAGTCTAGTTCCAGTCCTTGTCTACCTTGTCGACTTATACCCGGT 9541 AACAGGATATCTGTGGTAAGCAGTTCCTGCCCCGGCTCAGGGCAAGAACAGATGGAACA 9600
           TTGTCCTATAGACACCATTCGTCAAGGACGGGGCCGAGTCCCGGTTCTTGTCTACCTTGT 9601 GCTGAATATGGCCAAACAGGATATCTGTGGTAAGCAGTTCCTGCCCCGGCTCAGGGCA 9660
           CGACTTATACCGGTTTGTCCTATAGACACCATTCGTCAAGGACGGGGCCGAGTCCCGGT 9661 AGAACAGATGGTCCCCAGATGCGGTCCAGCCCTCAGCAGTTTCTAGAGAACCATCAGATG 9720
           TCTTGTCTACCAGGGGTCTACGCCAGGTCGGGAGTCGTCAAAGATCTCTTGGTAGTCTAC 9721 TTTCAGGGTCCCCAAGGACCTGAAATGACCCTGTGCCTTATTTGAACTAACCAATCAG 9780
           AAAGGTCCCAGGGGTTCCTGGACTTTACTGGGACACGGAATAAACTTGATTGGTTAGTC SacI
                                                           |
                                                          SstI
                                                           |
                             PauI                        Psp124BI
                              |                            |
                            BsePI                        EcoICRI
                              | |                          | |
                            BsaHII                       Ecl136II
                              | |                          | |
      9781 TTCGCTTCTCGCTTCTGTTCGCGCGCTTCTGCTCCCGAGCTCAATAAAAGAGCCCACAA 9840
           AAGCGAAGAGCGAAGACAAGCGCGCGAAGACGAGGGCTCGAGTTATTTTCTCGGGTGTT R Region(9855,9921)>>>>
                    |
      9841 CCCCTCACTCGGGGCGCCAGTCCTCCGATTGACTGAGTCGCCCGGGTACCCGTGTATCCA 9900
           GGGGAGTGAGCCCCGCGGTCAGGAGGCTAACTGACTCAGCGGGCCCATGGGCACATAGGT U5 Region(9922,9998)>>>>
                    |
      9901 ATAAACCCTCTTGCAGTTGCATCCGACTTGTGGTCTCGCTGTTCCTTGGGAGGGTCTCCT 9960
           TATTTGGGAGAACGTCAACGTAGGCTGAACACCAGAGCGACAAGGAACCCTCCCAGAGGA 9961 CTGAGTGATTGACTACCCGTCAGCGGGGGTCTTTCATTACATGTGAGCAAAAGGCCAGCA 10020
           GACTCACTAACTGATGGGCAGTCGCCCCCAGAAAGTAATGTACACTCGTTTTCCGGTCGT
```

*FIG. 3D-14* pBR322 origin(10045,10664)<<<

10021 AAAGGCCAGGAACCGTAAAAAGGCCGCGTTGCTGGCGTTTTTCCATAGGCTCCGCCCCC 10080
      TTCCGGTCCTTGGCATTTTTCCGGCGCAACGACCGCAAAAAGGTATCCGAGGCGGGGG

10081 TGACGAGCATCACAAAAATCGACGCTCAAGTCAGAGGTGGCGAAACCCGACAGGACTATA 10140
      ACTGCTCGTAGTGTTTTTAGCTGCGAGTTCAGTCTCCACCGCTTTGGGCTGTCCTGATAT

10141 AAGATACCAGGCGTTTCCCCCTGGAAGCTCCCTCGTGCGCTCTCCTGTTCCGACCCTGCC 10200
      TTCTATGGTCCGCAAAGGGGGACCTTCGAGGGAGCACGCGAGAGGACAAGGCTGGGACGG

FIG. 3D-14 (Cont'd)

```
10201 GCTTACCGGATACCTGTCCGCCTTTCTCCCTTCGGGAAGCGTGGCGCTTTCTCAATGCTC 10260
      CGAATGGCCTATGGACAGGCGGAAAGAGGGAAGCCCTTCGCACCGCGAAAGAGTTACGAG

10261 ACGCTGTAGGTATCTCAGTTCGGTGTAGGTCGTTCGCTCCAAGCTGGGCTGTGTGCACGA 10320
      TGCGACATCCATAGAGTCAAGCCACATCAGCAAGCGAGGTTCGACCCGACACACGTGCT

10321 ACCCCCCGTTCAGCCCGACCGCTGCGCCTTATCGGGTAACTATCGTCTTGAGTCCAACCC 10380
      TGGGGGGCAAGTCGGGCTGGCGACGCGGAATAGCCCATTGATAGCAGAACTCAGGTTGGG

10381 GGTAACACACGACTTATCGCCACTGGCAGCAGCCACTGGTAACAGGATTAGCAGAGCGAG 10440
      CCATTCTGTGCTGAATAGCGGTGACCGTCGTCGGTGACCATTGTCCTAATCGTCTCGCTC

10441 GTATGTAGGCGGTGCTACAGAGTTCTTGAAGTGGTGGCCTAACTACGGCTACACTAGAAG 10500
      CATACATCCGCCACGATGTCTCAAGAACTTCACCACCGGATTGATGCCGATGTGATCTTC

10501 GACAGTATTTCGTATCTCGGCCTCTGCTGAAGCCAGTTACCTTCGAAAAGAGTTGGTAG 10560
      CTGTCATAAAGCATAGACGCGAGACGACTTCGGTCAATGAAGCCTTTTCTCAACCATC

10561 CTCTTGATCCGGCAAACAAACCACCGCTGGTAGCGGTGGTTTTTTGTTGCAAGCAGCA 10620
      GAGAACTAGGCCGTTGTTTGGTGGCCACCATCGCCACCAAAAAACAAGCGTTCGTCGT

10621 GATTACGCGCAGAAAAAAAGGATCTCAAGAAGATCCTTTGATCTTTCTACGGGGTCTGA 10680
      CTAATGCGCGTCTTTTTTTCCTAGAGTTCTTCTAGGAAACTAGAAAGATGCCCCAGACT

10681 CGCTCAGTGGAACGAAAACTCACGTTAAGGGATTTTGGTCATGAGATTATCAAAAAGGAT 10740
      GCGAGTCACCTTGCTTTTGAGTGCAATTCCCTAAAACCAGTACTCTAATAGTTTTTCCTA

10741 CTTCACCTAGATCCTTTTAAATTAAAAATGAAGTTTTAAATCAATCTAAAGTATATATGA 10800
      GAAGTGGATCTAGGAAAATTTAATTTTTACTTCAAAATTAGTTAGATTTCATATATACT amp marker(10819,11679) <<<
              |
10801 GTAAACTTGGTCTGACAGTTACCAATGCTTAATCAGTGAGGCACCTATCTCAGCGATCTG 10860
      CATTTGAACCAGACTGTCAATGGTTACGAATTAGTCACTCCGTGGATAGAGTCGCTAGAC 10861 TCTATTTCGTTCATCCATAGTTGCCTGACTCCCCGTCGTGTAGATAACTACGATACGGGA 10920
      AGATAAAGCAAGTAGGTATCAACGGACTGAGGGGCAGCACATCTATTGATGCTATGCCCT 10921 GGGCTTACCATCTGGCCCCAGTGCTGCAATGATACCGCGAGACCCACGCTCACCGGCTCC 10980
      CCCGAATGGTAGACCGGGGTCACGACGTTACTATGGCGCTCTGGGTGCGAGTGGCCGAGG 10981 AGATTTATCAGCAATAAACCAGCCAGCCGGAAGGGCCGAGCGCAGAAGTGGTCCTGCAAC 11040
      TCTAAATAGTCGTTATTTGGTCGGTCGGCCTTCCCGGCTCGCGTCTTCACCAGGACGTTG
```

FIG. 3D-15

```
11041 TTTATCCGCCTCCAGCCAGTCTATTAATTGTTGCCGGGAAGCTAGAGTAAGTAGTTCGCC 11100
      AAATAGGCGGAGGTAGGTCAGATAATTAACAACGGCCCTTCGATCTCATTCATCAAGCGG

11101 AGTTAATAGTTTGCGCAACGTTGTTGCCATTGCTGCAGGCATCGTGGTGTCAGGCTCGTC 11160
      TCAATTATCAAACGCGTTGCAACAACGGTACGACGTCCGTAGCACCACAGTCCGAGCAG

11161 GTTTGGTATGGCTTCATTCAGCTCCGGTTCCCAACGATCAAGGCGAGTTACATGATCCCC 11220
      CAAACCATACCGAAGTAAGTCGAGGCCAAGGGTTGCTAGTTCCGCTCAATGTACTAGGGG

11221 CATGTTGTGCAAAAAAGCGGTTAGCTCCTTCGGTCCTCCGATCGTTGTCAGAAGTAAGTT 11280
      GTACAACACGTTTTTTCGCCAATCGAGGAAGCCAGGAGGCTAGCAACAGTCTTCATTCAA

11281 GGCCGCAGTGTTATCACTCATGGTTATGGCAGCACTGCATAATTCTCTTACTGTCATGCC 11340
      CCGGCGTCACAATAGTGAGTACCAATACCGTCGTGACGTATTAAGAGAATGACAGTACGG

11341 ATCCGTAAGATGCTTTTCTGTGACTGGTGAGTACTCAACCAAGTCATTCTGAGAATAGTG 11400
      TAGGCATTCTACGAAAAGACACTGACCACTCATGAGTTGGTTCAGTAAGACTCTTATCAC
```

*FIG. 3D-15 (Cont'd)*

```
11401 TATGCGGCGACCGAGTTGCTCTTGCCCGGCGTCAACACGGGATAATACCGCGCCACATAG 11460
      ATACGCCGCTGGCTCAACGAGAACGGGCCGCAGTTGTGCCCTATTATGGCGCGGTGTATC

11461 CAGAACTTTAAAAGTGCTCATCATTGGAAAACGTTCTTCGGGGCGAAAACTCTCAAGGAT 11520
      GTCTTGAAATTTTCACGAGTAGTAACCTTTTGCAAGAAGCCCCGCTTTTGAGAGTTCCTA

11521 CTTACCGCTGTTGAGATCCAGTTCGATGTAACCCACTCGTGCACCCAACTGATCTTCAGC 11580
      GAATGGCGACAACTCTAGGTCAAGCTACATTGGGTGAGCACGTGGGTTGACTAGAAGTCG

11581 ATCTTTTACTTTCACCAGCGTTTCTGGGTGAGCAAAAACAGGAAGGCAAAATGCCGCAAA 11640
      TAGAAAATGAAAGTGGTCGCAAAGACCCACTCGTTTTGTCCTTCCGTTTTACGGCGTTT

11641 AAAGGGAATAAGGGCGACACGGAAATGTTGAATACTCATACTCTTCCTTTTTCAATATTA 11700
      TTTCCCTTATTCCCGCTGTGCCTTTACAACTTATGAGTATGAGAAGGAAAAGTTATAAT amp pros (11721, 11749) <<<

11701 TTGAAGCATTTATCAGGGTTATTGTCTCATGAGCGGATACATATTTGAATGTATTTAGAA 11760
      AACTTCGTAAATAGTCCCAATAACAGAGTACTCGCCTATGTATAAACTTACATAAATCTT

11761 AAATAAACAAATAGGGGTTCCGCGCACATTTCCCCGAAAAGTGCCACCTGACGTCTAAGA 11820
      TTTATTTGTTTATCCCCAAGGCGCGTGTAAAGGGGCTTTTCACGGTGGACTGCAGATTCT

11821 AACCATTATTATCATGACATTAACCTATAAAAATAGGCGTATCACGAGGCCCTTTCGTCT 11880
      TTGGTAATAATAGTACTGTAATTGGATATTTTTATCCGCATAGTGCTCCGGGAAAGCAGA

11881 TCAAGAATTCAT 11892
      AGTTCTTAAGTA
```

FIG. 3F-5 pAC3-yCD2 (Unique Digest Sequence)

CMV Promotor (1-582)>>>

```
  1  TAGTTATTAATAGTAATCAATTACGGGGTCATTAGTTCATAGCCCATATATGGAGTTCCG  60
     ATCAATAATTATCATTAGTTAATGCCCCAGTAATCAAGTATCGGGTATATACCTCAAGGC

61  CGTTACATAACTTACGGTAAATGGCCCGCCTGGCTGACCGCCCAACGACCCCCGCCCATT 120
     GCAATGTATTGAATGCCATTTACCGGGCGGACCGACTGGCGGGTTGCTGGGGGCGGGTAA

121  CACGTCAATAATGACGTATGTTCCCATAGTAACGCCAATAGGGACTTTCCATTGACGTCA 180
     GTGCAGTTATTACTGCATACAAGGGTATCATTGCGGTTATCCCTGAAAGGTAACTGCAGT

181  ATGGGTGGAGTATTTACGGTAAACTGCCCACTTGGCAGTACATCAAGTGTATCATATGCC 240
     TACCCACCTCATAAATGCCATTTGACGGGTGAACCGTCATGTAGTTCACATAGTATACGG

241  AAGTACGCCCCCTATTGACGTCAATGACGGTAAATGGCCCGCCTGGCATTATGCCCAGTA 300
     TTCATGCGGGGGATAACTGCAGTTACTGCCATTTACCGGGCGGACCGTAATACGGGTCAT
```

Eco105I
                                    |
                                    SnaBI
                                    |
                                    BstSNI
                                    |

```
301  CATGACCTTATGGGACTTTCCTACTTGGCAGTACATCTACGTATTAGTCATCGCTATTAC 360
     GTACTGGAATACCCTGAAAGGATGAACCGTCATGTAGATGCATAATCAGTAGCGATAATG

361  CATGGTGATGCGGTTTTGGCAGTACATCAATGGGCGTGGATAGCGGTTTGACTCACGGGG 420
     GTACCACTACGCCAAAACCGTCATGTAGTTACCCGCACCTATCGCCAAACTGAGTGCCCC

421  ATTTCCAAGTCTCCACCCCATTGACGTCAATGGGAGTTTGTTTTGGCACCAAAATCAACG 480
     TAAAGGTTCAGAGGTGGGGTAACTGCAGTTACCCTCAAACAAAACCGTGGTTTTAGTTGC

481  GGACTTTCCAAAATGTCGTAACAACTCCGCCCCATTGACGCAAATGGGCGGTAGGCGTGT 540
     CCTGAAAGGTTTTACAGCATTGTTGAGGCGGGGTAACTGCGTTTACCCGCCATCCGCACA
```

R region (583-650)>>>
                                                |

```
541  ACGGTGGGAGGTCTATATAAGCAGAGCTGGTTTAGTGAACCGGCGCCAGTCCTCCGATTG 600
     TGCCACCCTCCAGATATATTCGTCTCGACCAAATCACTTGGCCGCGGTCAGGAGGCTAAC
```

FIG. 3F-6

```
                                                        U5 region (651-1202)>>>
                                                        |
601   ACTGAGTCGCCCGGGTACCCGTGTATCAATAAACCCTCTTGCAGTTGCATCGACTTGT 660
      TGACTCAGCGGGCCCATGGGCACATAGTTATTTGGGAGAACGTCAACGTAGCTGAACA 661   GGTCTGCTGTTCCTTGGAGGGTCTCCTCTGAGTGATTGACTACCCGTCAGCGGGGTC 720
      CCAGACGACAAGGAACCCTCCCAGAGGAGACTCACTAACTGATGGGCAGTCGCCCCAG 721   TTTCATTTGGGGGCTCGTCCGGATCGGGAGACCCCTGCCCAGGGACCACCGACCACCA 780
      AAAGTAAACCCCCGAGCAGGCCCTAGCCCTCTGGGGACGGGTCCCTGGTGGCTGGTGGT 5'SS (788)
          |
781   CCGGGAGGTAAGCTGGCCAGGAACTTATCTGTGTCTGTCCGATTGTCTAGTGTCTATGAC 840
      GGCCCTCCATTCGACCGGTCGTTGAATAGACACAGACAGGCTAACAGATCACAGATACTG

841   TGATTTATGGGCCTGCGTCGGTACTAGTTAGCTAACTAGCTCTGTATCTGCCGGACCG 900
```

```
1741 GAGAAGCGACCCCTGCGGAGAGGCACCGGACCCCTCCCAATGGCATCTCGCCTACGTG 1800
     CTCTTCGCTGGGGACGCCCTCTCCGTGGCCTGGGGAGGGGTTACCGTAGAGCGGATGCAC

1801 GGAGACGGGAGCCCCCTGTGGCCGACTCCACTACCTCGCAGGCATTCCCCTCCGGGCAG 1860
     CCTCTGCCCTCGGGGACACCGGCTGAGGTGATGGAGCGTCCGTAAGGGGAGGCGCGTC

1861 GAGGAAACGGACAGCTTCAATACTGGCCGTTCTCCTCTTCTGACCTTTACAACTGGAAAA 1920
     CTCCTTTGCCTGTCGAAGTTATGACCGGCAAGAGGAGAAGACTGGAAATGTTGACCTTTT

1921 ATAATAACCCTTCTTTTTCTGAAGATCCAGGTAAACTGACAGCTCTGATCGAGTCTGTC 1980
     TATTATTGGGAAGAAAAGACTTCTAGGTCCATTTGACTGTCGAGACTAGCTCAGACAGG

1981 TCATCACCCATCAGCCCACCTGGGACGACTGTCAGCAGCTGTTGGGGACTCTGCTGACCG 2040
     AGTAGTGGGTAGTCGGGTGGACCCTGCTGACAGTCGTCGACAACCCCTGAGACGACTGGC
```

FIG. 3F-7 (Cont'd)

```
2041 GAGAAGAAAACAACGGGTGCTCTTAGAGGCTAGAAAGCGGTGCGGGCGATGATGGGC 2100
     CTCTTCTTTTGTTGCCCACGAGAATCTCCGATCTTCCGCCACGCCCGCTACTACCCG

2101 GCCCCACTGACTGCCCAATGAAGTCGATGCCGCTTTTCCCCTCAGCGCCCAGACTGGG 2160
     CGGGGTGAGTTGACGGGTTACTTCAGCTACGGCGAAAGGGAGCTCGCGGGTCTGACCC

2161 ATTACACCACCCAGGCAGGTAGGAACCACCTAGTCCACTATGCCAGTTGCTCCTAGCGG 2220
     TAATGTGGTGGGTCCGTCCATCCTTGGTGGATCAGGTGATACGGTCAACGAGGATCGCC

2221 GTCTCCAAAACGCGGGCAGAAGCCCCACCAATTTGGCCAAGGTAAAAGGATAACACAAG 2280
     CAGAGGTTTTGCGCCCGTCTTCGGGGTGGTTAAACCGGTTCCATTTTCCTTATTGTGTTC

2281 GGCCAATGAGTCTCCCTCGGCCTTCCTAGAGAGACTTAAGGAAGCCTATCGAGGTACA 2340
     CCGGGTTACTCAGAGGGAGCCGGAAGGATCTCTCTGAATTCCTTCGGATAGCGTCCATGT

2341 CTCCTTATGACCCTGAGGACCCAGGGCAAGAAACTAATGTGTCTATGTCTTTCATTTGGC 2400
     GAGGAATACTGGGACTCCTGGGTCCCGTTCTTTGATTACACAGATACAGAAAGTAAACCG

2401 AGTCTGCCCAGACATTGGGAGAAAGTTAGAGAGGTTAGAAGATTTAAAAAACAAGACGC 2460
     TCAGACGGGTCTGTAACCCTCTTTCAATCTCTCCAATCTTCTAAATTTTTGTTCTGCG

2461 TTGGAGATTTGGTTAGAGAGGCAGAAAAGATCTTTAATAAACGAGAAACCCCGGAAGAAA 2520
     AACCTCTAAACCAATCTCTCCGTCTTTTCTAGAAATTATTGCTCTTTGGGGCCTTCTTT

2521 GAGAGGAACGTATCAGGAGAGAAACAGAGGAAAAGGAAGAACGCCGTAGGACAGAGGATG 2580
     CTCTCCTTGCATAGTCCTCTCTTTGTCTCCTTTTCTTCTTGCGGCATCCTGTCTCCTAC

2581 AGCAGAAAGAGAAAGAAGAGATCGTAGGAGACATAGGAGATGAGCAAGCTATTGGCCA 2640
     TCGTCTTTCTCTTTCTTCTCTAGCATCCTCTGTATCTCTACTCGTTCGATAACCGGT

2641 CTGTCGTTAGTGGACAGAAACAGGATAGACAGGGAGGAGAACGAAGGAGGTCCAACTCG 2700
     GACAGCAATCACCTGTCTTTGTCCTATCTGTCCCTCCTCTTGCTTCCTCCAGGGTTGAGC

NruI
              |
              BspEBI
              |
          BspDI
          | |
2701 ATCGGACCAGTGTGCCTACTGCAAAGAAAAGGGGCATGGCCTAAAGATTGTCCAAGA 2760
     TAGCCTGGTCACACGGATGACGTTTCTTTTCCCCGTACCGGATTTCTAACAGGTTCT pal(2820,6358)>>>
                                                              |
                        FIG. 3F-8
```

```
2761 AACCACGAGGACCTCGGGGACCAAGACCCCAGACCTCCTCCTGACCCTAGATGACTAGG 2820
     TTGGTGCTCCTGGAGCCCCTGGTTCTGGGGTCTGGAGGGAGGACTGGGATCTACTGATCC

2821 GAGGTCAGGGTCAGGAGCCCCCCCTGACCCAGGATAACCCTCAAAGTCGGGGGCAAC 2880
     CTCCAGTCCCAGTCCTGGGGGGGACTTGGGTCCTATTGGGAGTTTCAGCCCCCGTTG

2881 CGGTCACCTTCCTGGTAGATACTGGGCCCAACACTCCGTGCTGACCCAAAATCCTGGAC 2940
     GCCAGTGGAAGGACCATCTATGACCCGGGTTGTGAGGCACGACTGGGTTTTAGGACCTG

2941 CCCTAAGTGATAAGTCTGCCTGGGTCCAAGGGGTACTGGAGGAAAGCGGTATCGCTGGA 3000
     GGGATTCACTATTCAGACGGACCCAGGGTTCCCCGATGACCTCCTTTCGCCATAGCGACCT

3001 CCACGGATCGCAAAGTACATCTAGCTACCGGTAAGGTCACCCACTCTTTCCTCCATGTAC 3060
     GGTGCCTAGCGTTTCATGTAGATCGATGGCCATTCCAGTGGGTGAGAAAGGAGGTACATG

3061 CAGACTGTCCCTATCCTCTGTTAGGAAGAGATTGCTGACTAAACTAAAAGCCCAAATCC 3120
     GTCTGACAGGGATAGGAGACAATCCTTCTCTAAACGACTGATTTGATTTTCGGGTTTAGG
```

*FIG. 3F-8 (Cont'd)*

```
3121  ACTTTGAGGGATCAGGAGCCCAGGTTATGGGACCAATGGGCAGCCCCTGCAAGTGTTGA 3180
      TGAAACTCCCTAGTCCTCGGGTCCAATACCCTGGTTACCCCGTCGGGGACGTTCACAACT

3181  CCCTAAATATAGAAGATGAG*ATCGGCTACATGAGACCTCAAAAGAGCCAGATGTTTCTC 3240
      GGGATTTATATCTTCTACTCATAGCCGATGTACTCTGGAGTTTTCTCGGTCTACAAAGAG

3241  TAGGGTCCACATGGCTGTCTGATTTTCCTCAGGCCTGGGCGGAAACCGGGGGCATGGGAC 3300
      ATCCCAGGTGTACCGACAGACTAAAAGGAGTCCGGACCCGCCTTTGGCCCCGTACCCTG

3'SS (3314)
                    |
3301  TGGCAGTTCGCCAAGCTCCTCTGATCATACCTCTGAAAGCAACCTCTACCGCCCGTGTCCA 3360
      ACCGTCAAGCGGTTCGAGGAGACTAGTATGGAGACTTTCGTTGGAGATGGCGGCACAGGT

3361  TAAAACAATACCCCATGTCACAAGAAGCCAGACTGGGATCAAGCCCCACATACAGAGAC 3420
      ATTTTGTTATGGGGTACAGTGTTCTTCGGTCTGACCCCTAGTTCGGGGTGTATGTCTCTG

3421  TGTTGGACCAGGGAATACTGGTACCCTGCCAGTCCCCCTGGAACACGCCCCTGCTACCCG 3480
      ACAACCTGGTCCCTTATGACCATGGGACGGTCAGGGGGACCTTGTGCGGGGACGATGGGC

3481  TTAAGAAACCAGGGACTAATGATTATAGGCCTGTCCAGGATCTGAGAGAAGTCAACAAGC 3540
      AATTCTTTGGTCCCTGATTACTAATATCCGGACAGGTCCTAGACTCTCTTCAGTTGTTCG

3541  GGGTGGAAGACATCCACCCCACCGTGCCCAACCCTTACAACCTCTTGAGCGGCTCCAC 3600
      CCCACCTTCTGTAGGTGGGGTGGCACGGGTTGGGAATGTTGGAGAACTCGCCGAGGGTG

3601  CGTCCCACCAGTGGTACACTGTGCTTGATTTAAAGGATGCCTTTTTCTGCCTGAGACTCC 3660
      GCAGGGTGGTCACCATGTGACACGAACTAAATTTCCTACGGAAAAAGACGGACTCTGAGG

PfeI
                                                         |
                                                        TfiI
                                                         |
3661  ACCCCACCAGTCAGCCTCTCTTCGGCCTTTGAGTGGAGAGATCCAGAGATGGGATCTCAG 3720
      TGGGGTGGTCAGTCGGAGAGAAGCCGGAAACTCACCTCTCTAGGTCTCTACCCTAGAGTC

MfeI
          |
         MunI
          |
```

FIG. 3F-9

3721 GACAATTGACCTGGACCAGACTCCCACAGGGTTTCAAAAACAGTCCCACCCTGTTTGATG 3780
     CTGTTAACTGGACCTGGTCTGAGGGTGTCCCAAAGTTTTTGTCAGGGTGGGACAAACTAC

MroI
                              :
                              BseAI
                              :
                              Bsp13I
                              :
                              BspEI
                              :
                              Kpn2I
                              :
                              AccIII
                              :
3781 AGGCACTGCACAGAGACCTAGCAGACTTCCGGATCCAGCACCCAGACTTGATCCTGCTAC 3840
     TCCGTGACGTGTCTCTGGATCGTCTGAAGGCCTAGGTCGTGGGTCTGAACTAGGACGATG

3841 AGTACGTGGATGACTTACTGCTGGCCGCCACTTCTGAGCTAGACTGCCAACAAGGTACTC 3900
     TCATGCACCTACTGAATGACGACCGGCGGTGAAGACTCGATCTGACGGTTGTTCCATGAG

*FIG. 3F-9 (Cont'd)*

```
3901  GGGCCTGTTACAAACCCTAGGGAACCTCGGGTATCGGCCTCGGCCAAGAAAGCCAAA  3960
      CCCGGGACAATGTTTGGGATCCCTTGGAGCCCATAGCCGGAGCCGGTTCTTTCGGTTT

3961  TTTGCCAGAAACAGGTCAAGTATCTGGGGTATCTTCTAAAAGAGGGTCAGGATGGCTGA  4020
      AAACGGTCTTTGTCCAGTTCATAGACCCCATAGAAGATTTTCTCCCAGTCTCTACCGACT

4021  CTGAGGCCAGAAAAGAGACTGTGATGGGGCAGCCTACTCCGAAGACCCTCGACAACTAA  4080
      GACTCCGGTCTTTTCTCTGACACTACCCCGTCGGATGAGGCTTCTGGGGAGCTGTTGATT

4081  GGGAGTTCCTAGGGACGGCAGGCTTCTGTCGCCTCTGGATCCTGGGTTTGCAGAAATGG  4140
      CCCTCAAGGATCCCTGCCGTCCGAAGACAGCGGAGACCTAGGGACCCAAACGTCTTTACC

4141  CAGCCCCCTTGTACCCTCTCACCAAAACGGGGACTCTGTTTAATTGGGGCCCAGACCAAC  4200
      GTCGGGGAACATGGGAGTGGTTTTGCCCCTGAGACAAATTAACCCCGGGTCTGTTG

4201  AAAGGCCCTATCAAGAAATCAAGCAAGCTCTTCTAACTGCCCCAGCCCTGGGGTTGCAG  4260
      TTTCCGGGATAGTTCTTTAGTTCGTTCGAGAAGATTGACGGGGTCGGGACCCCAACGGTC

SalI
                              |
4261  ATTTGACTAAGCCCCTTTGAACTCTTTGTCGACGGGAAGCAGGGCTACGCCAAAGGTGTCC  4320
      TAAACTGATTCGGGAAACTTGAGAAACAGCTGCTCTTCGTCCCGATGCGGTTTCCACAGG

4321  TAACGCAAAAACTGGGACCTTGGCGTCGGCCGGTGGCCTACCTGTCCAAAAAGCTAGACC  4380
      ATTGCGTTTTTGACCCTGGAACCGCAGCCGGCCACCGGATGGACAGGTTTTTCGATCTGG

4381  CAGTAGCAGCTGGGTGGCCCCCTTGCCTACGGATGGTAGCAGCCATTGCCGTACTGACAA  4440
      GTCATCGTCGACCCACCGGGGAACGGATGCCTACCATCGTCGGTAACGGCATGACTGTT

4441  AGGATGCAGGCAAGCTAACCATGGACAGCCACTAGTCATTCTGCCCCCCATGCAGTAG  4500
      TCCTACGTCCGTTCGATTGGTACCTGTCGGTGATCAGTAAGACGGGGGTACGTCATC

4501  AGGCACTAGTCAAACAACCCCCCGACCGCTGGCTTTCCAACGCCCGGATGACTCACTATC  4560
      TCCGTGATCAGTTTGTTGGGGGGCTGGCGACCGAAAGGTTGCGGGCCTACTGAGTGATAG

4561  AGGCCTTGCTTTTGGACACGGACCCGGTCCAGTTCGGACCGGTGGTAGCCCTGAACCCGG  4620
      TCCGGAACGAAAACCTGTGCCTGGGCCAGGTCAAGCCTGGCCACCATCGGACTTGGGCC

4621  CTACGCTGCTCCCACTGCCTGAGGAAGGGCTGCAACACAACTGCCTTGATATCCTGGCCG  4680
      GATGCGACGAGGGTGACGGACTCCTTCCCGACGTTGTGTTGACGGAACTATAGGACGGC

4681  AAGCCCACGGAACCCGACCCGACCTAACGGACCAGCCGCTCCCAGACGCCGACCACACCT  4740
      TTCGGGTGCCTTGGGCTGGCTGGATTGCCTGGTCGGCGAGGGTCTGCGGCTGGTGTGGA

4741  GGTACACGGATGGAAGCAGTCTCTTACAAGAGGGACAGCGTAAGGCGGAGCTGCGGTGA  4800
      CCATGTGCCTACCTTCGTCAGAGAATGTTCTCCCTGTCGCATTCGCCCTCGACGCCACT
```

*FIG. 3F-10*

```
                                        BlpI
                                        |
                                        CeIII
                                        |
                                        Bpu1102I
                                        |
                                        Bsp1720I
                                        |
4801  CCACCGAGACCGAGGTAATCTGGGCTAAAGCCCTGCCAGCCGGGACATCCGCTCAGCGGG  4860
      GGTGGCTCTGGCTCCATTAGACCCGATTTCGGGACGGTCGGCCCTGTAGGCGAGTCGCCC

4861  CTGAACTGATAGCACTCACCCAGGCCCTAAAGATGGCAGAAGGTAAGAAGCTAAATGTTT  4920
      GACTTGACTATCGTGAGTGGGTCCGGGATTTCTACCGTCTTCCATTCTTCGATTTACAAA
```

FIG. 3F-10 (Cont'd)

```
4921  ATACTGATAGCCGTTATGCTTTTGCTACTGCCCATATCCATGGAGAAATATACAGAAGGC 4980
      TATGACTATCGGCAATACGAAAACGATGACGGGTATAGGTACCTCTTTATATGTCTTCCG

4981  GTGGGTTGCTCACATCAGAAGGCAAAGAGATCAAAAATAAAGACGAGATCTTGGCCCTAC 5040
      CACCCAACGAGTGTAGTCTTCCGTTTCTCTAGTTTTTATTTCTGCTCTAGAACCGGGATG

5041  TAAAAGCCCTCTTTCTGCCCAAAAGACTTAGCATAATCCATTGTCCAGGACATCAAAAGG 5100
      ATTTTCGGGAGAAAGACGGGTTTTCTGAATCGTATTAGGTAACAGGTCCTGTAGTTTTCC

5101  GACAGCGCCGAGGCTAGAGGCAACCGGATGGCTGACCAAGCGGCCCGAAAGGCAGCCA 5160
      CTGTCGCGGCTCCGATCTCCGTTGGCCTACCGACTGGTTCGCCGGGCTTTCCGTCGGT

5161  TCACAGAGACTCCAGACACCTCTACCCTCCTCATAGAAAATTCATCACCCTACACCTCAG 5220
      AGTGTCTCTGAGGTCTGTGGAGATGGGAGGAGTATCTTTTAAGTAGTGGGATGTGGAGTC

5221  AACATTTTCATTACACAGTGACTGATATAAAGGACCTAACCAAGTTGGGGGCCATTTATG 5280
      TTGTAAAAGTAATGTGTCACTGACTATATTTCCTGGATTGGTTCAACCCCCGGTAAATAC

5281  ATAAAACAAAGAAGTATTGGGTCTACCAAGGAAAACCTGTGATGCCTGACCAGTTTACTT 5340
      TATTTTGTTTCTTCATAACCCAGATGGTTCCTTTTGGACACTACGGACTGGTCAAATGAA

5341  TTGAATTATTAGACTTTCTTCATCAGCTGACTCACCTCAGCTTCTCAAAAATGAAGGCTC 5400
      AACTTAATAATCTGAAAGAAGTAGTCGACTGAGTGGAGTCGAAGAGTTTTACTTCCGAG

5401  TCCTAGAGAGAAGCCACAGTCCCTACTACATGCTGAACCGGGATCGAACACTCAAAAATA 5460
      AGGATCTCTCTTCGGTGTCAGGGATGATGTACGACTTGGCCCTAGCTTGTGAGTTTTTAT

5461  TCACTGAGACCTGCAAAGCTTGTGCACAAGTCAACGCCAGCAAGTCTGCCGTTAAACAGG 5520
      AGTGACTCTGGACGTTTCGAACACGTGTTCAGTTGCGGTCGTTCAGACGGCAATTTGTCC
```

```
SacII
|
SgrBI
|
Cfr42I
|
Sfr303I
|
KspI
|
```

FIG. 3F-11

```
5521 GAACTAGGGTCCGCGGGCATCGGCCCGGCACTCATTGGGAGATCGATTTCACCGAGATAA 5580
     CTTGATCCCAGGCGCCCGTAGCCGGGCCGTGAGTAACCCTCTAGCTAAAGTGGCTCTATT

5581 AGCCCGGATTGTATGGCTATAAATATCTTCTAGTTTTTATAGATACCTTTTCTGGCTGGA 5640
     TCGGGCCTAACATACCGATATTTATAGAAGATCAAAAATATCTATGGAAAGACCGACCT

5641 TAGAAGCCTTCCCAACCAAGAAGAAACCGCCAAGGTCGTACCAAGAAGCTACTAGAGG 5700
     ATCTTCGGAAGGGTTGGTTCTTCTTTGGCGGTTCCAGCATGGTTCTTCGATGATCTCC
```

```
                              PaeI
                               |
                              AbuI
                               |
                              SpaHI
                               |
                              SphI
                               |
5701 AGATCTTCCCCAGGTTCGGCATGCCTCAGGTATTGGGAACTGACAATGGGCCTGCCTTCG 5760
     TCTAGAAGGGGTCCAAGCCGTACGGAGTCCATAACCCTTGACTGTTACCCGGACGGAAGC
```

*FIG. 3F-11 (Cont'd)*

5761 TCTCCAAGGTGAGTCAGACAGTGGCCGATCGTTGGGATTGATTGGAATTACATTGTG 5820
     AGAGGTTCCACTCAGTCTGTCACCGGCTAGCAACCCCTAACTAACCTTTAAGTAACAC

5821 CATACAGACCCCAAAGCTCAGGCCGGTAGAAAGAATGAATAGAACCATCAAGGAGACTT 5880
     GTATGTCTGGGGTTTCGAGTCCGGCCATTTTCTTACTTATCTTGGTAGTCCTCTGAA

5881 TAACTAAATTAACGGCTTCGACTGGCTCTAGAGACTGGGTGCGCCTACTCCCTTAGCGC 5940
     ATTGATTAATTGCCGAAGCTGACCGAGATCTCTGACCCACGCGGATGAGGGAATCGCG

SfiI
                          |
5941 TGTACCGAGCCCGCAACAGCCGGGGCCCCATGGCTCATCCGTATGAGATCTTATATG 6000
     ACATGGCTCGGGCGTTGTCGGCCCCGGGGTACCGAGTAGGCATATACTCTAGAATATAC

6001 GGGCACCCCGCCCTTGTAAACTTCCCTGACCCTGACATGACAAGAGTTACTAACAGCC 6060
     CCCGTGGGGCGGGAACATTTGAAGGGACTGGGACTGTACTGTTCTCAATGATTGTCGG

6061 CCTCTCTCAAGCTCACTACAGGCTCTCTACTTAGTCCAGCACGAAGTCTGAGAACCTC 6120
     GGAGAGAGTTCGAGTGATGTCCGAGAGATGAATCAGGTCGTGCTTCAGACCTCTGGAG

6121 TGGGCAGCCTACCAAGAACAACTGACCGACCGGTGTACCTCACCCTACCGAGTCG 6180
     ACCCGTCGGATGGTTCTTGTTGACTGGCTGGCACCATGAGTGGGATGGCTCAGC

6181 GGGACACAGTGTGGGTCGGCCGACACCAGACTAAGAACCTAGAACCTCGCTGGAAGGAC 6240
     CCCTGTGTCACACCCAGCCGGCTGTGGTCTGATTCTTGGATCTTGGAGCGACCTTCCTG

6241 CTTACACAGTCCGTGCTGACCACCCCACGGCCCTCAAAGTAGCGGCATCGTAGCTTGGA 6300
     GAATGTGTCAGGCACGACTGGTGGGGGTGCCGGAGTTCATCTGCGTAGCATCGAACCT 4070A env (6359-8323) >>>
                                                     |
6301 TACACGGCCCCACGTGAAGGCTAGCGACCCCGGGTTGAACGTCCTGAGACTGACAT 6360
     ATGTGCCGGGGTGCACTTCCGAGCGCTGGGGCCCAACTTGCAGGACTCGACTGTA 6361 GGGCGTTCAACGCTCTCAAAACCCCCTCAAGATAAGATTAACCCGTGGAAGCCCTAAT 6420
     CCCGCAAGTTGCGAGAGTTTTGGGGGAGTTCTATTCTAATTGGGCACCTTCGGGATTA 6421 AGTCATGGAGTCCGTTAGAGTAGGATGGCAGAGAGCCCCATCAGGTCTTTAATGT 6480
     TCAGTACCCTCAGGCAATCTCATCCTACCGTCTCTCGGGGTAGTCAGAAATACA 6481 AACCTGGAGAGTCACCAACCTGATGACTGGGCGTACCGCCAATGCACCTCCTCCTGGG 6540
     TTGGACCTCTCAGTGGTTGGACTACTGACCCGCATGGCGGTTACGTGGAGGAGGACCC

*FIG. 3F-12*

```
6541  AACTGTACAAGATGCCTTCCAAAATTATATTTTGATCTATGTGATCTGTCGAGAGGA 6600
      TTGACATGTTCTACGGAAGGGTTTTAATATAAAACTAGATACACTAGACCAGCCTCTCCT

6601  GTGGGACCCTTCAGACCAGGAACCGTATGTCGGGTATGGCTGCAAGTACCCGCAGGAG 6660
      CACCCTGGGAAGTCTGGTCCTTGGCATACAGCCCATACCGACGTTCATGGGCGTCCTC

6661  ACAGCCGACCCGGACTTTTGACTTTACGTGTGCCCTGGCATACCGTAAAGTCGGGGTG 6720
      TGTCGGCTGGGCCTGAAAACTGAAATGCACACGGGACCGTATGGCATTTCAGCCCCAC

6721  TGGGGACCAGGAGAGGGCTACTGTGGTAAATGGGGTGTGAAACCACCGGACAGGCTTA 6780
      ACCCCTGGTCCTCTCCCGATGACACCATTTACCCCACACTTTGGTGGCCTGTCCGAAT

6781  CTGGAAGCCCACATCGTCGTGGGACCTAATCTCCCTTAAGCGCGGTAACACCCCCTGGGA 6840
      GACCTTCGGGTGTAGCAGCACCCTGGATTAGAGGGAATTCGCGCCATTGTGGGGACCCT

6841  CACGGGATGCTCTAAAGTTGCCTGTGGCCCCTGCTACGACCTCTCCAAAGTATCCAATTC 6900
      GTGCCCTACGAGATTCAACGGACACCGGGACGATGCTGGAGAGGTTTCATAGGTTAAG
```

*FIG. 3F-12 (Cont'd)*

```
6901 CTTCCAAGGGGCTACTCGAGGGGGCAGATGCAACCCTCTAGTCCTAGAATTCACTGATGC 6960
     GAAGGTTCCCCGATGAGCTCCCCCGTCTACGTTGGGAGATCAGGATCTTAAGTGACTACG

6961 AGGAAAAAGGCTAACTGGGACGGGCCCAAATCGTGGGGACTGAGACTGTACCGGACAGG 7020
     TCCTTTTTCCGATTGACCCTGCCCGGGTTTAGCACCCCTGACTCTGACATGGCCTGTCC

7021 AACAGATCCTATTACCATGTTCTCCCTGACCCGGCAGGTCCTTAATGTGGGACCCCGAGT 7080
     TTGTCTAGGATAATGGTACAAGAGGGACTGGGCCGTCCAGGAATTACACCCTGGGGCTCA

7081 CCCCATAGGGCCCAACCCAGTATTACCCGACCAAAGACTCCCTTCCTCACGAATAGAGAT 7140
     GGGGTATCCCGGGTTGGGTCATAATGGGCTGGTTTCTGAGGGAAGGAGTGGTTATCTCTA

7141 TGTACCGGCTCCACAGCCACCTAGCCCCCTCAATACCAGTTACCCCCCTTCCACTACCAG 7200
     ACATGGCCGAGGTGTCGGTGGATCGGGGAGTTATGGTCAATGGGGGAAGGTGATGGTC

7201 TACACCCTCAACCTGCCCTACAAGTCCAAGTGTCCGACAGCCACCCCCAGGAACTGGAGA 7260
     ATGTGGGAGTTGGAGGGGATGTTCAGGTTCACAGGGTGTCGGTGGGGGTCCTTGACCTCT

7261 TAGACTACTAGCTCTAGTCAAAGGAGCCTATCAGGCGCTTAACCTCACCAATCCCGACAA 7320
     ATCTGATGATCGAGATCAGTTTCCTCGGATAGTCCGCGAATTGGAGTGGTTAGGGCTGTT

7321 GACCCAAGAATGTTGGCTGTGCTTAGTGTCGGGACCTCCTTATTACGAAGGAGTAGCGGT 7380
     CTGGGTTCTTACAACCGACACGAATCACAGCCCTGGAGGAATAATGCTTCCTCATCGCCA

7381 CGTGGGCACTTATACCAATCATTCCACCGCTCCGGCCAACTGTACGGCCACTTCCAACA 7440
     GCACCCGTGAATATGGTTAGTAAGGTGGCGAGGCCGGTTGACATGCCGGTGAAGGGTTGT
```

BcoT22I
                                        |
                                      NsiI
                                        |
                                      Mph1103I
                                        |
                                      Zsp2I
                                        |
                                      BfrBI
                                        | |

FIG. 3F-13

```
7441  TAGCTTACCCTATCTGAAGTGACAGGACAGGGCCTATGCATGGGGCAGTACCTAAAAC  7500
      ATCGAATGGGATAGACTTCACTGTCCTGTCCCGGATACGTACCCCGTCATGGATTTTG
```

NaeI
                                     |
                                    PdiI
                                     |
                                   MroNI
                                    | |
                                   NgoMIV
                                    | |
```
7501  TCACCAGGCCTATGTACACCACCGAAGCGCCGGCTCAGGATCCTACTACTTGCAGC  7560
      AGTGGTCCGGAATACATGTGGTGGCTTCGCGGCCGAGTCCTAGGATGATGAACGTCG
```

AleI
                                                           |
                                                          OliI
                                                           |
```
7561  ACCGCCGGAACAATGTGGGCTTGCAGCACTGGATTGACTCCTGCTTGTCCACCACGGT  7620
      TGGCGGCCTTGTTACACCCGAACGTCGTGACCTAACTGAGGACGAACAGGTGGTGCCA

7621  GCTCAATCTAACCACAGAATTATTGTGTATTAGTTGAACTCTGGCCCAGAGTAATTACCA  7680
      CGAGTTAGATTGGTGTCTTAATAACACATAATCAACTTGAGACCGGGTCTCATTAATGGT
```

*FIG. 3F-13 (Cont'd)*

```
7681  CTCCCCCGATTATATGTATGGTCAGCTTGAACAGGGTACCAAATATAAAAGACAGCCAGT 7740
      GAGGGGGCTAATATACATACCAGTCGAACTTGTCCCATGGTTTATATTTTCTCTCGGTCA

7741  ATCATTGACCCTGGCCCTTCTACTAGGAGGATTAACCATGGGAGGGATTGCAGCTGGAAT 7800
      TAGTAACTGGGACCGGGAAGATGATCCTCCTAATTGGTACCCTCCCTAACGTCGACCTTA

7801  AGGGACGGGGACCACTGGCCTTAATTAAAACCCAGCAGTTTGAGCAGCTTCATGCCGCTAT 7860
      TCCCTGCCCCTGGTGACCGGAATTAATTTTGGGTCGTCAAACTCGTCGAAGTACGGCGATA

7861  CCAGACAGACCTCAACGAAGTCGAAAAGTCAATTACCAACCTAGAAAAGTCACTGACCTC 7920
      GGTCTGTCTGGAGTTGCTTCAGCTTTTCAGTTAATGGTTGGATCTTTTCAGTGACTGGAG

7921  GTTGTCTGAAGTAGTCCTACAGAACCGCAGAGGCCTAGATTTGCTATTCCTAAAGGAGGG 7980
      CAACAGACTTCATCAGGATGTCTTGGCGTCTCCGGATCTAAACGATAAGGATTTCCTCCC

7981  AGGTCTCTGGCAGCCCTAAAAGAAGAATGTTGTTTTTATGCAGACCACACGGGCTAGT 8040
      TCCAGAGACCGTCGGGATTTTCTTCTTACAACAAAATACGTCTGGTGTGCCCGATCA

8041  GAGAGACAGCATGGCCAAATTAAGAGAAAGGCTTAATCAGAGACAAAAACTATTTGAGAC 8100
      CTCTCTGTCGTACCGGTTTAATTCTCTTTCCGAATTAGTCTCTGTTTTTGATAAACTCTG

NspV
                          |
                          BstBI
                          |
                          Bsp119I
                          |
                          AsuII
                          |
                          Csp45I
                          |
                          SfuI
                          |
                          Bpu14I
                          |
                          BspT104I
                          |
8101  AGGCAAGGATGGTTCGAAGGCTGTTTAATAGATCCCCCTGGTTTACCACCTTAATCTC 8160
      TCCGGTTCCTACCAAGCTTCCGACAAATTATCTAGGGGACCAAATGGTGGAATTAGAG

8161  CACCATCATGGGACCTCTAATAGTACTCTTACTGATCTTACTCTTTGGACCTTGCATTCT 8220
      GTGGTAGTACCCTGGAGATTATCATGAGAATGACTAGAATGAGAAACCTGGAACGTAAGA

8221  CAATCGATTGGTCCAAATTTGTTAAAGACAGGATCTCAGTGGTCCAGGCTCTGGTTTTGAC 8280
      GTTAGCTAACCAGGTTTAAACAATTTCTGTCCTAGAGTCACCAGGTCCGAGACCAAAACTG
```

*FIG. 3F-14*

```
                                                      IRES reg(8327,8876)>>>
                                                      |
                                                   MluI(8325)
                                                      | |
8281  TCAGCAATATCACCAGCTAAAACCCATAGAGTACGAGCCATGAACCCGTTACTGGCCGAA  8340
      AGTCGTTATAGTGGTCGATTTTGGGTATCTCATGCTCGGTACTTGCGCAATGACCGGCTT ires_emcv reg(8378,8876)>>>
                                           |
8341  GCCGCTTGGAATAAGCCGGTGTGCGTTTGTCTATATGTTATTTTCCACCATATTGCCGT  8400
      CGGCGAACCTTATTCGGCCACACGCAAACAGATATACAATAAAAGGTGGTATAACGGCA 8401  CTTTTGGCAATGTGAGGGCCCGGAAACCTGGCCCTGTCTTCTTGACGAGCATTCCTAGG  8460
      GAAAACCGTTACACTCCCGGGCCTTTGGACCGGGACAGAAGAACTGCTCGTAAGGATCC
```

*FIG. 3F-14 (Cont'd)*

```
8461  GTCTTTCCCCTCTCGCCAAAGGAATGCAAGGTCTGTTGAATGTCGTGAAGGAAGCAGTTC  8520
      CAGAAAGGGGAGAGCGGTTTCCTTACGTTCCAGACAACTTACAGCACTTCCTTCGTCAAG

8521  CTCTGGAAGCTTCTTGAAGACAAACAACGTCTGTAGCGACCCTTTGCAGGCAGCGGAACC  8580
      GAGACCTTCGAAGAACTTCTGTTTGTTGCAGACATCGCTGGGAAACGTCCGTCGCCTTGG

8581  GGGGACCTGGCGACAGGTGCCTCTGCGGCCAAAAGCCACGTGTATAAGATACACCTGCAA  8640
      CCCCTGGACCGCTGTCCACGGAGACGCCGGTTTTCGGTGCACATATTCTATGTGGACGTT

8641  AGGCGGCACAACCCCAGTGCCACGTTGTGAGTTGGATAGTTGTGGAAAGAGTCAAATGGC  8700
      TCCGCCGTGTTGGGGTCACGGTGCAACACTCAACCTATCAACACCTTTCTCAGTTTACCG

8701  TCTCCTCAAGCGTATTCAACAAGGGGCTGAAGGATGCCCAGAAGGTACCCCATTGTATGG  8760
      AGAGGAGTTCGCATAAGTTGTTCCCCGACTTCCTACGGGTCTTCCATGGGGTAACATACC

8761  GATCTGATCTGGGGCCTCGGTGCACATGCTTTACATGTGTTTAGTCGAGGTTAAAAAAAC  8820
      CTAGACTAGACCCCGGAGCCACGTGTACGAAATGTACACAAATCAGCTCCAATTTTTTTG yC02 (8877,9353)>>>
                                                    |
                                                 PaiI (8874)
                                                    | |
8821  GTCTAGGCCCCCCGAACCACGGGGACGTGGTTTTCCTTTGAAAAACACGATTATAAATGG  8880
      CAGATCCGGGGGGCTTGGTGCCCCTGCACCAAAAGGAAACTTTTTGTGCTAATATTTACC

8881  TGACGGGGGCATGGCCTCCAAGTGGCATCAAAAGGCATGAATATCGCTTACAGGCAGG    8940
      ACTGCCCCCGTACCGGAGGTTCACCGTAGTTTTCCGTACCTATAGCGAATGTCCTCC

8941  CCTGCTGGCTACAAGGAGGCGGCGGTGCCTATCGCGGCTGTCTGATCAACAACAAGG    9000
      GGACGACCGATGTTCCTCCGCCGCCACGGATAGCGCCGACAGACTAGTTGTTGTTCC

9001  ACGGCAGTGTGCTGGCAGGGGCACAACATGAGGTTCCAAAGGCTCCGCCACCCTGC    9060
      TGCCGTCACACGACCGTCCCCGTGTTGTACTCCAAGGTTTCCGAGGCGGTGGGACG

9061  ACGGCGAGATCTCCACCTGGACAACTGTGCCAGCCTGAGGCAACGTGTACAAGGACA    9120
      TGCCGCTCTAGAGGTGGACCTGTTGACACGGTCGGACTCCGTTGCACATGTTCCTGT

9121  CCACCCTGTACACCACCCTGTCCCCTTGTGCCATGTGTACCGGCCTATCATCATGTACGG  9180
      GGTGGGACATGTGGTGGGACAGGGGAACAGGGGAACACTGTACACATGGCCGGATAGTAGTACATGCC
```

*FIG. 3F-15*

```
9181  GCATCCCTAGTGTGTGATCGCCGAGAACGTGAACTTCAAGTCCAAGGCCGAGAAGTACC  9240
      CGTAGGGATCACACACTAGCGGCTCTTGCACTTGAAGTTCAGGTTCCGGCTCTTCATGG

9241  TGAAACTAGGGCCACGAGGTGGTGGTTGTTGACGATGAGAGGTGTAAGAAGTGATGA  9300
      ACTTTGATCCCGGTGCTCCACCACCAACAACTGCTACTCTCCACATTCTTCACTACT
```

NotI (9356)
|
CciNI
|

```
9301  ACCAGTTCATCGACGAGAGGCCTCAGGACTGGTTCGAGGATATCGGCAGTAAGCGGCC  9360
      TGGTCAAGTAGCTGCTCTCCGGAGTCCTGACCAAGCTCCTATAGCCGCGCATTCGCCGG
```

U3 Region (9405, 9854) >>>
|

```
9361  GGATAAAATAAAAGATTTTATTTAGTCTCCAGAAAAAGGGGGGAATGAAAGACCCCACC  9420
      CCTATTTTATTTTCTAAAATAAATCAGAGGTCTTTTTCCCCCCTTACTTTCTGGGGTGG
```

*FIG. 3F-15 (Cont'd)*

```
                        BstI
                         |
              NheI
               |
           AsuNHI        5_LTR2 other(9447,9998)>>>>
             |  |           |
     9421 TGTAGGTTTGGCAAGCTAGCTTAAGTAAGGCCATTTTGCAAGGCATGGAAAAATACATAA 9480
          ACATCCAAACCGTTCGATCGAATTCATTCCGGTAAAACGTTCCGTACCTTTTATGTATT 9481 CTGAGAATAGAGAAGTTCAGATCAAGGTCAGGAACAGATGGAACAGCTGAATATGGGCCA 9540
          GACTCTTATCTCTTCAAGTCTAGTTCCAGTCCTTGTCTACCTTGTCGACTTATACCCGGT 9541 AACAGGATATCTGTGGTAAGCAGTTCCTGCCCCGGCTCAGGGCCAAGAACAGATGGAACA 9600
          TTGTCCTATAGACACCATTCGTCAAGGACGGGGCCGAGTCCCGGTTCTTGTCTACCTTGT 9601 GCTGAATATGGGCCAAACAGGATATCTGTGGTAAGCAGTTCCTGCCCCGGCTCAGGGCCA 9660
          CGACTTATACCCGGTTTGTCCTATAGACACCATTCGTCAAGGACGGGGCCGAGTCCCGGT 9661 AGAACAGATGGTCCCCAGATGCGGTCCAGCCCTCAGCAGTTTCTAGAGAACCATCAGATG 9720
          TCTTGTCTACCAGGGGTCTACGCCAGGTCGGGAGTCGTCAAAGATCTCTTGGTAGTCTAC 9721 TTTCCAGGGTGCCCCAAGGACCTGAAATGACCCTGTGCCTTATTTGAACTAACCAATCAG 9780
          AAAGGTCCCACGGGGTTCCTGGACTTTACTGGGACACGGAATAAACTTGATTGGTTAGTC SacI
                                                      |
                                                    SstI
                                                      |
                              PauI                 Psp1248I
                               |                    |
                             BsePI                EcoICRI
                               |  |                |  |
                             BssHII              Ecl136II
                               |  |                |  |
     9781 TTCGCTTCTCGCTTCTGTTCGCGCGCTTCTGCTCCCCGAGCTCAATAAAAGAGCCCACAA 9840
          AAGCGAAGAGCGAAGACAAGCGCGCGAAGACGAGGGGCTCGAGTTATTTTCTCGGGTGTT R Region(9855,9921)>>>>
                       |
     9841 CCCCTCACTCGGGGCGCCAGTCCTCCGATTGACTGAGTCGCCCGGGTACCCGTGTATCCA 9900
          GGGGAGTGAGCCCCGCGGTCAGGAGGCTAACTGACTCAGCGGGCCCATGGGCACATAGGT U5 Region(9922,9998)>>>>
                       |
     9901 ATAAACCCTCTTGCAGTTGCATCCGACTTGTGGTCTGCTGTTCCTTGGGAGGGTCTCCT 9960
          TATTTGGGAGAACGTCAACGTAGGCTGAACACCAGACGACAAGGAACCCTCCCAGAGGA 9961 CTGAGTGATTGACTACCCGTCAGCGGGGGTCTTTCATTACATGTGAGCAAAAGGCCAGCA 10020
          GACTCACTAACTGATGGGCAGTCGCCCCCAGAAAGTAATGTACACTCGTTTTCCGGTCGT
```

*FIG. 3F-16* pBR322 origin(10045,10664)<<<

```
10021 AAAGGCCAGGAACCGTAAAAAGGCCGCGTTGCTGGCGTTTTTCCATAGGCTCCGCCCCC 10080
      TTTCCGGTCCTTGGCATTTTTCCGGCGCAACGACCGCAAAAGGTATCCGAGGCGGGGGG

10081 TGACGAGCATCACAAAAATCGACGCTCAAGTCAGAGGTGGCGAAACCCGACAGGACTATA 10140
      ACTGCTCGTAGTGTTTTTAGCTGCGAGTTCAGTCTCCACCGCTTTGGGCTGTCCTGATAT

10141 AAGATACCAGGCGTTTCCCCCTGGAAGCTCCCTCGTGCGCTCTCCTGTTCCGACCCTGCC 10200
      TTCTATGGTCCGCAAAGGGGGACCTTCGAGGGAGCACGCGAGAGGACAAGGCTGGGACGG
```

FIG. 3F-16 (Cont'd)

```
10201 GCTTACCGGATACCTGTCCGCCTTTCTCCCTTCGGGAAGCGTGGCGCTTTCTCA[T]CTC 10260
      CGAATGGCCTATGGACAGGCGGAAAGAGGGAAGCCCTTCGCACCGCGAAAGACTATCGAG

10261 ACGCTGTAGGTATCTCAGTTCGGTGTAGGTCGTTCGCTCCAAGCTGGGCTGTGTGCACGA 10320
      TGCGACATCCATAGAGTCAAGCCACATCCAGCAAGCGAGGTTCGACCCGACACACGTGCT

10321 ACCCCCCGTTCAGCCCGACCGCTGCGCCTTATCCGGTAACTATCGTCTTGAGTCCAACCC 10380
      TGGGGGCAAGTCGGGCTGGCGACGCGGAATAGGCCATTGATAGCAGAACTCAGGTTGGG

10381 GGTAAGACACGACTTATCGCCACTGGCAGCAGCCACTGGTAACAGGATTAGCAGAGCGAG 10440
      CCATTCTGTGCTGAATAGCGGTGACCGTCGTCGGTGACCATTGTCCTAATCGTCTCGCTC

10441 GTATGTAGGCGGTGCTACAGAGTTCTTGAAGTGGTGGCCTAACTACGGCTACACTAGAAG 10500
      CATACATCCGCCACGATGTCTCAAGAACTTCACCACCGGATTGATGCCGATGTGATCTTC

10501 GACAGTATTTGGTATCTGCGCTCTGCTGAAGCCAGTTACCTTCGGAAAAAGAGTTGGTAG 10560
      CTGTCATAAACCATAGACGCGAGACGACTTCGGTCAATGGAAGCCTTTTTCTCAACCATC

10561 CTCTTGATCCGGCAAACAAACCACCGCTGGTAGCGGTGGTTTTTTTGTTTGCAAGCAGCA 10620
      GAGAACTAGGCCGTTTGTTTGGTGGCGACCATCGCCACCAAAAAAACAAACGTTCGTCGT

10621 GATTACGCGCAGAAAAAAAGGATCTCAAGAAGATCCTTTGATCTTTTCTACGGGGTCTGA 10680
      CTAATGCGCGTCTTTTTTTCCTAGAGTTCTTCTAGGAAACTAGAAAAGATGCCCCAGACT

10681 CGCTCAGTGGAACGAAAACTCACGTTAAGGGATTTTGGTCATGAGATTATCAAAAAGGAT 10740
      GCGAGTCACCTTGCTTTTGAGTGCAATTCCCTAAAACCAGTACTCTAATAGTTTTTCCTA

10741 CTTCACCTAGATCCTTTTAAATTAAAAATGAAGTTTTAAATCAATCTAAAGTATATATGA 10800
      GAAGTGGATCTAGGAAAATTTAATTTTTACTTCAAAATTTAGTTAGATTTCATATATACT amp marker (10819,11679) <<<
                        |
10801 GTAAACTTGGTCTGACAGTTACCAATGCTTAATCAGTGAGGCACCTATCTCAGCGATCTG 10860
      CATTTGAACCAGACTGTCAATGGTTACGAATTAGTCACTCCGTGGATAGAGTCGCTAGAC 10861 TCTATTTCGTTCATCCATAGTTGCCTGACTCCCCGTCGTGTAGATAACTACGATACGGGA 10920
      AGATAAAGCAAGTAGGTATCAACGGACTGAGGGGCAGCACATCTATTGATGCTATGCCCT 10921 GGGCTTACCATCTGGCCCCAGTGCTGCAATGATACCGCGAGACCCACGCTCACCGGCTCC 10980
      CCCGAATGGTAGACCGGGGTCACGACGTTACTATGGCGCTCTGGGTGCGAGTGGCCGAGG 10981 AGATTTATCAGCAATAAACCAGCCAGCCGGAAGGGCCGAGCGCAGAAGTGGTCCTGCAAC 11040
      TCTAAATAGTCGTTATTTGGTCGGTCGGCCTTCCCGGCTCGCGTCTTCACCAGGACGTTG
```

*FIG. 3F-17*

11041 TTTATCCGCCTCCATCCAGTCTATTAATTGTTGCCGGGAAGCTAGAGTAAGTAGTTCGCC 11100
      AAATAGGCGGAGGTAGGTCAGATAATTAACAACGGCCCTTCGATCTCATTCATCAAGCGG

11101 AGTTAATAGTTTGCGCAACGTTGTTGCCATTGCTGCAGGCATCGTGGTGTCACGCTCGTC 11160
      TCAATTATCAAACGCGTTGCAACAACGGTAACGACGTCCGTAGCACCACAGTGCGAGCAG

11161 GTTTGGTATGGCTTCATTCAGCTCCGGTTCCCAACGATCAAGGCGAGTTACATGATCCCC 11220
      CAAACCATACCGAAGTAAGTCGAGGCCAAGGGTTGCTAGTTCCGCTCAATGTACTAGGGG

11221 CATGTTGTGCAAAAAGCGGTTAGCTCCTTCGGTCCTCCGATCGTTGTCAGAAGTAAGTT 11280
      GTACAACACGTTTTTTCGCCAATCGAGGAAGCCAGGAGGCTAGCAACAGTCTTCATTCAA

11281 GGCCGCAGTGTTATCACTCATGGTTATGGCAGCACTGCATAATTCTCTTACTGTCATGCC 11340
      CCGGCGTCACAATAGTGAGTACCAATACCGTCGTGACGTATTAAGAGAATGACAGTACGG

11341 ATCCGTAAGATGCTTTTCTGTGACTGGTGAGTACTCAACCAAGTCATTCTGAGAATAGTG 11400
      TAGGCATTCTACGAAAAGACACTGACCACTCATGAGTTGGTTCAGTAAGACTCTTATCAC

*FIG. 3F-17 (Cont'd)*

11401 TATGCGGCGACCGAGTTGCTCTTGCCCGGCGTCAACACGGGATAATACCGCGCCACATAG 11460
      ATACGCCGCTGGCTCAACGAGAACGGGCCGCAGTTGTGCCCTATTATGGCGCGGTGTATC

11461 CAGAACTTTAAAAGTGCTCATCATTGGAAAACGTTCTTCGGGGCGAAAACTCTCAAGGAT 11520
      GTCTTGAAATTTTCACGAGTAGTAACCTTTTGCAAGAAGCCCCGCTTTTGAGAGTTCCTA

11521 CTTACCGCTGTTGAGATCCAGTTCGATGTAACCCACTCGTGCACCCAACTGATCTTCAGC 11580
      GAATGGCGACAACTCTAGGTCAAGCTACATTGGGTGAGCACGTGGGTTGACTAGAAGTCG

11581 ATCTTTTACTTTCACCAGCGTTTCTGGGTGAGCAAAAACAGGAAGGCAAATGCCGCAAA 11640
      TAGAAAATGAAAGTGGTCGCAAAGACCCACTCGTTTTTGTCCTTCCGTTTTACGGCGTTT

11641 AAAGGGAATAAGGGCGACACGGAAATGTTGAATACTCATACTCTTCCTTTTTCAATATTA 11700
      TTTCCCTTATTCCCGCTGTGCCTTTACAACTTATGAGTATGAGAAGGAAAAAGTTATAAT amp prom (11721,11749) <<<
                       |
11701 TTGAAGCATTTATCAGGGTTATTGTCTCATGAGCGGATACATATTTGAATGTATTTAGAA 11760
      AACTTCGTAAATAGTCCCAATAACAGAGTACTCGCCTATGTATAAACTTACATAAATCTT 11761 AAATAACAAATAGGGGTTCCGCGCACATTTCCCCGAAAAGTGCCACCTGACGTCTAAGA 11820
      TTTATTGTTTATCCCCAAGGCGCGTGTAAAGGGGCTTTTCACGGTGGACTGCAGATTCT 11821 AACCATTATTATCATGACATTAACCTATAAAAATAGGCGTATCACGAGGCCCTTTCGTCT 11880
      TTGGTAATAATAGTACTGTAATTGGATATTTTTATCCGCATAGTGCTCCGGGAAAGCAGA

11881 TCAAGAATTCGAT 11893
      AGTTCTTAAGCTA

*FIG. 3F-18*

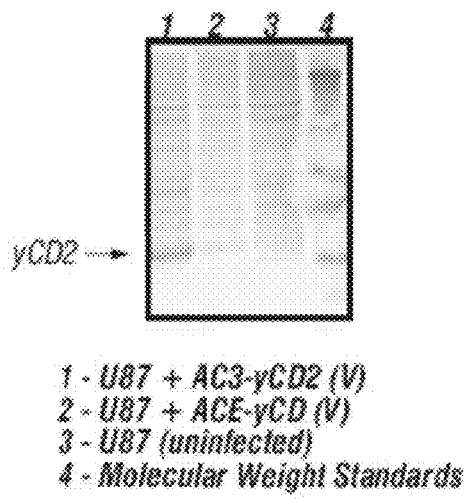

1 - U87 + AC3-yCD2 (V)
2 - U87 + ACE-yCD (V)
3 - U87 (uninfected)
4 - Molecular Weight Standards

*FIG. 4*

1. Separate synthesis of CDopt and UPRT genes with PSI1/Not1 sites

2. Digest with PSI1 and perform blunt end ligation

3. Deletion of CDopt gene STOP and UPRT START codon by site directed mutagenesis 4. CDopt-UPRT gene size: 1.3 kb 2. CDopt-Linker-UPRT gene size: 1.36 kb 1. Separate synthesis of CDopt gene and OPRT domain with PSI1/Not1 sites 2. Digest with PSI1 and perform blunt end ligation 3. Deletion of CDopt gene STOP and OPRT START codon by site directed mutagenesis 4. CDopt-OPRT gene size: 1.3 kb 2. CD-OPRT gene size: 1.33 kb hsa-miR-142-3p:  5'-UGUAGUGUUUCCUACUUUAUGGA-3' mmu-miR-142-3p:  5'-UGUAGUGUUUCCUACUUUAUGGA-3'

142-3pT: 5'- gcggccgcGTCGACTCCATAAAGTAGGAAACACTACAgcggccgc -3'

142-3pT4X:  5'-gcggccgcGTCGACTCCATAAAGTAGGAAACACTACACGATTCCATAAAGTAGGAAACACTACA
            accggtTCCATAAAGTAGGAAACACTACATCACTCCATAAAGTAGGAAACACTACAgcggccgc-3'

RECOMBINANT VECTORS

CROSS-REFERENCE TO RELATED APPLICATIONS

This application claims priority to U.S. Provisional Application Ser. No. 61/100,666, filed Sep. 26, 2008, U.S. Provisional Application Ser. No. 61/120,618, filed Dec. 8, 2008, U.S. Provisional Application Ser. No. 61/186,823, filed Jun. 13, 2009, U.S. Provisional Application Ser. No. 61/318,728, filed Mar. 29, 2010 and is a continuation-in-part of International Application No. PCT/US09/58512, filed Sep. 26, 2009, the disclosures of which are incorporated herein by reference.

TECHNICAL FIELD

This disclosure relates to replication competent retroviral vectors for treating cell proliferative. The disclosure further relates to the use of such replication competent retroviral vectors for delivery and expression of heterologous nucleic acids.

BACKGROUND

Effective methods of delivering genes and heterologous nucleic acids to cells and subjects has been a goal researchers for scientific development and for possible treatments of diseases and disorders.

SUMMARY

The disclosure provides a recombinant replication competent retrovirus (RCR) comprising: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising an internal ribosome entry site (IRES) operably linked to a heterologous polynucleotide, wherein the cassette is positioned 5' to the 3' LTR and 3' to the env nucleic acid domain encoding the retroviral envelope; and cis-acting sequences necessary for reverse transcription, packaging and integration in a target cell, wherein the RCR maintains higher replication competency after 6 passages compared to a pACE vector (SEQ ID NO:21). In one embodiment, the retroviral polynucleotide sequence is derived from murine leukemia virus (MLV), Moloney murine leukemia virus (MoMLV), Feline leukemia virus (FeLV) or Gibbon ape leukemia virus (GALV). In another embodiment, the MLV is an amphotropic MLV. In yet another embodiment, the retrovirus is an oncoretrovirus or gamma retrovirus. In yet another embodiment, the target cell is a cell having a cell proliferative disorder. The cell proliferative disorder can be selected from the group consisting of, but is not limited to, lung cancer, colon-rectum cancer, breast cancer, prostate cancer, urinary tract cancer, uterine cancer, brain cancer, head and neck cancer, pancreatic cancer, melanoma, stomach cancer and ovarian cancer, rheumatoid arthritis and other autoimmune diseases. In one embodiment, the promoter comprises a CMV promoter having a sequence as set forth in SEQ ID NO:19, 20 or 22 from nucleotide 1 to about nucleotide 582 and may include modification to one or more nucleic acid bases and which is capable of directing and initiating transcription. In yet a further embodiment, the promoter comprises a sequence as set forth in SEQ ID NO: 19, 20 or 22 from nucleotide 1 to about nucleotide 582. In a further embodiment, the promoter comprises a CMV-R-U5 domain polynucleotide. In one embodiment, the CMV-R-U5 domain comprises the immediately early promoter from human cytomegalovirus linked to an MLV R-U5 region. In yet another embodiment, the CMV-R-U5 domain polynucleotide comprises a sequence as set forth in SEQ ID NO: 19, 20 or 22 from about nucleotide 1 to about nucleotide 1202 or sequences that are at least 95% identical to a sequence as set forth in SEQ ID NO: 19, 20 or 22, wherein the polynucleotide promotes transcription of a nucleic acid molecule operably linked thereto. In another embodiment, the gag and pol of the polynucleotide are derived from an oncoretrovirus or gamma retrovirus. The gag nucleic acid domain can comprise a sequence from about nucleotide number 1203 to about nucleotide 2819 of SEQ ID NO: 19 or 22 or a sequence having at least 95%, 98%, 99% or 99.8% identity thereto. The pol domain can comprise a sequence from about nucleotide number 2820 to about nucleotide 6358 of SEQ ID NO: 19 or 22 or a sequence having at least 95%, 98%, 99% or 99.9% identity thereto. In one embodiment, the env domain encodes an amphotropic env protein. The env domain can comprise a sequence from about nucleotide number 6359 to about nucleotide 8323 of SEQ ID NO: 19 or 22 or a sequence having at least 95%, 98%, 99% or 99.8% identity thereto. The IRES domain of the vector can be any IRES, however, in one embodiment the IRES is derived from an encephalomyocarditis virus. In a further embodiment, the IRES comprises a sequence from about nucleotide number 8327 to about nucleotide 8876 of SEQ ID NO: 19 or 22 or a sequence having at least 95%, 98%, or 99% identity thereto.

The vector can comprise any number of different heterologous polynucleotides. For example, the heterologous polynucleotide can comprise a cytokine, an siRNA, miRNA or RNAi molecules, a targeting sequence, a binding domain, a cytotoxic gene, a single chain antibody or any combination thereof. When the heterologous polynucleotide is for a non-translated RNA such as siRNA, miRNA or RNAi then no IRES is necessary, but may be included for another translated gene RNA, and any kind of retrovirus can be used. In yet a further embodiment, the heterologous polynucleotide comprises a polynucleotide having a sequence as set forth in SEQ ID NO: 3, 5, 11, 13, 15 or 17. In a further embodiment, the heterologous sequence encodes a polypeptide comprising a sequence as set forth in SEQ ID NO: 4. The heterologous nucleic acid is human codon optimized and encodes a polypeptide as set forth in SEQ ID NO:4. In a further embodiment, the heterologous nucleic acid comprises a sequence as set forth in SEQ ID NO: 19 or 22 from about nucleotide number 8877 to about 9353. In one embodiment, the 3' LTR is derived from an oncoretrovirus or gamma-retrovirus. In a further embodiment, the 3' LTR comprises a U3-R-U5 domain. In yet a further embodiment, the 3' LTR comprises a sequence as set forth in SEQ ID NO: 19 from about nucleotide 9405 to about 9998 or a sequence that is at least 95%, 98% or 99.5% identical thereto.

The disclosure provides a polynucleotide comprising a sequence as set forth in SEQ ID NO: 19, 20 or 22.

The disclosure provides an isolated polynucleotide comprising from 5' to 3': a CMV-R-U5 fusion of the immediate early promoter from human cytomegalovirus to an MLV R-U5 region; a PBS, primer binding site for reverse transcriptase; a 5' splice site; ψ packaging signal; a gag coding sequence for MLV group specific antigen; a pol coding sequence for MLV polymerase polyprotein; a 3' splice site; a 4070A env coding sequence for envelope protein of MLV strain 4070A; an internal ribosome entry site (IRES) from encephalomyocarditis virus; a modified cytosine deaminase coding sequence; a polypurine tract; and a U3-R-U5 MLV long terminal repeat.

The disclosure provides a method of treating a subject with a cell proliferative disorder comprising contacting the subject with a polynucleotide encoding a polypeptide of the disclosure having cytosine deaminase activity under conditions such that the polynucleotide is expressed, and contacting the subject with 5-fluorocytosine.

The disclosure also provides a method of treating a cell proliferative disorder in a subject comprising contacting the subject with a retrovirus of the disclosure, wherein the heterologous nucleic acid sequence encodes a therapeutic protein that inhibits proliferation of a neoplastic cell. In one embodiment, the retrovirus comprises a polynucleotide encoding a polypeptide having a sequence as set forth in SEQ ID NO: 4, 12, 14, 16, or 18.

The disclosure provides a recombinant replication competent retrovirus (RCR) comprising recombinant replication competent retrovirus, wherein the vector infects the target multiple times leading to a mean of 5 or more copies of the retrovirus genome. The multiple copies provide a "super" infection useful for gene delivery and protein production in vivo and in vitro. In one embodiment, the recombinant replication competent retrovirus (RCR) comprises: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising an internal ribosome entry site (IRES) operably linked to a heterologous polynucleotide, wherein the cassette is positioned 5' to the 3' LTR and 3' to the env nucleic acid domain encoding the retroviral envelope; and cis-acting sequences necessary for reverse transcription, packaging and integration in a target cell, wherein the RCR maintains higher replication competency after 6 passages compared to a pACE vector (SEQ ID NO:21). In one embodiment, the retroviral polynucleotide sequence is derived from murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV). In another embodiment, the MLV is an amphotropic MLV. In yet another embodiment, the retrovirus is an oncoretrovirus or gamma retrovirus. In yet another embodiment, the target cell is a cell having a cell proliferative disorder. The cell proliferative disorder can be selected from the group consisting of, but is not limited to, lung cancer, colon-rectum cancer, breast cancer, prostate cancer, urinary tract cancer, uterine cancer, brain cancer, head and neck cancer, pancreatic cancer, melanoma, stomach cancer and ovarian cancer, rheumatoid arthritis and other autoimmune diseases. In one embodiment, the promoter comprises a CMV promoter having a sequence as set forth in SEQ ID NO:19, 20 or 22 from nucleotide 1 to about nucleotide 582 and may include modification to one or more nucleic acid bases and which is capable of directing and initiating transcription. In yet a further embodiment, the promoter comprises a sequence as set forth in SEQ ID NO: 19, 20 or 22 from nucleotide 1 to about nucleotide 582. In a further embodiment, the promoter comprises a CMV-R-U5 domain polynucleotide. In one embodiment, the CMV-R-U5 domain comprise the immediately early promoter from human cytomegalovirus linked to an MLV R-U5 region. In yet another embodiment, the CMV-R-U5 domain polynucleotide comprises a sequence as set forth in SEQ ID NO: 19, 20 or 22 from about nucleotide 1 to about nucleotide 1202 or sequences that are at least 95% identical to a sequence as set forth in SEQ ID NO: 19, 20 or 22, wherein the polynucleotide promotes transcription of a nucleic acid molecule operably linked thereto. In another embodiment, the gag and pol of the polynucleotide are derived from an oncoretrovirus or gamma retrovirus. The gag nucleic acid domain can comprise a sequence from about nucleotide number 1203 to about nucleotide 2819 of SEQ ID NO: 19 or 22 or a sequence having at least 95%, 98%, 99% or 99.8% identity thereto. The pol domain can comprise a sequence from about nucleotide number 2820 to about nucleotide 6358 of SEQ ID NO: 19 or 22 or a sequence having at least 95%, 98%, 99% or 99.9% identity thereto. In one embodiment, the env domain encodes an amphotropic env protein. The env domain can comprise a sequence from about nucleotide number 6359 to about nucleotide 8323 of SEQ ID NO: 19 or 22 or a sequence having at least 95%, 98%, 99% or 99.8% identity thereto. The IRES domain of the vector can be any IRES, however, in one embodiment the IRES is derived from an encephalomyocarditis virus. In a further embodiment, the IRES comprises a sequence from about nucleotide number 8327 to about nucleotide 8876 of SEQ ID NO: 19 or 22 or a sequence having at least 95%, 98%, or 99% identity thereto.

The disclosure provides a method of treating a cell proliferative disorder in a subject comprising contacting the subject with a retrovirus of the disclosure wherein the vector infects the target multiple times leading to a mean of 5 or more copies of the retrovirus genome.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 1A-C shows an alignment of the Wild-type yeast cytosine deaminase (SEQ ID NO: 2) and a cytosine deaminase of the disclosure (SEQ ID NO: 4) and other sequences of the disclosure (SEQ ID NOs:31-40).

Figure 3D-1:
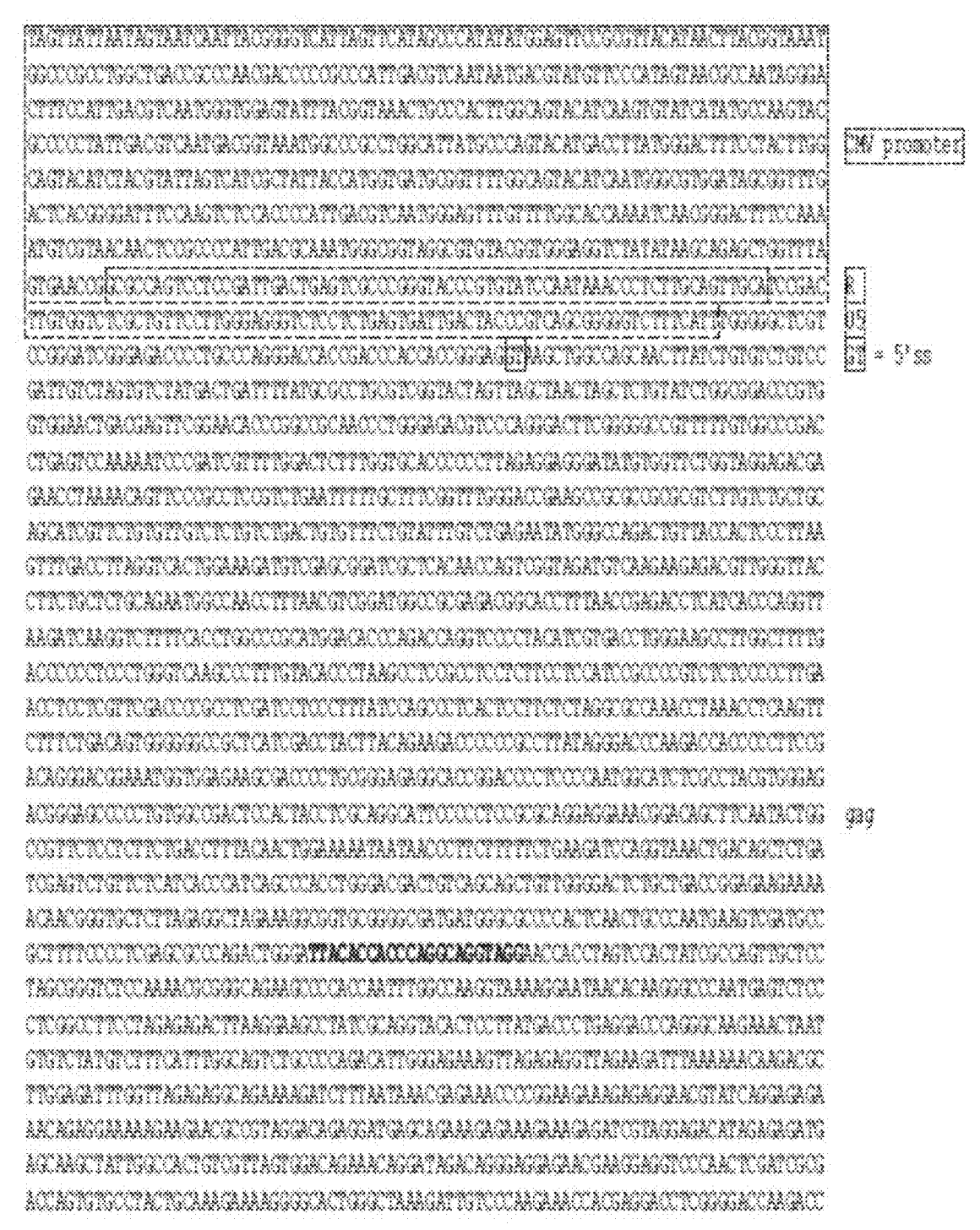
Figure 3D-1:
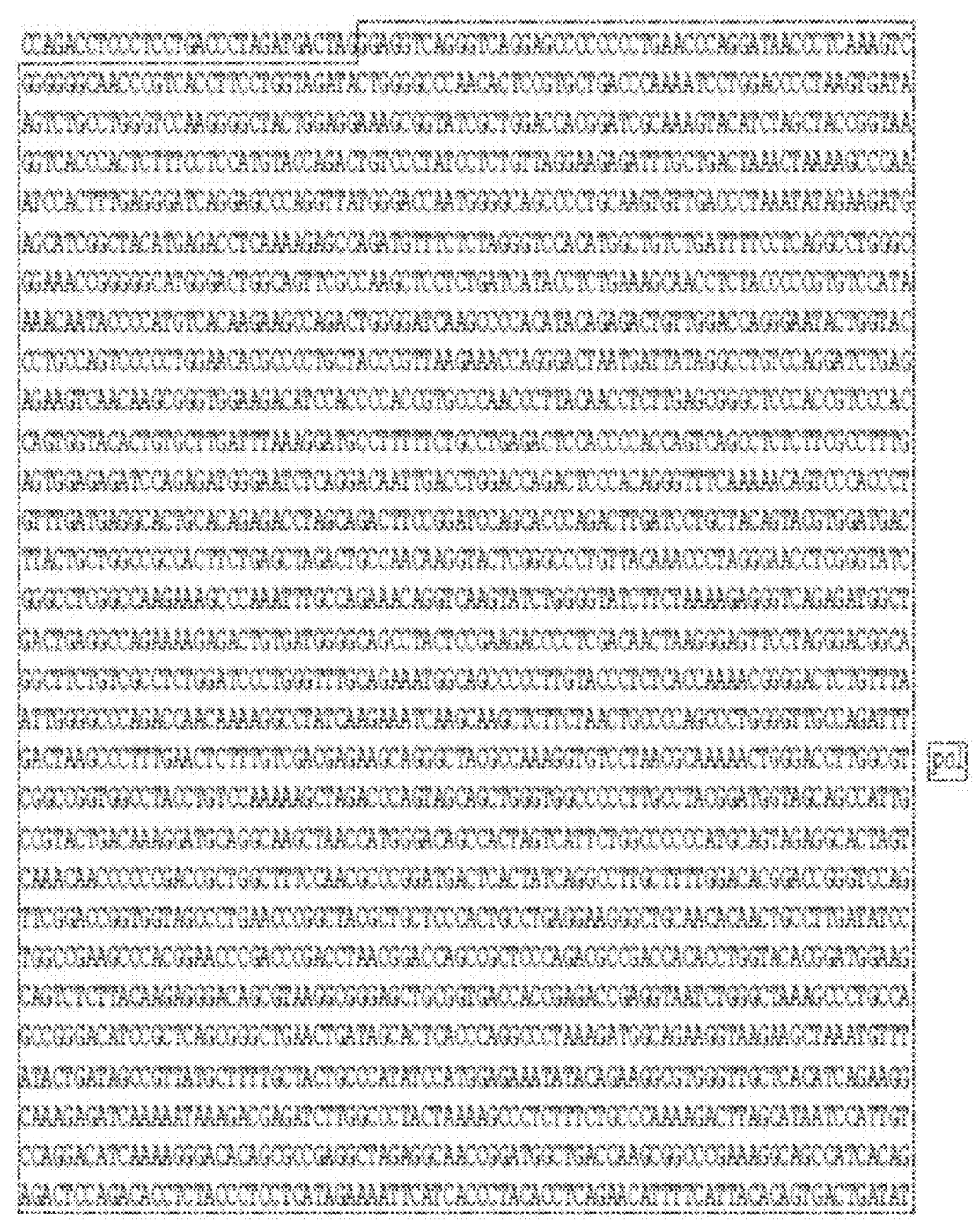
Figure 3D-2:
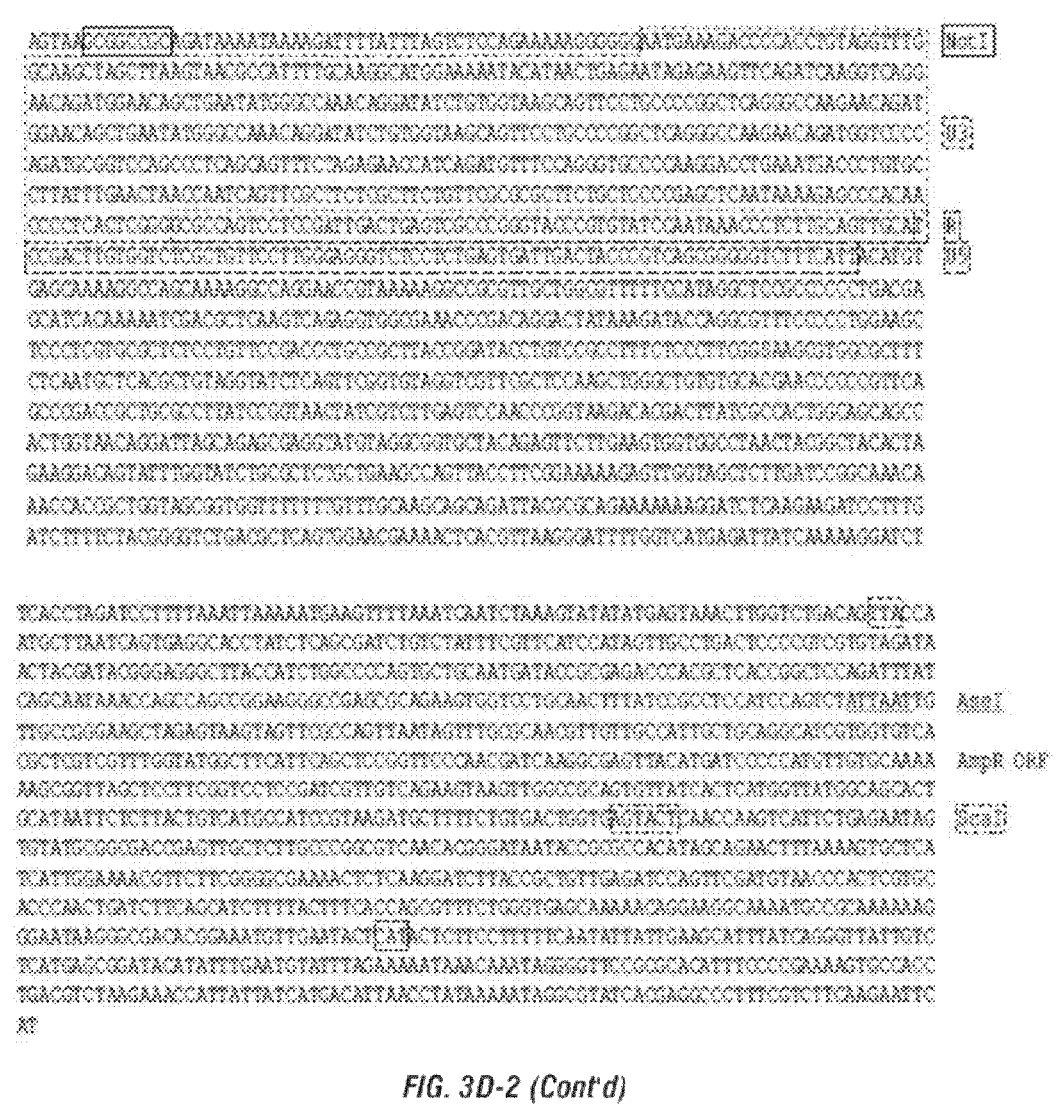

FIG. 3A-F shows (A) a schematic of a recombinant retroviral vector of the disclosure; (B-C) a plasmid map of a polynucleotide of the disclosure; (D) a sequence of a polynucleotide of the disclosure (SEQ ID NO:19); the vector coding region of pAC3-yCD2 in various formats (i.e., FIG. 3D-1 to 3D-2 shows the domains of the vector and 3D-3 to 3D-16 shows restriction sites in the vector of SEQ ID NO:19); (E) Diagram of changes between pACE-emdGFP and pAC3-emdGFP; (F-1 and F-2) show additional plasmid map details of SEQ ID NO:19; (F-3 to F-5) shows the sequence of SEQ ID NO:22 including identifying various domains; (F-6 to F-18) shows restriction sites in the vector of SEQ ID NO:22.

FIG. 4 shows that higher levels of yCD2 protein are observed compared to wild type yCD protein in infected U-87 cells.

FIG. 21B shows the placement of the two catheters into the tumor.

DETAILED DESCRIPTION

Figure 2:
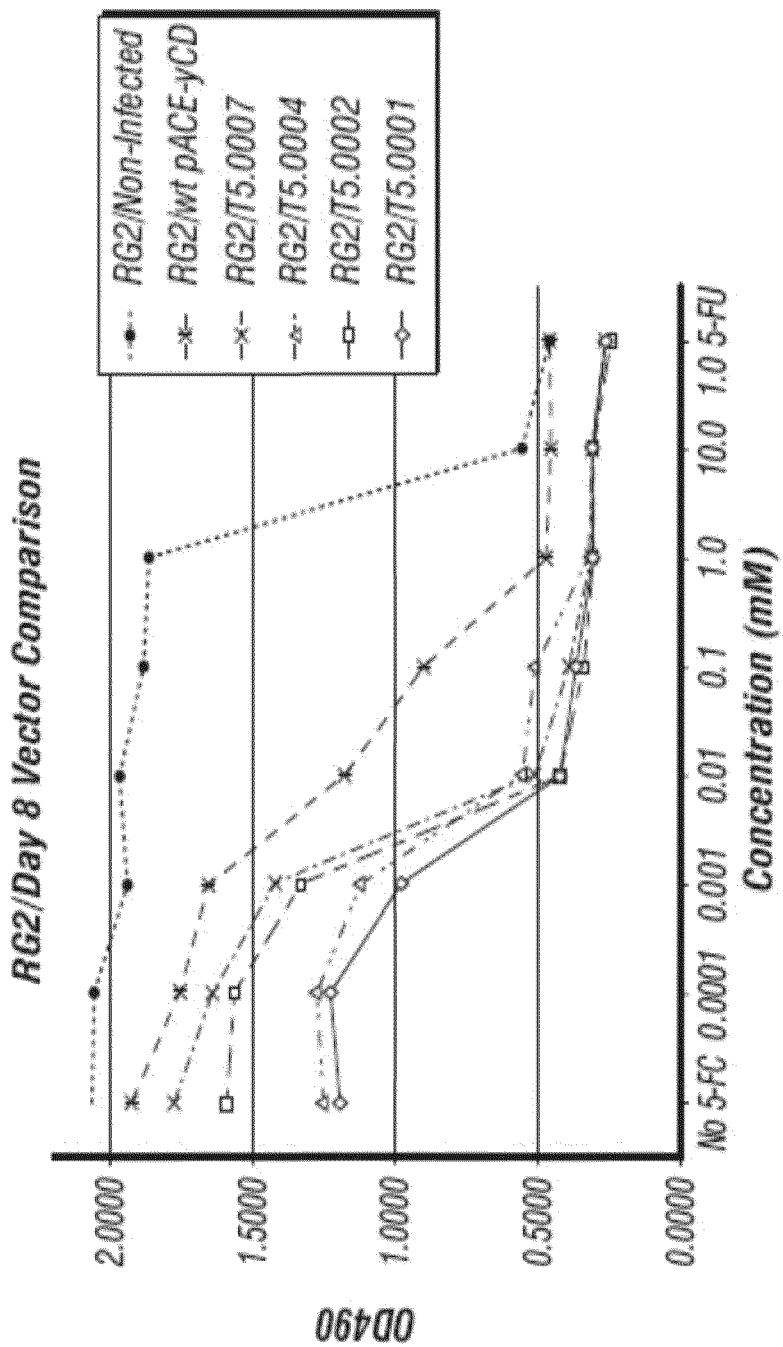
FIG. 2 shows a graph of cell killing data showing that modified vectors are more effective compared to the original wild type CD. The graph also shows that the new modified backbone (T5.0007) is more effective at killing than the old backbone (pACE-CD). Also shown is a table cataloguing the various vector constructs and their names.
Figure 2:
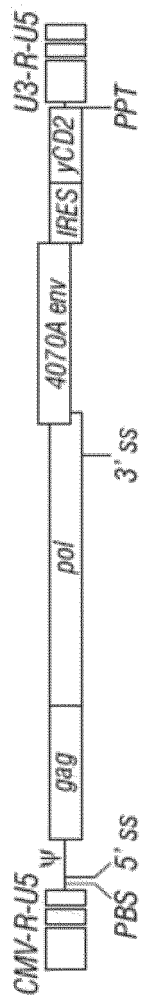

As used herein and in the appended claims, the singular forms "a," "and," and "the" include plural referents unless the context clearly dictates otherwise. Thus, for example, reference to "a cell" includes a plurality of such cells and reference to "the agent" includes reference to one or more agents known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

General texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The publications discussed throughout the text are provided solely for their disclosure prior to the filing date of the present application. Nothing herein is to be construed as an admission that the inventors are not entitled to antedate such disclosure by virtue of prior disclosure.

The disclosure provides methods and compositions useful for gene or protein delivery to a cell or subject. Such methods and compositions can be used to treat various diseases and disorders in a subject including cancer and other cell proliferative diseases and disorders. The disclosure provides replication competent retroviral vectors for gene delivery.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The disclosure provides replication competent viral vectors the contain a heterologous polynucleotide encoding, for example, a cytosine deaminase or mutant thereof, an miRNA or siRNA, a cytokine, an antibody binding domain etc., that can be delivered to a cell or subject. The viral vector can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art (see also, e.g., *Concepts in Genetic Medicine*, ed. Boro Dropulic and Barrie Carter, Wiley, 2008, Hoboken, N.J.; *The Development of Human Gene Therapy*, ed. Theodore Friedmann, Cold Springs Harbor Laboratory Press, Cold springs Harbor, N.Y., 1999; *Gene and Cell Therapy*, ed. Nancy Smyth Templeton, Marcel Dekker Inc., New York, N.Y., 2000 and *Gene Therapy: Therapeutic Mechanism and Strategies*, ed. Nancy Smyth Templetone and Danilo D Lasic, Marcel Dekker, Inc., New York, N.Y., 2000; the disclosures of which are incorporated herein by reference).

In one embodiment, the viral vector can be a replication competent retroviral vector capable of infecting only replicating mammalian cells. In one embodiment, a replication competent retroviral vector comprises an internal ribosomal entry site (IRES) 5' to the heterologous polynucleotide encoding, e.g., a cytosine deaminase, miRNA, siRNA, cytokine, receptor, antibody or the like. When the heterologous polynucleotide encodes a non-translated RNA such as siRNA, miRNA or RNAi then no IRES is necessary, but may be included for another translated gene, and any kind of retrovirus (see below) can be used. In one embodiment, the polynucleotide is 3' to a ENV polynucleotide of a retroviral vector. In one embodiment the viral vector is a retroviral vector capable of infecting target cells multiple times (5 or more per diploid cell).

In other embodiments, host cells transfected with a replication competent retroviral vector of the disclosure are provided. Host cells include eukaryotic cells such as yeast cells, insect cells, or animal cells. Host cells also include prokaryotic cells such as bacterial cells.

Also provided are engineered host cells that are transduced (transformed or transfected) with a vector provided herein (e.g., a replication competent retroviral vector). The engineered host cells can be cultured in conventional nutrient media modified as appropriate for activating promoters, selecting transformants, or amplifying a coding polynucleotide. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; or plant cells or explants, etc. Typically human cells or cell lines will be used; however, it may be desirable to clone vectors and polynucleotides of the disclosure into non-human host cells for purposes of sequencing, amplification and cloning.

The disclosure also provides replication competent retroviral vectors having increased stability relative to prior retroviral vectors. Such increased stability during infection and replication is important for the treatment of cell proliferative disorders. The combination of transduction efficiency, transgene stability and target selectivity is provided by the replication competent retrovirus. The compositions and methods provide insert stability and maintain transcription activity of the transgene and the translational viability of the encoded polypeptide.

The disclosure provides modified retroviral vectors. The modified retroviral vectors can be derived from members of the retroviridae family. The Retroviridae family consists of three groups: the spumaviruses-(or foamy viruses) such as the human foamy virus (HFV); the lentiviruses, as well as visna virus of sheep; and the oncoviruses (although not all viruses within this group are oncogenic). The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2) and simian immunodeficiency virus (SIV). The oncoviruses have historically been further subdivided into groups A, B, C and D on the basis of particle morphology, as seen under the electron microscope during viral maturation. A-type particles represent the immature particles of the B- and D-type viruses seen in the cytoplasm of infected cells. These particles are not infectious. B-type particles bud as mature virion from the plasma membrane by the enveloping of intracytoplasmic A-type particles. At the membrane they possess a toroidal core of 75 nm, from which long glycoprotein spikes project. After budding, B-type particles contain an eccentrically located, electron-dense core. The prototype B-type virus is mouse mammary tumor virus (MMTV). No intracytoplasmic particles can be observed in cells infected by C-type viruses. Instead, mature particles bud directly from the cell surface via a crescent 'C'-shaped condensation which then closes on itself and is enclosed by the plasma membrane. Envelope glycoprotein spikes may be visible, along with a uniformly electron-dense core. Budding may occur from the surface plasma membrane or directly into intracellular vacuoles. The C-type viruses are the most commonly studied and include many of the avian and murine leukemia viruses (MLV). Bovine leukemia virus (BLV), and the human T-cell leukemia viruses types I and II (HTLV-I/II) are similarly classified as C-type particles because of the morphology of their budding from the cell surface. However, they also have a regular hexagonal morphology and more complex genome structures than the prototypic C-type viruses such as the murine leukemia viruses (MLV). D-type particles resemble B-type particles in that they show as ring-like structures in the infected cell cytoplasm, which bud from the cell surface, but the virion incorporate short surface glycoprotein spikes. The electron-dense cores are also eccentrically located within the particles. Mason Pfizer monkey virus (MPMV) is the prototype D-type virus.

Retroviruses have been classified in various ways but the nomenclature has been standardized in the last decade (see ICTVdB—The Universal Virus Database, v 4 on the World Wide Web (www) at ncbi.nlm.nih.gov/ICTVdb/ICTVdB/ and the text book "Retroviruses" Eds Coffin, Hughs and Varmus, Cold Spring Harbor Press 1997; the disclosures of which are incorporated herein by reference). In one embodiment, the replication competent retroviral vector can comprise an Orthoretrovirus or more typically a gamma retrovirus vector.

Retroviruses are defined by the way in which they replicate their genetic material. During replication the RNA is converted into DNA. Following infection of the cell a double-stranded molecule of DNA is generated from the two molecules of RNA which are carried in the viral particle by the molecular process known as reverse transcription. The DNA form becomes covalently integrated in the host cell genome as a provirus, from which viral RNAs are expressed with the aid of cellular and/or viral factors. The expressed viral RNAs are packaged into particles and released as infectious virion.

The retrovirus particle is composed of two identical RNA molecules. Each wild-type genome has a positive sense, single-stranded RNA molecule, which is capped at the 5' end and polyadenylated at the 3' tail. The diploid virus particle contains the two RNA strands complexed with gag proteins, viral enzymes (pol gene products) and host tRNA molecules within a 'core' structure of gag proteins. Surrounding and protecting this capsid is a lipid bilayer, derived from host cell membranes and containing viral envelope (env) proteins. The env proteins bind to a cellular receptor for the virus and the particle typically enters the host cell via receptor-mediated endocytosis and/or membrane fusion.

After the outer envelope is shed, the viral RNA is copied into DNA by reverse transcription. This is catalyzed by the reverse transcriptase enzyme encoded by the pol region and uses the host cell tRNA packaged into the virion as a primer for DNA synthesis. In this way the RNA genome is converted into the more complex DNA genome.

The double-stranded linear DNA produced by reverse transcription may, or may not, have to be circularized in the nucleus. The provirus now has two identical repeats at either end, known as the long terminal repeats (LTR). The termini of the two LTR sequences produces the site recognized by a pol product—the integrase protein—which catalyzes integration, such that the provirus is always joined to host DNA two base pairs (bp) from the ends of the LTRs. A duplication of cellular sequences is seen at the ends of both LTRs, reminiscent of the integration pattern of transposable genetic elements. Retroviruses can integrate their DNAs at many sites in host DNA, but different retroviruses have different integration site preferences. HIV-1 and simian immunodeficiency virus DNAs preferentially integrate into expressed genes, murine leukemia virus (MLV) DNA preferentially integrates near transcriptional start sites (TSSs), and avian sarcoma leukosis virus (ASLV) and human T cell leukemia virus (HTLV) DNAs integrate nearly randomly, showing a slight preference for genes (Derse D, et al. (2007) Human T-cell leukemia virus type 1 integration target sites in the human genome: comparison with those of other retroviruses. J Virol 81:6731-6741; Lewinski M K, et al. (2006) Retroviral DNA integration: viral and cellular determinants of target-site selection. PLoS Pathog 2:e601).

Transcription, RNA splicing and translation of the integrated viral DNA is mediated by host cell proteins. Variously spliced transcripts are generated. In the case of the human retroviruses HIV-1/2 and HTLV-I/II viral proteins are also used to regulate gene expression. The interplay between cellular and viral factors is a factor in the control of virus latency and the temporal sequence in which viral genes are expressed.

Retroviruses can be transmitted horizontally and vertically. Efficient infectious transmission of retroviruses requires the expression on the target cell of receptors which specifically recognize the viral envelope proteins, although viruses may use receptor-independent, nonspecific routes of entry at low efficiency. Normally a viral infection leads to a single or few copies of viral genome per cell because of receptor masking or down-regulation that in turn leads to resistance to superinfection (Ch 3 p 104 in "Retroviruses" J M Coffin, S H Hughes, & H E Varmus 1997 Cold Spring Harbor Laboratory Press, Cold Spring Harbor N.Y.; Fan et al. J. Virol 28:802, 1978). By manipulating the situation in tissue culture it is possible to get some level of multiple infection but this is less than 5 copies/diploid genome. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

In many situations for using a recombinant replication competent retrovirus therapeutically, it is advantageous to have high levels of expression of the transgene that is encoded by the recombinant replication competent retrovirus. For example, with a prodrug activating gene such as the cytosine deaminase gene it is advantageous to have higher levels of expression of the CD protein in a cell so that the conversion of the prodrug 5-FC to 5-FU is more efficient. Similarly high levels of expression of siRNA or shRNA lead to more efficient suppression of target gene expression. Also for cytokines or single chain antibodies (scAbs) it is usually advantageous to express high levels of the cytokine or scAb. In addition, in the case that there are mutations in some copies of the vector that inactivate or impair the activity of the vector or transgene, it is advantageous to have multiple copies of the vector in the target cell as this provides a high probability of efficient expression of the intact transgene. The disclosure provides recombinant replication competent retroviruses capable of infecting a target cell or target cell population multiple times resulting in an average number of copies/diploid genome of 5 or greater. The disclosure also provides methods of testing for this property. Also provided are methods of treating a cell proliferative disorder, using a recombinant replication competent retrovirus capable of infecting a target cell or target cell population multiple times resulting in an average number of copies/diploid genome of 5 or greater.

As mentioned above, the integrated DNA intermediate is referred to as a provirus. Prior gene therapy or gene delivery systems use methods and retroviruses that require transcription of the provirus and assembly into infectious virus while in the presence of an appropriate helper virus or in a cell line containing appropriate sequences enabling encapsidation without coincident production of a contaminating helper virus. As described below, a helper virus is not required for the production of the recombinant retrovirus of the disclosure, since the sequences for encapsidation are provided in the genome thus providing a replication competent retroviral vector for gene delivery or therapy.

Other existing replication competent retroviral vectors also tend to be unstable and lose sequences during horizontal or vertical transmission to an infected cell or host cell and during replication. This may be due in-part from the presence of extra nucleotide sequences that include repeats or which reduce the efficiency of a polymerase.

The retroviral genome and the proviral DNA of the disclosure have at least three genes: the gag, the pol, and the env, these genes may be flanked by one or two long terminal (LTR) repeat, or in the provirus are flanked by two long terminal repeat (LTR) and sequences containing cis-acting sequences such as psi. The gag gene encodes the internal structural (matrix, capsid, and nucleocapsid) proteins; the pol gene encodes the RNA-directed DNA polymerase (reverse transcriptase), protease and integrase; and the env gene encodes viral envelope glycoproteins. The 5' and/or 3' LTRs serve to promote transcription and polyadenylation of the virion RNAs. The LTR contains all other cis-acting sequences necessary for viral replication. Lentiviruses have additional genes including vif, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virion) are missing from the viral genome, the result is a cis defect which prevents encapsidation of genomic viral RNA. This type of modified vector is what has typically been used in prior gene delivery systems (i.e., systems lacking elements which are required for encapsidation of the virion) as 'helper' elements providing viral proteins in trans that package a non-replicating, but packageable, RNA genome.

In a first embodiment, the disclosure provides a recombinant retrovirus capable of infecting a non-dividing cell, a dividing cell, or a cell having a cell proliferative disorder. The recombinant replication competent retrovirus of the disclosure comprises a polynucleotide sequence encoding a viral GAG, a viral POL, a viral ENV, a heterologous polynucleotide preceded by an internal ribosome entry site (IRES) encapsulated within a virion.

The phrase "non-dividing" cell refers to a cell that does not go through mitosis. Non-dividing cells may be blocked at any point in the cell cycle, (e.g., $G_0/G_1$, $G_{1/S}$, $G_{2/M}$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector is capable of infecting non-dividing cells. Examples of pre-existing non-dividing cells in the body include neuronal, muscle, liver, skin, heart, lung, and bone marrow cells, and their derivatives. For dividing cells oncoretroviral vectors can be used.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous cell cancer, malignant melanoma, sinonasal undifferentiated carcinoma (SNUC), brain (including glioblastomas) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer, skin cancer and ovarian cancer. The cell proliferative disease also includes rheumatoid arthritis (O'Dell NEJM 350:2591 2004) and other auto-immune disorders (Mackay et al NEJM 345:340 2001) that are often characterized by inappropriate proliferation of cells of the immune system.

The heterologous nucleic acid sequence is operably linked to an IRES. As used herein, the term "heterologous" nucleic acid sequence or transgene refers to (i) a sequence that does not normally exist in a wild-type retrovirus, (ii) a sequence that originates from a foreign species, or (iii) if from the same species, it may be substantially modified from its original form. Alternatively, an unchanged nucleic acid sequence that is not normally expressed in a cell is a heterologous nucleic acid sequence.

Depending upon the intended use of the retroviral vector of the disclosure any number of heterologous polynucleotide or nucleic acid sequences may be inserted into the retroviral vector. For example, for in vitro studies commonly used marker genes or reporter genes may be used, including, antibiotic resistance and fluorescent molecules (e.g., GFP). Additional polynucleotide sequences encoding any desired polypeptide sequence may also be inserted into the vector of the disclosure. Where in vivo delivery of a heterologous nucleic acid sequence is sought both therapeutic and non-therapeutic sequences may be used. For example, the heterologous sequence can encode a therapeutic molecule including antisense molecules (miRNA, siRNA) or ribozymes directed to a particular gene associated with a cell proliferative disorder or other gene-associated disease or disorder, the heterologous sequence can be a suicide gene (e.g., HSV-tk or PNP or cytosine deaminase; either modified or unmodified), a growth factor or a therapeutic protein (e.g., Factor IX, IL2, and the like). Other therapeutic proteins applicable to the disclosure are easily identified in the art.

In one embodiment, the heterologous polynucleotide within the vector comprises a cytosine deaminase that has been optimized for expression in a human cell. In a further embodiment, the cytosine deaminase comprises a sequence that has been human codon optimized and comprises mutations that increase the cytosine deaminase's stability (e.g., reduced degradation or increased thermo-stability) compared to a wild-type cytosine deaminase. In yet another embodiment, the heterologous polynucleotide encodes a fusion construct comprising a cytosine deaminase (either human codon optimized or non-optimized, either mutated or non-mutated) operably linked to a polynucleotide encoding a polypeptide having UPRT or OPRT activity. In another embodiment, the heterologous polynucleotide comprises a CD polynucleotide of the disclosure (e.g., SEQ ID NO:3, 5, 11, 13, 15, or 17).

In another embodiment, replication competent retroviral vector can comprise a heterologous polynucleotide encoding a polypeptide comprising a cytosine deaminase (as described herein) and may further comprise a polynucleotide comprising a miRNA or siRNA molecule either as part of the primary transcript from the viral promoter or linked to a promoter, which can be cell-type or tissue specific.

MicroRNAs (miRNA) are small, non-coding RNAs. They are located within introns of coding or non-coding gene, exons of non-coding genes or in inter-genic regions. miRNA genes are transcribed by RNA polymerase II that generate precursor polynucleotides called primary precursor miRNA (pri-miRNA). The pri-miRNA in the nucleus is processed by the ribonuclease Drosha to produce the miRNA precursor (pre-miRNA) that forms a short hairpin structure. Subsequently, pre-miRNA is transported to the cytoplasm via Exportin 5 and further processed by another ribonuclease called Dicer to generate an active, mature miRNA.

A mature miRNA is approximately 21 nucleotides in length. It exerts in function by binding to the 3' untranslated region of mRNA of targeted genes and suppressing protein expression either by repression of protein translation or degradation of mRNA. miRNA are involved in biological processes including development, cell proliferation, differentiation and cancer progression. Studies of miRNA profiling indicate that some miRNA expressions are tissue specific or enriched in certain tissues. For example, miR-142-3p, miR-181 and miR-223 expressions have demonstrated to be enriched in hematopoietic tissues in human and mouse (Baskerville et al., 2005 *RNA* 11, 241-247; Chen et al., 2004 *Science* 303, 83-86).

Some miRNAs have been observed to be up-regulated (oncogenic miRNA) or down-regulated (repressor) in several tumors (Spizzo et al., 2009 *Cell* 137, 586e1). For example, miR-21 is overexpressed in glioblastoma, breast, lung, prostate, colon, stomach, esophageal, and cervical cancer, uterine leiomyosarcoma, DLBCL, head and neck cancer. In contrast, members of let-7 have reported to be down-regulated in glioblastoma, lung, breast, gastric, ovary, prostate and colon cancers. Re-establishment of homeostasis of miRNA expression in cancer is an imperative mechanism to inhibit or reverse cancer progression.

As a consequence of the vital functions modulated by miRNAs in cancers, focus in developing potential therapeutic approaches has been directed toward antisense-mediated inhibition (antigomers) of oncogenic miRNAs. However, miRNA replacement might represent an equally efficacious strategy. In this approach, the most therapeutically useful miRNAs are the ones expressed at low levels in tumors but at high level, and therefore tolerated, in normal tissues.

miRNAs that are down-regulated in cancers could be useful as anticancer agents. Examples include mir-128-1, let-7, miR-26, miR-124, and miR-137 (Esquela-Kerscher et al., 2008 *Cell Cycle* 7, 759-764; Kumar et al., 2008 *Proc Natl Acad Sci USA* 105, 3903-3908; Kota et al., 2009 *Cell* 137, 1005-1017; Silber et al., 2008 BMC Medicine 6:14 1-17). miR-128 expression has reported to be enriched in the central nervous system and has been observed to be down-regulated in glioblastomas (Sempere et al., 2004 *Genome Biology* 5:R13.5-11; Godlewski et al., 2008 *Cancer Res* 68: (22) 9125-9130). miR-128 is encoded by two distinct genes, miR-128-1 and miR-128-2. Both are processed into identical mature sequence. Bmi-1 and E2F3a have been reported to be the direct targets of miR-128 (Godlewski et al., 2008 *Cancer Res* 68: (22) 9125-9130; Zhang et al., 2009 *J. Mol Med* 87:43-51). In addition, Bmi-1 expression has been observed to be up-regulated in a variety of human cancers, including gliomas, mantle cell lymphomas, non-small cell lung cancer B-cell non-Hodgkin's lymphoma, breast, colorectal and prostate cancer. Furthermore, Bmi-1 has been demonstrated to be required for the self-renewal of stem cells from diverse tissues, including neuronal stem cells as well as "stem-like" cell population in gliomas.

Although there have been a number of in vitro demonstrations of the possibilities of miRNA mediated inhibition of cellular function, it has been difficult to deliver these as oligonucleotides or in viral vectors as efficiently as necessary to have in vivo effects (e.g. Li et al. Cell Cycle 5:2103-2109 2006), as has been true for other molecules. Non-replicative vectors do not appear to be efficient enough in any case to achieve delivery of a therapeutic gene into a significant portion of tumors. However it is also not simple to see how to use replicative vectors to deliver miRNA types of agents. In particular it is not clear how to incorporate extra RNA sequences into the RNA genome of replication competent retroviruses and maintain the replication efficiency and keep the addition stably incorporated into the genome.

Replication-defective retroviral and lentiviral vectors have been used to stably express pri-mi RNA by a polymerase II promoter such as CMV or LTR and demonstrated production of mature miRNA. However, these vectors do not have to go through the entire lifecycle of the retrovirus or lentivirus multiple times as is required for replicating vectors. The genome has to be able to accommodate many more events than simple entry, integration and transcription. The concerns associated with the use of a RNA-based virus to express miRNA include: (1) the integrity of the viral RNA genome at post transcriptional step during RNA processing; (2) the stability of the inserted cassette during replication; and (3) proper processing of pri-miRNA as part of the viral RNA transcribed from the LTR promoter producing mature miRNA.

Thus, incorporation of type III RNA polymerase III promoters such as the U6 and the H1 promoter in non-replicative retroviral and lentiviral vectors has been used widely to express functional small interference RNA (siRNA) producing a short hairpin structured RNA (Bromberg-White et al., 2004 *J Virol* 78:9, 4914-4916; Sliva et al., 2006 *Virology* 351, 218-225; Haqa et. al., 2006, *Transplant Proc* 38(10):3184-8). The loop sequence is cleaved by Dicer producing the mature siRNAs that are 21-22 nucleotides in length. shRNA can be stably expressed in cells to down-regulate target gene expression. However the incorporation of such cassettes into the recombinant replication competent retroviral vector, the expression and the processing by Dicer to produce mature miRNA remain problematic.

In one embodiment, the disclosure provides a recombinant replication competent retroviral vector that contains a heterologous polynucleotide sequence of a primary precursor miRNA.

In a further embodiment the primary precursor miRNA is of human origin. In another embodiment the primary precursor RNA sequence is downstream of the env gene.

In another embodiment, the disclosure provides a recombinant replication competent retroviral vector that contains a heterologous polynucleotide sequence of the human primary precursor miR-128-2 (SEQ ID NO:32) downstream of the env gene. miRNAs that are down-regulated in cancers can be incorporated into the vector for therapeutic gene delivery. For example, let-7, miR-26, miR-124, and miR-137 (Esquela-Kerscher et al., 2008 *Cell Cycle* 7, 759-764; Kumar et al., 2008 *Proc Natl Acad Sci USA* 105, 3903-3908; Kota et al., 2009 *Cell* 137, 1005-1017; Silber et al., 2008 *BMC Medicine* 6:14 1-17).

In yet another embodiment, the disclosure provides a recombinant replication competent retroviral vector that contains a heterologous polynucleotide sequence of the short hairpin structured human pre-miR-128 linked to a human H1 promoter (SEQ ID NO: 33 and SEQ ID NO:34) downstream of the env gene. miRNAs that are down-regulated in cancers can be incorporated into the vector for therapeutic gene delivery. For example, let-7, miR-26, miR-124, and miR-137 (Esquela-Kerscher et al., 2008 *Cell Cycle* 7, 759-764; Kumar et al., 2008 *Proc Natl Acad Sci USA* 105, 3903-3908; Kota et al., 2009 *Cell* 137, 1005-1017; Silber et al., 2008 *BMC Medicine* 6:14 1-17).

Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, Anal. Biochem., 172:289, 1988).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism, and other diseases. Of particular interest are the blocking of genes associated with cell-proliferative disorders. Antisense nucleic acids are also useful for the inhibition of expression of proteins associated with toxicity.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., Antisense Res. and Dev., 1(3):227, 1991; Helene, C., Anticancer Drug Design, 6(6): 569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

As used herein, the term "RNA interference" (RNAi) refers to the process of sequence-specific post-transcriptional gene silencing mediated by short interfering nucleic acids (siRNAs or microRNAs (miRNA)). The term "agent capable of mediating RNA interference" refers to siRNAs as well as DNA and RNA vectors that encode siRNAs when transcribed within a cell. The term siRNA or miRNA is meant to encompass any nucleic acid molecule that is capable of mediating sequence specific RNA interference, for example short interfering RNA (siRNA), double-stranded RNA (d5RNA), micro-RNA (miRNA), short hairpin RNA (siRNA), short interfering oligonucleotide, short interfering nucleic acid, short interfering modified oligonucleotide, chemically-modified siRNA, post-transcriptional gene silencing RNA (ptgsRNA), and others.

Suitable range for designing stem lengths of a hairpin duplex, includes stem lengths of 20-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides, and 600-700 nucleotides. Suitable range for designing loop lengths of a hairpin duplex, includes loop lengths of 4-25 nucleotides, 25-50 nucleotides, or longer if the stem length of the hair duplex is substantial. In certain context, hairpin structures with duplexed regions that are longer than 21 nucleotides may promote effective siRNA-directed silencing, regardless of the loop sequence and length.

The replicating retroviral vectors of the disclosure can be used to treat disease by expressing engineered siRNA or miRNA (Dennis, Nature, 418: 122 2002) that switches off or lowers expression of key genes that govern the proliferation or survival of diseased cells including tumor cells. Such targets include genes like Rad 51 a central enzyme in DNA repair, and without which cell growth is drastically restricted. Other targets include many of the signaling pathway molecules that control cell growth (Marquez & McCaffrey Hum Gene Ther. 19:27 2008). The siRNA or miRNA may be combined with expression of a cytotoxic gene from the same or different retroviral vector of the disclosure. An example of a suitable cytotoxic gene comprise a cytosine deaminase or modified cytosine deaminase of the disclosure. Examples of siRNA or miRNA that can be expressed from the same vector or a different vector with cytosine deaminase are siRNA or miRNA's that target Thymidilate synthase, Dihydropyrimidine dehydrogenase or other nucleic acid anabolic or synthetic enzymes, that can enhance or complement the action of 5-FU produced locally in a tumor or tissue from 5-FC activation by cytosine deaminase.

In use, the retroviral vector(s) will replicate through the tumor or other target tissue and before growth inhibition occurs the virus first integrates into the host genome and continues to make virus after growth of that cell is inhibited. Methods for selecting functional miRNA or siRNA sequences are known in the art. Key feature in general in designing effective siRNA or miRNA sequences is usually avoiding "off-target" effects. However for the use of replicating vectors that are highly specific to tumor cells such as those of the disclosure, these side effects are not very important, as the cells are expected to eventually die. A retroviral vector of this disclosure can be made using cells from other species for which the corresponding protein is not significantly targeted. Such cells include dog cell lines or chicken cell line. Alternatively the virus is made by transient transfection on human 293 derived cells or other cell line that allows efficient transient transfection. For this use the virus does not need to utilize an IRES, and the siRNA or miRNA sequence can simply be inserted at a convenient site on the viral genome. This site includes the region downstream of the envelope and upstream of the 3'LTR of the replicating retrovirus. Alternatively polIII transcription units can be inserted in the viral genome with the appropriate siRNA or miRNA's, typically downstream of the 3' envelope gene. Several different siRNA or miRNA sequences can be inserted to ensure efficient down regulation of the target gene or down regulation of more than one gene. Suitable sequences and targets can be obtained from sources known to those skilled in the art. For example:

The MIT/ICBP siRNA Database http:(//)web.mit.edu/sirna/—"The MIT [Massachusetts Institute of Technology]/ICBP [Integrative Cancer Biology Program] siRNA Database is a university-wide effort to catalog these experimentally validated reagents and make that information available to other researchers, both within and outside the MIT community. (Massachusetts Institute of Technology).

RNAi Central—http:(//)katandin.cshl.org:9331/RNAi_web/scripts/main2.pl RNAi resources, including siRNA and shRNA design tools. (Hannon Lab, Cold Spring Harbor Laboratory)

The RNAi Web—http://www.rnaiweb.com/ General resource.

siDIRECT—http://genomics.jp/sidirect/ Online target-specific siRNA design program for mammalian RNA interference. (University of Tokyo, Japan).

siRNA Database—A comprehensive siRNA database that contains siRNA targets against all known mRNA sequences throughout a variety of organisms. (Part of the Protein Lounge systems biology Web site)

siRNA Database and Resources for RNA Interference Studies http://www.rnainterference.org/ siRNA Selector—http://bioinfo.wistar.upenn.edu/siRNA/siRNA.htm. A set of rules was used for evaluating siRNA functionality based on thermodynamics parameters (Khvorova et al., 2003, Schwarz et al., 2003) and sequence-related determinants developed by Dharmacon (Reynolds et al., 2004). Specificity is determined using BLAST against UniGene databases. (Wistar Institute)

siRNA Target Finder http://www.ambion.com/techlib/misc/siRNA finder.html (Ambion).

The replicating retroviruses of the disclosure can also express targets for naturally occurring siRNA's that are restricted in expression to particular cell types so that replication of the vector is significantly inhibited in those cell types. The generation of murine leukemia virus-based recombinant replication competent retroviral vector allows high level of transduction and thus high efficiency of gene delivery in vivo. One major concern of using replication competent retroviral vector has been the uncontrolled spread of virus as reported previously (Donahue et al., *J. Exp Med.* 1992, 176: 1124-1135; Calmes et al., *Blood* 2005, 106: 2530-2533; Seggewiss et al., *Blood* 2006, 107: 3865-3867). Because of the nature of the virus, the viral spread may be achieved initially within lymphatic cells and subsequently spread to peripheral tissues. For anti-tumor purposes some normal cells in the body that are naturally replicating at some level are hematopoietic cells, cells of the lining of the gut, and some endothelial cells. These are then potential sites where virus that is in the circulation could productively infect. In general this would be undesirable. Any stray infection of cells such as these can be inhibited by including a target for naturally occurring miRNA's or for a combination of miRNA's in these cell types. Some feasibility of using miRNA targets to suppress immune responses has already been shown. (Brown et al. Nat Biotechnol. 2007 25:1457-67). These targets are small RNA sequences with a homologous match to the miRNA sequences that are naturally occurring. These sequences can be inserted in any convenient site in the vectors of the disclosure without, in general significant deleterious consequence for vector viability, other than in a cell of the type desired. Vectors can be made and used as described herein.

In one embodiment, the disclosure provides a recombinant replication competent retroviral vector that contains a single copy of the miR-142-3p target sequence (142-3pT, SEQ ID NO:35) downstream of the transgene, such as yCD2 or GFP, linked to the IRES. In addition to miR181 and miR-223, the target sequence of other tissue or cell-enriched miRNA can be incorporated into the vector to restrict viral spread in specific tissue or cell type manner. For example, miR-133 and miR206 expressions are highly enriched in muscle cells (Kelly et al., 2008 Nature Medicine 14:11 1278-1283.

In another embodiment, the disclosure provides a recombinant replication competent retroviral vector that contains 4 copies of the 142-3pT (SEQ ID NO: 36) downstream of the transgene, such as yCD2 or GFP, linked to the IRES. In addition to miR181 and miR-223, the target sequence of other tissue or cell-enriched miRNA can be incorporated into the vector to restrict viral spread in specific tissue or cell type manner. For example, miR-133 and miR206 expressions are highly enriched in muscle cells. The disclosure provides flexibility of single, multiple or combination of target sequence of miRNA and thereby provides restriction of uncontrolled viral spread in a tissue- and/or cell-specific fashion in vitro and in vivo (e. g. hematopoietic and/or muscle cells), (Kelly et al., 2008 Nature Medicine 14:11 1278-1283).

The miRNA target can be inserted 3' to the transgene but before the 3'LTR or upstream of the IRES but after the 3' end of the envelope. In general the target would not be inserted into protein coding sequences.

In yet further embodiments, the heterologous polynucleotide may comprise a cytokine such as an interleukin, interferon gamma or the like. Cytokines that may expressed from a retroviral vector of the disclosure include, but are not limited to, IL-lalpha, IL-lbeta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21, anti-CD40, CD40L, IFN-gamma and TNF-alpha, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TRANK, TR9 (International Publication No. WO 98/56892), TR10 (International Publication No. WO 98/54202), 312C2 (International Publication No. WO 98/06842), and TR12, and soluble forms CD154, CD70, and CD153. Angiogenic proteins may be useful in some embodiments, particularly for protein production from cell lines. Such angiogenic factors include, but are not limited to, Glioma Derived Growth Factor (GDGF), Platelet Derived Growth Factor-A (PDGF-A), Platelet Derived Growth Factor-B (PDGF-B), Placental Growth Factor (PIGF), Placental Growth Factor-2 (PIGF-2), Vascular Endothelial Growth Factor (VEGF), Vascular Endothelial Growth Factor-A (VEGF-A), Vascular Endothelial Growth Factor-2 (VEGF-2), Vascular Endothelial Growth Factor B (VEGF-3), Vascular Endothelial Growth Factor B-1 86 (VEGF-B186), Vascular Endothelial Growth Factor-D (VEGF-D), Vascular Endothelial Growth Factor-D (VEGF-D), and Vascular Endothelial Growth Factor-E (VEGF-E). Fibroblast Growth Factors may be delivered by a vector of the disclosure and include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15. Hematopoietic growth factors may be delivered using vectors of the disclosure, such growth factors include, but are not limited to, granulocyte macrophage colony stimulating factor (GM-CSF) (sargramostim), granulocyte colony stimulating factor (G-CSF) (filgrastim), macrophage colony stimulating factor (M-CSF, CSF-1) erythropoietin (epoetin alfa), stem cell factor (SCF, c-kit ligand, steel factor), megakaryocyte colony stimulating factor, PIXY321 (a GMCSF/IL-3) fusion protein and the like.

Generally, the recombinant virus of the disclosure is capable of transferring a nucleic acid sequence into a target cell.

The term "regulatory nucleic acid sequence" refers collectively to promoter sequences, polyadenylation signals, transcription termination sequences, upstream regulatory domains, origins of replication, enhancers and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro.

An internal ribosome entry sites ("IRES") refers to a segment of nucleic acid that promotes the entry or retention of a ribosome during translation of a coding sequence usually 3' to the IRES. In some embodiments the IRES may comprise a splice acceptor/donor site, however, preferred IRESs lack a splice acceptor/donor site. Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that, in particular, of picornaviruses such as the poliomyelitis virus (Pelletier et al., 1988, Mol. Cell. Biol., 8, 1103-1112) and the EMCV virus (encephalo-myocarditis virus (Jang et al., J. Virol., 1988, 62, 2636-2643). The disclosure provides the use of an IRES in the context of a replication-competent retroviral vector.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter as described above.

The heterologous nucleic acid sequence is typically under control of either the viral LTR promoter-enhancer signals or an internal promoter, and retained signals within the retroviral LTR can still bring about efficient integration of the vector into the host cell genome. Accordingly, the recombinant retroviral vectors of the disclosure, the desired sequences, genes and/or gene fragments can be inserted at several sites and under different regulatory sequences. For example, a site for insertion can be the viral enhancer/promoter proximal site (i.e., 5' LTR-driven gene locus). Alternatively, the desired sequences can be inserted into a regulatory sequence distal site (e.g., the IRES sequence 3' to the env gene) or where two or more heterologous sequences are present one heterologous sequence may be under the control of a first regulatory region and a second heterologous sequence under the control of a second regulatory region. Other distal sites include viral promoter sequences, where the expression of the desired sequence or sequences is through splicing of the promoter proximal cistron, an internal heterologous promoter as SV40 or CMV, or an internal ribosome entry site (IRES) can be used.

In one embodiment, the retroviral genome of the disclosure contains an IRES comprising a cloning site downstream of the IRES for insertion of a desired/heterologous polynucleotide. In one embodiment, the IRES is located 3' to the env gene in the retroviral vector, but 5' to the desired heterologous polynucleotide. Accordingly, a heterologous polynucleotide encoding a desired polypeptide may be operably linked to the IRES.

In another embodiment, a targeting polynucleotide sequence is included as part of the recombinant retroviral vector of the disclosure. The targeting polynucleotide sequence is a targeting ligand (e.g., peptide hormones such as heregulin, a single-chain antibodies, a receptor or a ligand for a receptor), a tissue-specific or cell-type specific regulatory element (e.g., a tissue-specific or cell-type specific promoter or enhancer), or a combination of a targeting ligand and a tissue-specific/cell-type specific regulatory element. Preferably, the targeting ligand is operably linked to the env protein of the retrovirus, creating a chimeric retroviral env protein. The viral GAG, viral POL and viral ENV proteins can be derived from any suitable retrovirus (e.g., MLV or lentivirus-derived). In another embodiment, the viral ENV protein is non-retrovirus-derived (e.g., CMV or VSV).

In one embodiment, the recombinant retrovirus of the disclosure is genetically modified in such a way that the virus is targeted to a particular cell type (e.g., smooth muscle cells, hepatic cells, renal cells, fibroblasts, keratinocytes, mesenchymal stem cells, bone marrow cells, chondrocyte, epithelial cells, intestinal cells, mammary cells, neoplastic cells, glioma cells, neuronal cells and others known in the art) such that the recombinant genome of the retroviral vector is delivered to a target non-dividing, a target dividing cell, or a target cell having a cell proliferative disorder.

In one embodiment, the retroviral vector is targeted to the cell by binding to cells having a molecule on the external surface of the cell. This method of targeting the retrovirus utilizes expression of a targeting ligand on the coat of the retrovirus to assist in targeting the virus to cells or tissues that have a receptor or binding molecule which interacts with the targeting ligand on the surface of the retrovirus. After infection of a cell by the virus, the virus injects its nucleic acid into the cell and the retrovirus genetic material can integrate into the host cell genome.

In another embodiment, targeting uses cell- or tissue-specific regulatory elements to promote expression and transcription of the viral genome in a targeted cell which actively utilizes the regulatory elements, as described more fully below. The transferred retrovirus genetic material is then transcribed and translated into proteins within the host cell. The targeting regulatory element is typically linked to the 5' and/or 3' LTR, creating a chimeric LTR.

By inserting a heterologous polynucleotide of interest into the viral vector of the disclosure, along with another gene which encodes, for example, the ligand for a receptor on a specific target cell, the vector is now target specific. Viral vectors can be made target specific by attaching, for example, a sugar, a glycolipid, or a protein. Targeting can be accomplished by using an antibody to target the viral vector. Those of skill in the art will know of, or can readily ascertain, specific polynucleotide sequences which can be inserted into the viral genome or proteins which can be attached to a viral envelope to allow target specific delivery of the viral vector containing the nucleic acid sequence of interest.

Thus, the disclosure includes in one embodiment, a chimeric env protein comprising a retroviral ENV protein operably linked to a targeting polypeptide. The targeting polypeptide can be a cell specific receptor molecule, a ligand for a cell specific receptor, an antibody or antibody fragment to a cell specific antigenic epitope or any other ligand easily identified in the art which is capable of binding or interacting with a target cell. Examples of targeting polypeptides or molecules include bivalent antibodies using biotin-streptavidin as linkers (Etienne-Julan et al., J. Of General Virol., 73, 3251-3255 (1992); Roux et al., Proc. Natl. Acad. Sci USA 86, 9079-9083 (1989)), recombinant virus containing in its envelope a sequence encoding a single-chain antibody variable region against a hapten (Russell et al., Nucleic Acids Research, 21, 1081-1085 (1993)), cloning of peptide hormone ligands into the retrovirus envelope (Kasahara et al., Science, 266, 1373-1376 (1994)), chimeric EPO/env constructs (Kasahara et al., 1994), single-chain antibody against the low density lipoprotein (LDL) receptor in the ecotropic MLV envelope, resulting in specific infection of HeLa cells expressing LDL receptor (Somia et al., Proc. Natl. Acad. Sci USA, 92, 7570-7574 (1995)), similarly the host range of ALV can be altered by incorporation of an integrin ligand, enabling the virus to now cross species to specifically infect rat glioblastoma cells (Valsesia-Wittmann et al., J. Virol. 68, 4609-4619 (1994)), and Dornberg and co-workers (Chu and Dornburg, J. Virol 69, 2659-2663 (1995); M. Engelstadter et al. Gene Therapy 8, 1202-1206 (2001)) have reported tissue-specific targeting of spleen necrosis virus (SNV), an avian retrovirus, using envelopes containing single-chain antibodies directed against tumor markers.

The disclosure provides a method of producing a recombinant retrovirus capable of infecting a target cell comprising transfecting a suitable host cell with the following: a vector comprising a polynucleotide sequence encoding a viral gag, a viral pol and a viral env, and a heterologous polynucleotide, operably linked to a regulatory nucleic acid sequence, and recovering the recombinant virus.

The retrovirus and methods of the disclosure provide a replication competent retrovirus that does not require helper virus or additional nucleic acid sequence or proteins in order to propagate and produce virion. For example, the nucleic acid sequences of the retrovirus of the disclosure encode a group specific antigen and reverse transcriptase, (and integrase and protease-enzymes necessary for maturation and reverse transcription), respectively, as discussed above. The viral gag and pol can be derived from a lentivirus, such as HIV or an oncovirus or gammaretrovirus such as MoMLV. In addition, the nucleic acid genome of the retrovirus of the disclosure includes a sequence encoding a viral envelope (ENV) protein. The env gene can be derived from any retroviruses. The env may be an amphotropic envelope protein which allows transduction of cells of human and other species, or may be an ecotropic envelope protein, which is able to transduce only mouse and rat cells. Further, it may be desirable to target the recombinant virus by linkage of the envelope protein with an antibody or a particular ligand for targeting to a receptor of a particular cell-type. As mentioned above, retroviral vectors can be made target specific by inserting, for example, a glycolipid, or a protein. Targeting is often accomplished by using an antibody to target the retroviral vector to an antigen on a particular cell-type (e.g., a cell type found in a certain tissue, or a cancer cell type). Those of skill in the art will know of, or can readily ascertain without undue experimentation, specific methods to achieve delivery of a retroviral vector to a specific target. In one embodiment, the env gene is derived from a non-retrovirus (e.g., CMV or VSV). Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G), cytomegalovirus envelope (CMV), or influenza virus hemagglutinin (HA) can also be used.

In one embodiment, the retroviral genome is derived from an onco-retrovirus, and more particularly a mammalian onco-retrovirus. In a further embodiment, the retroviral genome is derived from a gamma retrovirus, and more particularly a mammalian gamma retrovirus. By "derived" is meant that the parent polynucleotide sequence is an wild-type oncovirus which has been modified by insertion or removal of naturally occurring sequences (e.g., insertion of an IRES, insertion of a heterologous polynucleotide encoding a polypeptide or inhibitory nucleic acid of interest, swapping of a more effective promoter from a different retrovirus or virus in place of the wild-type promoter and the like).

Unlike recombinant retroviruses produced by standard methods in the art that are defective and require assistance in order to produce infectious vector particles, the disclosure provides a retrovirus that is replication-competent.

In another embodiment, the disclosure provides retroviral vectors that are targeted using regulatory sequences. Cell- or tissue-specific regulatory sequences (e.g., promoters) can be utilized to target expression of gene sequences in specific cell populations. Suitable mammalian and viral promoters for the disclosure are described elsewhere herein. Accordingly, in one embodiment, the disclosure provides a retrovirus having tissue-specific promoter elements at the 5' end of the retroviral genome. Typically, the tissue-specific regulatory elements/sequences are in the U3 region of the LTR of the retroviral genome, including for example cell- or tissue-specific promoters and enhancers to neoplastic cells (e.g., tumor cell-specific enhancers and promoters), and inducible promoters (e.g., tetracycline).

Transcription control sequences of the disclosure can also include naturally occurring transcription control sequences naturally associated with a gene encoding a superantigen, a cytokine or a chemokine.

In some circumstances, it may be desirable to regulate expression. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV can be used. Other viral promoters that can be used include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific or selective promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. The Whey accessory protein (WAP) may be used for breast tissue expression (Andres et al., PNAS 84:1299-1303, 1987). Other promoters/regulatory domains that can be used are set forth in Table 1.

"Tissue-specific regulatory elements" are regulatory elements (e.g., promoters) that are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the disclosure typically has a selectivity ratio of greater than about 5. Preferably, the selectivity ratio is greater than about 15.

In certain indications, it may be desirable to activate transcription at specific times after administration of the recombinant replication competent retrovirus of the disclosure (RRCR). This may be done with promoters that are hormone or cytokine regulatable. For example in therapeutic applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones may be used. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1990), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin. Tumor specific promoters such as osteocalcin, hypoxia-responsive element (HRE), MAGE-4, CEA, alpha-fetoprotein, GRP78/BiP and tyrosinase may also be used to regulate gene expression in tumor cells.

In addition, this list of promoters should not be construed to be exhaustive or limiting, those of skill in the art will know of other promoters that may be used in conjunction with the promoters and methods disclosed herein.

TABLE 1

TISSUE SPECIFIC PROMOTERS

| Tissue | Promoter |
|---|---|
| Pancreas | Insulin Elastin Amylase pdr-1 pdx-1 glucokinase |
| Liver | Albumin PEPCK HBV enhancer α fetoprotein apolipoprotein C α-1 antitrypsin vitellogenin, NF-AB Transthyretin |
| Skeletal muscle | Myosin H chain Muscle creatine kinase Dystrophin Calpain p94 Skeletal alpha-actin fast troponin 1 |
| Skin | Keratin K6 Keratin K1 |
| Lung | CFTR Human cytokeratin 18 (K18) Pulmonary surfactant proteins A, B and C CC-10 P1 |
| Smooth muscle | sm22 α SM-alpha-actin |
| Endothelium | Endothelin-1 E-selectin von Willebrand factor TIE (Korhonen et al., 1995) KDR/flk-1 Melanocytes Tyrosinase |
| Adipose tissue | Lipoprotein lipase (Zechner et al., 1988) Adipsin (Spiegelman et al., 1989) acetyl-CoA carboxylase (Pape and Kim, 1989) glycerophosphate dehydrogenase (Dani et al., 1989) adipocyte P2 (Hunt et al., 1986) |
| Breast | Whey Acidic Protien (WAP) (Andres et al. PNAS 84:1299-1303 1987 |
| Blood | β-globin |

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the disclosure. For example, promoters that are active in a variety of central nervous system (CNS) neurons may be therapeutically useful in protecting against damage due to stroke, which may affect any of a number of different regions of the brain. Accordingly, the tissue-specific regulatory elements used in the disclosure, have applicability to regulation of the heterologous proteins as well as a applicability as a targeting polynucleotide sequence in the present retroviral vectors.

In yet another embodiment, the disclosure provides plasmids comprising a recombinant retroviral derived construct. The plasmid can be directly introduced into a target cell or a cell culture such as NIH 3T3 or other tissue culture cells. The resulting cells release the retroviral vector into the culture medium.

The disclosure provides a polynucleotide construct comprising from 5' to 3': a promoter or regulatory region useful for initiating transcription; a psi packaging signal; a gag encoding nucleic acid sequence, a pol encoding nucleic acid sequence; an env encoding nucleic acid sequence; an internal ribosome entry site nucleic acid sequence; a heterologous polynucleotide encoding a marker, therapeutic or diagnostic polypeptide; and a LTR nucleic acid sequence. As described elsewhere herein and as follows the various segment of the polynucleotide construct of the disclosure (e.g., a recombinant replication competent retroviral polynucleotide) are engineered depending in part upon the desired host cell, expression timing or amount, and the heterologous polynucleotide. A replication competent retroviral construct of the disclosure can be divided up into a number of domains that may be individually modified by those of skill in the art.

For example, the promoter can comprise a CMV promoter having a sequence as set forth in SEQ ID NO:19, 20 or 22 from nucleotide 1 to about nucleotide 582 and may include modification to one or more (e.g., 2-5, 5-10, 10-20, 20-30, 30-50, 50-100 or more nucleic acid bases) so long as the modified promoter is capable of directing and initiating transcription. In one embodiment, the promoter or regulatory region comprises a CMV-R-U5 domain polynucleotide. The CMV-R-U5 domain comprises the immediately early promoter from human cytomegalovirus to the MLV R-U5 region. In one embodiment, the CMV-R-U5 domain polynucleotide comprises a sequence as set forth in SEQ ID NO:19, 20 or 22 from about nucleotide 1 to about nucleotide 1202 or sequences that are at least 95% identical to a sequence as set forth in SEQ ID NO:19, 20, or 22 wherein the polynucleotide promotes transcription of a nucleic acid molecule operably linked thereto. The gag domain of the polynucleotide may be derived from any number of retroviruses, but will typically be derived from an oncoretrovirus and more particularly from a mammalian oncoretrovirus. In one embodiment the gag domain comprises a sequence from about nucleotide number 1203 to about nucleotide 2819 or a sequence having at least 95%, 98%, 99% or 99.8% (rounded to the nearest $10^{th}$) identity thereto. The pol domain of the polynucleotide may be derived from any number of retroviruses, but will typically be derived from an oncoretrovirus and more particularly from a mammalian oncoretrovirus. In one embodiment the pol domain comprises a sequence from about nucleotide number 2820 to about nucleotide 6358 or a sequence having at least 95%, 98%, 99% or 99.9% (roundest to the nearest $10^{th}$) identity thereto. The env domain of the polynucleotide may be derived from any number of retroviruses, but will typically be derived from an oncoretrovirus or gamma-retrovirus and more particularly from a mammalian oncoretrovirus or gamma-retrovirus. In some embodiments the env coding domain comprises an amphotropic env domain. In one embodiment the env domain comprises a sequence from about nucleotide number 6359 to about nucleotide 8323 or a sequence having at least 95%, 98%, 99% or 99.8% (roundest to the nearest $10^{th}$) identity thereto. The IRES domain of the polynucleotide may be obtained from any number of internal ribosome entry sites. In one embodiment, IRES is derived from an encephalomyocarditis virus. In one embodiment the IRES domain comprises a sequence from about nucleotide number 8327 to about nucleotide 8876 or a sequence having at least 95%, 98%, or 99% (roundest to the nearest $10^{th}$) identity thereto so long as the domain allows for entry of a ribosome. The heterologous domain can comprise a cytosine deaminase of the disclosure. In one embodiment, the CD polynucleotide comprises a human codon optimized sequence. In yet another embodiment, the CD polynucleotide encodes a mutant polypeptide having cytosine deaminase, wherein the mutations confer increased thermal stabilization that increase the melting temperature (Tm) by 10° C. allowing sustained kinetic activity over a broader temperature range and increased accumulated levels of protein. In one embodiment, the cytosine deaminase comprises a sequence as set forth in SEQ ID NO:19 or 22 from about nucleotide number 8877 to about 9353. The heterologous domain may be followed by a polypurine rich domain. The 3' LTR can be derived from any number of retroviruses, typically an oncoretrovirus and preferably a mammalian oncoretrovirus. In one embodiment, the 3' LTR comprises a U3-R-U5 domain. In yet another embodiment the LTR comprises a sequence as set forth in SEQ ID NO:19 or 22 from about nucleotide 9405 to about 9998 or a sequence that is at least 95%, 98% or 99.5% (rounded to the nearest $10^{th}$) identical thereto.

The disclosure also provides a recombinant retroviral vector comprising from 5' to 3' a CMV-R-U5, fusion of the immediate early promoter from human cytomegalovirus to the MLV R-U5 region; a PBS, primer binding site for reverse transcriptase; a 5' splice site; a ψ packaging signal; a gag, ORF for MLV group specific antigen; a pol, ORF for MLV polymerase polyprotein; a 3' splice site; a 4070A env, ORF for envelope protein of MLV strain 4070A; an IRES, internal ribosome entry site of encephalomyocarditis virus; a modified cytosine deaminase (thermostabilized and codon optimized); a PPT, polypurine tract; and a U3-R-U5, MLV long terminal repeat. This structure is further depicted in FIG. 3.

The disclosure also provides a retroviral vector comprising a sequence as set forth in SEQ ID NO:19, 20 or 22.

The retroviral vectors can be used to treat a wide range of disease and disorders including a number of cell proliferative diseases and disorders (see, e.g., U.S. Pat. Nos. 4,405,712 and 4,650,764; Friedmann, 1989, Science, 244:1275-1281; Mulligan, 1993, Science, 260:926-932, R. Crystal, 1995, Science 270:404-410, each of which are incorporated herein by reference in their entirety, see also, The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

The disclosure also provides gene therapy for the treatment of cell proliferative disorders. Such therapy would achieve its therapeutic effect by introduction of an appropriate therapeutic polynucleotide (e.g., antisense, ribozymes, suicide genes, siRNA), into cells of subject having the proliferative disorder.

Delivery of polynucleotide constructs can be achieved using the recombinant retroviral vector of the disclosure, particularly if it is based on MLV, which is capable of infecting dividing cells.

In addition, the therapeutic methods (e.g., the gene therapy or gene delivery methods) as described herein can be performed in vivo or ex vivo. It may be preferable to remove the majority of a tumor prior to gene therapy, for example surgically or by radiation. In some aspects, the retroviral therapy may be preceded or followed by surgery, chemotherapy or radiation therapy.

Thus, the disclosure provides a recombinant retrovirus capable of infecting a non-dividing cell, a dividing cell or a neoplastic cell, therein the recombinant retrovirus comprises a viral GAG; a viral POL; a viral ENV; a heterologous nucleic acid operably linked to an IRES; and cis-acting nucleic acid sequences necessary for packaging, reverse transcription and integration. The recombinant retrovirus can be a lentivirus, such as HIV, or can be an oncovirus. As described above for the method of producing a recombinant retrovirus, the recombinant retrovirus of the disclosure may further include at least one of VPR, VIF, NEF, VPX, TAT, REV, and VPU protein. While not wanting to be bound by a particular theory, it is believed that one or more of these genes/protein products are important for increasing the viral titer of the recombinant retrovirus produced (e.g., NEF) or may be necessary for infection and packaging of virion.

The disclosure also provides a method of nucleic acid transfer to a target cell to provide expression of a particular nucleic acid (e.g., a heterologous sequence). Therefore, in another embodiment, the disclosure provides a method for introduction and expression of a heterologous nucleic acid in a target cell comprising infecting the target cell with the recombinant virus of the disclosure and expressing the heterologous nucleic acid in the target cell. As mentioned above, the target cell can be any cell type including dividing, non-dividing, neoplastic, immortalized, modified and other cell types recognized by those of skill in the art, so long as they are capable of infection by a retrovirus.

It may be desirable to modulate the expression of a gene in a cell by the introduction of a nucleic acid sequence (e.g., the heterologous nucleic acid sequence) by the method of the disclosure, wherein the nucleic acid sequence give rise, for example, to an antisense or ribozyme molecule. The term "modulate" envisions the suppression of expression of a gene when it is over-expressed, or augmentation of expression when it is under-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

It may be desirable to transfer a nucleic acid encoding a biological response modifier (e.g., a cytokine) into a cell or subject. Included in this category are immunopotentiating agents including nucleic acids encoding a number of the cytokines classified as "interleukins". These include, for example, interleukins 1 through 15, as well as other response modifiers and factors described elsewhere herein. Also included in this category, although not necessarily working according to the same mechanisms, are interferons, and in particular gamma interferon, tumor necrosis factor (TNF) and granulocyte-macrophage-colony stimulating factor (GM-CSF). Other polypeptides include, for example, angiogenic factors and anti-angiogenic factors. It may be desirable to deliver such nucleic acids to bone marrow cells or macrophages to treat enzymatic deficiencies or immune defects. Nucleic acids encoding growth factors, toxic peptides, ligands, receptors, or other physiologically important proteins can also be introduced into specific target cells.

The disclosure can be used for delivery of heterologous polynucleotides that promote drug specific targeting and effects. For example, HER2 (see, e.g., SEQ ID NO:23 and 24), a member of the EGF receptor family, is the target for binding of the drug trastuzumab (Herceptin™, Genentech). Trastuzumab is a mediator of antibody-dependent cellular cytotoxicity (ADCC). Activity is preferentially targeted to HER2-expressing cells with 2+ and 3+ levels of overexpression by immunohistochemistry rather than 1+ and non-expressing cells (Herceptin prescribing information, Crommelin 2002). Enhancement of expression of HER2 by introduction of vector expressing HER2 or truncated HER2 (expressing only the extracellular and transmembrane domains) in HER2 low tumors may facilitate optimal triggering of ADCC and overcome the rapidly developing resistance to Herceptin that is observed in clinical use.

The substitution of yCD2 (comprising SEQ ID NO:19 from about 8877 to 9353) for the intracellular domain of HER2 allows for cell surface expression of HER2 and cytosolic localization of yCD2. The HER2 extracellular domain (ECD) and transmembrane domain (TM) (approximately 2026 by from about position 175 to 2200 of SEQ ID NO:23) can be amplified by PCR (Yamamoto et al., Nature 319:230-234, 1986; Chen et al., Canc. Res., 58:1965-1971, 1998) or chemically synthesized (BioBasic Inc., Markham, Ontario, Canada) and inserted between the IRES and yCD2 gene in the vector pAC3-yCD2 SEQ ID NO: 19 (e.g., between about nucleotide 8876 and 8877 of SEQ ID NO:19). Alternatively, the yCD gene can be excised and replaced with a polynucleotide encoding a HER2 polypeptide or fragment thereof. A further truncated HER2 with only the Herceptin binding domain IV of the ECD and TM domains (approximately 290 by from position 1910 to 2200) can be amplified or chemically synthesized and used as above (Landgraf 2007; Garrett et al., J. of Immunol., 178:7120-7131, 2007). A further modification of this truncated form with the native signal peptide (approximately 69 bp from position 175-237) fused to domain IV and the TM can be chemically synthesized and used as above. The resulting viruses can be used to treat a cell proliferative disorder in a subject in combination with trastuzumab or trastuzumab and 5-FC.

Alternatively, HER2 and the modifications described above can be expressed in a separate vector containing a different ENV gene or other appropriate surface protein. This vector can be replication competent (Logg et al. J. Mol Biol. 369:1214 2007) or non-replicative "first generation" retroviral vector that encodes the envelope and the gene of interest (Emi et al. J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses (Palu 2000, Baum et al., Mol. Therapy, 13(6):1050-1063, 2006). For example, a polynucleotide can comprise a sequence wherein the GAG and POL and yCD2 genes of SEQ ID NO: 19 are deleted, the ENV corresponds to a xenotropic ENV domain of NZB MLV or VSV-g, and the IRES or a promoter such as RSV is operatively linked directly to HER2, HER2 ECDTM, HER2 ECDIVTM, or HER2 SECDIVTM.

Mixed infection of cells by VSVG pseudotyped virus and amphotropic retrovirus results in the production of progeny virions bearing the genome of one virus encapsidated by the envelope proteins of the other. The same is true for other envelopes that pseudotype retroviral particles. For example, infection by retroviruses derived as above results in production of progeny virions capable of encoding yCD2 and HER2 (or variant) in infected cells. The resulting viruses can be used to treat a cell proliferative disorder in a subject in combination with trastuzumab or trastuzumab and 5-FC.

Recently, a gamma retrovirus, XMRV, has been associated with prostate cancer in humans with the virus showing a strong preference for replication in prostate tissue (R. Schlaberg et al. PNAS 106: 16351-16356 2009). The virus appears very similar to xenotropic MLV. In one embodiment of the disclosure, non-replicative retroviral vectors are provided which carry both a therapeutic gene (cytosine deaminase, thymidine kinase, other prodrug activating genes, interferons, IL-2, IL-12, other cytokines, p53 other anti-oncogenes, anti-cancer miRNA or the like) and an envelope gene that is capable of being complemented by the XMRV gag and gag-pol functions such as an amphotropic envelope, a GALV envelope, a VSVg protein envelope, or other envelopes known to those skilled in the art. The non-replicative vector polynucleotide is delivered to the prostate cancer in a patient or animal as a DNA or RNA molecule using one of: non-viral or physical delivery systems; a heterologous viral delivery system such as an adenoviral vector, or as a manufactured retroviral particle. Once delivered the non-replicative vector will be spread by complementation by XMRV and infection of neighboring cells will take place until the boundary of XMRV infection is reached, when the XMRV complementation will not be available. The therapeutic gene can then have its effect (e.g. after a prodrug is administered) in the XMRV infected area only. The same rescue effect can be achieved using a replicative retroviral vector of the disclosure. This strategy (complementary non-replicative vector with a therapeutic gene) can be used with any retroviral disease (HIV infection, HTLV1 infection, other cancer associated retroviruses), or with any viral or viral associated disease (HPV infection and HPV E6 & E7 expression in cervical cancers, EBV associated lymphomas or carcinomas etc.).

Another aspect of the development of resistance to trastuzumab relates to the interference with intracellular signaling required for the activity of trastuzumab. Resistant cells show loss of PTEN and lower expression of p27kip1 [Fujita, Brit J. Cancer, 94:247, 2006; Lu et al., Journal of the National Cancer Institute, 93(24): 1852-1857, 2001; Kute et al., Cytometry Part A 57A:86-93, 2004). For example, a polynucleotide encoding PTEN (SEQ ID NO:25) can be recombinantly generated or chemically synthesized (BioBasic Inc., Markham, Canada) and operably inserted directly after the yCD2 polynucleotide in the vector pAC3-yCD2 SEQ ID NO: 19 or 22, or with a linker sequence as previously described, or as a replacement for yCD2. In a further example, the PTEN encoding polynucleotide can be synthesized as above and inserted between the IRES and yCD2 sequences or with a linker as previously described.

Alternatively, PTEN can be expressed in a separate vector containing a different ENV gene or other appropriate surface protein. This vector can be replication competent (Logg et al. J. Mol Biol. 369:1214 2007) or non-replicative "first generation" retroviral vector that encodes the envelope and the gene of interest (Emi et al., J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses (Palu, Rev Med Virol. 2000, Baum, Mol. Ther. 13(6):1050-1063, 2006). For example, a polynucleotide can comprise a sequence wherein the GAG and POL and yCD2 genes of SEQ ID NO: 19 are deleted, the ENV corresponds to a xenotropic ENV domain of NZB MLV or VSV-g, and the IRES or a promoter such as RSV is operatively linked directly to PTEN.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above results in production of progeny virions capable of encoding yCD2 and PTEN (or variant) or PTEN alone in infected cells. The resulting viruses can be used to treat a cell proliferative disorder in a subject in combination with trastuzumab or trastuzumab and 5-FC.

Similarly, a polynucleotide encoding p27kip1 (SEQ ID NO:27 and 28) can be chemically synthesized (BioBasic Inc., Markham, Canada) and operably inserted directly after the yCD2 gene in the vector pAC3-yCD2 SEQ ID NO: 19 or with a linker sequence. In a further example, the p27kip1 encoding polynucleotide can be synthesized as above and inserted between the IRES and yCD2 sequences or with a linker as previously described or in place of the yCD2 gene.

Alternatively, p27kip1 can be expressed in a separate vector containing a different ENV gene or other appropriate surface protein. This vector can be replication competent (C R. Logg et al. J. Mol Biol. 369:1214 2007) or non-replicative "first generation" retroviral vector that encodes the envelope and the gene of interest (Emi et al. J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses (Palu 2000, Baum 2006, supra). For example, a polynucleotide can comprise a sequence wherein the GAG and POL and yCD2 genes of SEQ ID NO: 19 are deleted, the ENV corresponds to a xenotropic ENV domain of NZB MLV or VSV-g, and the IRES or a promoter such as RSV is operatively linked directly to p27kip1.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above from both SEQ ID NO: 19 and 22 results in production of progeny virions capable of encoding yCD2 and p27kip1 (or variant) in infected cells. The resulting viruses can be used to treat a cell proliferative disorder in a subject in combination with trastuzumab or trastuzumab and 5-FC.

In another example, CD20 is the target for binding of the drug rituximab (Rituxan™, Genentech). Rituximab is a mediator of complement-dependent cytotoxicity (CDC) and ADCC. Cells with higher mean fluorescence intensity by flow cytometry show enhanced sensitivity to rituximab (van Meerten et al., Clin Cancer Res 2006; 12(13):4027-4035, 2006). Enhancement of expression of CD20 by introduction of vector expressing CD20 in CD20 low B cells may facilitate optimal triggering of ADCC.

For example, a polynucleotide encoding CD20 (SEQ ID NO:29 and 30) can be chemically synthesized (BioBasic Inc., Markham, Canada) and operably inserted directly after the yCD2 gene in the vector pAC3-yCD2(-2) SEQ ID NO: 19 or 22 with a linker sequence as previously described, or as a replacement for the yCD2 gene. In a further example, the CD20 encoding polynucleotide can be synthesized as above and inserted between the IRES and yCD2 sequences or with a linker as previously described. As a further alternative the CD20 sequence can be inserted into the pAC3-yCD2 vector after excision of the CD gene by Psi1 and Not1 digestion.

In still a further example, a polynucleotide encoding CD20 (SEQ ID NO:29 and 30) can be chemically synthesized (BioBasic Inc., Markham, Canada) and inserted into a vector containing a non amphotropic ENV gene or other appropriate surface protein (Tedder et al., PNAS, 85:208-212, 1988). Alternate ENV and glycoproteins include xenotropic and polytropic ENV and glycoproteins capable of infecting human cells, for example ENV sequences from the NZB strain of MLV and glycoproteins from MCF, VSV, GALV and other viruses [Palu 2000, Baum 2006]. For example, a polynucleotide can comprise a sequence wherein the GAG and POL and yCD2 genes of SEQ ID NO: 19 are deleted, the ENV corresponds to a xenotropic ENV domain of NZB MLV or VSV-g, and the IRES or a promoter such as RSV is operatively linked directly to CD20.

Mixed infection of cells by VSVG pseudotyped virus and amphotropic retrovirus results in the production of progeny virions bearing the genome of one virus encapsidated by the envelope proteins of the other [Emi 1991]. The same is true for other envelopes that pseudotype retroviral particles. For example, infection by retroviruses derived as above from both SEQ ID NO: 19 or 22 results in production of progeny virions capable of encoding yCD2 and CD20 in infected cells. The resulting viruses can be used to treat a cell proliferative disorder in a subject in combination with Rituxan and/or 5-FC. Similarly, infection of a tumor with a vector encoding only the CD20 marker can make the tumor treatable by the use of Rituxan.

Levels of the enzymes and cofactors involved in pyrimidine anabolism can be limiting. OPRT, thymidine kinase (TK), Uridine monophosphate kinase, and pyrimidine nucleoside phosphorylase expression is low in 5-FU resistant cancer cells compared to sensitive lines (Wang et al., Cancer Res., 64:8167-8176, 2004). Large population analyses show correlation of enzyme levels with disease outcome (Fukui et al., Int'l. J. OF Mol. Med., 22:709-716, 2008). Coexpression of CD and other pyrimidine anabolism enzymes (PAE) can be exploited to increase the activity and therefore therapeutic index of fluoropyrimidine drugs.

To further increase the genetic stability (see, e.g., FIG. 5) of yCD2/PAE containing vectors, the enzyme encoding gene can be chemically synthesized with random mutations throughout the sequence. These mutations can be essentially random or can consist of only mutations at the wobble position for each amino acids. The library of mutated sequences is inserted downstream or in place of the yCD2 gene as was previously described for SEQ ID NO: 11 and 13 to create a library of plasmids that can then be used to generate a library of infectious particles by transient transfection of 293T cells or equivalent. Sensitive cells can be infected with retrovirus encoding the fusion polypeptide and subjected to selection with appropriate chemicals.

DNA shuffling or "molecular breeding" allows genetic information to be shuffled, leading to recombinants with desired properties. Different proteins and enzymes have been improved using DNA shuffling (Stemmer 1994 *Proc Natl Acad Sci USA* 91(22): 10747-51; Stemmer 1994 *Nature* 370 (6488):389-91). Genetic recombination is a major force driving the evolution of many viruses. In retrovirus, recombination between two co-packaged retroviral genomes may occur at rates as high as 40% per replication cycle. High rates of recombination at each replication cycle enables genetic information to be shuffled rapidly, leading to recombinants with new pattern of mutations and phenotypes within a short period of time. For example, molecular breeding of retrovirus containing a library of recombinant ecotropic envelope sequences from six murine leukemia virus resulted in a viral clone with a new tropism. Using the same method, several viral clones were selected with improved stability and processing yields (Soong et al., 2000 *Nat Genet* 25(4):436-9; Powell et al., 2000 *Nat Blotechnol* 18(12):1279-82). In order to generate vectors that can replicate in cells that are resistant to retroviral infection because of viral restriction or inhibitory factors, such as APOBEC, Trim5alpha, tetherin, Zap or other elements in cells that render them resistant to retroviral infection (D. Wolf & S P. Goff, Annu. Rev. Genet. 2008. 42:143-63) the vectors of the disclosure can be used to express libraries of random peptide libraries normally expressed in yeast libraries (F. Hoppe-Seyler & K. Butz J Mo Med 78:426-430 (2000); R. Wolkowicz et al. J. Biol. Chem. 280:15195-15201 (2005); both incorporated by reference), made from inserts of random nucleotide syntheses into the vectors. These inserts can be expressed as stand-alone peptides expressed from the IRES or otherwise, or can be tagged at the beginning, in the middle of, or at the end of the protein that it is desired to express. For example it is known that yeast cytosine deaminase tolerates fusion to the C terminus of a protein (K N. Barton et al. Mol Ther 13:347-356 2006). Alternatively the peptides can be inserted at the beginning, middle or end of viral structural proteins in the same way. Not all insertion sites will be well tolerated but various useful sites are known. The peptides can be from 6 to 60 amino acids in length, typically between 8 and 20 amino acids. Peptides that bind to and inactivate known antiviral agents may be select by conventional yeast two hybrid methods but this is laborious and has no functional guarantee of success. However, if the virus itself is expressing the peptide library by bulk insertion of library nucleotide sequences into the vector as a DNA plasmid followed by transient transfection on 293T cells or equivalent to generate a library of infectious particles, then the vector that grows best in the target cell or tumor type is selected by serial growth in that cell type or tumor explants. Serial passage in the target cell type rapidly select for viruses that carry an inhibitor peptide for any factor that inhibits viral replication in that cell type. In order to maintain a good diversity of peptides, and supply an opportunity for mutations to occur, if necessary, the target cell is grown mixed with a cell type that supports viral replication well (e.g. HT1080 human fibrosarcoma) to provide further copies of the library of viruses and to let the error prone reverse transcriptase introduce occasional random mutations, that may be advantageous.

The virus coming from the cells is monitored on each passage for its diversity, by direct sequencing of the insert or otherwise, and may be recycled through the selection procedure several times. The selected viruses are cloned out from the viral supernatant or the cells by PCR across the insert, insertion in a plasmid and sequencing of individual plasmid clones. The identified peptide aptamers are then rechecked for their ability to confer replication advantage in a particular cell type such as a particular tumor type or particular blood cell types etc. The peptide aptamers are also used directly to identify the cellular element with which it interacts by methods known to those in the art.

The peptide aptamer sequence is then incorporated as before in a viral vector that has the desired replication capacity, and carries a therapeutic gene as described elsewhere in the disclosure. Such a vector is used for therapeutic purposes as described in this disclosure.

Polynucleotide sequence incorporated into vectors are sometimes unstable resulting in deletion of the polynucleotide sequence from the viral genome over time. The basis for this is not well understood, but it is believed to be sequence dependent Molecular breeding using the vectors described herein to select for recombinant viral clones that have acquired optimal recombinations within the heterologous polynucleotide sequence is employed to select for viral clones that have greater vector stability.

For example, the HSV-TK coding sequence is not as stable as desired in some situations. Molecular breeding of recombinant retroviral vectors encompass a pool of degenerated coding sequence of HSV-TK is performed to select recombinant vectors that have great vector stability. Randomly mutagenized Herpes Thymidine Kinase (TK) is chemically synthesized (Bio Basic Inc., Markham, Canada). The synthetic sequence is inserted 3' of the yCD2 sequence in SEQ ID NO:19, or by itself in the pAC3-yCD2 vector back bones after excision of the CD2 gene. The retroviral vector mixture is packaged as described elsewhere herein. Mouse fibroblast LMTK-cells or humans 143Tk- are infected with vector and selected for TK activity in HAT media (Hiller et al., Mol. Cell Biol. 8(8):3298-3302, 1988). Serial passage of supernatants of resistant cells to fresh LMTK-/143Tk- cells again selected in HAT media results in selection of stable vectors expressing TK. TK+ resistant cells can be isolated and TK sequences rescued by standard PCR based techniques for mutation analysis (Cowell et al., CDNA Library Protocols, Published by Humana Press, 1996). In this manner, sequences are selected for both expression of functional protein and genomic stability of retroviral vector construct. Similar strategies can be employed for UPRT (SEQ ID NO: 11, 13), OPRT (SEQ ID NO: 15, 17) and other genes of interest. In addition, the serial passage strategy can be used for non-selectable genes and the genomic DNA after serial passage screened for full length inserts by PCR across the IRES-insert gene (see FIG. 5). The full length inserts can be purified and cloned out back into the viral vector then retested. Several cycles of this procedure can be performed to select the most stable gene. This strategy can also be used for passage in animals with or without tumors, and even in patient tissue.

Alternatively, OPRT, UPRT, TK or other PAE can be expressed in a separate vector containing a different env gene or other appropriate surface glycoprotein. This vector can be replication competent (Logg et al. J. Mol Biol. 369:1214 2007) or non-replicative "first generation" retroviral vector that encodes the envelope and the gene of interest (Emi et al. J. Virol 65:1202 1991). In the latter case the pre-existing viral infection will provide complementary gag and pol to allow infective spread of the "non-replicative" vector from any previously infected cell. Alternate ENV and glycoproteins include xenotropic and polytropic ENV and glycoproteins capable of infecting human cells, for example ENV sequences from the NZB strain of MLV and glycoproteins from MCF, VSV, GALV and other viruses [Palu 2000, Baum 2006, supra]. For example, a polynucleotide can comprise a sequence wherein the GAG and POL genes are deleted, the ENV corresponds to a xenotropic ENV domain from NZB MLV or VSV-g, and the IRES or a promoter such as RSV is operatively linked directly to OPRT, UPRT, TK, or other PAE gene.

Mixed infection of cells by VSV-g pseudotyped virus and amphotropic retrovirus results in the production of progeny virions bearing the genome of one virus encapsidated by the envelope proteins of the other (Emi et al., J. Virol. 65:1202, 1991). The same is true for other envelopes that pseudotype retroviral particles. For example, infection by retroviruses derived as above from both SEQ ID NO: 19 and 22 results in production of progeny virions capable of encoding yCD2 and OPRT in infected cells. The resulting viruses can be used to treat a cell proliferative disorder in a subject in combination with 5-FC.

The recombinant retrovirus of the disclosure can be used for the treatment of a neuronal disorder for example, may optionally contain an exogenous gene, for example, a gene which encodes a receptor or a gene which encodes a ligand. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by an infected donor cell would be beneficial in a disorder where the subject's neural cell is defective in the production of such a gene product. A cell genetically modified to secrete a neurotrophic factor, such as nerve growth factor, (NGF), might be used to prevent degeneration of cholinergic neurons that might otherwise die without treatment.

Alternatively, cells being grafted into a subject with a disorder of the basal ganglia, such as Parkinson's disease, can be modified to contain an exogenous gene encoding L-DOPA, the precursor to dopamine. Parkinson's disease is characterized by a loss of dopamine neurons in the substantia-nigra of the midbrain, which have the basal ganglia as their major target organ.

Other neuronal disorders that can be treated similarly by the method of the disclosure include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic cells infected with a recombinant retrovirus of the disclosure containing an exogenous gene for a factor which would promote survival of these neurons can be accomplished by the method of the disclosure, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this disclosure. For example, antisense sequences, or a gene encoding an antagonist can be transferred to a neuronal cell and implanted into the hippocampal region of the brain.

For diseases due to deficiency of a protein product, gene transfer could introduce a normal gene into the affected tissues for replacement therapy, as well as to create animal models for the disease using antisense mutations. For example, it may be desirable to insert a Factor IX encoding nucleic acid into a retrovirus for infection of a muscle or liver cell.

The disclosure also provides gene therapy for the treatment of cell proliferative or immunologic disorders. Such therapy would achieve its therapeutic effect by introduction of an antisense or dominant negative encoding polynucleotide into cells having the proliferative disorder, wherein the polynucleotide binds to and prevents translation or expression of a gene associated with a cell-proliferative disorder. Delivery of heterologous nucleic acids useful in treating or modulating a cell proliferative disorder (e.g., antisense polynucleotides) can be achieved using a recombinant retroviral vector of the disclosure. In another embodiment, a cell proliferative disorder is treated by introducing a CD polynucleotide of the disclosure, expressing the polynucleotide to produce a polypeptide comprising cytosine deaminase activity and contacting the cell with 5-fluorocytosine in an amount and for a period of time to produce a cytotoxic amount of 5-FU.

A number of chemotherapeutic agents are currently on the market having varying degrees of success from full remission to temporary remission and prolonged life with expected recurrence. Some of the cancer therapeutic agents on the market target the vascular angiogenic properties of tumor. The composition target the angiogenesis of tumors seeking to reduces blood supply and nutrients to the tumor or cancer and thereby reduce the tumor and prolong a subject's life. VEGF is an angiogenic factor known to play a role in tumor growth. Thus, antagonists of VEGF have been developed as anticancer agents.

Human VEGF mediates neoangiogenesis in normal and malignant vasculature; it is overexpressed in most malignancies and high levels have correlated with a greater risk of metastases and poor prognosis in many. When VEGF interacts with its receptor in in vitro models of angiogenesis, endothelial cell proliferation and new blood vessel formation occur. In animal models, VEGF has been demonstrated to induce vascular endothelial-cell proliferation/migration, sustain survival of newly-formed blood vessels, and enhance vascular permeability.

A VEGF antagonist agent is one that targets or negatively regulates the VEGF signaling pathway. Examples include VEGF inhibitors (e.g., agents that directly inhibit VEGF (e.g., VEGF-A, -B, -C, or -D), such as by binding VEGF (e.g., anti-VEGF antibodies such as bevacizumab (AVASTIN®) or ranibizumab (LUCENTIS®), or other inhibitors such as pegaptanib, NEOVASTAT®, AE-941, VEGF Trap, and PI-88)), modulators of VEGF expression (e.g., INGN-241, oral tetrathiomolybdate, 2-methoxyestradiol, 2-methoxyestradiol nanocrystal dispersion, bevasiranib sodium, PTC-299, Veglin), inhibitors of a VEGF receptor (e.g., KDR or VEGF receptor III (Flt4), for example anti-KDR antibodies, VEGFR2 antibodies such as CDP-791, IMC-1121B, VEGFR2 blockers such as CT-322), modulators of VEGFR expression (e.g., VEGFR1 expression modulator Sirna-027) or inhibitors of VEGF receptor downstream signaling. In some aspects described herein, the VEGF antagonist agent is bevacizumab, pegaptanib, ranibizumab, sorafenib, sunitinib, AE-941, VEGF Trap, pazopanib, vandetanib, vatalanib, cediranib, fenretinide, squalamine, INGN-241, oral tetrathiomolybdate, tetrathiomolybdate, Panzem NCD, 2-methoxyestradiol, AEE-788, AG-013958, bevasiranib sodium, AMG-706, axitinib, BIBF-1120, CDP-791, CP-547632, PI-88, SU-14813, SU-6668, XL-647, XL-999, IMC-1121B, ABT-869, BAY-57-9352, BAY-73-4506, BMS-582664, CEP-7055, CHIR-265, CT-322, CX-3542, E-7080, ENMD-1198, OSI-930, PTC-299, Sirna-027, TKI-258, Veglin, XL-184, or ZK-304709.

Bevacizumab (AVASTIN®) (rhuMAb-VEGF)(Anti-VEGF monoclonal antibody) is a recombinant human/murine chimeric monoclonal antibody directed against vascular endothelial growth factor (VEGF)). It is prepared by engineering VEGF-binding residues of a murine anti-VEGF monoclonal antibody into framework regions of human immunoglobulin-1 (IgG1) (Prod Info Avastin, 2004). Only 7% of the amino acid sequence is derived from the murine antibody, with 93% from IgG1. Bevacizumab binds and neutralizes all human VEGF forms via recognition of binding sites for the two human VEGF receptor types (flt-1 and flk-1). In animal models, the antibody has been shown to stabilize established tumors or suppress tumor growth by inhibiting angiogenesis induced by VEGF.

The pharmacokinetics of bevacizumab are linear after doses of 0.3 mg/kg or greater (Anon, 2002). Following 90-minute intravenous infusions of 0.3, 1, 3, and 10 mg/kg in advanced cancer patients (n=25), peak serum concentrations of bevacizumab ranged from 5 to 9 mcg/mL, 21 to 39 mcg/mL, 52 to 92 mcg/mL, and 186 to 294 mcg/mL, respectively; slight accumulation was observed with repeat doses (weekly), but this was not significant and pharmacokinetics remained linear. Steady-state levels of bevacizumab were obtained in 100 days after 1 to 20 mg/kg weekly, every 2 weeks, or every 3 week.

The recommended dose of bevacizumab is 5 milligrams/kilogram infused intravenously over 30 minutes every 2 weeks until disease progression diminishes. Bevacizumab should follow chemotherapy. Efficacy of single-agent bevacizumab has not been established. Bevacizumab (which may be co-administered with the gemcitabine and docetaxel, or within a week before or after chemotherapy), is administered intravenously, at about 1 mg/kg to about 15 mg/kg, preferably about 5 mg/kg.

The methods and compositions of the disclosure are useful in combination therapies including therapies with bevacizumab. As described herein a replication competent retrovirus (RCR) of the disclosure comprising a therapeutic (e.g., a cytotoxic gene) is useful in treating cell proliferative disorders. An advantage of the RCR of the disclosure includes its ability to infect replicating cells cancer cells. Where the transgene of the vector comprises a cytotoxic gene (e.g., a gene that encodes a polypeptide that converts a non-cytotoxic agent to a cytotoxic agent) provides the ability to kill cancer cells.

The disclosure provides methods for treating cell proliferative disorders such as cancer and neoplasms comprising administering an RCR vector of the disclosure followed by treatment with a chemotherapeutic agent or anti-cancer agent. In one aspect, the RCR vector is administered to a subject for a period of time prior to administration of the chemotherapeutic or anti-cancer agent that allows the RCR to infect and replicate. The subject is then treated with a chemotherapeutic agent or anti-cancer agent for a period of time and dosage to reduce proliferation or kill the cancer cells. In one aspect, if the treatment with the chemotherapeutic or anti-cancer agent reduces, but does not kill the cancer/tumor (e.g., partial remission or temporary remission), the subject may then be treated with a non-toxic therapeutic agent (e.g., 5-FC) that is converted to a toxic therapeutic agent in cells expression a cytotoxic gene (e.g., cytosine deaminase) from the RCR.

Using such methods the RCXR vectors of the disclosure are spread during a replication process of the tumor cells, such cells can then be killed by treatment with an anti-cancer or chemotherapeutic agent and further killing can occur using the RCR treatment process described herein.

In yet another embodiment of the disclosure, the heterologous gene can comprise a coding sequence for a target antigen (e.g., a cancer antigen). In this embodiment, cells comprising a cell proliferative disorder are infected with an RCR comprising a heterologous polynucleotide encoding the target antigen to provide expression of the target antigen (e.g., overexpression of a cancer antigen). An anticancer agent comprising a targeting cognate moiety that specifically interacts with the target antigen is then administered to the subject. The targeting cognate moiety can be operably linked to a cytotoxic agent or can itself be an anticancer agent. Thus, a cancer cell infected by the RCR comprising the targeting antigen coding sequences increases the expression of target on the cancer cell resulting in increased efficiency/efficacy of cytotoxic targeting.

Blocking of interactions between cells of the immune system has been shown to have significant immunological effects, either activating or suppressing (Waldmann Annu Rev Med. 57:65 2006). For example, blockade of the interaction of CTLA-4 (CD 152) and B7.1 (CD80) which modulates the activation of T cells has been shown to cause immune stimulation, presumably by blocking this suppressive interaction (Peggs et al. Curr. Opin. Immunol. 18:206, 2006). This blockade can potentially be achieved either by antibodies against CTLA-4 or by soluble B7.1. Systemic administration of these types of molecules can have undesirable global effects which can at a minimum lead to deleterious side-effects or even death in the case of one CD28 agonist (Suntharalingam et al. NEJM 355 1018 2006). Pfizer has been developing one such anti-CTLA-4 blockading antibody (CP-675,206) as an anticancer reagent but has recently stopped development because of significant side effects. Local delivery of blockading molecules that are released into the local environment, from the tumor after infection with a replication competent vector encoding such molecules that are released into the extracellular space, provides the immune modulation locally and can avoid these serious side effects. The blockading molecules are antibodies, single chain antibodies, soluble versions of the natural ligand or other peptides that bind such receptors.

In yet another embodiment, an RCR of the disclosure can comprise a coding sequence comprising a binding domain (e.g., an antibody, antibody fragment, antibody domain or receptor ligand) that specifically interacts with a cognate antigen or ligand. The RCR comprising the coding sequence for the binding domain can then be used to infect cells in a subject comprising a cell proliferative disorder such as a cancer cell or neoplastic cell. The infected cell will then express the binding domain or antibody. An antigen or cognate operably linked to a cytotoxic agent or which is cytotoxic itself can then be administered to a subject. The cytotoxic cognate will then selectively kill infected cells expressing the binding domain. Alternatively the binding domain itself can be an anti-cancer agent.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$, a Fd fragment, a Fv fragments, and dAb fragments) as well as complete antibodies.

The VH and VL regions can be further subdivided into regions of hypervariability, termed "complementarity determining regions" (CDR), interspersed with regions that are more conserved, termed "framework regions" (FR). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two .beta.-sheets formed of about seven .beta.-strands, and a conserved disulphide bond (see, e.g., A. F. Williams and A. N. Barclay 1988 Ann. Rev Immunol. 6:381-405). The canonical structures of hypervariable loops of an immunoglobulin variable can be inferred from its sequence, as described in Chothia et al. (1992) J. Mol. Biol. 227:799-817; Tomlinson et al. (1992) J. Mol. Biol. 227:776-798); and Tomlinson et al. (1995) EMBO J. 14(18):4628-38.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site"), e.g., a structure that interacts with Tie1, e.g., binds to or inhibits Tie1.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity.

The term "monospecific antibody" refers to an antibody that displays a single binding specificity and affinity for a particular target, e.g., epitope. This term includes a "monoclonal antibody" which refers to an antibody that is produced as a single molecular species, e.g., from a population of homogenous isolated cells. A "monoclonal antibody composition" refers to a preparation of antibodies or fragments thereof of in a composition that includes a single molecular species of antibody. In one embodiment, a monoclonal antibody is produced by a mammalian cell. One or more monoclonal antibody species may be combined.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human or effectively human. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human or effectively human. For example, FR1, FR2, and FR3 collectively can be at least 70, 75, 80, 85, 90, 92, 95, 98, or 99% identical to a human sequence encoded by a human germline V segment of a locus encoding a light or heavy chain sequence.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin light chains (about 25 Kd or 214 amino acids) are encoded by a variable region gene at the NH2-terminus (about 110 amino acids) and a kappa or lambda constant region gene at the COOH— terminus. Full-length immunoglobulin heavy chains (about 50 Kd or 446 amino acids), are similarly encoded by a variable region gene (about 116 amino acids) and one of the other aforementioned constant region genes, e.g., gamma (encoding about 330 amino acids). A light chain refers to any polypeptide that includes a light chain variable domain. A heavy chain refers to any polypeptide that a heavy chain variable domain.

The term "antigen-binding fragment" of a full-length antibody (or simply "antibody portion," or "fragment"), as used herein, refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab').sub.2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition. As used herein, "isotype" refers to the antibody class (e.g., IgM or IgG1) that is encoded by heavy chain constant region genes.

The disclosure provides a method of treating a subject having a cell proliferative disorder. The subject can be any mammal, and is preferably a human. The subject is contacted with a recombinant replication competent retroviral vector of the disclosure. The contacting can be in vivo or ex vivo. Methods of administering the retroviral vector of the disclosure are known in the art and include, for example, systemic administration, topical administration, intraperitoneal administration, intra-muscular administration, intracranial, cerebrospinal, as well as administration directly at the site of a tumor or cell-proliferative disorder. Other routes of administration known in the art.

Thus, the disclosure includes various pharmaceutical compositions useful for treating a cell proliferative disorder. The pharmaceutical compositions according to the disclosure are prepared by bringing a retroviral vector containing a heterologous polynucleotide sequence useful in treating or modulating a cell proliferative disorder according to the disclosure into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

For example, and not by way of limitation, a retroviral vector useful in treating a cell proliferative disorder will include an amphotropic ENV protein, GAG, and POL proteins, a promoter sequence in the U3 region retroviral genome, and all cis-acting sequence necessary for replication, packaging and integration of the retroviral genome into the target cell.

The following Examples are intended to illustrate, but not to limit the disclosure. While such Examples are typical of those that might be used, other procedures known to those skilled in the art may alternatively be utilized.

EXAMPLES

Example 1

Figure 3A:
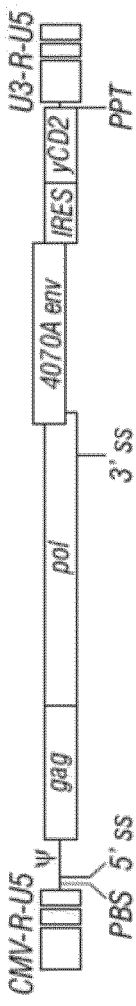
Figure 3B:
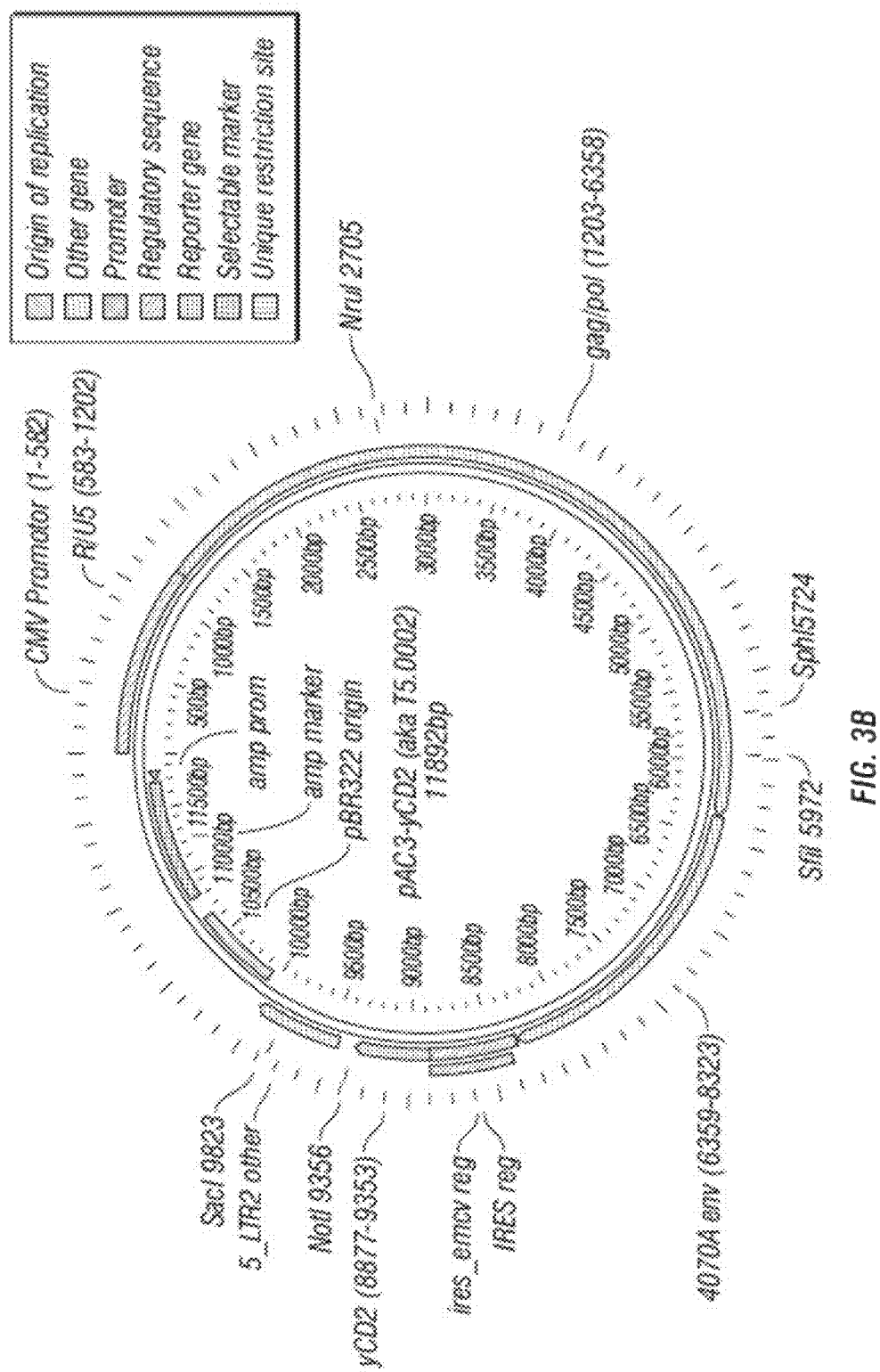
Figure 3C:
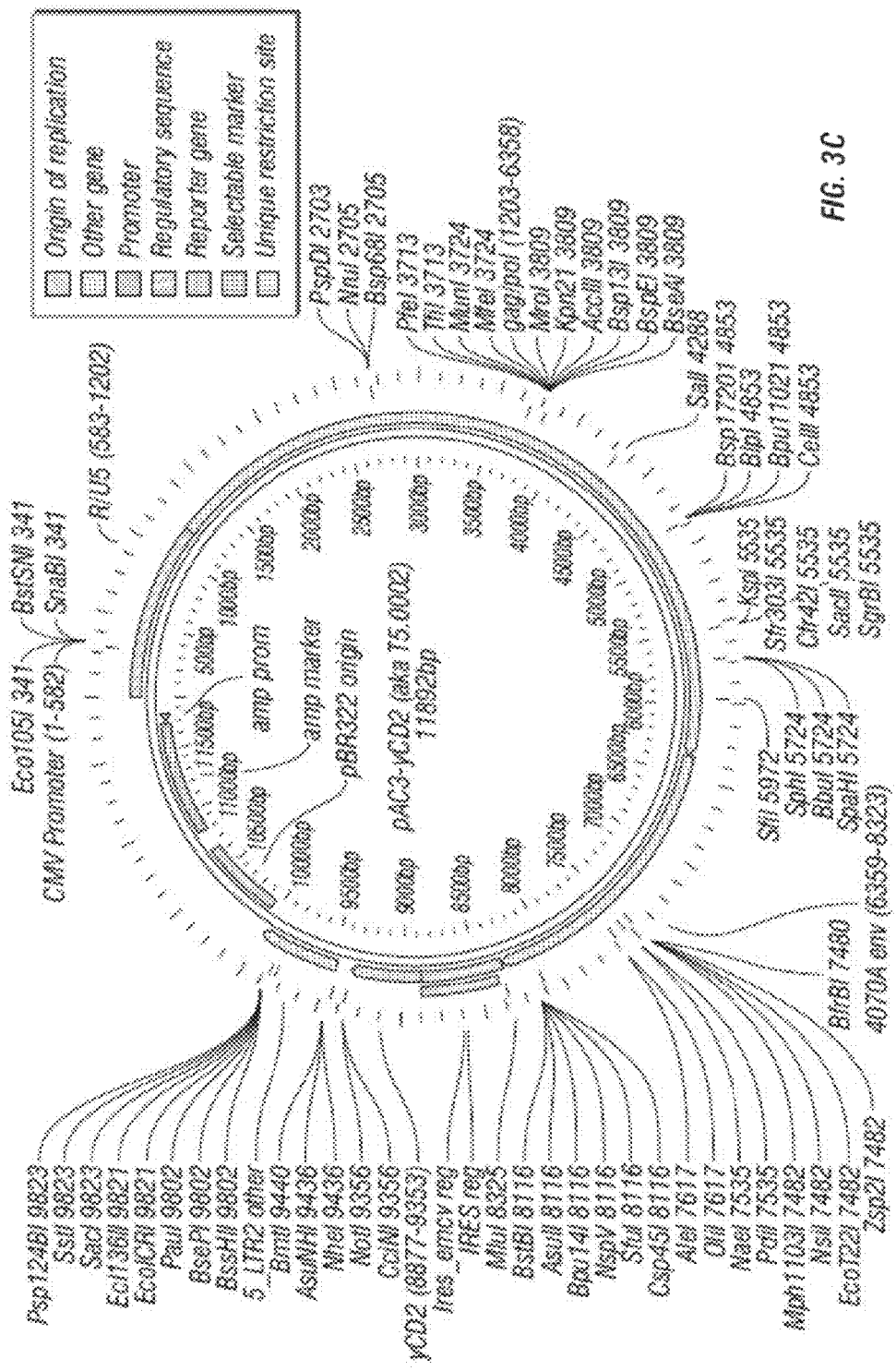
Figure 3E:
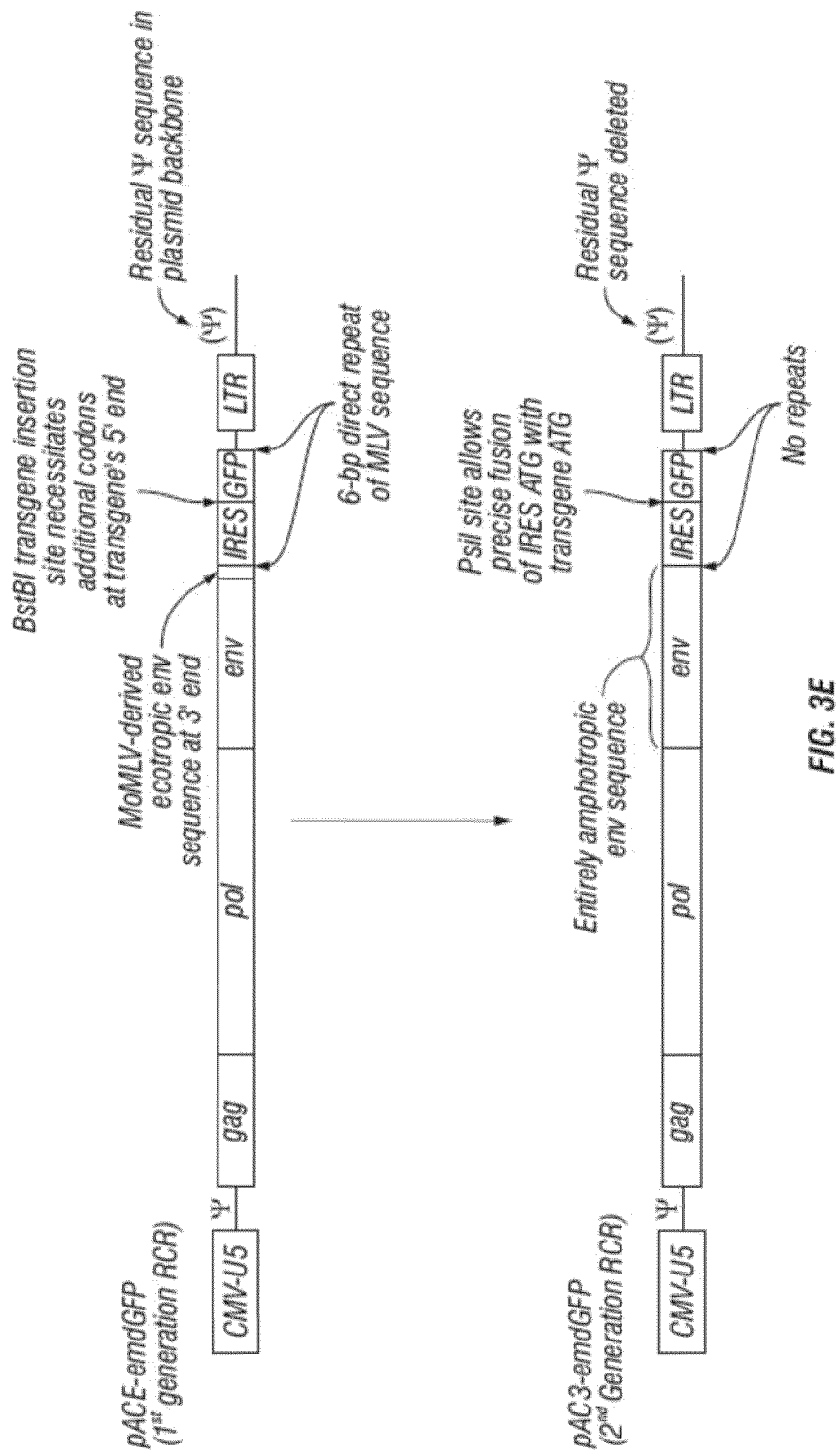

Modification of Vector Backbone of pACE-GFPemd to pAC3-GFPemd and Insertion of Cytosine Deaminase Gene Sequences in Place of GFP The previous back bone of the pACE-GFPemd plasmid (U.S. Pat. No. 6,899,871, Wang et al. Hum Gene Ther 14:117 2003) was modified in 3 ways as shown in FIG. 3E. The modifications were made by PCR-mediated, oligonucleotide-directed mutagenesis (Logg et al., J. Mol Biol 369: 1214, 2007; see also "Molecular Biology and Biotechnology" Eds. J M. Walker, R. Rapley, Royal Society of Chemistry, London UK, 2000). The following modifications were made. 1) The nucleic acid sequence at the p15 region at 3' end of the amphotropic env gene was originally derived from the ecotropic envelope—this sequence was replaced by the corresponding sequence from the 4070A amphotropic envelope; the encoded envelope amino acids are identical in the two constructs. 2) The IRES sequence 3' end was modified to allow easier insertion of transgenes of choice with insertion of a PstI1 site and small imperfect repeats at either end of the IRES transgene site were removed. 3) Residual viral sequence downstream of the 3'LTR was removed. The resultant plasmid is pACE-emdGFP (aka pACE-GFP, pACE-eGFP and T5.0006) was used as a basis for the vectors encoding cytosine deaminase and variants. Two methods of inserting the coding sequence cassettes were used initially. The first method resulted in the sequence 5'TTATAAT3' (SEQ ID NO:73), and the second in the sequence 5'TTATAA3' (SEQ ID NO:74) immediately upstream of the ATG start codon. The second method was simpler, as it involved simple PstI1 and Not1 enzyme cuts in the vector and the synthetic cytosine deaminase genes, followed by religation. Vectors with cytosine deaminase inserts were made both ways with the CDopt (CD1) and the CDopt+3pt (CD2) (see FIG. 2) coding sequences and infectious virus preps made by transient transfection of 293T cells as described in Example 3. U87 cells were then infected in culture, at an MOI of 0.1, and the cells grown until 100% infected. Cell extracts of 100% infected cells were assayed for cytosine deaminase activity as described in Example 6 and the specific activity of the enzyme was found to be equivalent for constructs with either upstream sequence, that were otherwise identical. Therefore in the table in FIG. 2, pACE-eGFP (T5.0006) and pACE-yCD (T5.0007) have the first upstream sequence, while all other constructs that were further tested have the second. Subsequently vectors with different gene inserts have been routinely constructed with straightforward PStI1 and Not 1 cuts.

See FIG. 3A below for a diagram of the vector construct for the initial transfected replication-competent retrovirus. CMV is the human CMV immediate early promoter, U3, R and U5 are the corresponding regions of the viral long terminal repeat (LTR). Gag, pol and env are the viral protein coding regions. FIGS. 3B and 3D shows the plasmid structure and a sequence of the disclosure.

Figure 5:
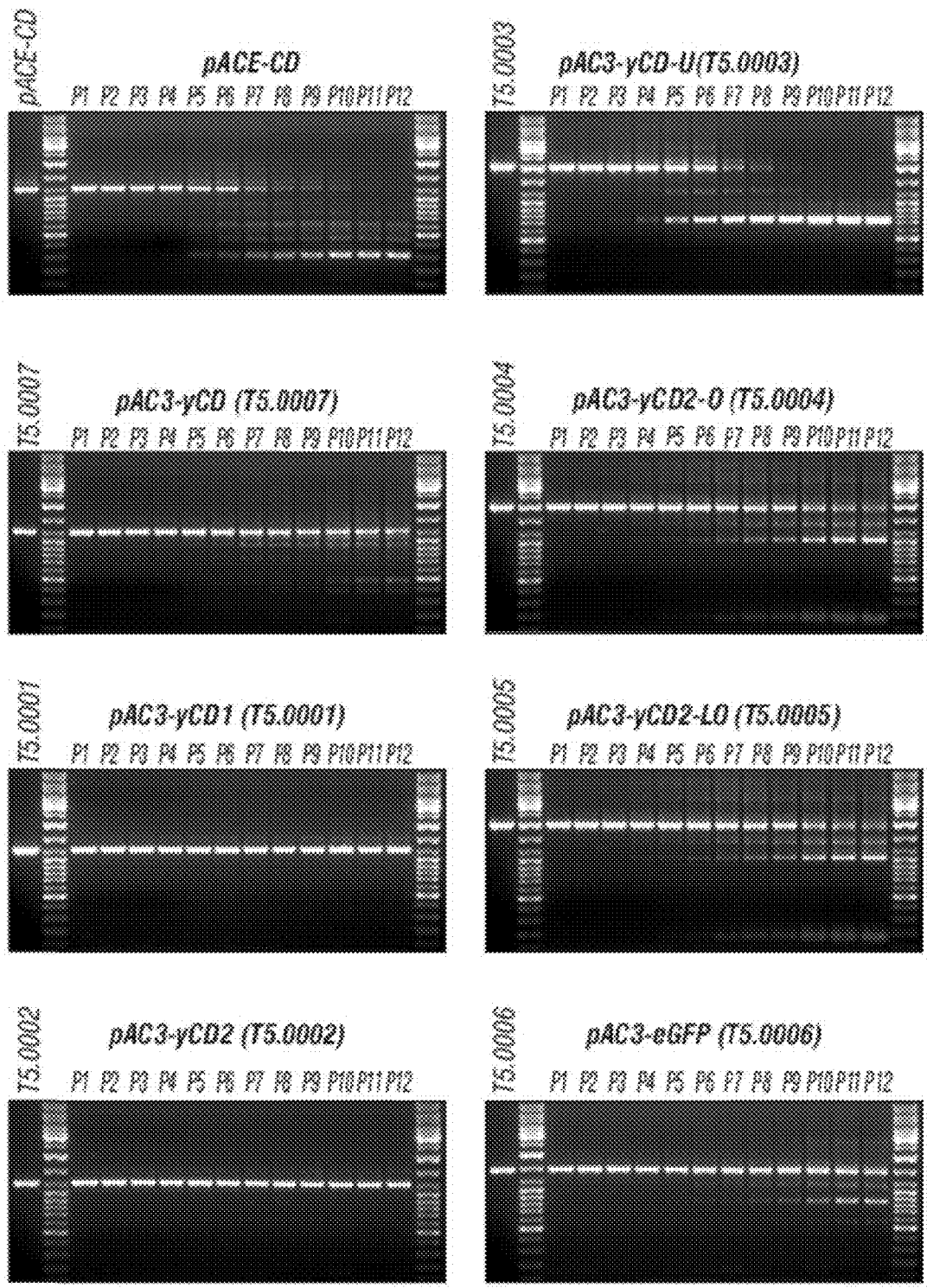
FIG. 5 shows that a vector of the disclosure is genetically stable after 12 cycles of viral passages as assessed using PCR amplification. The figure also demonstrates that the vectors of the disclosure are more stable after longer passages compared to the vector pACE-CD (Kasahara et al.). In particular pAC3-CD is more stable than pACE-CD, demonstrating that the changed backbone has made the vector more stable. In addition pACE-yCD1 (T5.0001) and -yCD2 (T5.0002) are very much more stable than pAC-yCD, demonstrating that small and silent changes to the coding sequence of the transgene can have a very large effect on stability, leading to superior properties.

The vector of the disclosure provides a number of differences compared to the vector of Tai et al., Mol. Ther. 12:842, 2005. The Tai et al. vector has been altered to eliminate about 70 bp of MLV sequence downstream from the 3'LTR. The DNA sequence downstream of the ClaI site in the envelope was changed to an amphotropic envelope sequence. This change does not change the amino acid sequence of the envelope. In addition, small repeats on either side of the IRES-CD cassette have been eliminated to avoid instability due to homologous recombination. These changes also unexpectedly provided increased stability of the vector during replication and passaging in host cells (FIG. 5).

It is recognized that after reverse transcription and the first integration event into treated cells, the DNA provirus and any subsequent progeny retrovirus has a conventional LTR structure from MLV on either end. This configuration has been shown to be stable after multiple cycles of infection (See FIG. 5 below).

Example 2

Genetic Enhancements to the Wild Type Yeast Cytosine Deaminase Gene

Two sets of changes have been made: (1) three positional mutations which change three amino acids (A23L, I140L and V108I) to increase thermal stability of the yeast cytosine deaminase protein and (2) additional gene sequence modifications to enhance human codon usage sequences to improve protein translation efficiency in human cells without further changes to the amino acid sequence.

Sequence design for CD included CD-optimized, CD-UPRT (+/− linker) and CD-OPRTase (+/− linker). The final cytosine deaminase coding sequence can comprise at the 5' end a PSI1 site (full length) and 3' end Not1 site plus poly A tail for PSI1/Not1 cassette based strategy. Sequences cassettes were ordered from, and provided by, a commercial vendor (BioBasic Inc., Markham, Ontario, Canada).

Figures 1, 3F:
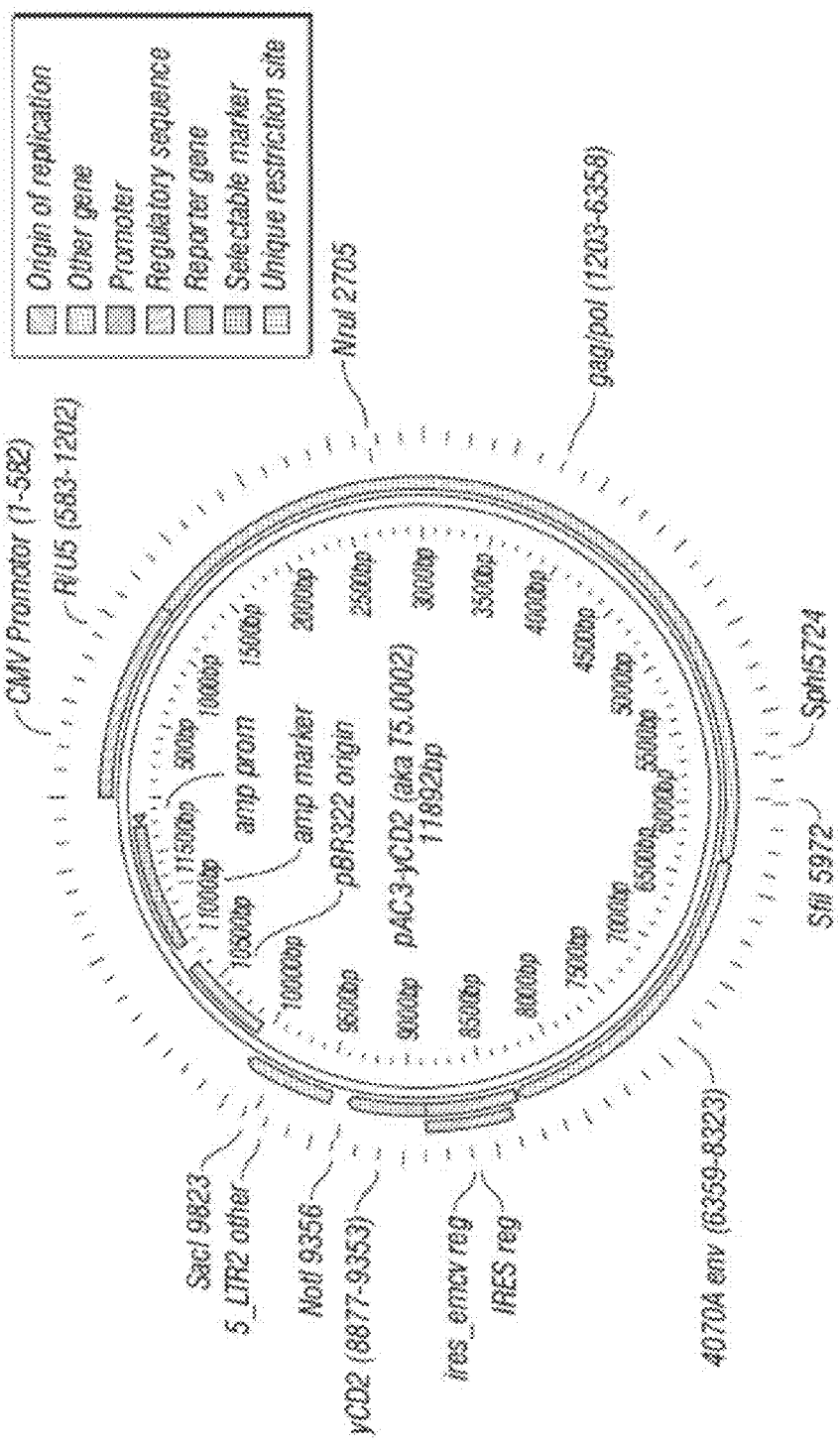
Figures 2, 3F:
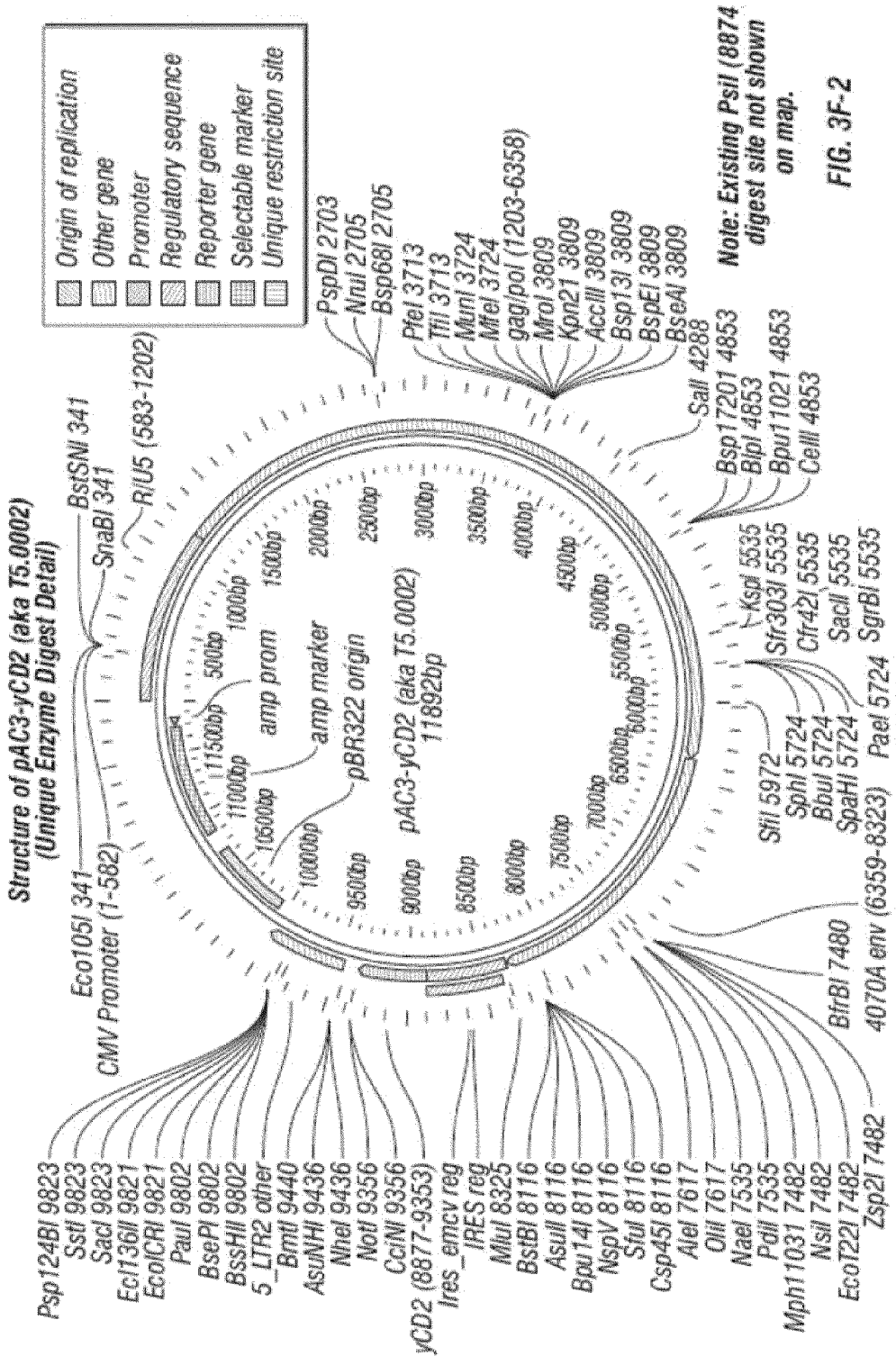
Figures 3, 3F:

The following sequence comprising a yeast cytosine deaminase was used for cloning, optimizing and mutation (the boxed nucleic acids comprise the restriction sites—Psi1 and Not1—used in subsequent methods for cloning:

After the genes were synthesized at a contractor (Bio Basic Inc., Markham, Ontario, Canada) they were inserted into the Psi1-Not1 site of the pAC3 vector backbone (FIG. 3). The plasmid backbone was normally generated by cutting the plasmid pAC3-eGFP with Psi1 and Not1 and purifying the large (about 11 kb) fragment encoding the plasmid and retroviral backbone.

A. Humanized Codon Optimized CD Gene (CDopt, Aka CD1, T5.0001).

A comparison of a human codon optimized cytosine deaminase of Conrad et al. and PCT WO 99/60008 indicates (SEQ ID NO: 43)
AACACGA TTATAA ATGGTGACAGGGGGAATGGCAAGCAAGTGGGATCAGAAGGGTATGGACATTGCCT

ATGAGGAGGCGGCCTTAGGTTACAAAGAGGGTGGTGTTCCTATTGGCGGATGTCTTATCAATAACAAA

GACGGAAGTGTTCTCGGTCGTGGTCACAACATGAGATTTCAAAAGGGATCCGCCACACTACATGGTGA

GATCTCCACTTTGGAAAACTGTGGGAGATTAGAGGGCAAAGTGTACAAAGATACCACTTTGTATACGA

CGCTGTCTCCATGCGACATGTGTACAGGTGCCATCATCATGTATGGTATTCCACGCTGTGTTGTCGGT

GAGAACGTTAATTTCAAAAGTAAGGGCGAGAAATATTTACAAACTAGAGGTCACGAGGTTGTTGTTGT

TGACGATGAGAGGTGTAAAAAGATCATGAAACAATTTATCGATGAAAGACCTCAGGATTGGTTTGAAG

ATATTGGTGAGTAG GCGGCCGC GCCATAGATAAAATAAAAGATTTTATTTAGTCTCCAGAAAAAGGGG

GG

The following Table summarizes the genes and resulting plasmid vectors that were made and their names.

TABLE

Vector constructs and names

| Identity Code | Reference name | Original Name | 5'LTR Prom | Envelope | Vector | IRES | Transgene | 3'LTR |
|---|---|---|---|---|---|---|---|---|
| T5.0000 | pACE-yCD | pACE-CD (Tai et al. 2005) | CMV | Ampho (4070A) | pACE | EMCV | Wt yeast CD | MLV U3 |
| T5.0001 | pAC3-yCD1 | CDopt sequence | CMV | Ampho (4070A) | pAC3 | EMCV | modified CD | MLV U3 |
| T5.0002 | pAC3-yCD2 | CDopt + 3pt | CMV | Ampho (4070A) | pAC3 | EMCV | Modified CD | MLV U3 |
| T5.0003 | pAC3-yCD2-U | Cdopt + 3pt-UPRT | CMV | Ampho (4070A) | pAC3 | EMCV | CD2-UPRT | MLV U3 |
| T5.0004 | pAC3-yCD2-O | CDopt + 3pt-OPRT | CMV | Ampho (4070A) | pAC3 | EMCV | CD2-OPRT | MLV U3 |
| T5.0005 | pAC3-yCD2-LO | CDopt + 3pt-LINK-OPRT | CMV | Ampho (4070A) | pAC3 | EMCV | CD2-L-OPRT | MLV U3 |
| T5.0006 | pAC3-eGFP | pAC3-emd, pAC3GFP | CMV | Ampho (4070A) | pAC3 | EMCV | Emerald GFP | MLV U3 |
| T5.0007 | pAC3-yCD | pAC3-yCD | CMV | Ampho (4070A) | pAC3 | EMCV | Wt yeast CD | MLV U3 |

The replication competent retroviral vector described by Kasahara et al. pACE-CD (U.S. Pat. No. 6,899,871, the disclosure of which is incorporated herein) was used as a basis for additional modifications. A vector (pAC3-yCD) was modified to express a modified yeast cytosine deaminase gene as described herein and was used in the contructs. See FIG. 3A below for a diagram of the vector construct for the initial transfected replication-competent retrovirus. CMV is the human CMV immediate early promoter, U3, R and U5 are the corresponding regions of the viral long terminal repeat (LTR). Gag, pol and env are the viral protein coding regions. FIGS. 3B and 3D shows the plasmid structure and a sequence of the disclosure.

91 total codons optimized in both, 36 codons identical, 47 codons had third base pair changes (all encode same amino acid) and 9 codons were different (however they encoded same amino acid). Of the 9 codons that differed:

AGC (Ser) to TCC (Ser)

CGT (Arg) to AGG (Arg)

CCA (Pro) to CCT (Pro)

All have equivalent GC content and encode the same amino acid. The native yeast gene sequence above was separately codon optimized to give the following CD gene (CD1) and was called T5.0001 when inserted into the plasmid vector pAC3 which encodes the replication competent retrovirus (RCR) with IRES.

(SEQ ID NO: 44)
TTATAAATGGTGACCGGCGGCATGGCCTCCAAGTGGGATCAAAAGGGCATGGATATCGCTTACGAGGA

GGCCGCCCTGGGCTACAAGGAGGGCGGCGTGCCTATCGGCGGCTGTCTGATCAACAACAAGGACGGCA

GTGTGCTGGGCAGGGGCCACAACATGAGGTTCCAGAAGGGCTCCGCCACCCTGCACGGCGAGATCTCC

ACCCTGGAGAACTGTGGCAGGCTGGAGGGCAAGGTGTACAAGGACACCACCCTGTACACCACCCTGTC

CCCTTGTGACATGTGTACCGGCGCTATCATCATGTACGGCATCCCTAGGTGTGTGGTGGGCGAGAACG

TGAACTTCAAGTCCAAGGGCGAGAAGTACCTGCAAACCAGGGGCCACGAGGTGGTGGTTGTTGACGAT

GAGAGGTGTAAGAAGATCATGAAGCAGTTCATCGACGAGAGGCCTCAGGACTGGTTCGAGGATATCGG

CGAGTGATAAGCGGCCGCAGATAAAATAAAAGATTTTATTTAGTCTCCAGAAAAAGGGGGG.

B. Heat Stabilized CD Gene.

Additional modifications were made to enhance the stability of the cytosine deaminase. Genetic enhancements to the wild type yeast cytosine deaminase gene were made to include three positional mutations which change three amino acids (A23L, I140L and V108I) to increase thermal stability of the yeast cytosine deaminase protein.

The following primer pairs were used in the generation of the gene for the cytosine deaminase polypeptide of the disclosure:

Site directed mutagenesis primers: Primers sense: 5'-tcgag-gatatcggcgagtgaaacccgttattcttttggc-3' (SEQ ID NO:45)
Primers antisense: 5'-gccaaaaagaataacgggtttcactcgc-cgatatcctcga-3' (SEQ ID NO:46)
Primers sense:
5'tcggcgagtgatccggcggcggcgcctc-cggcggcggcgcctccggcggcggcgcctccggcggcg gcgccaac-ccgttatt-3' (SEQ ID NO:47)
Primers antisense:
5'-aataacgggttggcgccgccgccggag-gcgccgccgccggaggcgccgccgccggag gcgccgccgccggat-cactcgccga-3' (SEQ ID NO:48)

The three amino acid substitutions are: A23L, V108I, I140L. A sequence encoding these substitutions is shown below.

(SEQ ID NO: 3)
ATGGTGACAGGGGGAATGGCAAGCAAGTGGGATCAGAAGGGTATGGACA

TTGCCTATGAGGAGGCGTTATTAGGTTACAAAGAGGGTGGTGTTCCTAT

TGGCCGGATGTCTTATCAATAACAAAGACGGAAGTGTTCTCGGTCGTGGT

CACAACATGAGATTTCAAAAGGGATCCGCCACACTACATGGTGAGATCT

CCACTTTGGAAAACTGTGGGAGATTAGAGGGCAAAGTGTACAAAGATAC

CACTTTGTATACGACGCTGTCTCCATGCGACATGTGTACAGGTGCCATC

ATCATGTATGGTATTCCACGCTGTGTCATCGGTGAGAACGTTAATTTCA

AAAGTAAGGGCGAGAAATATTTACAAACTAGAGGTCACGAGGTTGTTGT

TGTTGACGATGAGAGGTGTAAAAAGTTAATGAAACAATTTATCGATGAA

AGACCTCAGGATTGGTTTGAAGATATTGGTGAGTAG

The encoded polypeptide comprises the following sequence (substituted amino acids in underlined):

(SEQ ID NO: 4)
1 MVTGGMASKWDQKGMDIAYEEA_L_LGYKEGGVPIGGCLINNKDGSVLGRGHNMRFQKGSAT

61 LHGEISTLENCGRLEGKVYKDTTLYTTLSPCDMCTGAIIMYGIPRCV_I_GENVNFKSKGEK

121 YLQTRGHEVVVVDDERCKK_L_MKQFIDERPQDWFEDIGE-

To increase the stability of the native yeast CD protein, three amino acid substitutions were engineered into the protein. These substitutions were alone or in combination with human codon optimization.

Final construct design that integrates 3 amino acid substitutions A23L/V108I/I140L utilizing preferred codons and uses preferred human codon usage for entire sequence (this gene is called CDopt+3pt [aka CD2] (SEQ ID NO:49):

1 ATGGTGACCGGCGGCATGGCCTCCAAGTGGGATCAAAAGGGCATGGATATCGCTTACGAG

61 GAGGCC_CTG_CTGGGCTACAAGGAGGGCGGCGTGCCTATCGGCGGCTGTCTGATCAACAAC

121 AAGGACGGCAGTGTGCTGGGCAGGGGCCACAACATGAGGTTCCAGAAGGGCTCCGCCACC

181 CTGCACGGCGAGATCTCCACCCTGGAGAACTGTGGCAGGCTGGAGGGCAAGGTGTACAAG

241 GACACCACCCTGTACACCACCCTGTCCCCTTGTGACATGTGTACCGGCGCTATCATCATG

301 TACGGCATCCCTAGGTGTGTG_ATC_GGCGAGAACGTGAACTTCAAGTCCAAGGGCGAGAAG

361 TACCTGCAAACCAGGGGCCACGAGGTGGTGGTTGTTGACGATGAGAGGTGTAAGAAG_CTG_

421 ATGAAGCAGTTCATCGACGAGAGGCCTCAGGACTGGTTCGAGGATATCGGCGAGTGATAA

T5.0002 refers to the above modified CD when inserted into the plasmid vector pAC3 which encodes the RCR with IRES. Underlined codons denotes preferred codons for amino acid substitutions.

Protein translation sequence alignment indicates preferred codon changes and amino acid substitutions result in desired protein structure:

CD-optimized sequence design (human codon preference+3 amino acid substitutions)

```
                                                                (SEQ ID NO: 50)
AACACGATTATAAATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA

GATCTCCACCCTGGAGAACTGTGGCAGGCTGGAGGGCAAGGTGTACAAGGACACCACCCTGTACACCA

CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGTAAGCGGCCGCGCCATAGATAAAATAAAAGATTTTATTTAGTCTCCAGAAAAAGGGG

GG
```

C. Construction of CD-UPRT Fusion Gene (CDopt+3Pt-UPRT, [Aka CDopt-UPRT and CD2-UPRT], T5.0003 in the pAC3 Plasmid RCR Vector).

Figure 10A:
FIG. 10A-D shows schemes for the generation of various embodiments of the disclosure comprising polypeptide with CD, OPRT and UPRT activity.
Figure 10A:
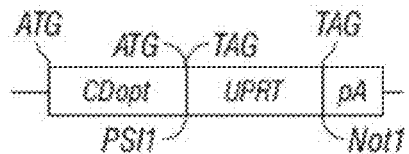
Figure 10A:
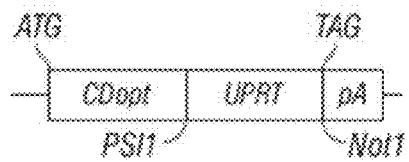

A fusion construct was also developed comprising a CD polypeptide as described above linked to a UPRT polypeptide to generate a CD-optimized-UPRT sequence using Scheme I as set forth in FIG. 10A. The following primers were used to delete the stop-start between the CD and UPRT.

Primer sequences:

| Primer Name | Primer Sequence (5' to 3') | (SEQ ID NO:) |
|---|---|---|
| del118-123 | 5'-tcgaggatatcggcgagtgaaacccgttattcttttttggc-3' | (51) |
| del118-123-antisense | 5'-gccaaaaagaataacgggtttcactcgccgatatcctcga-3' | (52) |

| Primer Name | Length (nt.) | Tm | Duplex Energy at 68° C. | Energy Cost of Mismatches |
|---|---|---|---|---|
| del118-123 | 40 | 79.06° C. | -44.37 kcal/mole | 21.1% |
| del118-123-antisense | 40 | 79.06° C. | -47.95 kcal/mole | 20.3% |

| Primer Name | Primer-Template Duplex |
|---|---|
| del118-123 (SEQ ID NOs: 51 and 53, respectively) | 5'-tcgaggatatcggcgagtga------aacccgttattcttttttggc-3'<br>\|\|\|\|\|\|\|\|\|\|\|\|\|\|\|\|\|\|\|\|  \|\|\|\|\|\|\|\|\|\|\|\|\|\|\|\|\|\|\|\|\|<br>ccaagctcctatagccgctcactatctacttgggcaataagaaaaaccgaag |
| del118-123-antisense SEQ ID NO: 54 and 52 respectively) | ggttcgaggatatcggcgagtgatagatgaacccgttattcttttttggcttc<br>\|\|\|\|\|\|\|\|\|\|\|\|\|\|\|\|\|\|\|\|  \|\|\|\|\|\|\|\|\|\|\|\|\|\|\|\|\|\|\|\|\|\|<br>3'-agctcctatcgccgctcact------ttgggcaataagaaaaaccg |

The resulting fusion polynucleotide comprises 1296 bp and the sequence set forth immediately below:

```
                                                                (SEQ ID NO: 55)
AACACGATTATAAATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA
```

-continued

```
GATCTCCACCCTGGAGAACTGTGGCAGGCTGGAGGGCAAGGTGTACAAGGACACCACCCTGTACACCA

CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGAACCCGTTATTCTTTTTGGCTTCTCCATTCTTGTACCTTACATATCTTATATATTAT

CCAAACAAAGGGTCTTTCGTTAGCAAACCTAGAAATCTGCAAAAAATGTCTTCGGAACCATTTAAGAA

CGTCTACTTGCTACCTCAAACAAACCAATTGCTGGGTTTGTACACCATCATCAGAAATAAGAATACAA

CTAGACCTGATTTCATTTTCTACTCCGATAGAATCATCAGATTGTTGGTTGAAGAAGGTTTGAACCAT

CTACCTGTGCAAAAGCAAATTGTGGAAACTGACACCAACGAAAACTTCGAAGGTGTCTCATTCATGGG

TAAAATCTGTGGTGTTTCCATTGTCAGAGCTGGTGAATCGATGGAGCAAGGATTAAGAGACTGTTGTA

GGTCTGTGCGTATCGGTAAAATTTTAATTCAAAGGGACGAGGAGACTGCTTTACCAAAGTTATTCTAC

GAAAAATTACCAGAGGATATATCTGAAAGGTATGTCTTCCTATTAGACCCAATGCTGGCCACCGGTGG

TAGTGCTATCATGGCTACAGAAGTCTTGATTAAGAGAGGTGTTAAGCCAGAGAGAATTTACTTCTTAA

ACCTAATCTGTAGTAAGGAAGGGATTGAAAAATACCATGCCGCCTTCCCAGAGGTCAGAATTGTTACT

GGTGCCCTCGACAGAGGTCTAGATGAAAACAAGTATCTAGTTCCAGGGTTGGGTGACTTTGGTGACAG

ATACTACTGTGTTTAA[GCGGCCGC]GCCATAGATAAAATAAAAGATTTTATTTAGTCTCCAGAAAAAGG

GGGG
```

D. Construction of CD-Linker UPRT Fusion Gene (CDopt+3Pt-LINK-UPRT [Aka CDopt-LINKER-UPRT and CD2-L-UPRT].

Figure 10B:
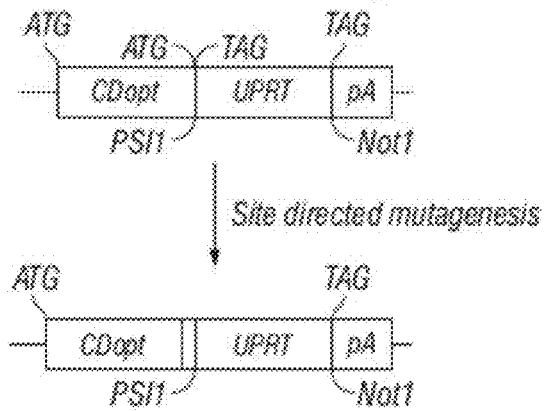

A fusion construct was also developed by cloning a linker (Ser-Gly-Gly-Gly-Gly)$_4$ (SEQ ID NO:56) domain between and in frame with the CD polypeptide and the UPRT polypeptide to generated a CD-optimized-linker-UPRT sequence using Scheme II as depicted in FIG. 10B. The following primers were used to insert the linker.

| Primer Name | Primer Sequence (5' to 3')(SEQ ID NO:) |
|---|---|
| ins_60nt_after_477 | 5'-tcggcgagtgatccggcggcggcgcctccggcggcggcgcctccggcg gcggcgcctccggcggcggcgccaacccgttatt-3' (57) |
| ins_60nt_after_477-antisense | 5'-aataacgggttggcgccgccgccggaggcgccgccgccggaggcgcc gccgccggaggcgccgccgccggatcactcgccga-3' (58) |

| Primer Name | Length (nt.) | Tm | Duplex Energy at 68° C. | Energy Cost of Mismatches |
|---|---|---|---|---|
| ins_60nt_after_477 | 82 | 79.77° C. | -30.19 kcal/mole | 83.3% |
| ins_60nt_after_477-antisense | 82 | 79.77° C. | -32.31 kcal/mole | 82.2% |

The resulting construct has size: 1356 bp and the sequence immediately below:

(SEQ ID NO: 59)
```
AACACGA[TTATAA]ATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA

GATCTCCACCCTGGAGAACTGTGGCAGGCTGGAGGGCAAGGTGTACAAGGACACCACCCTGTACACCA
```

```
CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGTCCGGCGGCGGCGCCTCCGGCGGCGGCGCCTCCGGCGGCGGCGCCTCCGGCGGCGGC

GCCAACCCGTTATTCTTTTTGGCTTCTCCATTCTTGTACCTTACATATCTTATATATTATCCAAACAA

AGGGTCTTTCGTTAGCAAACCTAGAAATCTGCAAAAAATGTCTTCGGAACCATTTAAGAACGTCTACT

TGCTACCTCAAACAAACCAATTGCTGGGTTTGTACACCATCATCAGAAATAAGAATACAACTAGACCT

GATTTCATTTTCTACTCCGATAGAATCATCAGATTGTTGGTTGAAGAAGGTTTGAACCATCTACCTGT

GCAAAAGCAAATTGTGGAAACTGACACCAACGAAAACTTCGAAGGTGTCTCATTCATGGGTAAAATCT

GTGGTGTTTCCATTGTCAGAGCTGGTGAATCGATGGAGCAAGGATTAAGAGACTGTTGTAGGTCTGTG

CGTATCGGTAAAATTTTAATTCAAAGGGACGAGGAGACTGCTTTACCAAAGTTATTCTACGAAAAATT

ACCAGAGGATATATCTGAAAGGTATGTCTTCCTATTAGACCCAATGCTGGCCACCGGTGGTAGTGCTA

TCATGGCTACAGAAGTCTTGATTAAGAGAGGTGTTAAGCCAGAGAGAATTTACTTCTTAAACCTAATC

TGTAGTAAGGAAGGGATTGAAAAATACCATGCCGCCTTCCCAGAGGTCAGAATTGTTACTGGTGCCCT

CGACAGAGGTCTAGATGAAAACAAGTATCTAGTTCCAGGGTTGGGTGACTTTGGTGACAGATACTACT

GTGTTTAA[SCGGCCGG]GCCATAGATAAAATAAAAGATTTTATTTAGT

CTCCAGAAAAAGGGGGG
```

E. Construction of CD-OPRT Fusion Gene (CDopt+3Pt-OPRT [Aka CDopt-OPRT and CD2-OPRT], T5.0004 when Inserted into the pAC3 Plasmid RCR Vector).

Figure 10C:
Figure 10C:
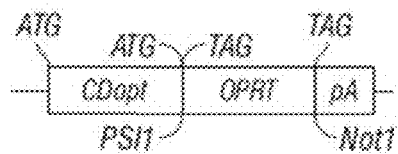
Figure 10C:
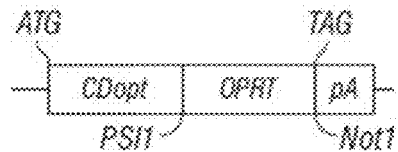

A fusion construct was also developed comprising a CD polypeptide as described above linked to an OPRT polypeptide to generated a CD-optimized-OPRTase (CD humanized+ 3ptmutation+OPRTase functional domain human) using Scheme III as shown in FIG. 10C.

The resulting construct comprises a size of 1269 bp and the sequence immediately below:

```
                                                               (SEQ ID NO: 60)
AACACGA[TTATAA]ATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA

GATCTCCACCCTGGAGAACTGTGGCAGGCTGGAGGGCAAGGTGTACAAGGACACCACCCTGTACACCA

CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGGCGGTCGCTCGTGcagctttggggccattggtgacgggtctgtacgacgtgcaggct ttcaagtttggggacttcgtgctgaagagcgggctttcctcccccatctacatcgatctgcggggcat cgtgtctcgaccgcgtcttctgagtcaggttgcagatattttattccaaactgcccaaaatgcaggca tcagttttgacaccgtgtgtggagtgccttatacagctttgccattggctacagttatctgttcaacc aatcaaattccaatgcttattagaaggaaagaaacaaaggattatggaactaagcgtcttgtagaagg aactattaatccaggagaaacctgtttaatcattgaagatgttgtcaccagtggatctagtgttttgg aaactgttgaggttcttcagaaggagggcttgaaggtcactgatgccatagtgctgttggacagagag cagggaggcaaggacaagttgcaggcgcacgggatccgcctccactcagtgtgtacattgtccaaaat gctggagattctcgagcagcagaaaaaagttgatgctgagacagttgggagagtgaagaggtttattc
```

```
aggagaatgtctttgtggcagcgaatcataatggttctcccctttctataaaggaagcacccaaagaa ctcaGCTTCGGTGCACGTGCAGAGCTGCCCAGGATCCACCCAGTTGCATCGAAGTAAGCGGCCGCGCC

ATAGATAAAATAAAAGATTTTATTTAGTCTCCAGAAAAAGGGGGG
```

F. Construction of CD-Linker-OPRT Fusion Gene (CDopt+3Pt-LINK-OPRT, [Aka CDopt-LINKER-OPRT and CD2-L-OPRT], T5.0005 in the pAC3 Plasmid RCR Vector).

Figure 10D:
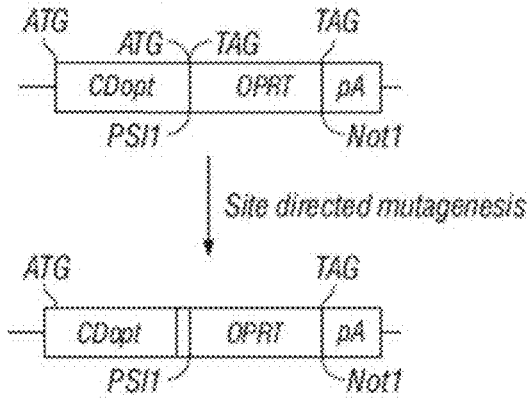

A fusion construct was also developed by cloning a linker (Ser-Gly-Gly-Gly-Gly)$_4$ (SEQ ID NO:56) domain between and in frame with the CD polypeptide and the OPRT polypeptide to generated a CD-optimized-linker-OPRT sequence using Scheme IV as shown in FIG. 10D.

The resulting construct comprises a size of 1329 bp and the sequence immediately below:

generated other methods of production can be implemented by those skilled in the art. Vector particles were generated by transient transfection of 293T cells (Pear et al. Proc Natl Acad Sci USA. 90:8392-8396 1993).

The 293T cells were thawed and put into culture, then passaged twice in T-75 flasks containing 15 mL of the DMEM medium that was prepared by mixing DMEM High Glucose medium (Hyclone#30081, 500 mL) with FBS (Hyclone#SH30070, 50 mL), L-Glutamine (Cellgro#25-005-CI, 5 mL), NEAA (Hyclone #SH30238, 5 mL), and Penicil-

```
                                                           (SEQ ID NO: 61)
AACACGATTATAAATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA

GATCTCCACCCTGGAGAACTGTGGCAGGCTGGAGGGCAAGGTGTACAAGGACACCACCCTGTACACCA

CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGTCCGGCGGCGGCGCCTCCGGCGGCGGCGCCTCCGGCGGCGGCGCCTCCGGCGGCGGC

GCCGCGGTCGCTCGTGcagctttggggccattggtgacgggtctgtacgacgtgcaggctttcaagtt tggggacttcgtgctgaagagcgggctttcctccccatctacatcgatctgcggggcatcgtgtctc gaccgcgtcttctgagtcaggttgcagatattttattccaaactgcccaaaatgcaggcatcagtttt gacaccgtgtgtggagtgccttatacagctttgccattggctacagttatctgttcaaccaatcaaat tccaatgcttattagaaggaaagaaacaaaggattatggaactaagcgtcttgtagaaggaactatta atccaggagaaacctgtttaatcattgaagatgttgtcaccagtggatctagtgttttggaaactgtt gaggttcttcagaaggagggcttgaaggtcactgatgccatagtgctgttggacagagagcagggagg caaggacaagttgcaggcgcacgggatccgcctccactcagtgtgtacattgtccaaaatgctggaga ttctcgagcagcagaaaaagttgatgctgagacagttgggagagtgaagaggtttattcaggagaat gtctttgtggcagcgaatcataatggttctcccctttctataaaggaagcacccaaagaactcaGCTT

CGGTGCACGTGCAGAGCTGCCCAGGATCCACCCAGTTGCATCGAAGTAAGCGGCCGCGCCATAGATAA

AATAAAAGATTTTATTTAGTCTCCAGAAAAAGGGGGG
```

FIG. 4 demonstrates that higher levels of the human codon optimized with the three mutations for higher stability are observed compared to wild type yCD protein in infected U-87 cells.

Example 3

Vector Production by Transient Transfection

Vector can be produced in a number of ways, but the first step is to introduce the DNA vector into cells to allow production of infectious particles, that can then be harvested from the cell supernatant. Once infectious particles have been lin-strep (Cellgro#30-002-CI, 5 mL). The flasks were incubated at 37° C. and 5% $CO_2$. After the $3^{rd}$ passage cells were seeded in 6 T-25's, each containing 5 mL of the medium, at a cell density of $1.8 \times 10^6$ cells/T-25 (or $7.2 \times 10^4$ cells/cm$^2$). One day after seeding the T-25's, the cells were transfected with the T5.0002 plasmid that expressed the viral vector using the Calcium Phosphate Transfection Kit from Promega (Cat#E1200). Eighteen hours following transfection, the media in one set of the flasks (3 flasks each set) were replaced with fresh medium containing 10 mM NaB. The media in the $2^{nd}$ set of the flasks were not replaced, which served as a control (zero NaB). Eight hours post NaB treatment the media in all flasks were replaced with the fresh medium containing no NaB. The expression was allowed to continue for both sets of flasks until the next day (22 hours duration). The supernatants from both sets of flasks were harvested and assayed for their titers by qPCR expressed in Transducing Units (TU)/ml (see Example 4).

The titer results are shown in the following table.

| Condition | First titer | Second titer (after storing at −80° C. for 68 days) |
|---|---|---|
| Without NaB | 1.5 (±0.05) × $10^6$ TU/mL | 1.2 (±0.2) × $10^6$ TU/mL |
| 10 mM NaB | 1.4 (±0.3) × $10^6$ TU/mL | 7.0 (±0.14) × $10^5$ TU/mL |

TU = transduction unit

Subsequent vector preparations were produced in this manner, without sodium butyrate. Other vector plasmids (Table 2) have been used in the same way to generate vector preparations with titers between 1E5 TU/ml and 1E7 TU/ml. Such material can be further purified and concentrated, if desired, as described below see also: U.S. Pat. No. 5,792,643; T. Rodrigues et al. J Gene Med 9:233 2007.

In certain embodiments of the disclosure the dosing was calculated by grams of brain weight. In such embodiments, the dosing of a replication competent retroviral vector of the disclosure useful in the methods for treatment can range from $10^4$ to $10^6$ TU per gram brain weight.

Example 4

Quantitative PCR Tittering Assay

The functional vector concentration, or titer, is determined using a quantitative PCR-based (qPCR) method. In this method, vector is titered by infecting a transducible host cell line (e.g. PC-3 human prostatic carcinoma cells, ATCC Cat#CRL-1435) with a standard volume of vector and measuring the resulting amount of provirus present within the host cells after transduction. The cells and vector are incubated under standard culturing condition (37° C., 5% $CO_2$) for 24 hr to allow for complete infection prior to the addition of the anti-retroviral AZT to stop vector replication. Next, the cells are harvested from the culture dish and the genomic DNA (gDNA) is purified using an Invitrogen Purelink gDNA purification kit and eluted from the purification column with sterile RNase-/DNase-free water. The $A_{260}/A_{280}$ absorbance ratio is measured on a spectrophotometer to determine the concentration and relative purity of the sample. The gDNA concentrations are normalized with additional RNase-/DNase-free water to the lowest concentration of any given set of gDNA preparations such that the input DNA for the qPCR is constant for all samples analyzed. Genomic DNA purity is further assessed by electrophoresis of an aliquot of each sample on an ethidium bromide stained 0.8% agarose gel. If the sample passes an $A_{260}/A_{280}$ absorbance range of 1.8-2.0 and shows a single band of gDNA, then the sample is ready for qPCR analysis of provirus copy number of the vector. Using primers that interrogate the LTR region of the provirus (reverse-transcribed vector DNA and vector DNA that is integrated into the host gDNA), qPCR is performed to estimate the total number of transduction events that occurred when the known volume of vector was used to transduce the known number of cells. The number of transduction events per reaction is calculated from a standard curve that utilizes a target-carrying plasmid of known copy-number that is serial diluted from $10^7$ to 10 copies and measured under identical qPCR conditions as the samples. Knowing how many genomic equivalents were used for each qPCR reaction (from the concentration previously determined) and how many transduction events that occurred per reaction, we determine the total number of transduction events that occurred based on the total number of cells that were present at the time of transduction. This value is the titer of the vector after dilution into the medium containing the cells during the initial transduction. To calculate the corrected titer value, the dilution is corrected for by multiplying through by the volume of culture and the volume of titer divided by the volume of titer. These experiments are performed in replicate cultures and analyzed by qPCR using triplicate measurements for each condition to determine an average titer and with its associated standard deviation and coefficient of variance.

Example 5

Vector Testing

In order to be effective vector constructs and their derived infectious particles need to: (1) make good titer of virus by transient transfection (see Examples 3 and 4); (2) be stable upon multiple passages; (3) kill cells efficiently in the presence of 5-FC; and (4) express enzyme activity upon infection of target cells. Example 3 shows that useful titers can be obtained from the vectors.

Genetic Stability of Viral Vectors.

To demonstrate the stability the following experiment was performed. Approximately $10^6$ naive U-87 cells were initially infected with the viral vector at an MOI of 0.01, and grown until fully infected to complete a single cycle of infection. Supernatant is then repassed onto uninfected cells and the cycle repeated. In this experiment, twelve cycles have been completed in duplicate trials (FIG. 5 shows one of each of the duplicate trials; the other duplicates gave similar results). Genomic stability of the yCD2 or other transgene sequence is assessed by PCR amplification of the integrated provirus from the infected cells using MLV specific primers flanking the transgene insertion site. The appearance of any bands smaller than full-length amplicon would be an indicator of vector instability. FIG. 5 demonstrates that a vector of the disclosure (T5.0007—comprising the modified vector and CD heterologous polynucleotide) maintains stability for more passages than pACE-CD. Furthermore T5.0003 is somewhat less stable while T5.0004 and T5 appear about as stable as pACE-CD. pACE-CD has been used in mouse tumor studies and shows good anti-tumor effects in mouse models. However a more stable viral genome will be much more potent and long lasting in treatment of animals and humans, especially if multiple cycles of 5-FC treatment are required. Both T5.0001 and T5.0002 are markedly more stable than even T5.0007, showing that silent changes in a protein coding sequence or small changes that result in point mutations can lead to unexpectedly superior properties with more stable vector genomes.

Cell Killing Experiments.

The Cell Titer 96 Aqueous One Solution Cell Proliferation Assay (MTS) is a colorimetric method for determining the number of viable cells in proliferation assays. We have utilized this assay to determine cell growth kinetics, as well as to determine the dose response of various cell lines to 5-Fluorocytosine (5-FC) and 5-Fluorouracil (5-FU).

Cells 100% infected with vector were seeded at 1000 cells/well in 96-well plates. They were monitored over an eight day period following treatment with various concentrations of 5-FC (5-FU for controls). An analysis of their cell growth was assessed every two days utilizing Promega's Cell Titer 96

AQueous One Solution reagent (MTS). Briefly, 20 μl of MTS was mixed with 100 μl media (as recommended by the manufacturer) and added to the samples in the 96-well plate. The samples were incubated for 60 minutes in a 37° C./5% $CO_2$ incubator. Thereafter, absorbance readings were taken on a plate reader at a 490 nm wavelength. The plates were then discarded.

Figure 6A:
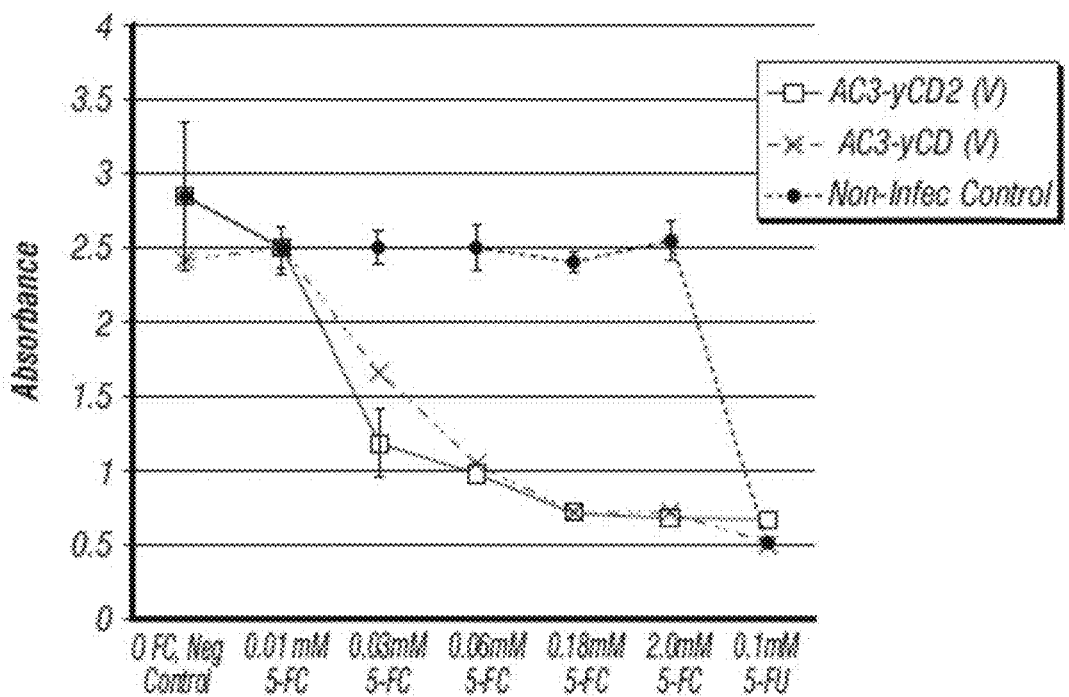
FIG. 6 shows (A) cell killing assays; and (B) cytosine deaminase specific activity of cells infected with different vectors. (A) shows that cytosine deaminase and vector of the disclosure kill infected cells at least as well and perhaps better than the original pACE-CD when U87 infected cells are exposed to increasing levels of 5-FC. (B) Shows that the specific CD activity of the disclosure (T5.0007, T5.0001 and T5.0002) are all increased compared to pACE-CD (T5.0000), and is in the order T5.0000<T5.0007<T5.0001<T5.0002.

FIG. 6A shows the results of an experiment that demonstrates that the cytosine deaminase in cells expressing the yCD2 protein is at least as active as that from cells expressing the wild type yCD protein, by performing 5-FC titrations on U-87 cells infected either with AC3-yCD2 (vector) or AC3-yCD (vector). Briefly, U-87 cells 5 days post infection at a multiplicity of infection of 0.1 (i.e. 100% infected) with either AC3-yCD (wild type CD) vector or AC3-yCD2 (thermostabilized & codon optimized) vector were subject to increasing amounts of 5-FC or 0.1 mM of 5-FU as a positive control for 8 days. On day 8, cell cultures were assessed for viability using an MTS assay (Promega Cell Titer 96 AQUEOUS One Solution Proliferation Assay). Data shows comparable killing between the two retroviral vectors at increasing doses of 5-FC treatment.

In similar in-vitro cell culture experiments with RG2 cells (ATCC Cat#CRL-2433), the RG2 cell line was transduced with 5 different vectors (pACE-CD, T5.0001, T5.0002, T5.0004, and T5.0007). It was subsequently subject to increasing concentrations of 5-FC (5-FU for controls) for 8 days and monitored as described above. The results are shown in FIG. 2. Concentrations of 0.01 mM were sufficient to induce complete killing throughout all vectors tested with the exception of wild type-yeast Cytosine Deaminase (pACE-yCD). It was less sensitive and required 1.0 mM of 5-FC for complete killing.

CD Expression Assay.

Figure 6B:
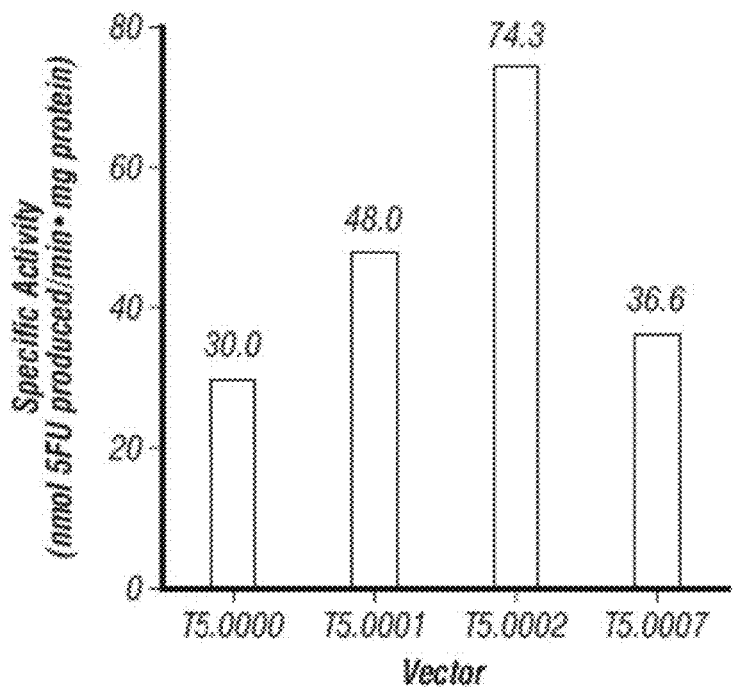
Figure 7:
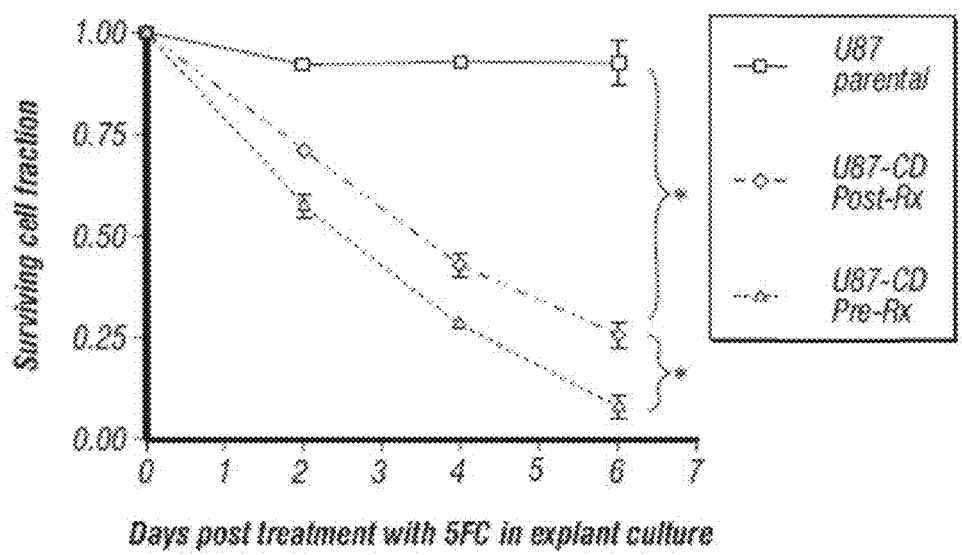
FIG. 7 shows U-87 tumors treated with CD vector of the disclosure in vivo and explanted from mice treated with 4 cycles of 5-FC are still sensitive to the drug.

U87 cells were transduced at a multiplicity of infection (MOI) of 0.1, cultivated for 5 days to allow viral spread and cells from day 5 post transduction were harvested. The cells were then collected by centrifugation at 800×g for 5 min. The supernatant was aspirated away from the cell pellet and washed with 5 mL of phosphate buffered saline (PBS) and again centrifuged at 800×g for 5 min. The resulting cell pellet was taken up in 1.5 mL of PBS, resuspended by passage through a pipette tip and placed in a freezer at −20 C. Cells were lysed by a freeze/thaw method. Previously resuspended cells were allowed to thaw at room temperature, passed through a pipette tip, mixed with protease inhibitor cocktail and again refrozen at −20 C. Previous to the enzyme assay, the sample was again thawed at room temperature and passed through a pipette tip. The suspension was then centrifuged at 14,000 rpm in a tabletop centrifuge for 5 min. The supernatant was decanted away from the pellet and placed in a fresh eppendorf tube and placed on ice.

yCD enzyme activity was assessed by using an HPLC assay. The HPLC assay was performed on a Shimadzu LC20AT unit connected in series with a photoarray detector and autoinjector. The solid phase was a Hypersil BDS $C_{18}$ HPLC column with a 5 um sphere size and 4.0×250 mm column dimensions. The mobile phase was 50 mM ammonium phosphate, pH 2.1, containing 0.01% tert-butylammonium perchlorate and 5% methanol; the system was equilibrated at 22 C. All reagents were ACS grade and solvents were HPLC grade. A reaction mix was made consisting of 800 μL with a final concentration of 0.125 mg/mL 5FC (1 mM) in PBS and placed in a 1.5 mL autosampler vial. The reaction was then initiated by adding 200 uL of each cell lysate. The reaction/autosampler vials were placed in the auto sampler and 5 uL of the reaction mixture was injected. Time points were taken periodically by retrieving a 5 uL aliquot from each reaction vial and analyzing on the HPLC column. The conversion rates of 5FC to 5FU were calculated by comparing the peak areas with known amounts from a previously generated standard curve of 5FU. The rate of 5FC conversion to 5FU was derived by plotting the amount of 5FU (in nmol) generated against its corresponding time interval. Protein concentration for the cell sample was derived and the Specific Activity of the cell lysate samples were calculated by dividing the conversion rate (nmol/min) by the amount of protein used in the assay in mg. FIG. 6B shows the specific activity of various vectors after 5 days on transduction at an MOI of 0.1. The data demonstrate that pACE-yCD (T5.0000)<pAC3-yCD1(T5.0001)<pAC3-CD2 (T5.0002) in terms of the specific activity of cytosine deaminase in tissue culture cells.

Example 6

Vector Purification and Concentration

A vector of the disclosure is manufactured by transient transfection on 293T cells (Example 3), followed by harvesting of the cell supernatant, filtration, benzonase treatment, diafiltration/concentration and dialysis. A further chromatography column step may be included, known to those skilled in the art (see for example U.S. Pat. No. 5,792,643; T. Rodriguez et al. J Gene Med 9:233 2007; WO 2010/148203). Clinical material is released based on standard testing such as sterility, mycoplasma and endotoxins, plus product specific potency, strength, and identity testing. Titer is determined as Transducing Units (TU) by PCR quantitation of integrated viral vector DNA in target cells (Example 4). The final product is targeted to have a titer of up to $10^9$ TU/ml formulated in isotonic Tris-buffered sucrose solution, as a sterile injectable.

In general, to accurately and precisely determine the strength of vector lots, a quantitative PCR-based titer assay has been developed (described in general terms in example 4). The details of the assay procedure consist of the following steps:

Transduction.

Transductions are performed in a 12-well plate format using the stable human prostate adenocarcinoma derived PC-3 cell line. For each test sample, three dilutions of un-titered vector preparation are used to transduce PC-3 cells in triplicate wells. Viral replication is stopped 24 hours post-transduction with azidothymidine (AZT). Cells are maintained for an additional 24-64 hours prior to harvesting and genomic DNA purification.

Genomic DNA Preparation.

Qiagen DNeasy DNA Minikits is used to prepare genomic DNA from transduced harvested cells as per the manufacturer's protocol. DNA concentrations and quality are assessed by direct absorbance measurement using UV/vis spectrophotometry to determine the A260 and A260/A280 ratio.

Real-Time Quantitative PCR.

The BioRad CFX96 real-time PCR instrument or equivalent is used for performing quantitative PCR. Provector copy numbers present in each test sample are measured by using specific DNA oligonucleotide primers in conjunction with a TaqMan probe designed to amplify the integrated, or pro-retroviral, U3/Psi packaging versus the CMV/Psi plasmid promoter. Vector titer is expressed relative to a copy number standard curve. To generate the vector copy number standard curve, genomic DNA from PC-3 cells is spiked with a unique plasmid containing the pro-retroviral U3/Psi sequence. Vector test sample titers are obtained by calculating the number of transduced genomes in multiple dilutions using multiple reactions per dilution.

For each titer assessment, a non-template control (wells containing all components except plasmid or genomic DNA) and a negative control (all components including equivalent genomic DNA from non-transduced PC-3 cells), is performed in triplicate. The titer values are expressed in transduction units per milliliter (TU/mL).

The potency of the vector of the disclosure is dependent on both the replication of the vector and the resultant cytosine deaminase (CD) activity in target cells. Therefore the potency assay measures the increase in CD activity over time as vector infection spreads in a previously uninfected cell line in tissue culture. The assay measures the enzymatic activity of the transferred yCD2 protein in transduced cells during early, middle and late stages of infection by monitoring the conversion of 5-fluorocytosine (5-FC) to 5-fluorouracil (5-FU), using reverse phase HPLC separation with UV detection. The increase of CD activity over the course of the infection is a function of the percent of cells infected over time and indicative of the TOCA 511 vector's ability to replicate. CD activity based on the 5-FC to 5-FU conversion rate is measured for each time point in CD units per mg of protein (the specific activity, SA). The increase in SA is then plotted over time, and reflects both the increase in the percentage of cells transduced as a result of viral replication in the culture, and the resultant transfer of CD activity. Accumulated data from multiple assays and vector lots has been used to determine an appropriate specification for this increase in SA of CD, for product release. The assay has 1, 3 and 5 day time points after an initial infection at an MOI of about 0.1 and a non-infected control.

CD activity from late stage infected cells (day 5 time point) was compared between lots to evaluate the use of this activity as an Identity test. The assay includes the following steps:

Transductions.

Transductions are performed in multi-well plate format on U87 cells. For each transduction, three suitable dilutions are used and each performed in triplicate. Cells are harvested at 0, 1, 3 and 5 days post transduction.

Set-Up of CD Reaction.

Cells are lysed and the total protein concentration determined using the BCA protein assay using BSA as a standard. For the yCD2 enzyme assay, an appropriate amount of cell lysate is added to buffer containing 5-FC such that the rate of 5-FU formation remains linear over 1-2 hours at 37° C. The final volume for the reaction mixture is 100 μL. After 2 h, the enzyme reaction is terminated by the addition of trichloroacetic acid, briefly vortexed and prepared for subsequent HPLC analyses. Cell lysates from non-transduced cells are used as a negative control while a similar assay using samples from 100% infected cells is used as a positive control.

HPLC Analysis.

The terminated reaction mixture is centrifuged at 12,000 rpm for 5 minutes at room temperature in a micro-centrifuge. The supernatant is then decanted away from the pellet and passed through a 0.2μ filter to further remove particulates before injection onto a reverse phase HPLC column previously equilibrated with an aqueous based mobile phase containing phosphate buffer at a pH around 4.0. The chromatograms is followed at 260 nm and 280 nm to monitor both substrate consumption and product formation. Concentrations of either substrate or product are determined using the graphing and analysis capabilities of GraphPad by comparing them to previously generated standard curves calculated from known substrate or product concentrations. Amounts of 5-FU generated over 1-2 h are used to determine CD units of activity (1 unit of CD activity is defined as the formation 1 nmol of 5-FU per min) and the Specific Activity is calculated dividing this number by the amount of protein (from the cell lysate) used in the assay.

Example 7

Construction and Use of a Vector Encoding a Single Chain Antibody to CTLA-4 (CD 152)

Single chain antibodies are derived from known full antibody sequences that have a desired effect. Such sequences are available (e.g. WO2006048749, US2006165706, U.S. Pat. No. 7,034,121, Genbank Accession Numbers DJ437648, CS441506, CS441500, CS441494, CS441488, the disclosures of which are incorporated herein by reference). Such conventional antibody gene sequences are converted into single chain antibody (scFv) sequences by commonly used methods known to those skilled in the art (see for example Gilliland et al. "Rapid and reliable cloning of antibody variable regions and generation of recombinant single chain antibody fragments." Tissue Antigens 47, 1-20, 1996). Phage single chain antibodies to CTLA-4 are also available from screening phage-scFv libraries directly (Pistillo et al. Tissue Antigens 55:229 2000), and can be used directly for insertion into the replicating retroviral vectors of the disclosure. Regardless of how the sequence is derived scFv are typically about 700-900 bp in length and are synthesized by a commercial vendor (BioBasic) with a Psi1 site at the 5' end and compatible Not1 site at the 3' end, as described previously. This sequence is then inserted into the replicating retroviral back bone from pAC3-yCD2 at the Psi1-Not1 sites after removal of the yCD2 sequence. Vector is produced and titered as described, and further purified if necessary as described above. Human and Mouse CTLA4 are very homologous in sequence and the replicating retrovirus of the disclosure is first tested in a suitable syngeneic immunocompetent mouse models such as the CT26/Balb/c model and s91 mouse melanoma models, well known to those skilled in the art (see for example Hodge et al J. Immunol. 174:5994 2005). Outcome is measured by one or more of: modulation of tumor growth; lack of toxicity; generation of antitumor responses; shrinkage of remote lesions indicating systemic immunity. Doses are in the range of $10^3$ to $10^7$ TU in mice. In patients the vector is administered by intralesional injection into tumor, or by administration into the circulation that then carries the virus to the tumor. Doses are in the range of $10^5$ to $10^{11}$ TU.

Example 8

Anti-Melanoma Efficacy Studies with Anti CD152 Single Chain Antibody Expressing Vector in a Mouse Melanoma Model Objective.

The objective of this study is to assess the effect of a novel MLV based replication-competent retroviral vector carrying single chain antibody directed against Cytotoxic T-Lymphocyte Antigen 4 (CTLA-4) also referred to as Cluster of differentiation 152 (CD152) sequence (pAC3-αCD152) on melanoma growth, when delivered via intratumoral (IT) injection in DBA/2 mice bearing subcutaneous melanoma (Cloudman S91).

Mice.

Female DBA/2 or BALB/c mice (age ~8 weeks) are purchased from Jackson Laboratories (Bar Harbor, Me.). Mice are acclimated for 7 days after arrival before start of studies.

Cells.

Cloudman S91 cells (ATCC, Manassas Va.) are a spontaneously arising melanoma derived from DBA/2 mice. Cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. S91 cells (1E6 in 100 µL) are injected into the right flank of DBA/2 mice.

Vector.

Vectors preparations are made by transient transfection (or from a producer cell line in HT1080 cells) with titers of approximately 7E6TU/ml. For initial studies vector is not further purified or concentrated. For follow on experiments to determine full dose response curves, high titer purified material is prepared with a titer expected around $10^8$/ml. Vector is administered IT in a volume of 50-100 µL and IV in 100 µL the total dose/mouse of approximately 7E5 TU/mouse. Vector expressing αCD152 is identified as Toca αCD152.

Tumor Implantation and Vector Injection.

Five groups of female DBA/2 (55 mice, 9-10 weeks of age) are implanted subcutaneously with S91 melanoma cells (Day 0) and then dosed (day 4-7 depending on growth rate of the S91 tumor; approximately 50-100 mm$^3$) with vehicle (Groups 1), with control vector [AC3-GFP(V), (Group2), intratumor (IT) Toca αCD152 vector injection (Groups 3), or intravenous Toca αCD152 vector injection (Groups 4). Group 5 mice have no tumor implanted and are intravenously injected with Toca αCD152 only.

Data Analysis.

Tumor growth analysis is carried out to 2000 mm$^3$ or to 60 days based on whichever comes first. 10 mice from each group will be plotted for tumor size over time. Statistical significance will be determined using analysis of variance (ANOVA). P values of <0.05 are considered statistically significant in all analyses, which are performed with Prism 5 statistical software (GraphPad Software) or equivalent. In-life observations are also taken to assess any adverse events to αCD152 expression during treatment.

Results.

Delivery of αCD152 by replicating MLV IT shows a statistically significant retardation of growth compared to the controls. Delivery of αCD152 by replicating MLV intravenously shows a statistically significant retardation of growth compared to the controls abrogates melanoma burden from the DBA/2-Cloudman S91 mouse melanoma model. Further animal studies were performed as described more fully below.

Example 9

ACE-yCD2 Viral Vector is Therapeutic in an Intracranial Human Xenograft (U87) in Nude Mice An intracranial xenograft model using the U87 human glioma cell line was established to test RCR vector spread and biodistribution as well as therapeutic efficacy of RCR-vector mediated cytosine deaminase suicide gene therapy in a nude mouse host.

Following acclimation, mice were randomly assigned to one of 8 Treatment groups (see group description below). Seven groups underwent intracranial administration into the right striatum of 1×10$^5$ U87 cells administered/mouse on Day 0. Group 8 mice were not implanted with tumor. At Day 5, mice were injected with Formulation Buffer only, or an RCR vector at 9×10$^5$/5 ul, 9×10$^4$/5 ul, or 9×10$^3$/5 ul. Mice receiving no vector, or vector at 9×10$^5$/5 ul or 9×10$^3$/5 ul were randomized to receive 5-FC (500 mg/kg/day), administered as a single IP injection, beginning on Day 19, or no 5-FC. Mice receiving vector at mid dose all received 5-FC (i.e., No separate control group for this dose). 5-FC administration continued daily for 7 consecutive days followed by 15 days of no treatment. Cycles of drug plus rest were repeated up to 4 cycles. 10 mice from each group except group 8 were randomly assigned to the survival analysis category. The remaining mice were sacrificed according to a predetermined schedule.

| | | | | | N per Analysis Category | |
|---|---|---|---|---|---|---|
| Group | Test article | Volume | Drug TX | N | (A) Survival analysis | (B) Scheduled Sacrifice |
| 1 | Form buffer | 5 ul | none | 4 | | 4 before first drug cycle |
| 2 | Form buffer | 5 ul | 5FC | 10 | 10 | |
| 3 | T5.0002 | 9e5/5ul | PBS | 10 | 10 | |
| 4 | T5.0002 | 9e5/5ul | 5FC | 25 | 10 | 3 before start of each cycle, 15 total |
| 5 | T5.0002 | 9e4/5ul | 5FC | 10 | 10 | |
| 6 | T5.0002 | 9e3/5ul | 5FC | 25 | 10 | 3 before start of each cycle, 15 total |
| 7 | T5.0002 | 9e3/5ul | PBS | 10 | 10 | |
| 8 NO TUMOR | none | | 5FC | 15 | | 3 before start of each cycle, 15 total |
| Total Number of Animals | | | | 109 | 60 | 49 |

Intravenous dosing was done via injection into the tail vein. Intraperitoneal dosing was done via injection into the abdomen with care taken to avoid the bladder. For intracranial injection mice were anesthetized with isoflurane and positioned in a stereotaxic device with blunt ear bars. The skin was shaved and betadine was used to treat the scalp to prepare the surgical site. The animal was placed on a heating pad and a scalpel used under sterile conditions to make a midline incision through the skin. Retraction of the skin and reflection of the fascia at the incision site will allow for visualization of the skull. A guide cannula with a 3 mm projection, fitted with a cap with a 3.5 mm projection, will be inserted through a small burr hole in the skull and attached with dental cement and three small screws to the skull. After hardening of the cement, the skin will be closed with sutures. The projected stereotaxic coordinates are AP=0.5-1.0 mm, ML=1.8-2.0 mm, DV=3.0 mm. Exact stereotaxic coordinates for the cohort of animals received will be determined in a pilot experiment (2-3 animals) by injecting dye and determining its location. The animals will be monitored during anesthesia recovery. Analgesics, buprenorphine, will be administered subcutaneously (SC) before the end of the procedure then buprenorphine will be administered approximately every 12 hrs for up to 3 days. Animals will be monitored on a daily basis. Cells or vector were intracranially infused through an injection cannula with a 3.5 mm projection inserted through the guide cannula. The rate was controlled with a syringe pump fitted with a Hamilton syringe and flexible tubing. For cell injection, 1 microliter of cells was delivered at a flow rate of 0.2 microliters per minute (5 minutes total). For vector injection, 5 microliters of vector was delivered at a flow rate 0f 0.33 microliters per minute (15 minutes total).

Figure 8:
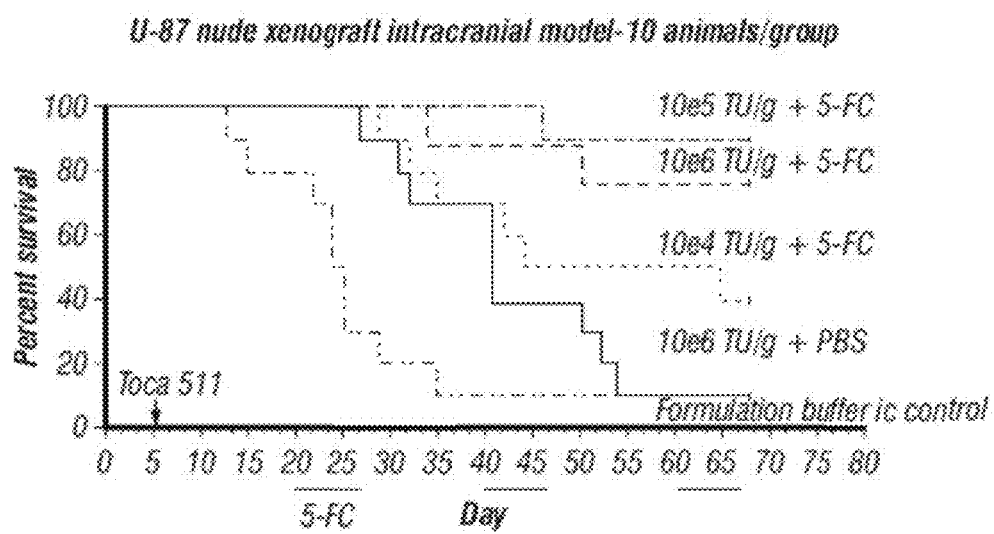
FIG. 8 shows dosing information and therapeutic effect in a Kaplan-Meyer survival analysis in a mouse model of brain cancer.

Vector was delivered and calculated as transforming units (TU) per gram of brain weight to the mice. Using such calculation the translation of dose can be calculated for other mammals including humans. FIG. 8 shows the effect on vector dose in this mouse model.

Example 10

AC3-yCD2(V) is Therapeutic in a Syngeneic Mouse Model of Brain Cancer

Additional experiments to demonstrate the methods and compositions of the disclosure in a syngeneic animal model were performed.

An intracranial implant model using the CT26 colorectal cancer cell line in syngeneic BALB/c mice was established to test RCR vector spread and biodistribution as well as therapeutic efficacy of RCR-vector mediated cytosine deaminase suicide gene therapy and its immunological impact.

This study included 129 animals, 0 Male, 119 Female and 10 contingency animals (10 Female). Following acclimation, mice were randomly assigned to one of 8 Treatment groups (see group description below). Seven groups underwent intracranial administration into the right striatum of $1\times10^4$ CT26 cells administered/mouse on Day 0. Group 8 mice were not implanted with tumor. At Day 4, mice were injected with Formulation Buffer only, or vector at $9\times10^5/5$ ul, $9\times10^4/5$ ul, or $9\times10^3/5$ ul. Mice receiving no vector, or vector at $9\times10^5/5$ ul or $9\times10^3/5$ ul were randomized to receive 5-FC (500 mg/kg/BID), administered by IP injection, beginning on Day 13, or no 5-FC. Mice receiving vector at mid dose received 5-FC (i.e. No separate control group for this dose). 5-FC administration continued daily for 7 consecutive days followed by 10 days of no treatment. Cycles of drug plus rest were repeated up to 4 cycles. 10 mice from each group except group 8 were randomly assigned to the survival analysis category. The remaining mice were sacrificed according to a predetermined schedule.

Naïve sentinel mice were co-housed with the scheduled sacrifice animals and taken down at the same time points to assess vector transmittal through shedding.

| | | | | | N per Analysis Category | | |
|---|---|---|---|---|---|---|---|
| Group | Test article | Volume | Drug TX | N | (A) Surivival analysis | (B) Scheduled Sacrifice | (C) Sentinels |
| 1 | Form buffer | 5 ul | PBS | 4 | | 4 before first drug cycle | |
| 2 | Form buffer | 5 ul | 5FC | 10 | 10 | | |
| 3 | T5.0002 | 9e5/5ul | PBS | 10 | 10 | | |
| 4 | T5.0002 | 9e5/5ul | 5FC | 25 | 10 | 3 before start of each cycle, 15 total | 1 before start of each cycle, 5 total |
| 5 | T5.0002 | 9e4/5ul | 5FC | 10 | 10 | | |
| 6 | T5.0002 | 9e3/5ul | 5FC | 25 | 10 | 3 before start of each cycle, 15 total | 1 before start of each cycle, 5 total |
| 7 | T5.0002 | 9e3/5ul | PBS | 10 | 10 | | |
| 8 NO TUMOR | none | | 5FC | 15 | | 3 before start of each cycle, 15 total | |
| Total Number of Animals | | | | 119 | 60 | 49 | 10 |

Intravenous dosing was done via injection into the tail vein. Intraperitoneal dosing was done via injection into the abdomen with care taken to avoid the bladder. For intracranial administration, mice with a guide cannula with a 3.2 mm projection implanted into the right striatum, and fitted with a cap with a 3.7 mm projection were used. The projected stereotaxic coordinates are AP=0.5-1.0 mm, ML=1.8-2.0 mm, DV=3.2 mm (from bregma). Cells or vector were intracranially infused through an injection cannula with a 3.7 mm projection inserted through the guide cannula. The rate was controlled with a syringe pump fitted with a Hamilton syringe and flexible tubing.

For cell injection, 1 microliter of cells was delivered at a flow rate of 0.2 microliter per minute (5 minutes total). For vector injection, 5 microliter of vector was delivered at a flow rate of 0.33 microliter per minute (15 minutes total).

Figure 9:
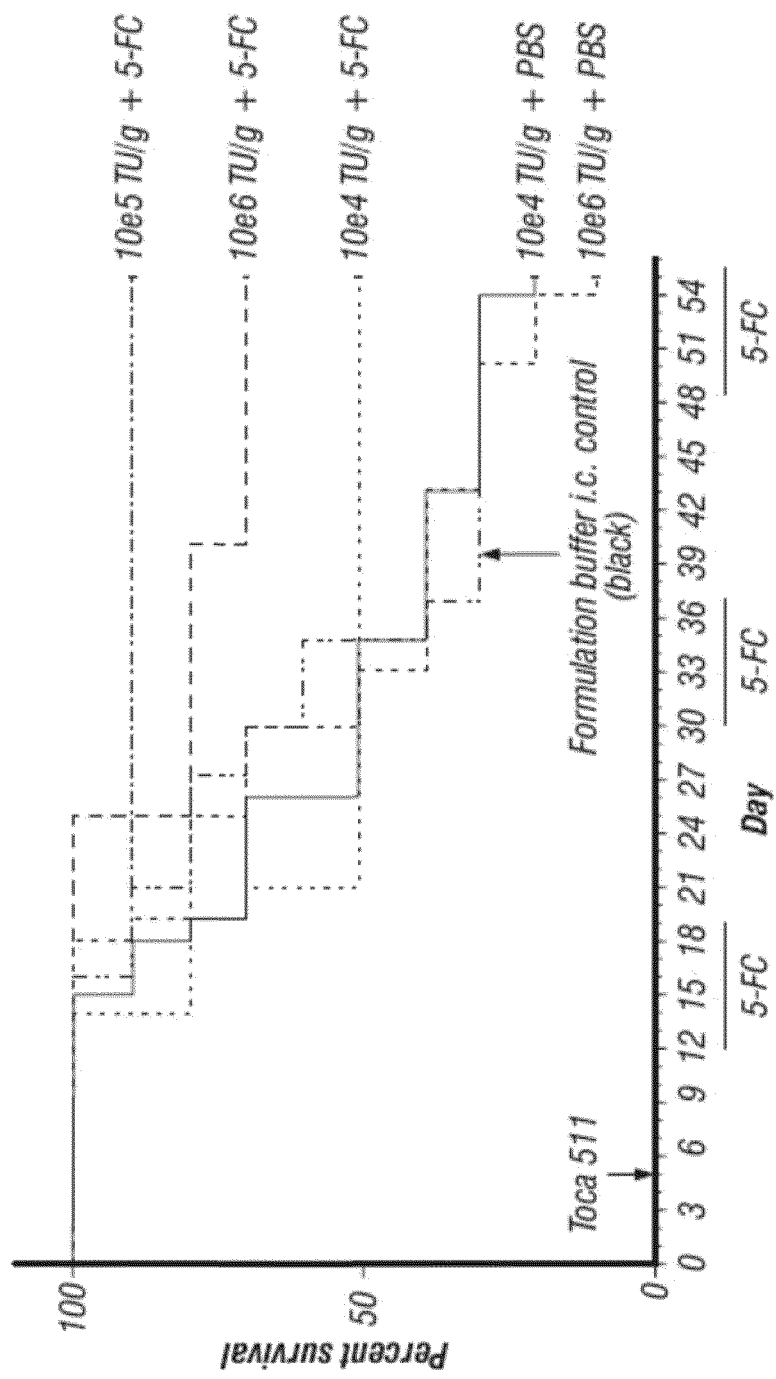
FIG. 9 shows dosing information and therapeutic effect in a Kaplan-Meyer survival analysis in a syngeneic mouse model.

Vector was delivered and calculated as transforming units (TU) per gram of brain weight to the mice. Using such calculation the translation of dose can be calculated for other mammals including humans. FIG. 9 shows the effect on vector dose in this mouse model when the vector is delivered intracranially.

Example 11

Construction and Testing of RCR Vectors Expressing miR-128-1 and miR128-2

Construction of Recombinant Replication Competent Retroviral Vector Containing a Heterologous Polynucleotide Sequence of Human Pri-miRNA-128-1.

The replication competent retroviral vector, pAC3-miR-128-1 expressing miR-128-1 was derived from the backbone of pAC3-yCD2 described in one of the embodiment. The pAC3 backbone in the pAC3-miR-128-1 vector was isolated by endonuclease digestion of the pAC3-yCD2 plasmid DNA with Mlu I and Not I to remove the IRES-yCD2 polynucleotide sequence. The polynucleotide DNA sequence of pri-miR-128-1 was obtained from the product sheet of the pEP-mir-128-1 expression vector (Cell BioLabs Inc.) (SEQ ID NO: 31). DNA sequence of pri-miR-128-1 was synthesized with a Mlu I restriction enzyme site at the 5' end and a Not I restriction enzyme site at the 3'end of the double-stranded DNA fragment for subsequent insertion at the corresponding site in the Mlu I and Not I digested pAC3-yCD2 plasmid DNA described above. The resulting construct, pAC3-miR-128-1, encodes 3 genes: the gag, the pol, and the env, and the non-coding pri-miR-128-1 sequence (FIG. 11).

Vector stock was produced by transient transfection of the vector-encoding plasmid DNA into 293T cells using calcium phosphate method. Eighteen hours post transfection, the culture was replaced with fresh medium. Twenty-four hours post medium replacement, the supernatant containing the vector was collected and filtered through a 0.45 µm filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

Construction of Recombinant Replication Competent Retroviral Vector Containing a Heterologous Polynucleotide Sequence of Human Pri-miRNA-128-2.

The replication competent retroviral vector, pAC3-miR-128-2 expressing miR-128-2 was derived from the backbone of pAC3-yCD2 described in one of the embodiment. The pAC3 backbone in the pAC3-miR-128-1 vector was isolated by endonuclease digestion of the pAC3-yCD2 plasmid DNA with Mlu I and Not I to remove the IRES-yCD2 polynucleotide sequence. The polynucleotide DNA sequence of pri-miR-128-2 was obtained from the sequence analysis of the expression vector Lenti-miR-128-2 expressing the pri-miR128-2 (System Biosciences) (SEQ ID NO:32). DNA sequence of pri-miR128-2 was synthesized with a Mlu I restriction enzyme site at the 5' end and a Not I restriction enzyme site at the 3'end of the double-stranded DNA fragment for subsequent insertion at the corresponding site in the Mlu I and Not I digested pAC3-yCD2 plasmid DNA described above. The resulting construct, pAC3-miR-128-1, encodes 3 genes: the gag, the pol, and the env, and the non-coding pri-miR-128-2 sequence (FIG. 11).

Vector stock was produced by transient transfection of the vector-encoding plasmid DNA into 293T cells using calcium phosphate method. Eighteen hours post transfection, the culture was replaced with fresh medium. Twenty-four hours post medium replacement, the supernatant containing the vector was collected and filtered through a 0.45 m filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

Construction of Recombinant Replication Competent Retroviral Vector Containing Heterologous Polynucleotide Sequences of Human H1 Promoter and Human Pre-miRNA-128.

The replication competent retroviral vector, pAC3-miR-128-2 expressing miR-128-2 was derived from the backbone of pAC3-yCD2 described in one of the embodiment. The pAC3 backbone in the pAC3-miR-128-1 vector was isolated by endonuclease digestion of the pAC3-yCD2 plasmid DNA with Mlu I and Not I to remove the IRES-yCD2 polynucleotide sequence. The polynucleotide DNA sequence of the human H1 promoter was obtained from the product information of pSilencer 3.1 H1 hygro expression vector (Ambion), and the polynucleotide DNA sequence of the short hairpin structured pre-miR-128-1 was obtained from the http://(///)www.mirbase.org/. DNA sequence of pre-miR128-1 linked to the human H1 promoter (SEQ ID NO: 33) was synthesized with a Mlu I restriction enzyme site at the 5' end and a Not I restriction enzyme site at the 3'end of the double-stranded DNA fragment for subsequent insertion at the corresponding site in the Mlu I and Not I digested pAC3-yCD2 plasmid DNA described above. The resulting construct, pAC3-H1-shRNAmiR128, encodes 3 genes: the gag, the pol, and the env, and the non-coding short hairpin structured pre-miR-128-1 sequence (FIG. 11).

Vector stock was produced by transient transfection of the vector-encoding plasmid DNA into 293T cells using calcium phosphate method. Eighteen hours post transfection, the culture was replaced with fresh medium. Twenty-four hours post medium replacement, the supernatant containing the vector was collected and filtered through a 0.45 m filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

Analysis of Replication Kinetics of Recombinant Replication Competent Retroviral Vector by qPCR Assay.

Figure 12A:
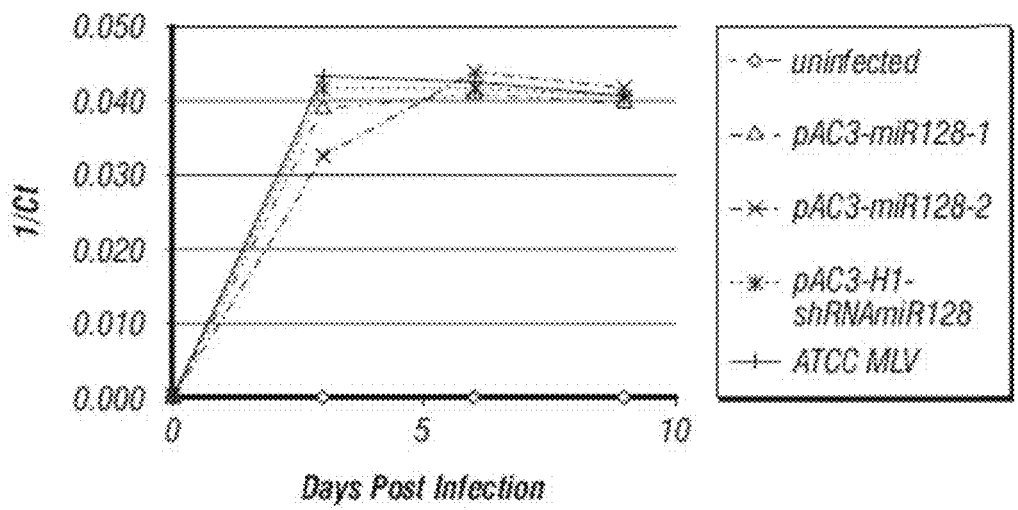
FIG. 12A-B: A. shows a comparison of replication kinetics of miR-128 containing vectors (pAC3-miR-128-1, pAC3-miR-128-2, and pAC3-H1-shRNAmiR128) in human fibrosarcoma cells HT1080 analyzed by qPCR. The graph is generated by plotting of inversed C(t) values obtained from qPCR vs. various time points during viral replication. B. shows a comparison of replication kinetics of miR-128 containing vectors (pAC3-miR-128-1, pAC3-miR-128-2, and pAC3-H1-shRNAmiR128) in human glioma cells U87-MG analyzed by qPCR. The graph is generated by plotting of inversed C(t) values obtained from qPCR vs. various time points during viral replication.
Figure 12B:
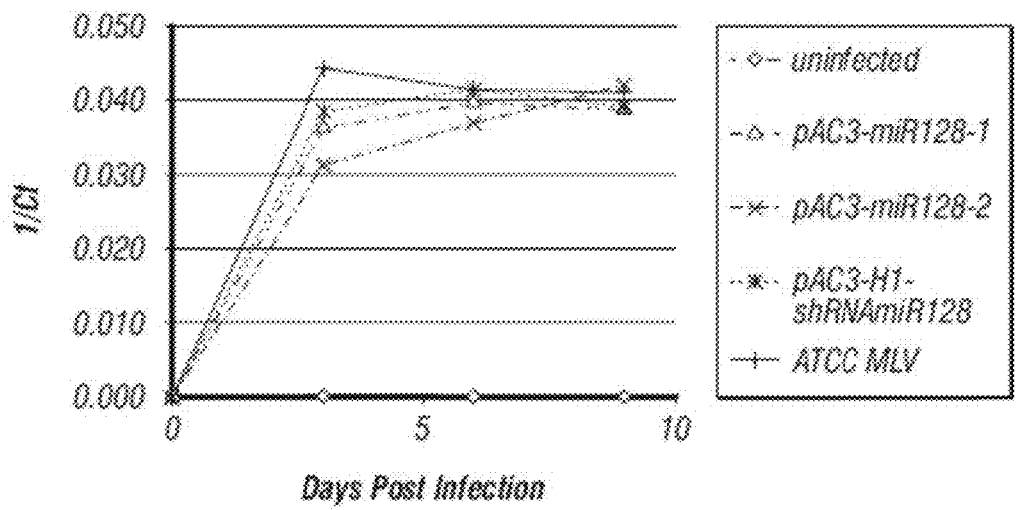

Currently, there are at least two common ways to obtain replication kinetics of recombinant replication competent retroviral vector: (1) analysis of GFP expression with vectors expressing the GFP protein by flow cytometric analysis, and (2) reversed transcriptase assay by measuring the reverse transcriptase activity of the vector stock collected from cultured medium of transduced cells. Titers assessed by DNA analysis of transduced cells provide the most reliable estimate of the functional titers as compared to titers obtained by RNA and transgene expression in which titers were over-estimated and under-estimated, respectively, (Sastry et al., 2002 *Gene Therapy* 9, 1155-1162). The replication kinetics of viral spread correlates with the percent of a cell population being transduced in which an integrated proviral DNA of the viral genome can be detected by qPCR with primers specific to the viral sequence is being tested in culture. The present assay requires equal amount of genomic DNA input from all time points within the same vector tested and among various vectors if a comparison of replication kinetics is being tested. The replication kinetics graph was generated by plotting inversed C(t) values vs. time points. FIG. 12A and FIG. 12B show comparisons of replication kinetics of various recombinant replication competent retroviral vectors. The assay is sensitive to reveal the small difference in replication kinetics among various vectors.

Testing of Replication Kinetics of miR-128 Containing Recombinant Replication Competent Retroviral Vectors in Culture.

In order to confirm that the incorporation of pri-miR-128-1, pri-miR-128-2 and H1-pre-miR-128-1 sequence, respectively, replicates normally, calculated volume of each vector stocks collected from transient transfection mentioned above was used to infect fresh human fibrosarcoma cells, HT1080 and human glioma cells, U87-MG, respectively, at a MOI of 0.1. Transduced cells were passaged at day 3, 6 and 9 post infection. At each time point, a portion of cells were collected for genomic DNA extraction for qPCR. Dilutions of genomic DNA were made to generate aliquots of genomic DNA with same concentration for equal amount of genomic in-put in qPCR. Replication kinetics of each vectors were generated by plotting inversed C(t) values vs. time points. FIGS. 12A and 12B show that all vectors tested replicated at similar kinetics compared to control MLV virus.

Testing of Expression of Mature miR-128 from Cells Transduced with miR-128 Containing Recombinant Replication Competent Retroviral Vector.

Figure 13:
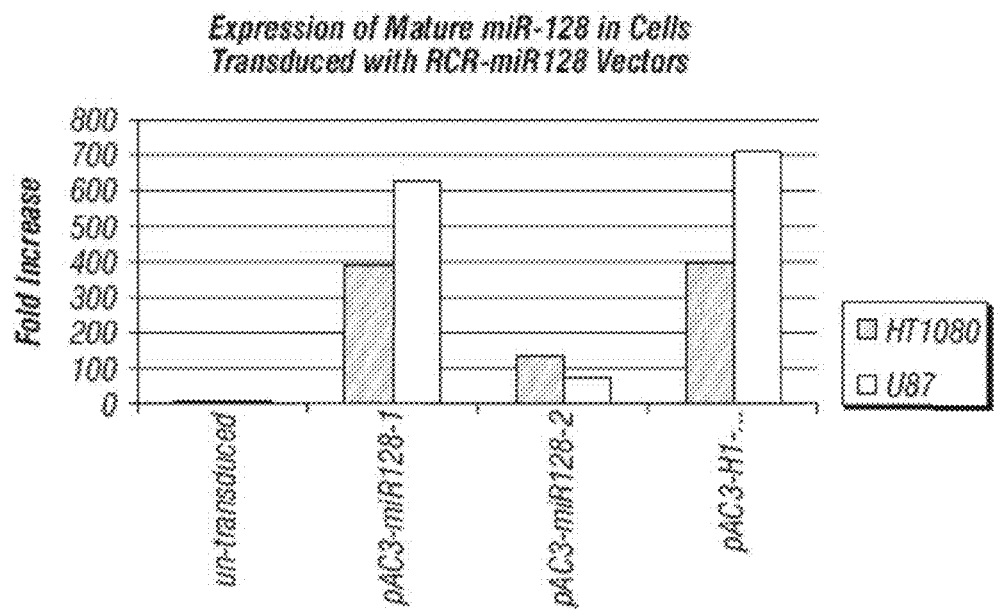
FIG. 13 shows a relative quantification of mature miR-128 expression from cells transduced with miR-128 containing vectors.

In order to confirm the expression of miR-128 from cells transduced with miR-128 containing recombinant replication competent retroviral vectors, cells from day 9 post infection at which the maximal infectivity has reached (FIG. 12A and FIG. 12B) were expanded and harvested to extract total RNA for detection of mature miRNA expression. The results from Taqman microRNA assay showed an over expression of mature miR-128 from both HT1080 and U87-MG cells transduced with pAC3-miR-128-1, pAC3-miR-128-2, and pAC3-H1-shRNAmiR128 vectors, respectively, compared to untransduced cells (FIG. 13). In both cell lines, cells transduced with pAC3-miR-128-1 and pAC3-H1-shRNAmiR128 vector expressed higher level of mature miR-128 than cells transduced with pAC3-miR-128-2 vector.

Testing of Bmi-1 Expression from Cells Transduced with miR-128 Containing Recombinant Replication Competent Retroviral Vectors to Demonstrate Target Engagement of miR-12.

Figure 14:
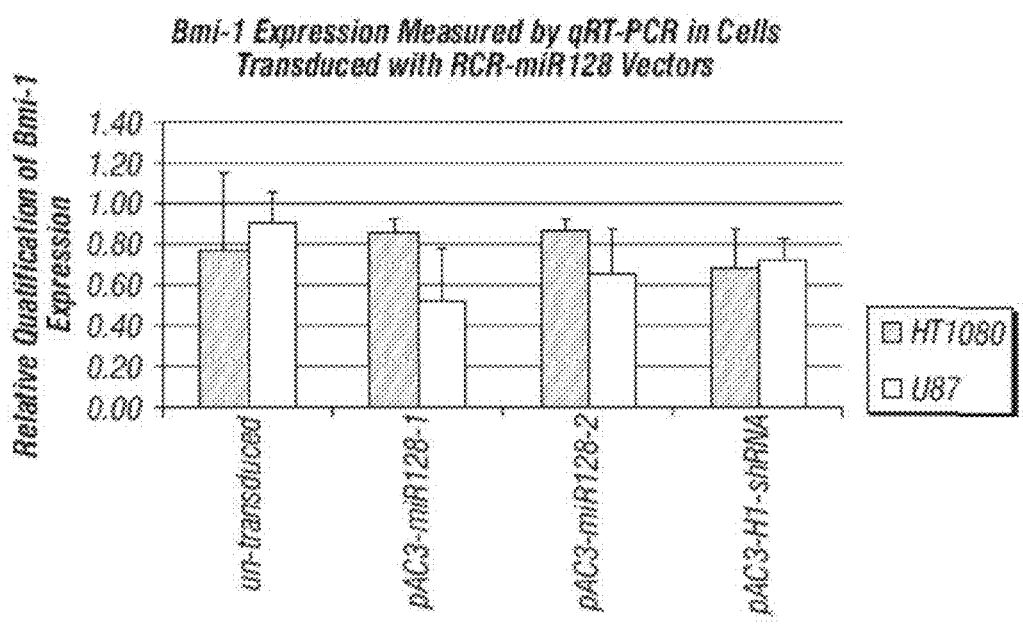
FIG. 14 shows a relative quantification of Bmi-1 gene expression from cells transduced with miR-128 containing vectors.

Bmi-1 expression has been observed to be up-regulated in a variety of human cancers including glioblastoma, and has been shown to be the target of miR-128. To confirm target engagement of miR-128, Bmi-1 expression from cells transduced with pAC3-miR-128-1, pAC3-miR-128-2 and pAC3-H1-shRNAmiR128 vector, respectively, was detected by qRT-PCR. FIG. 14 shows that U87-MG cells transduced with pAC3-miR-128-1, pAC3-miR-128-2 and pAC3-H1-shRNAmiR128 vector, respectively, expressed lower level of Bmi-1 than untransduced cells, whereas in HT1080 cells no significant difference was observed between transduced and untransduced cells. The data support the concept that miR-128 plays an important functional role in the central nervous system.

Example 12

Construction and Testing of Recombinant Replication Competent Retroviral Vector Containing Heterologous Polynucleotide Sequences of IRES, yCD2, Human H1 Promoter and Human pre-miR128-1

Construction.

The replication competent retroviral vector, pAC3-yCD2-H1-shRNAmiR128 is derived from the backbone of pAC3-yCD2 described in one of the embodiments. The pAC3-yCD2 backbone in the pAC3-yCD2-H1-shRNAmiR128 vector is isolated by endonuclease digestion of the pAC3-yCD2 plasmid DNA with Not I. The polynucleotide DNA sequence of the human H1 promoter is obtained from the product information of pSilencer 3.1 H1 hygro expression vector (Ambion), and the polynucleotide DNA sequence of the short hairpin structured pre-miR-128-1 is obtained from the http://)www.mirbase.org/. DNA sequence of pre-miR128-1 linked to the human H1 promoter (SEQ ID NO: 34) is synthesized with a Not I restriction enzyme site at both ends of the double-stranded DNA fragment for subsequent insertion at the corresponding site in Not I digested pAC3-yCD2 plasmid DNA described above. The resulting construct, pAC3-H1-shRNAmiR128, encodes 4 genes: the gag, the pol, and the env, and the yCD2, and the non-coding short hairpin structured pre-miR-128-1 sequence (FIG. 11).

Vector stock is produced by transient transfection of the vector-encoding plasmid DNA into 293T cells using calcium phosphate method. Eighteen hours post transfection, the culture is replaced with fresh medium. Twenty-four hours post medium replacement, the supernatant containing the vector is collected and filtered through a 0.45 μm filter and used immediately or stored in aliquots at −80° C. for later use. Twenty micro-liter of the collected vector stocks is used to infect human prostate cancer cells, PC3. Twenty-four hours post infection, AZT is added to the cells to inhibit further viral replication. Forty-eight hours post infection, genomic DNA of infected PC3 cells is extracted for titer assay. The titer of the vector stocks is determined by qPCR with an inclusion of standards of known copy numbers.

Testing of Replication Kinetics of the pAC3-yCD2-H1-shRNAmiR128 Recombinant Replication Competent Retroviral Vectors in Culture.

In order to confirm that the incorporation of H1-pre-miR-128-1 replicates normally, calculated volume of each vector stocks collected from transient transfection mentioned above is used to infect fresh human fibrosarcoma cells, HT1080 and human glioma cells, U87-MG, respectively, at a MOI of 0.1. Transduced cells are passaged at day 3, 6 and 9 post infection. At each time point, a portion of cells are collected for genomic DNA extraction for qPCR. Dilutions of genomic DNA are made to generate aliquots of genomic DNA with same concentration for equal amount of genomic in-put in qPCR. Replication kinetics of each vectors are generated by plotting inversed C(t) values vs. time points. Result show that the vector replicates at similar kinetics compared to control MLV virus.

Testing of Expression of Mature miR-128 from Cells Transduced with the pAC3-yCD2-H1-shRNAmiR128 Recombinant Replication Competent Retroviral Vector.

To confirm the expression of miR-128 from cells transduced with pAC3-yCD2-H1-shRNAmiR128 recombinant replication competent retroviral vector, cells from day 9 post infection, at which the maximal infectivity is reached, are expanded and harvested to extract total RNA for detection of mature miRNA expression. Result from Taqman microRNA assay shows an over expression of mature miR-128 from both HT1080 and U87-MG cells transduced with the pAC3-yCD2-H1-shRNAmiR128compared to untransduced cells.

Testing of Bmi-1 Expression from Cells Transduced with pAC3-yCD2-H1-shRNAmiR128 Recombinant Replication Competent Retroviral Vectors to Demonstrate Target Engagement of miR-128.

Bmi-1 expression has been observed to be up-regulated in a variety of human cancers including glioblastoma, and has been shown to be the target of miR-128. To confirm target engagement of miR-128, Bmi-1 expression from cells transduced with pAC3-yCD2-H1-shRNAmiR128 is detected by qRT-PCR. The result shows that U87-MG cells transduced with pAC3-yCD2-H1-shRNAmiR128 express lower level of Bmi-1 than untransduced cells, whereas in HT1080 cells no significant difference was observed between transduced and untransduced cells. The data support the concept that miR-128 plays an important functional role in the central nervous system.

Testing of yCD2 Expression from Cells Transduced with pAC3-yCD2-H1-shRNAmiR128 by Immune-Blot.

To confirm the expression of yCD2 from cells transduced with pAC3-yCD2-H1-shRNAmiR128 recombinant replication competent retroviral vector, cells from day 9 post infection, at which the maximal infectivity is reached, are expanded and harvested to extract total protein for detection of yCD2 expression. The result from immune-blot shows normal expression yCD2 from both HT1080 and U87-MG cells transduced with the pAC3-yCD2-H1-shRNAmiR128 compared to pAC3-yCD2 transduced cells.

Example 13

Testing of Vector Stability of miR-128 Containing Recombinant Retroviral Vectors in Culture Multiple serial infection cycles of miR-128 containing recombinant retroviral vectors (pAC3-miR-128-1, pAC3-miR-128-2, pAC3-H1-shRNAmiR128 and pAC3-yCD2-H1-shRNAmiR128) is tested to assess the stability of the vectors. HT1080 and U87-MG cells are initially infected with vectors at a low MOI and are allowed to spread in culture. Vector stocks at each infection cycles are collected, filtered diluted to infect fresh cells. At the end of each infection cycles, cells are harvested and genomic DNA are extracted for assessment of transgene stability by standard PCR using primers that bind to the 3' of the env gene and 3' of the untranslated region in the vector upstream of the 3'LTR. The result shows that all vectors tested remain stable for at least over 8-20 cycles.

Example 14

Anti-Tumor Efficacy Studies with miRNA Expressing Vector in a Mouse/Human Xenograft Model Objective.

The objective of this study is to assess the effect of a novel MLV based replication-competent retroviral vectors carrying the miR128 sequence (AC3-miR128-1(V); AC3-miR128-2 (V); AC3-miR128-3(V) on survival, when delivered via intracranial (IC) injection in nude mice bearing a human glioma xenograft, at three Toca 511 dose levels.

Mice.

Female athymic nude-Foxn1^nu (nude) mice (age ~8 weeks) are purchased from Harlan (Indianapolis Ind.). Mice are acclimated for 7 days after arrival. Mice undergo surgical placement of an indwelling guide cannula with a 3.0 mm projection implanted into the right striatum, and fitted with a cap containing a 3.5 mm projection. The stereotaxic coordinates are AP=+0.5 mm, ML=−1.8 mm (from bregma).

Cells.

U-87 MG cells (ATCC, Manassas Va.) are derived from a malignant glioma from a 44 year old Caucasian female. Cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. U-87 MG cells (1E5 in 1 μL) are infused at 0.2 μL per minute (5 minutes, followed by a hold of 5 minutes) IC through an injection cannula with a 3.5 mm projection inserted through the guide cannula.

Vectors preparations are made by transient transfection (or from a producer cell line) and all have titers of approximately 5E6TU/ml. For initial studies vector is not further purified or concentrated. For follow on experiments to determine full dose response curves, high titer purified material is prepared with a titer of around 10E8/ml. Vector is administered IC in a volume of 5 ul or less for a minimum total dose/mouse of approximately 2.5E4TU/mouse.

Tumor Implantation and Vector Injection.

Six groups of female athymic nude-Foxn1^nu mice (65 mice, 9-10 weeks of age) are implanted IC with U-87 tumor cells (Day 0) then dosed IC (day 4-7 depending on growth rate of the U87 cells) with vehicle (Groups 1), with control vector (AC3-GFP(V), Group2) or IC with AC3-miR128-1(V); AC3-miR128-2(V); AC3-miR128-3(V) (Groups 3-5). Group 6 mice were not implanted with tumor or vector.

Data Analysis.

Survival analysis to day 60 is performed on 10 mice each from Groups 1-6 and plotted as a Kaplan Meyer plot. Survival curves are compared by the log-rank test. P values of <0.05 are considered statistically significant in all analyses, which are performed with Prism 5 statistical software (GraphPad Software) or equivalent.

Results from treatment with the vectors show a statistically significant survival advantage in this human glioma xenograft model compared to treatment with control vector or vehicle alone.

Example 15

Anti-Tumor Efficacy Studies with yCD2 and miRNA Expressing Vector in a Mouse/Human Xenograft Model The objective of this study is to assess the effect of a novel MLV based replication-competent retroviral vector expressing yCD2 and miR-128, designated AC3-yCD2-H1-shRNAmiR128 (V) on survival when delivered via intracranial (IC) injection in nude mice bearing a "stem-cell" like enriched human glioma xenograft, at three dose levels.

Female athymic nude-Foxn1^nu (nude) mice (age ~8 weeks) are purchased from Harlan (Indianapolis Ind.). Mice are acclimated for 7 days after arrival. Mice undergo surgical placement of an indwelling guide cannula with a 3.0 mm projection implanted into the right striatum, and fitted with a cap containing a 3.5 mm projection. The stereotaxic coordinates are AP=+0.5 mm, ML=−1.8 mm (from bregma).

Early passages of primary human glioma (Dr. Carol Kruse, Burnham Biomedical Res Inst, San Diego, Calif.) are cultured in serum-free medium with EGF, bFGF and B27 supplement. Cells are resuspended in PBS (Hyclone, Logan Utah) for implantation. Approximately 1000 cells in 1 μL are infused at 0.2 μL per minute (5 minutes, followed by a hold of 5 minutes) IC through an injection cannula with a 3.5 mm projection inserted through the guide cannula.

Vectors preparations are made by transient transfection (or from a producer cell line) and all have titers of approximately 5E6TU/ml. For initial studies vector is not further purified or concentrated. For follow on experiments to determine full dose response curves, high titer purified material is prepared with a titer of around 10E8/ml. Vector is administered IC in a volume of 5 ul or less for a minimum total dose/mouse of approximately 2.5E4TU/mouse.

Tumor Implantation and Vector Injection.

Six groups of female athymic nude-Foxn1^nu mice (66 mice, 9-10 weeks of age) are implanted IC with "stem-like" cells (Day 0) then dosed IC at day 7-14 post tumor implantation depending on growth rate of the cells with Groups 1: vehicle; Group2: control vector AC3-GFP(V); Group 3: TOCA511; Group 4: AC3-yH1-shRNAmiR128(V); Group 5: AC3-yCD2-H1-shRNAmiR128(V); and Group 6: untreated mice that are not implanted with tumor or vector.

Data Analyses.

Survival analysis to day 60 is performed on 10 mice each from Groups 1-5 and plotted as a Kaplan Meyer plot. Survival curves are compared by the log-rank test. P values of <0.05 are considered statistically significant in all analyses, which are performed with Prism 5 statistical software (GraphPad Software) or equivalent.

Results.

Results from treatment with the vectors show a statistically significant survival advantage in this human glioma xenograft model compared to treatment with control vector or vehicle alone.

Example 16

Construction of Vectors with miR Target Sequences

Construction of Replication Competent Retroviral Vector Expressing GFP and Containing a Single Copy of 142-3p Target Sequence.

Figure 15:
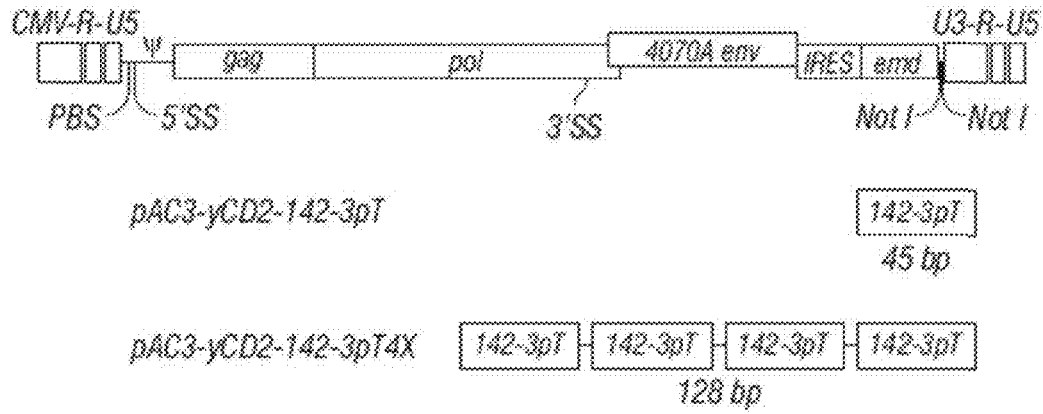
FIG. 15 is a schematic vector map of the MLV retroviral vector pAC3-emd containing a single copy of 142-3pT target sequence, designated pAC3-emd-142-3pT and 4 tandem repeats of 142-3pT, designated pAC3-emd-142-3pT4X.

The replication competent retroviral vector, pAC3-emd-142-3pT, encoding a GFP was derived from the backbone of pAC3-emd described above (current existing patent). The pAC3-emd backbone in the pAC3-emd-142-3pT vector was isolated by endonuclease digestion of the pAC3-emd plasmid DNA with Not I. The perfect complementary target sequence of miR142-3pT was obtained from published literature (Brown et al., 2006 *Nature Medicine* 12:5 585-591). The target sequence of the miR-142-3p (SEQ ID NO: 35) was synthesized with a Not I restriction enzyme site present at each end of the double-stranded DNA fragment for subsequent insertion at the corresponding site in the pAC3-emd plasmid DNA. The orientation of the 142-3pT insert was confirmed by sequencing analysis. The resulting construct, pAC3-emd-142-3pT, encodes 4 genes: the gag, the pol, the env, and the emd, and the non-coding 142-3pT sequence (FIG. 15).

Vector stock was produced by transient transfection of the vector-encoding plasmid DNA into 293T cells using calcium phosphate method. Eighteen hours post transfection, the culture was replaced with fresh medium. Twenty-four hours post medium replacement the supernatant containing the vector was collected and filtered through a 0.45 µm filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

Construction of Replication Competent Retroviral Vector Expressing yCD2 and Containing a Single Copy of 142-3p Target Sequence.

Figure 16:
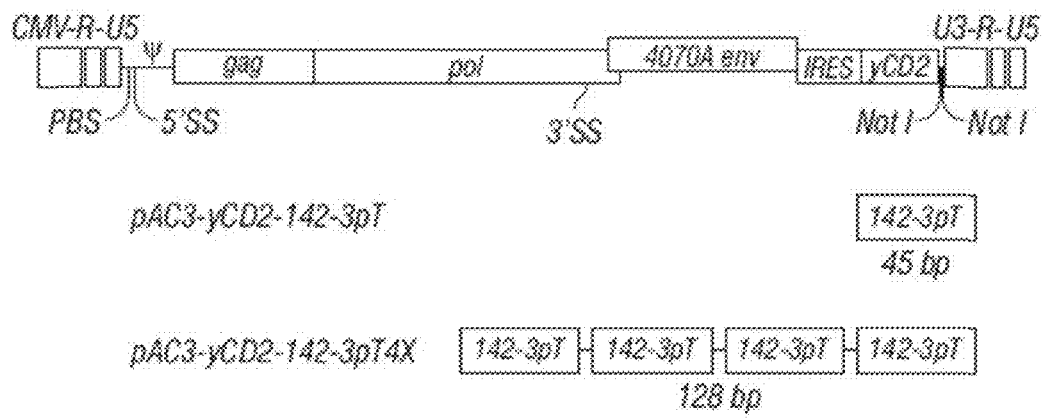
FIG. 16 is a schematic vector map of the MLV retroviral vector pAC3-yCD2 containing a single copy of 142-3pT target sequence, designated pAC3-yCD2-142-3pT and 4 tandem repeats of 142-3pT, designated pAC3-yCD2-142-3pT4X.

The replication competent retroviral vector, pAC3-yCD2-142-3pT, encoding a yCD2 gene was derived from the backbone of pAC3-yCD2 described above (current existing patent). The pAC3-yCD2 backbone in the pAC3-yCD2-142-3pT vector was isolated by endonuclease digestion of the pAC3-yCD2 plasmid DNA with Not I. The perfect complementary target sequence of miR142-3pT was obtained from published literature (Brown et al., 2006 *Nature Medicine* 12:5 585-591). The target sequence of the miR-142-3p (SEQ ID NO: 35) was synthesized with Not I restriction enzyme site present at each end of the double-stranded DNA fragment for subsequent insertion at the corresponding site in the pAC3-yCD2 plasmid DNA. The resulting construct, pAC3-yCD2-142-3pT, encodes 4 genes: the gag, the pol, the env, and the yCD2, and the non-coding 142-3pT sequence (FIG. 16).

Vector stock was produced by transient transfection of the vector-encoding plasmid DNA into 293T cells using calcium phosphate method. Eighteen hours post transfection, the culture was replaced with fresh medium. Twenty-four hours post medium replacement the supernatant containing the vector was collected and filtered through a 0.45 µm filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

Construction of Replication Competent Retroviral Vector Expressing GFP and Containing 4 Copies of 142-3p Target Sequence.

The replication competent retroviral vector, pAC3-emd-142-3pT4X, encoding yCD2 (modified cytosine deaminase) was derived from the backbone of pAC3-emd described above. The pAC3-yCD2 backbone in the pAC3-emd-142-3pT 4X vector was isolated by endonuclease digestion of the pAC3-emd plasmid DNA with Not I. Four tandem repeat of the perfect complementary target sequence of miR142-3pT4X was obtained from published literature (Brown et al., 2006 *Nature Medicine* 12:5 585-591). The target sequence of the miR-142-3p4X (SEQ ID NO: 36) was synthesized with a Not I restriction enzyme site present at each end of the double-stranded DNA fragment for subsequent insertion at the corresponding site in the pAC3-emd plasmid DNA. The orientation of the 142-3pT insert was confirmed by sequencing analysis. The resulting construct, pAC3-emd-142-3pT4X, encodes 4 genes: the gag, the pol, the env, and the emd, and the non-coding 142-3pT4X sequence (FIG. 15).

Vector stock was produced by transient transfection of the vector-encoding plasmid DNA into 293T cells using calcium phosphate method. Eighteen hours post transfection, the culture was replaced with fresh medium. Twenty-four hours post medium replacement the supernatant containing the vector was collected and filtered through a 0.45 µm filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

Construction of Replication Competent Retroviral Vector Expressing yCD2 and Containing 4 Copies of 142-3p Target Sequence.

The replication competent retroviral vector, pAC3-yCD2-142-3pT4X, encoding a GFP was derived from the backbone of pAC3-emd described above. The pAC3-emd backbone in the pAC3-yCD2-142-3pT 4Xvector was isolated by endonuclease digestion of the pAC3-yCD2 plasmid DNA with Not I.

Four tandem repeat of the perfect complementary target sequence of miR142-3pT4X was obtained from published literature (Brown et al., 2006 *Nature Medicine* 12:5 585-591). The target sequence of the miR-142-3pT4X (SEQ ID NO: 36) was synthesized with a Not I restriction enzyme site present at each end of the double-stranded DNA fragment for subsequent insertion at the corresponding site in the pAC3-yCD2 plasmid DNA. The orientation of the 142-3pT4X insert was confirmed by sequencing analysis. The resulting construct, pAC3-emd-142-3pT4X, encodes 4 genes: the gag, the pol, the env, and the emd, and the non-coding 142-3pT4X sequence (FIG. 16).

Vector stock was produced by transient transfection of the vector-encoding plasmid DNA into 293T cells using calcium phosphate method. Eighteen hours post transfection, the culture was replaced with fresh medium. Twenty-four hours post medium replacement the supernatant containing the vector was collected and filtered through a 0.45 µm filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

Example 17

Testing of Replication Kinetics 142-3pT Containing Recombinant Retroviral Vectors in Non-Hematopoietic Human Cell Lines.

In order to confirm that the incorporation of the 142-3pT sequence in a vector of the disclosure replicates similar to their parental vectors, calculated volume of each vector stocks collected from transient transfection mentioned above was used to infect fresh human fibrosarcoma cells, HT1080 and human glioma cells, U87-MG, respectively, at a MOI of 0.1. Transduced cells were passaged at day 3, 6 and 9 post infection. At each time point, a portion of cells were collected for genomic DNA extraction for qPCR. Dilutions of genomic DNA were made to generate aliquots of genomic DNA with same concentration for equal amount of genomic in-put in qPCR.

Figure 17A:
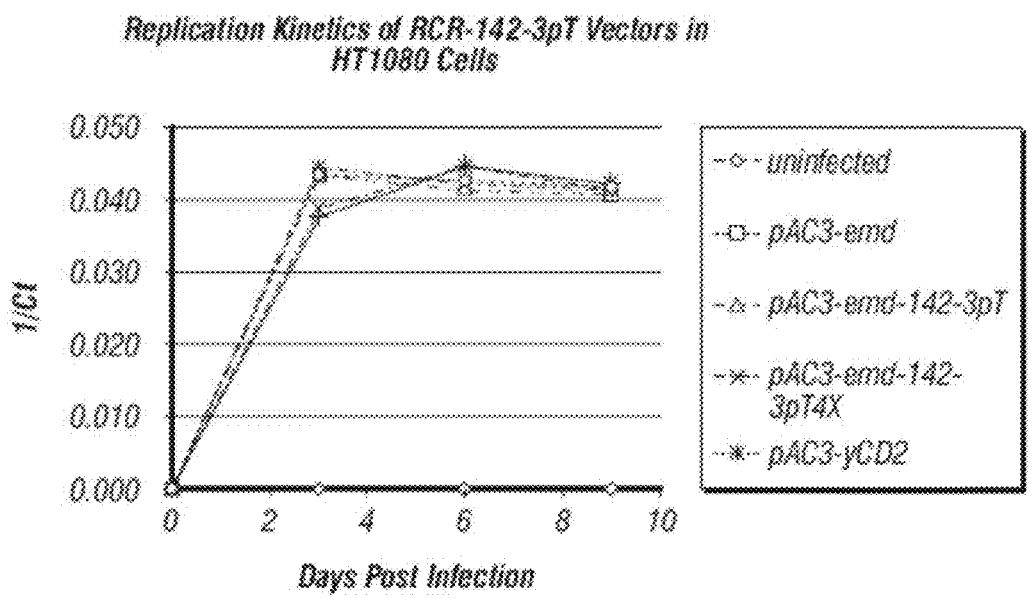
FIG. 17: A. shows a comparison of replication kinetics of 142-3pT containing vectors (pAC3-emd-142-3pT pAC3-emd-142-3pT4X, pAC3-yCD2-142-3pT and pAC3-yCD2-142-3pT4X) and their parental vectors (pAC3-emd and pAC3-yCD2) in human fibrosarcoma cells HT1080 analyzed qPCR. The graph is generated by plotting by inversed C(t) values obtained from qPCR vs. various time points during viral replication. B. shows a comparison of replication kinetics of GFP containing vectors (pAC3-emd, pAC3-emd-142-3pT and pAC3-emd-142-3pT4X) in human fibrosarcoma cells HT1080 analyzed by flow cytometric analysis of GFP expression at various time points during vector spread.
Figure 17B:
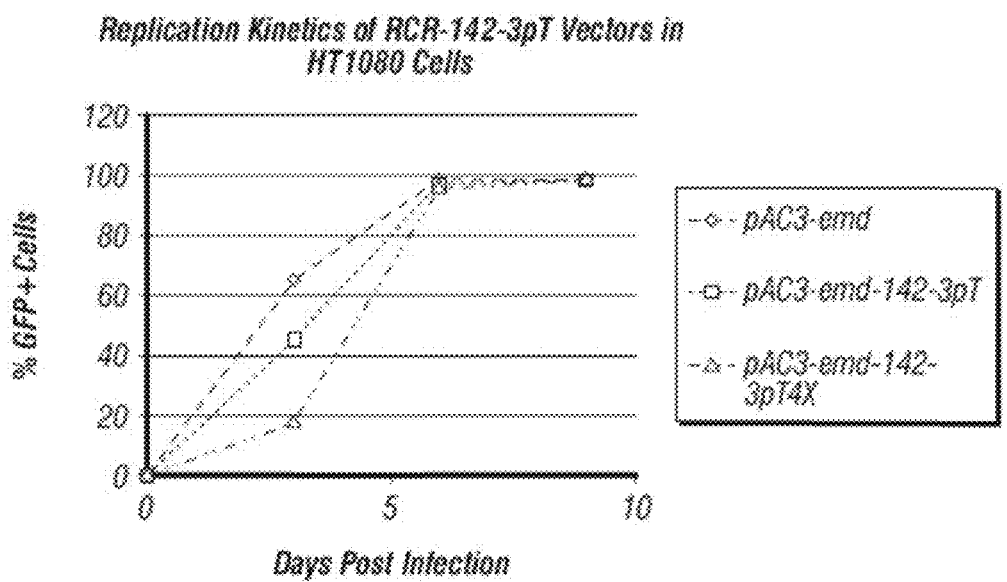
Figure 18A:
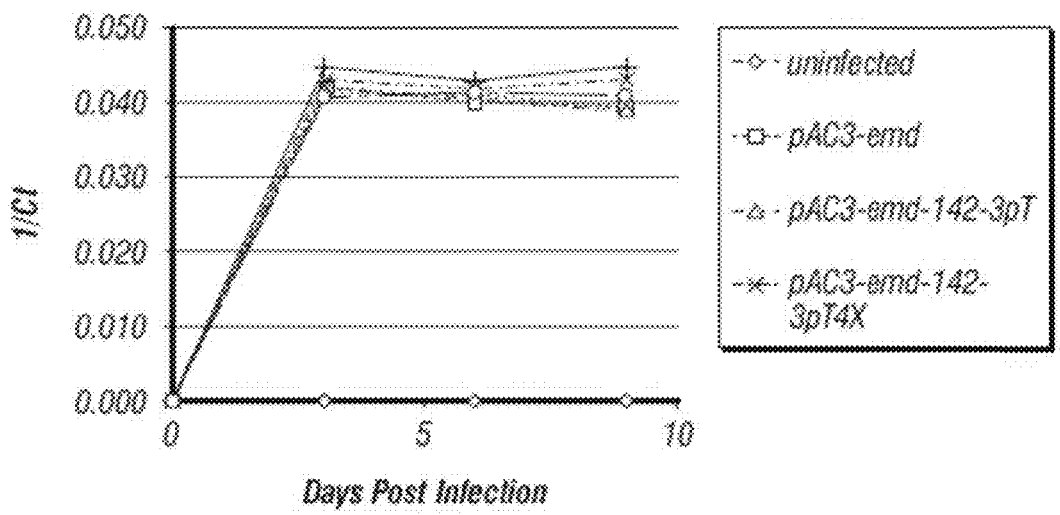
FIG. 18: A. shows a comparison of replication kinetics of 142-3pT containing vectors (pAC3-emd-142-3pT pAC3-emd-142-3pT4X, pAC3-yCD2-142-3pT and pAC3-yCD2-142-3pT4X) and their parental vectors (pAC3-emd and pAC3-yCD2) in human glioma cells U87-MG analyzed qPCR. The graph is generated by plotting by inversed C(t) values obtained from qPCR vs. various time points during viral replication. B. shows a comparison of replication kinetics of GFP containing vectors (pAC3-emd, pAC3-emd-142-3pT and pAC3-emd-142-3pT4X) in human glioma cells U87-MG analyzed by flow cytometric analysis of GFP expression at various time points during vector spread.
Figure 18B:
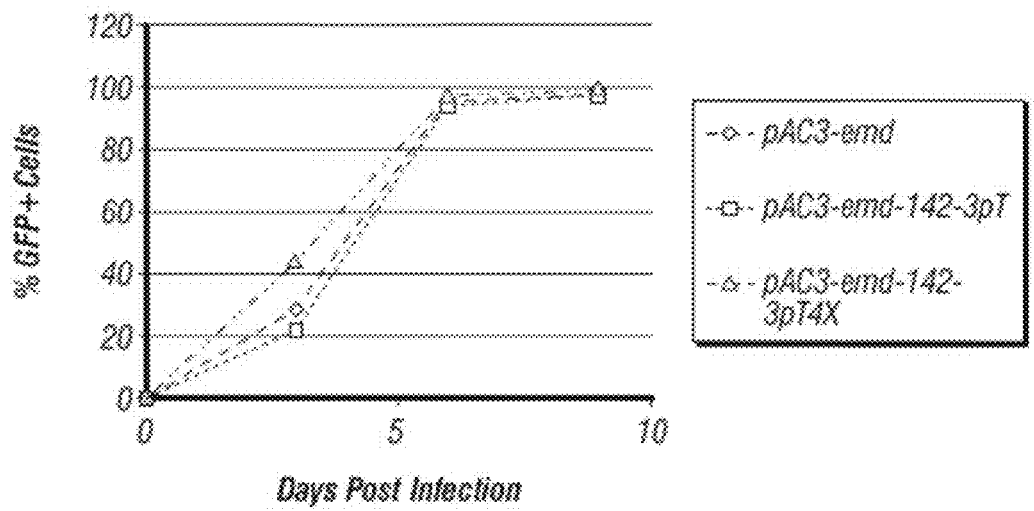

Replication kinetics of each vectors were generated by plotting inversed C(t) values vs. time points. FIGS. 17A and 18A show that all vectors tested replicated at similar kinetics compared to their parental vectors (pAC3-emd and pAC3-yCD2). Replication kinetics of vectors expressing GFP protein (pAC3-emd, pAC3-emd-142-3pT and pAC3-emd-142-3pT4X) was also assessed by flow cytometric analysis. FIGS. 17 and 18 show that pAC3-emd-142-3pT and pAC3-emd-142-3pT4X vectors replicated at a similar kinetic as their parental vector, pAC3-emd in these cell lines.

Testing of Replication Kinetics of 142-3pT Containing Recombinant Retroviral Vectors in Human and Mouse Hematopoietic Cells.

Figure 19:
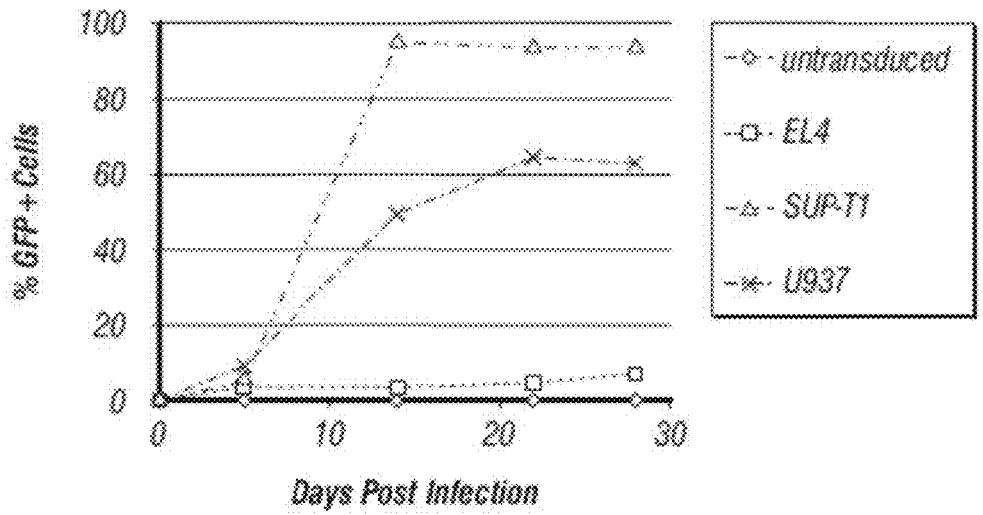
FIG. 19 shows the replication kinetics of GFP containing vector (pAC3-emd) in mouse and human hematopoietic cells analyzed by flow cytometric analysis of GFP expression at various time points during vector spread.

The expression of mature miR-142-3p was first confirmed in a mouse T-lymphocytic cell line EL4, a human T-lymphocytic cell line SUP-T1 and a human monocytic cell line U937 by Taqman microRNA assay using the primer set specific for mouse and human miR-142-3p as the sequences of mature miR-142-3p of the two species are identical. The replication kinetics of recombinant retroviral vector expressing the GFP (pAC3-emd) was tested in all three cell lines with an initial infection at a MOI of 2. FIG. 19 shows that the pAC3-emd vector replicated efficiently in human T-lymphocytes and monocytes (SUP-T1 and U937) as the viral spread reached 65% and 95% of cell population, respectively, by day 28 post infection. Vector spread in EL4 cells remained less than 5% during the time frame tested in FIG. 19, but eventually spread to 40% of cells by day 60 and 70% by day 75 was observed (FIG. 20D).

Example 18

Figure 20A:
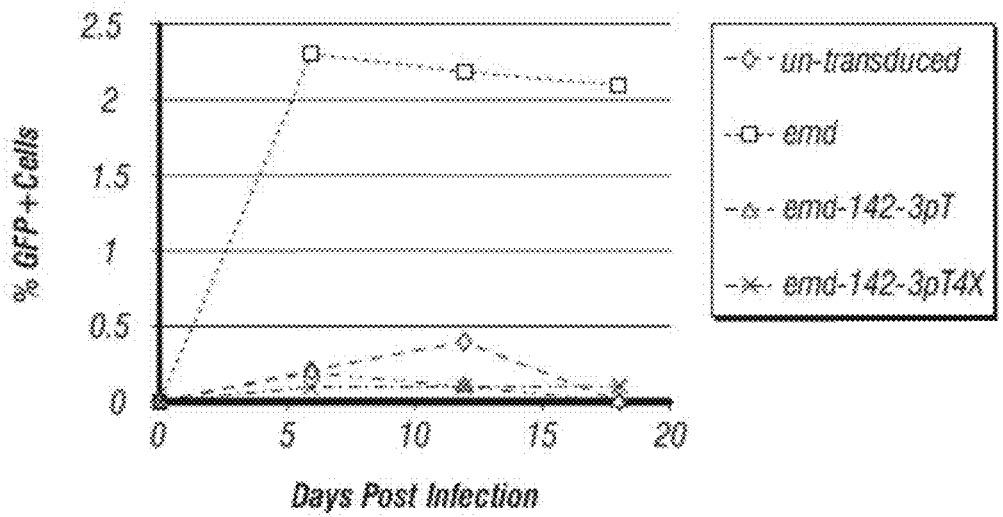
FIG. 20A-C shows comparison of replication kinetics. A. shows a comparison of replication kinetics of GFP containing vectors (pAC3-emd, pAC3-emd-142-3pT and pAC3-emd-142-3pT4X) in mouse T-lymphocytes EL4 analyzed by flow cytometric analysis of GFP expression at various time points during vector spread. B. shows a comparison of replication kinetics of GFP containing vectors (pAC3-emd, pAC3-emd-142-3pT and pAC3-emd-142-3pT4X) in human T-lymphocytes SUP-T1 analyzed by flow cytometric analysis of GFP expression at various time points during vector spread. C. shows a comparison of replication kinetics of GFP containing vectors (pAC3-emd, pAC3-emd-142-3pT and pAC3-emd-142-3pT4X) in human monocytes U937 analyzed by flow cytometric analysis of GFP expression at various time points during vector spread.
Figure 20B:
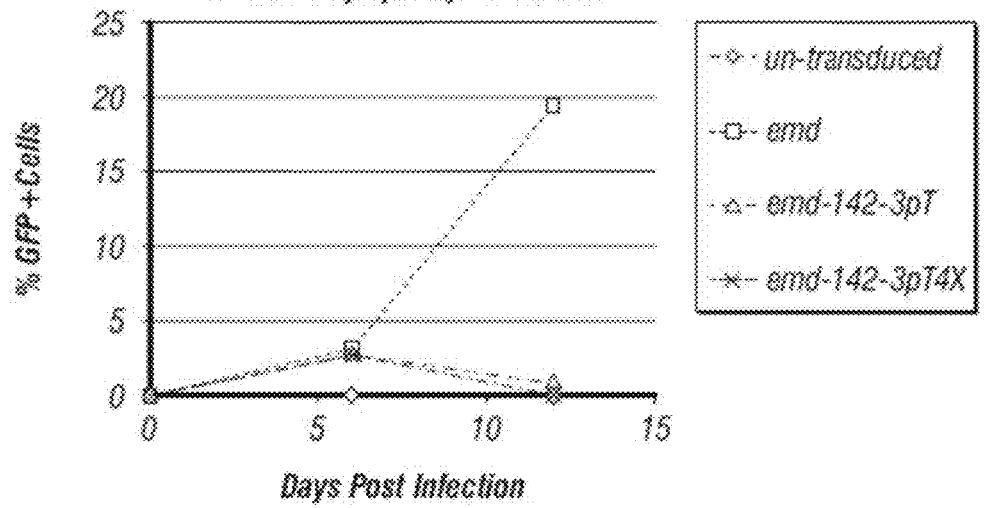
Figure 20C:
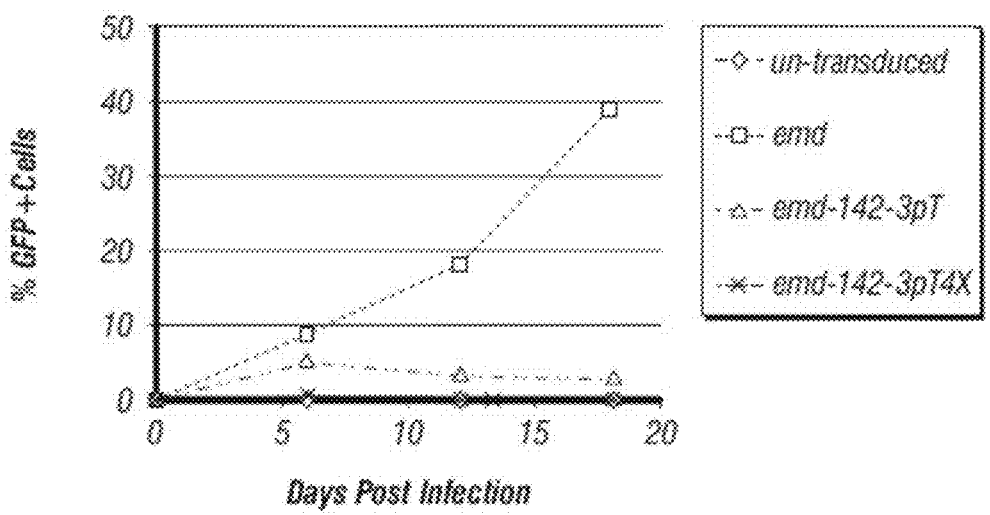

Testing of Vector Spread of 142-3pT Containing Recombinant Retroviral Vectors in Human and Mouse Hematopoietic Cells The functional effect of miR-142-3p in suppressing the GFP expression in the recombinant retroviral vector expressing GFP was tested by flow cytometric analysis. Calculated volume of pAC3-emd, pAC3-emd-142-3pT and pAC3-emd-142-3pT4X vector stock collected from transient transfection mentioned above was used to infect fresh EL4, SUP-T1 and U937 cells at a MOI of 2. A portion of cells were collected at day 6, 12 and 18 post infection for analysis of GFP expression by flow cytometric analysis. FIG. 20A shows the GFP expression was suppressed to background level in EL4 cells transduced with pAC3-emd-142-3pT and pAC3-emd-142-3pT4X vector compared to their parental vector pAC3-emd. The GFP suppression remained persistent within the time frame tested. FIG. 20B and FIG. 20C show remarkable suppression of GFP expression in SUP-T1 and U937 cells transduced with pAC3-emd-142-3pT and pAC3-emd-142-3pT4X vector, respectively, compared to their parental vector pAC3-emd. FIG. 20D shows that even when time is allowed for spread of the pAC3-emd vector to approximately 30% at 55 days, expression of pAC3-emd-142-3pT and pAC3-emd-142-3pT4X vector continues to be suppressed. The results confirm that the miR-142-3p expression in mouse and human hematopoietic cells effectively suppress the GFP expression in cells transduced with recombinant retroviral vectors containing the 142-3pT sequence. In U937 cells, the result suggested that the vector containing 4 copies of 142-3pT (pAC3-emd-142-3pT4X) may be more effective in suppressing GFP expression than the vector containing single copy of 142-3pT (pAC3-emd-142-3pT4X).

Example 19

Testing of Viral RNA Genome

It is unclear whether the functional effect of miR-142-3pT in suppressing the GFP expression mentioned above is due direct suppression of GFP expression at the translational level or due to degradation of viral genome at post transcriptional level. A portion of cells at the end of the experimental time point is collected for total RNA extraction using standard molecular biology method. qRT-PCR using primers (e.g. pol primer set and env2 primer set) specific to cDNA derived from reverse transcribed viral RNA is performed to assess viral load of transduced cells. The result shows that the viral load of cells transduced with pAC3-emd-142-3pT and pAC3-emd-142-3pT4X, respectively, is significantly lower than cells transduced with pAC3-emd vector. The result supports the concept that miR-142-3p in mouse and human hematopoietic cells effectively degrades the viral RNA genome at post transcriptional level, thereby, restricts the vector spread in mouse and human hematopoietic cells.

Example 20

Testing of Integrated Proviral DNA by qPCR

It is unclear whether the functional effect of miR-142-3pT in suppressing the GFP expression mentioned above is due direct suppression of GFP expression at the translational level or due to degradation of viral genome and thus integration of proviral DNA. A portion of cells at the end of the experimental time point is collected for genomic DNA extraction using standard molecular biology methods. qPCR using primers specific to integrated proviral DNA is performed to assess the copy number of integrated proviral DNA per cell. The result shows that the copy number per cells of cells transduced with pAC3-emd-142-3pT and pAC3-emd-142-3pT4X, respectively, is significantly lower than cells transduced with pAC3-emd vector. The result supports the concept that miR-142-3p in mouse and human hematopoietic cells effectively degrades the viral RNA genome at post transcriptional level, and thereby restricts the vector spread in mouse and human hematopoietic cells.

Example 21

Testing of Vector Stability of 142-3pT Containing Recombinant Retroviral Vectors in Culture Multiple serial infection cycles of 142-3pT containing recombinant retroviral vectors is tested to assess the stability of the vectors. HT1080 and U87-MG cells are initially infected with vectors at a low MOI and are allowed to spread in culture. Vector stocks at each infection cycles are collected, filtered and diluted to infect fresh cells. At the end of each infection cycles, cells are harvested and genomic DNA are extracted for assessment of transgene stability by standard PCR using primers that bind to the 3' of the env gene and 3' of the untranslated region in the vector downstream of the heterologous polynucleotide sequence linked to the IRES. The result shows that vectors containing single copy of 142-3pT (pAC3-emd-142-3pT and pAC3-yCD2-142-3pT) remains stable for at least over 10-20 cycles, whereas vectors containing 4 tandem repeats of 142-3pT (pAC3-emd-142-3pT4X and pAC3-yCD2-142-3pT4X) can show deletion of 142-3pT sequence in early infection cycles.

Example 22

Testing of Controlled Vector Spread of 142-3pT Containing Recombinant Retroviral Vectors in In Vivo This experiment is conducted with the same design as example 27 below. The functional effect of miR-142-3p in restricting vector spread via hematopoietic cells is tested in vivo by intravenous injection of the recombinant retroviral vectors (pAC3-emd, pAC3-emd-142-3pT and pAC3-emd-142-3pT4X) in 8-wk-old nude Balb/C mice with implanted U87 xenografts. For each vector, there are three groups of mice each represents a time point (e.g. 30 day, 60 day and 90 day post viral vector administration). A dose of 1E4 to 1E7 TU of each vector stock is administered by intravenous injection to all animals. Animals from each time point are sacrificed to harvest spleen, lymph nodes and bone marrow and tumor. GFP expression of subpopulation of cells (e.g. CD4+, CD8+ and etc.) are harvested and analyzed by flow cytometric analysis. In a duplicate experiment, animals from each time point are sacrificed and tissues (e.g. liver, kidney, spleen, tumor etc.) are collected for genomic DNA extraction. qPCR is performed to assess the presence of integrated proviral DNA in tissues collected. The result shows vector spread of vectors containing the 142-3pT is significantly reduced in hematopoietic tissues demonstrating the reduction of vector replication in these tissues. At the same time GFP and PCR signal is still observed in the tumor, showing that the miR target sequences have depressed spread in the lymphoid tissues, but still allowed spread in the tumor tissue.

Example 23

Extended Survival in a Patient Dog with Spontaneous Recurrent Malignant Glioma and Treated with T5.0002 Vector Plus 5-FC A male 35 kg Boxer dog, presenting with recurrent anaplastic oligodendroglioma 3 months following complete surgical resection, was treated with T5.0002 virus, purified and formulated (see U.S. Pat. No. 5,792,643; T. Rodriguez et al. J Gene Med 9:233 2007; WO 2010/148203) in isotonic Tris/NaCl pH7.2 rendered isotonic with mannitol & sucrose, 1 mg/ml HSA, 0.1 mg/ml ascorbate) in combination with 5-FC. The tumor measured approximately 13 $cm^3$, and caused major lateral ventricle compression and significant midline shift (See FIG. 1) Due to the large size of the tumor, Toca 511 was infused through 2 separate catheters (400 μL and 480 μL), using Convection Enhanced Delivery (CED). The total Toca 511 dose administered was approximately $4.1 \times 10^6$ TU/g brain. ProHance® (gadoteridol) was added to Toca 511 prior to injection to allow visualization of delivery by MRI. The volume of distribution of the vector was estimated to be approximately 10-12% of the tumor volume.

Figure 21A:
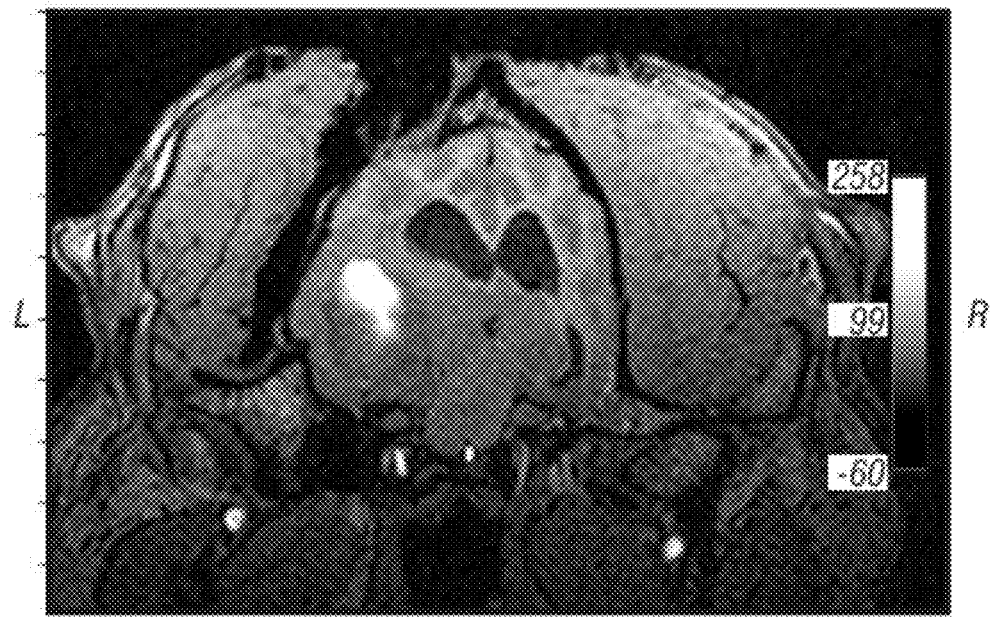
FIGS. 21A-B are still frames from the MRI images obtained from the patient dog during intratumoral CED infusion of Toca 511 and gadolinium. Note the large tumor on the left side of the image compressing both sides of the brain and shifting midline structures to the right. The white areas are the gadolinium-Toca 511 infusion.
Figure 21B:
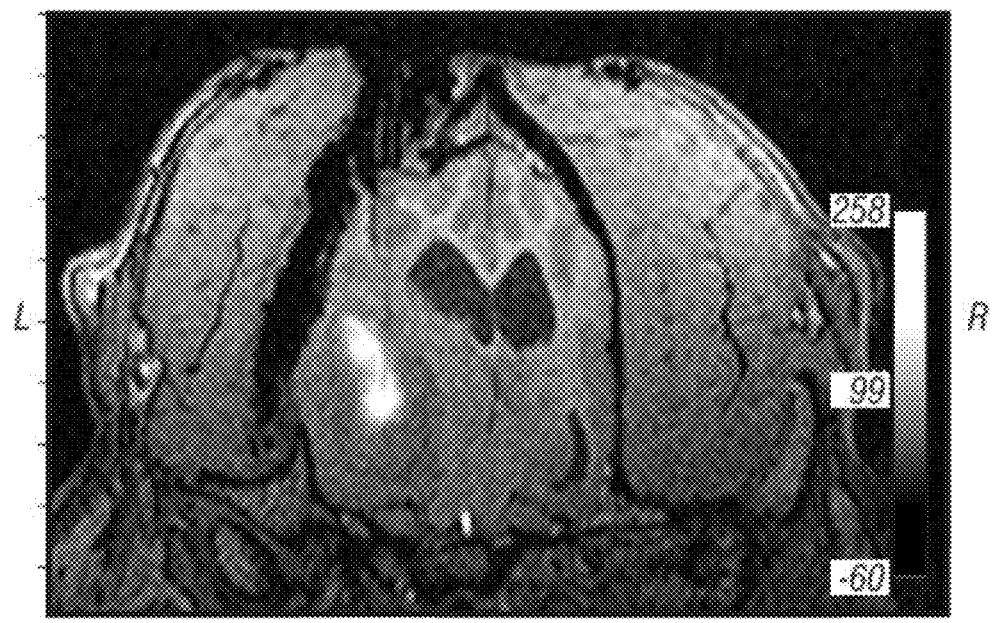

FIGS. 21A and 21B are still frames from the MRI images obtained from the patient dog during intratumoral CED infusion of Toca 511 and gadolinium. Note the large tumor on the left side of the image compressing both sides of the brain and shifting midline structures to the right. The white areas are the gadolinium-Toca 511 infusion. FIG. 21B shows the placement of the two catheters into the tumor.

Toca 511 was allowed to spread for 8 days. The dog was treated with 5-FC at a divided dose of 130 mg/kg/day, by mouth, three times daily with food for 5 days. The dose was increased to 160 mg/kg/day for 2 more days (7 days of 5-FC total). A follow-up MRI showed no change in tumor size and some possible changes to the internal area of the tumor. After 21 days of viral spread, a second cycle of 5-FC was initiated at the higher dose of 160 mg/kg/day (divided, three times a day with food). The drug was stopped after the fifth day of dosing due to the development of rash.

MRI performed at 2 weeks after the first course of 5-FC and 2 weeks after the second course of 5-FC (7 weeks after treatment began) has shown that the tumor volume has plateaued while the rate of tumor growth has declined. The patient became more alert and active, and remained clinically stable, 13 weeks after injection of vector. At 15.5 weeks the dog was euthanized because of stomach bleeding due to prolonged high dose steroid administration (and not because of the tumor). The estimated lifespan of the dog was no more than 3-4 weeks at the time of initial injection of the vector. Efficacy of the Toca 511/5-FC combination in this patient dog is shown by survival 3 to 4 times longer than that originally estimated by his attending veterinarian. At autopsy low levels (20-30 copies/microgram genomic DNA) of vector DNA were detectable in the residual tumor, but nowhere else in the dog.

Example 24

Construction of Gamma Interferon Vectors

Construction and Testing of a Replication Competent Retroviral Vector Encoding the Human IFN-Gamma Gene.

Figure 22:
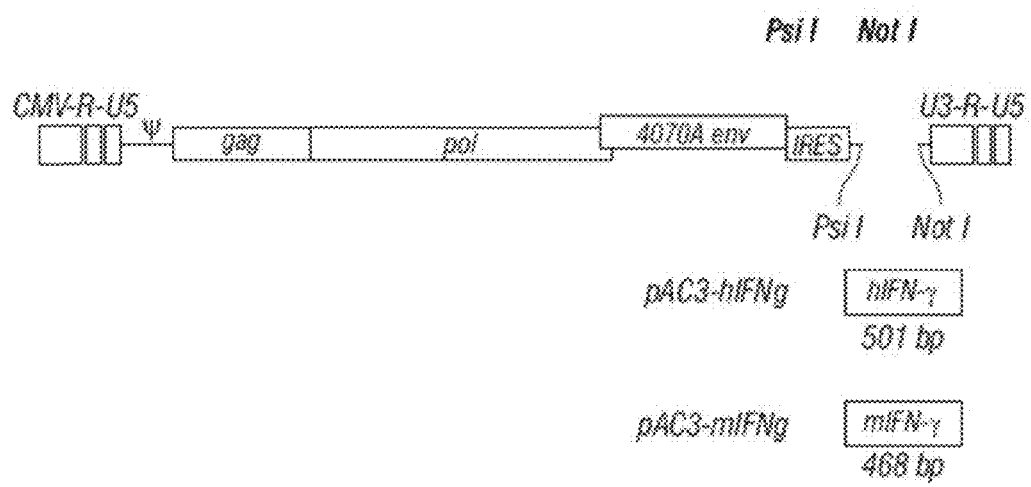
FIG. 22 is a schematic vector map of the MLV retroviral vectors encoding the human IFN-gamma (hIFNg) and mouse IFN-gamma (mIFNg), respectively, in pAC3 backbone.

The replication competent retroviral vector, pAC3-hIFNg, encoding the human IFN-gamma gene, was derived from the backbone of pAC3-yCD2 described above. The pAC3 backbone in the pAC3-hIFNg vector was isolated by endonuclease digestion of the pAC3-yCD2 plasmid DNA with Psi I and Not I. The cDNA sequence of human IFN-gamma gene was identified and confirmed among three sequences obtained from different accession numbers (AM903379, BC070256, and NM000619). Sequence alignment showed identical sequence among the three. The open reading frame of the human IFN-gamma (SEQ ID NO: 38) was synthesized with Psi I and Not I restriction enzyme site present at each end of the DNA fragment for subsequent insertion at the corresponding site in the pAC3 backbone. The resulting construct, pAC3-hIFNg, encodes 4 genes: the gag, the pol, the env, and the human IFN-gamma (FIG. 22).

Vector stock was produced by transient transfection of the vector-encoding plasmid DNA into HT1080 cells using FUGENE HD transfection Reagent. Forty-eight hours post transfection the supernatant containing the vector was collected and filtered through a 0.45 μm filter and used immediately or stored in aliquots at −80° C. for later use. Specific volume of the undiluted vector stock was used to infect fresh 75% confluent HT1080. At day 4 and day 5 post infection, the supernatant containing the vector was collected and filtered through a 0.45 μm filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

The expression of human IFN-gamma was first tested at the RNA level. Total RNA was extracted from transduced HT1080 cells at 5 days post infection in the second infection using standard RNA extraction method. RT-PCR was performed to detect the expression of human IFN-γ. Fifty nano-gram of total RNA was used in the RT reaction to generate cDNA. One tenth of the volume from RT reaction was subsequently used for PCR using PCR primer set specific for human IFN-γ. Result from RT-PCR showed that human IFN-gamma is expressed in HT1080 cells infected with pAC3-hIFNg vector.

Figure 24:
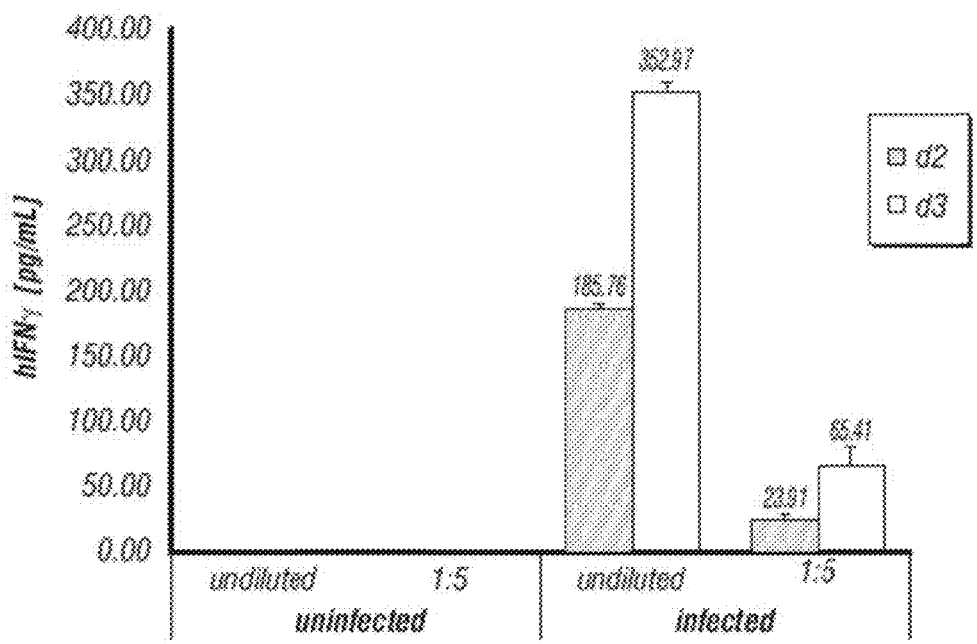
FIG. 24 shows the expression of hIFN-gamma protein secreted from human fibrosarcoma cell line HT1080 infected with pAC3-hIFNg vector.

The expression of secreted human IFN-protein was tested by standard ELISA. Vector stock collected from day 4 and day 5 post infection was serially diluted in the ELISA assay in order to obtain a linear range between protein concentration and dilution factor. The result showed that human IFN-γ protein is secreted at a higher concentration by the HT1080 cells at day 5 post infection than by the cells at day 4 post infection (FIG. 24). Cells at post d5 infection secreted approximately 325-355 pg/mL human IFN-γ protein.

Construction and Testing of a Replication Competent Retroviral Vector Encoding the Mouse IFN-Gamma Gene.

The replication competent retroviral vector, pAC3-mIFNg, encoding the mouse IFN-γ gene was derived from the backbone of pAC3-yCD2 described above. The pAC3 backbone in the pAC3-mIFNg vector was isolated by endonuclease digestion of the pAC3-yCD2 plasmid DNA with Psi I and Not I. The cDNA sequence of mouse IFN-γ gene was identified and confirmed among three sequences obtained from different accession numbers (BC119063, BC119065 and NM008337). Sequence alignment showed identical sequence among the three. The open reading frame of the mouse IFN-gamma (SEQ ID NO: 39) was synthesized with Psi I and Not I restriction enzyme site present at each end of the DNA fragment for insertion at the corresponding site in the pAC3 backbone. The resulting construct, pAC3-mIFNg, encodes 4 genes: the gag, the pol, the env, and the mouse IFN-gamma (FIG. 22).

Vector stock was produced by transient transfection of the vector-encoding plasmid DNA into HT1080 cells using FUGENE HD transfection Reagent. Forty-eight hours post transfection the supernatant containing the vector was collected and filtered through a 0.45 micron filter and used immediately or stored in aliquots at −80° C. for later use. Specific volume of the undiluted vector stock was used to infect fresh 75% confluent HT1080. At day 4 and day 5 post infection the supernatant containing the vector was collected and filtered through a 0.45 micron filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

Figure 23:
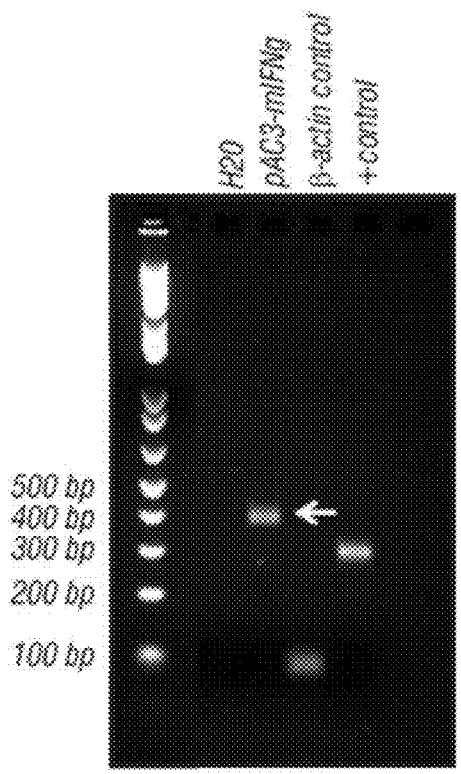
FIG. 23 shows the expression of mIFN-gamma at the RNA level from human fibrosarcoma cell line HT1080 infected with pAC3-mIFNg vector. Expression is detected by RT-PCR.

The expression of mouse IFN-gamma was first tested at the RNA level. Total RNA was extracted from transduced HT1080 cells at 5 days post infection in the second infection using standard RNA extraction method. RT-PCR was performed to detect the expression of mouse IFN-gamma. Fifty nano-gram of total RNA was used in the RT reaction to generate cDNA. One tenth of the volume from RT reaction was subsequently used for PCR using PCR primer set specific for mouse IFN-gamma (FIG. 23). Result from RT-PCR showed that mouse IFN-gamma is expressed in HT1080 cells infected with pAC3-mIFNg vector.

Figure 25:
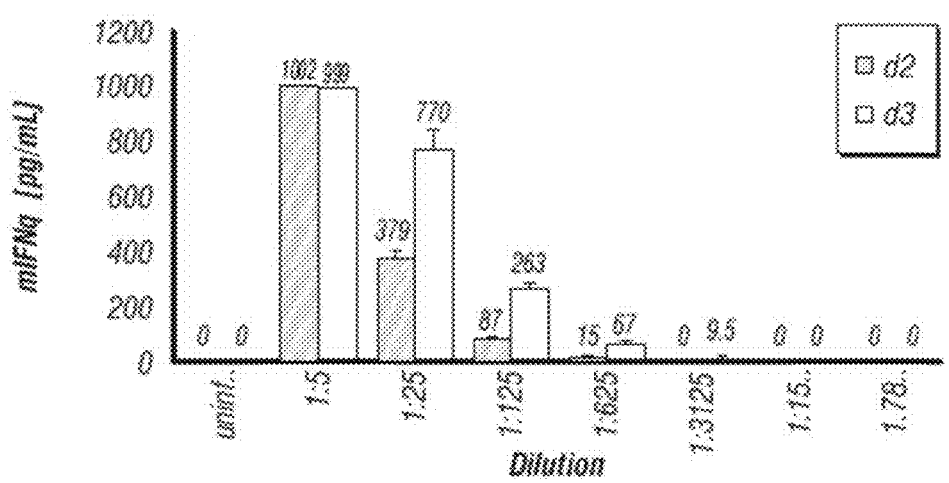
FIG. 25 shows the expression of mIFN-gamma protein secreted from human fibrosarcoma cell line HT1080 infected with pAC3-mIFNg vector.

The expression of secreted human IFN-gamma protein was tested by standard ELISA. Vector stock collected from day 4 and day 5 post infection was serially diluted in the ELISA assay in order to obtain a linear range between protein concentration and dilution factor. The result showed that mouse IFN-γ protein is secreted at a higher concentration by the HT1080 cells at day 5 post infection than by the cells at day 4 post infection (FIG. 25). Cells at post d5 infection secreted approximately 33-42 ng/mL mouse IFN-gamma protein.

Example 25

Anti-Tumor Efficacy Studies with Gamma Interferon Expressing Vector in a Mouse Subcutaneous Tumor Model Objective.

The objective of this study is to assess the effect of a novel MLV based replication-competent retroviral vector carrying the murine gamma interferon sequence (pAC3-mIFNg) on tumor growth, when delivered via intratumoral (IT) injection in BALB/c mice bearing subcutaneous colon carcinoma (CT26.WT).

Mice.

Female BALB/c mice (age ~8 weeks) are purchased from Jackson Laboratories (Bar Harbor, Me.). Mice will be acclimated for 7 days after arrival before start of studies.

Cells.

CT26.WT cells (ATCC, Manassas Va.) are an N-nitroso-N-methylurethane-(NNMU) induced, undifferentiated colon carcinoma cell line. Cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. CT26.WT cells (2E5 in 100 µL) are injected into the right flank of BALB/c mice.

Vectors.

Vectors preparations are made by transient transfection (or from a producer cell line after infection of a second cell line with the infectious virus from the initial transfection; see, e.g., International Application No. PCT/US10/38996, the disclosure of which is incorporated herein by reference) with titers of approximately $3 \times 10^6$ TU/ml. For initial studies vector is not further purified or concentrated. For follow on experiments to determine full dose response curves, high titer purified material is prepared with a titer expected around $10^8$/ml. To achieve high titer material, canine cell line CF2 are chosen for production as gamma interferon is poorly cross-species reactive and use of xenogeneic cell lines will prevent the inhibitory action of gamma interferon on the producing cells. The vector is purified and concentrated as described in the specification (see also T. Rodriguez et al. J Gene Med 9:233 2007). Vector is administered IT in a volume of 100 µL and the total dose/mouse of approximately 3E3, 3E4 and 3E5 TU/mouse. Vector expressing gamma interferon is identified as Toca 621.

Tumor Implantation and Vector Injection.

Nine groups of female BALB/c (99 mice, 9-10 weeks of age) are implanted subcutaneously with CT26.WT tumor cells (Day 0) and then dosed (day 4-7 depending on growth rate of the CT26 tumor; approximately 50-100 mm$^3$) with vehicle (Groups 1), with control vector [AC3-GFP(V), (Group2), IT Toca 621 vector injection (Groups 3-5), or intravenous Toca 621 vector injection (group 6-8). Group 9 mice have no tumor implanted and are intravenously injected with vector only.

Data Analysis.

Tumor growth analysis is carried out to 2000 mm$^3$ or to 60 days based on whichever comes first. 10 mice from each group will be plotted for tumor size over time. Statistical significance are determined using analysis of variance (ANOVA). P values of <0.05 are considered statistically significant in all analyses, which are performed with Prism 5 statistical software (GraphPad Software) or equivalent. In-life observations are also taken to assess any adverse events to Toca 621 administration.

Results.

The results of measurement of tumor size over time show a statistically significant difference in the growth of tumors treated with the vector expressing gamma IFN over the tumors in animals that received control vector or vehicle.

Example 26

Anti-Tumor Efficacy Studies with Gamma Interferon Expressing Vector in a Mouse Subcutaneous Tumor Model Objective.

The objective of this study was to assess the effect of a novel MLV based replication-competent retroviral vector carrying the murine gamma interferon sequence (pAC3-mIFNg) on tumor growth, when delivered via intratumoral (IT) injection in BALB/c mice bearing subcutaneous melanoma (Cloudman S91).

Mice.

Female BALB/c mice (age ~8 weeks) were purchased from Jackson Laboratories (Bar Harbor, Me.). Mice were acclimated for 7 days after arrival before start of studies.

Cells.

Clone M-3 Cloudman S91 cells (ATCC, Manassas Va.) are derived from an irradiation induced malignant melanoma from a C×DBA F1 mouse. Cells were cultured in Dulbecco's modified Eagles medium with 10% fetal bovine serum, sodium pyruvate, and Glutamax (Hyclone, Logan Utah, and Invitrogen, San Diego Calif.). Cells were resuspended in PBS (Hyclone, Logan Utah) for implantation. S91 cells (1E5 in 100 µL) were injected into the right flank of BALB/c mice.

Vectors.

Vectors preparations are made by transient transfection (or from a producer cell line after infection of a second cell line with the infectious virus from the initial transfection with titers of approximately 3E6TU/ml. For initial studies vector was not further purified or concentrated. For follow on experiments to determine full dose response curves, high titer purified material was prepared with a titer approximately $10^8$ TU/ml. To achieve high titer material, the human cell line HT1080 was used for production of the mouse gamma interferon vector as gamma interferon is poorly cross-species reactive and use of xenogeneic cell lines prevents the inhibitory action of gamma interferon on the producing cells. The vector was purified and concentrated as described in the specification above. Vector was administered IT in a volume of 100 µL and the total dose/mouse of approximately 3E3, 3E4 and 3E5 TU/mouse. Vector expressing gamma interferon is identified as Toca 621.

Tumor Implantation and Vector Injection.

Two groups of female BALB/c (approx. 20 mice, 9-10 weeks of age) were implanted subcutaneously with S91 tumor cells. Mice with tumors reaching approximately 50-125 mm3 were randomized and injected IT with control vector, Toca 511 (Groups 1, N=10), or Toca 621 vector (Group 2, N=5).

Data Analyses.

Tumor growth analysis was carried out to 600 mm3 or to 45 days based on whichever comes first. All mice from each group were plotted for tumor size over time. Statistical significance was determined using analysis of variance (ANOVA). P values of <0.05 are considered statistically significant in all analyses, which are performed with Prism 5 statistical software (GraphPad Software) or equivalent. In-life observations were also taken to assess any adverse events to Toca 621 administration.

Results.

A statistically significant reduction in average tumor volume was measured in mice with tumors injected with a single dose of Toca 621 vector expressing gamma IFN compared to mice with tumors injected with control Toca 511 vector (p=0.003) see FIG. 35.

Example 27

Intravenous Gene Delivery Using a Replicative Retroviral Vector

Objective.

The objective of this study was to assess the effectiveness of intravenous delivery of a novel MLV based replication-competent retroviral vector carrying the marker green fluorescent protein (AC3-GFP(V)) to U87 gliomas implanted in the brains of nude mice.

Mice.

Female athymic nude-Foxn1^nu (nude) mice (age ~8 weeks) were purchased from Harlan (Indianapolis Ind.). Mice were acclimated for 7 days after arrival. Mice underwent surgical placement of an indwelling guide cannula with a 3.0 mm projection implanted into the right striatum, and fitted with a cap containing a 3.5 mm projection. The stereotaxic coordinates are AP=+0.5 mm, ML=−1.8 mm (from bregma).

Cells.

U-87 MG cells (ATCC, Manassas Va.) are derived from a malignant glioma from a 44 year old Caucasian female. Cells were cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. U-87 MG cells (1E5 in 1 µL) were infused at 0.2 µL per minute (5 minutes, followed by a hold of 5 minutes) intracranially (IC) through an injection cannula with a 3.5 mm projection inserted through the guide cannula.

Vectors.

Vector preparations were made by transient transfection and all had a titer of approximately 2.8E7TU/ml. Vector was administered intratumorally (IT) in a volume of 5 ul or less for a minimum total dose/mouse of approximately 1.4E45 TU/mouse. Intravenous injections were done through the tail vein with 2.8E6/100 uL.

Tumor Implantation and Vector Injection.

Five groups of female athymic nude-Foxn1^nu mice (16 mice, 9-10 weeks of age) were implanted IC with U-87 tumor cells (Day 0) then dosed IT or IV (day 4-7 depending on growth rate of the U87 cells) with vehicle IV (Group 1), with vector IV (Group2), IT with a blood/brain barrier disruptor Vardenafil and vector (Group 3), IT with Vardenafil and vector (Groups 4), or IT with vector (group 5). 14 days after vector injection mice were sacrificed and tumors are isolated and analyzed for GFP expression.

Data Analysis.

Figure 26:
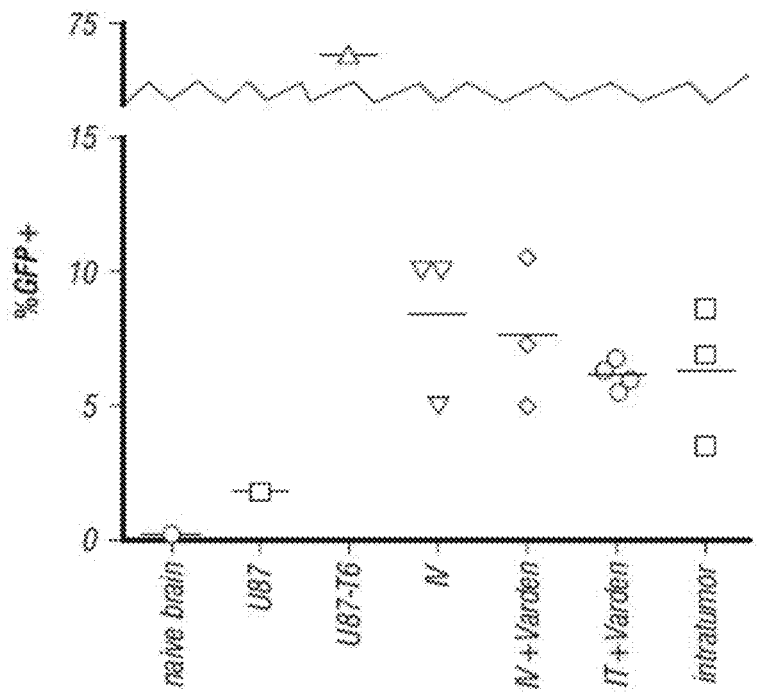
FIG. 26 shows flow cytometry analysis of GFP expression in U87 cells after intratumor or intravenous delivery of AC3-GFP vector in a nude mouse model. Cells are measured by flow cytometry for percent GFP positive. Cells isolated from naive nude mouse brains, U87 cells from tissue culture, or U87 cells transduced at an multiplicity of infection of 1 with AC3-GFP(V) in vitro serve as controls. From example 27 (iv injection of GFP vector).
Figure 27:
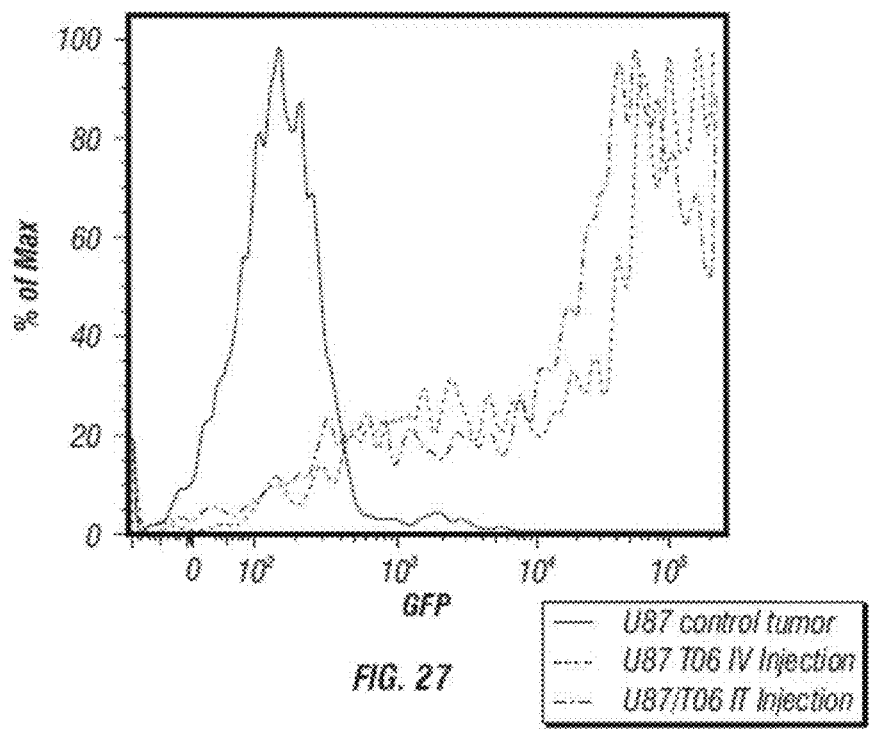
FIG. 27 shows a histogram analysis was also done on groups 1,3 and 5 from example 27 (iv injection of GFP vector) to measure the distribution of GFP signal in isolated U87 cells. GFP expression is from U87 tumor cells isolated from mouse brains after 14 days after vector treatment.

U87 cells from disrupted tumors isolated from the mice were analyzed by flow cytometry for the percentage GFP positive from groups 2-5 (FIG. 26). Histogram analysis was also done on groups 1, 3, and 5 to measure the distribution of GFP signal in isolated U87 cells (FIG. 27).

Results.

Intravenous delivery of GFP was as equally effective as intratumor injection of U87 glioma cells intracranially implanted into nude mice.

Example 28

Figure 28:
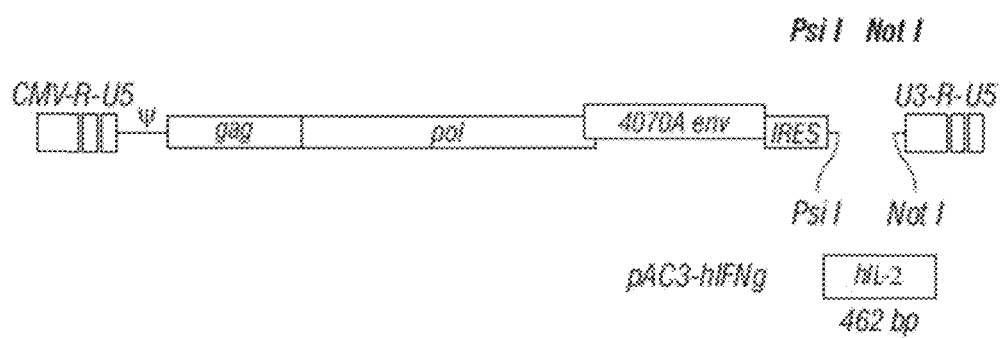
FIG. 28 is a schematic vector map of the MLV retroviral vectors encoding the human IL-2 in the pAC3 backbone.

Construction of Replication Competent Retroviral Vector Encoding the Human IL-2 Gene The replication competent retroviral vector, pAC3-hIL2, encoding the human IL2 gene, is derived from the backbone of pAC3-yCD2 vector. The pAC3 backbone in the pAC3-hIL2 vector-encoding plasmid DNA was isolated by endonuclease digestion of the pAC3-yCD2 plasmid DNA with Psi I and Not I. The cDNA sequence of human IFN-γ gene was identified and confirmed using sequences obtained from different accession numbers (BC066255 and BC066257). Sequence alignment of the two revealed identical sequence. The open reading frame of the human IFN-γ (SEQ ID NO: 40) was synthesized with Psi I and Not I restriction enzyme site present at each end of the DNA fragment for subsequent insertion at the corresponding site in the pAC3 backbone. The resulting construct, pAC3-hIL2, encodes 4 genes: the gag, the pol, the env, and the human IL2. (FIG. 28).

Vector stock is produced by transient transfection of the vector-encoding plasmid DNA into 293T cells using calcium phosphate method. Eighteen hours post transfection, the culture was replaced with fresh medium. Twenty-four hours post medium replacement, the supernatant containing the vector was collected and filtered through a 0.45 µm filter and used immediately or stored in aliquots at −80° C. for later use. Twenty micro-liter of the collected vector stocks was used to infect human prostate cancer cells, PC3. Twenty-four hours post infection, AZT was added to the cells to inhibit further viral replication. Forty-eight hours post infection, genomic DNA of infected PC3 cells was extracted for titer assay. The titer of the vector stocks was determined by qPCR with an inclusion of standards of known copy numbers.

The expression of human IL-2 is first tested at the RNA level. Total RNA is extracted from transduced CF2TH and HT1080 cells at 5 days post infection using standard RNA extraction method. RT-PCR was performed to detect the expression of human IL-2. Fifty nano-gram of total RNA was used in the RT reaction to generate cDNA. One tenth of the volume from RT reaction was subsequently used for PCR using PCR primer set specific for human IL-2. Result from RT-PCR shows that human IL-2 is expressed in HT1080 cells transduced with pAC3-hIL2 vector.

The expression of secreted human IL-2 protein was tested by standard ELISA. Vector stock collected from day 5 post infection was serially diluted in the ELISA assay in order to obtain a linear range between protein concentration and dilution factor. The result showed that human IL-2 protein is secreted at a higher concentration by the CF2TH cells than HT1080 at day 5 post infection.

Example 29

Anti-Tumor Efficacy Studies with Interleukin 2 Expressing Vector in a Mouse Subcutaneous Tumor Model Objective.

The objective of this study is to assess the effect of a novel MLV based replication-competent retroviral vector carrying the murine leukocytotrophic hormone interleukin 2 (IL-2) sequence (pAC3-mIL2) on tumor growth, when delivered via intratumoral (IT) injection in BALB/c mice bearing subcutaneous colon carcinoma (CT26.WT).

Mice.

Female BALB/c mice (age ~8 weeks) are purchased from Jackson Laboratories (Bar Harbor, Me.). Mice will be acclimated for 7 days after arrival before start of studies.

Cells.

CT26.WT cells (ATCC, Manassas Va.) are an N-nitroso-N-methylurethane-(NNMU) induced, undifferentiated colon carcinoma cell line. Cells are cultured in Dulbecco's modified Eagles medium with 10% fetal bovine serum, sodium pyruvate, and Glutamax (Hyclone, Logan Utah, and Invitrogen, San Diego Calif.). Cells are resuspended in PBS (Hyclone, Logan Utah) for implantation. CT26.WT cells (2E5 in 100 µL) are injected into the right flank of BALB/c mice.

Vectors.

Vector preparations are made by transient transfection (or from a producer cell line) with titers of approximately 6E6TU/ml. For initial studies vector is not further purified or concentrated. For follow on experiments to determine full dose response curves, high titer purified material is prepared with a titer expected around 10E8/ml. Vector is administered IT in a volume of 100 µL and the total dose/mouse of approximately 6E5 TU/mouse. Vector expressing gamma interferon is identified as Toca IL2.

Tumor Implantation and Vector Injection.

Five groups of female BALB/c (55 mice, 9-10 weeks of age) are implanted subcutaneously with CT26.WT tumor cells (Day 0) and then dosed (day 4-7 depending on growth rate of the CT26 tumor; approximately 50-100 mm$^3$) with vehicle (Groups 1), with control vector [AC3-GFP(V), (Group2), IT Toca IL2 vector injection (Groups 3), or intravenous Toca IL2 vector injection (group 4). Group 5 mice have no tumor implanted and are intravenously injected with vector only.

Data Analysis.

Tumor growth analysis is carried out to 2000 mm$^3$ or to 60 days based on whichever comes first. 10 mice from each group will be plotted for tumor size over time. Statistical significance will be determined using analysis of variance (ANOVA). P values of <0.05 are considered statistically significant in all analyses, which are performed with Prism 5 statistical software (GraphPad Software) or equivalent. In-life observations are also taken to assess any adverse events to IL-2 expression during treatment.

Results.

Delivery of IL-2 by replicating MLV reduces and in some instances clears tumors burden from the BALB/c CT26 mouse model.

Example 30

Tumor Explants Have Multiple Copies of the Vector Genome and Show Continued Susceptibility to Super-Infection In order to examine in more detail the mechanism of action of the replicating retrovirus tumors from some animals in the mouse and human tumor models described in example 9 (athymic nude-Foxn1^nu (nude) mice with Human U87 intracranial implants) and example 10 (BALB/c mice with syngeneic CT26 intracranial implants) were explanted and examined for 5-FC sensitivity, vector copy number/diploid genome, and CD protein expression.

Explant Assignments.

The experimental design is summarized below. The study consisted of 5 tumor explants. The history of each tumor removed for implantation is given below.
Explant History:

| Animal # | Study | Treatment | # of 5-FC dosings before explant | Cell Type | Dosing regimen |
|---|---|---|---|---|---|
| 833 | Example 9 FIG. 8 | AC3-yCD2(V) E6 + 5-FC | 4 | Human U87 | QD, 7 days every 21 days |
| 953 | Example 9 FIG. 8 | AC3-yCD2(V) E5 + 5-FC | 4 | Human U87 | QD, 7 days every 21 days |
| 969 | Example 9 FIG. 8 | AC3-yCD2(V) E5 + 5-FC | 4 | Human U87 | QD, 7 days every 21 days |
| 31 | Example 10 FIG. 9 | AC3-yCD2(V) E5 + 5-FC | 3.5 | Mouse CT26 | BID 7 days, every 17 days |
| 61 | Example 10 FIG. 9 | AC3-yCD2(V) E4 + 5-FC | 3 | Mouse CT26 | BID 7 days, every 17 days |

The 5-FC cell killing assays were carried out as described in Example 5 above, measuring viability after 8 days of 5-FC treatment.

Copy number/microgram of DNA was determined by PCR as described for the vector titering assay in Example 5, and converted to copy number/diploid genome by dividing by 150,000, the approximate number of diploid mouse/human genomes in 1 microgram of genomic DNA. Western Blot analysis was performed on 1E6 cells/lysate in RIPA buffer using antibodies from clone 83A25 for GP70 and Abcam anti-CD antibody ab3525 for the CD protein. Cell explants underwent super-infection procedures with a AC3-eGFP(V) and a mock procedure to determine which explants were potentially further infectable. The extent of GFP expression was measured by FACS analyses, with uptake and expression of GFP indicating the relative susceptibility to further infection.

Results. 5-FC Cell Killing Assay and Copy Number of Integrated Vector.

Cultured explants were tested for 5-FC sensitivity by generating a killing profile from treated cell lines at varying 5-FC concentrations (summarized in the Table below). Results from the killing profile measured by MTS viability assay show that U87 human tumors derived from animals #833, 953, 969 on average ($IC_{50}$=0.009 mM) had a similar response compared to an in vitro U87 positive control ($IC_{50}$=0.008 mM) to 5-FC treatment (FIG. 29A). Analysis of CT26 murine tumors (Example 10) showed that the 5-FC responsive animal #61 had an $IC_{50}$ of 0.003 mM (FIG. 29B) which is similar to in vitro 100% transduced CT26 results ($IC_{50}$=0.001 mM). Animal #31 was poorly responsive to 5-FC (FIG. 29B). PCR results for copy number per cell are also shown in the table below.

| Animal # | Study | 5-FC sensitivity IC50 (mM) | Vector copy number per diploid genome |
|---|---|---|---|
| 833 | Example 9 | 0.009 | 22.3 |
| 953 | Example 9 | 0.009 | 9.6 |
| 969 | Example 9 | 0.009 | 18.7 |
| 61 | Example 10 | 0.003 | 6.0 |
| 31 | Example 10 | Not sensitive | 0.9 |

Western Blot Analysis of GP70 and CD Protein Expression.

Further analysis of cells by western blot from the CT26 study showed that both tumor explants derived from mice #31 and #61 had observable GP70 protein expression when using U87+AC3-yCD2(V) infected lysates as a reference positive control (FIG. 30).

However, analysis of CD expression showed that only #61 still had observable CD expression. Cells from #31 were run in duplicate wells (#31(A) and #31(B)) to verify negative CD gene expression results.

GFP Expression after AC3-eGFP(V) Transduction.

Attempts to transduce explants with an MLV vector expressing GFP showed that U87 tumors derived from animals #833, 953, 969 were scarcely transducible (<0.5%). CT26 explanted tumor cells derived from animal #61 could be partially transduced (7% GFP positive) while explanted cells from animal #31 could not (FIG. 31).

All U87 gliomas isolated from the brains of nude mice after 4 full cycles of 5-FC treatment were still sensitive to 5-FC treatment in vitro with an $IC_{50}$ the same as in vitro transduced U87 and, surprisingly, showed multiple vector superinfections had taken place. Two CT26 tumors were isolated from BALB/c mice after 3 and 3.5 cycles of 5-FC treatment. Of the two, only one tumor showed 5-FC sensitivity while the other did not. Further analysis showed that the 5-FC resistant tumor is refractory to further MLV transduction, expresses GP70 but no longer expresses the CD, and has low copy number compared to the other CT26 and all U87 explants tested. These observations show that whereas a virus that has undergone a deletion of the CD gene behaves as expected for a normal retrovirus and excludes further infection, cells infected with vector carrying the CD transgene behave atypically and allow multiple superinfections (range: 6.0-23.3, mean 14.5 copies per diploid genome). Typical tumors are not diploid but are polyploid with a genome larger than the diploid genome. This would further increase the actual vector copy number per cell. The multiple vector copy numbers contributes to the therapeutic effect as more of the protein derived from the transgene (in this case CD) is produced than from a single vector integration. It also means that in general, even if some members of a viral vector population undergo rearrangements, other members will donate protein activity (in this case sensitivity to 5-FC). The experiments described here also provide a method of testing a recombinant replication competent retrovirus for the property of multiple infections of a target cell population.

Example 31

Direct Measurement from Excised Tumors Treated with AC3-yCD2(V) Shows Unexpectedly High Levels of Viral Vector Copies Per Genome and Susceptibility to Superinfection in the Syngeneic Tu2449 Glioma Model Objective.

This study was conducted to compare the efficacy of two dose levels of AC3(V)-yCD2 (aka Toca511) delivered via IC injection in combination with 5-FC treatment in a TU-2449 glioma tumor bearing, immunocompetent mouse model, and examined survival in the setting of active tumor growth. TU-2449 cells implanted IC in syngeneic B6C3F1 mice have been used as an experimental murine glioma model. This model was also used for survival and short term (15-18 day) experiments where tumors were implanted, treated with vector and dosed short term with 5-FC then excised for further characterization of gene copy number and CD activity.

Mice.

Female B6C3F1 mice (age ~8 weeks) were purchased from Harlan (Indianapolis Ind.). Mice were acclimated for 7 days after arrival.

Mice underwent surgical placement of an indwelling guide cannula with a 3.0 mm projection implanted into the right striatum, and fitted with a cap containing a 3.5 mm projection. The stereotaxic coordinates were AP=+0.5 mm, ML=−1.8 mm (from bregma).

Cells.

TU-2449 cells (Smilowitz et al. J Neurosurg. 2007 106: 652-659 2007) derived originally from Glial fibrillary acidic protein (GFAP)-v-src transgenic mice, were cultured in Dulbecco's modified Eagles medium with 10% fetal bovine serum, sodium pyruvate, and Glutamax (Hyclone, Logan Utah, and Invitrogen, San Diego Calif.). Cells were resuspended in PBS (Hyclone, Logan Utah) for implantation. TU-2449 cells (1E4 in 1 µL) were infused at 0.2 µL per minute (5 minutes, followed by a hold of 5 minutes) IC through an injection cannula with a 3.5 mm projection inserted through the guide cannula.

The study consisted of 6 groups of female mice (see Table below). On day 0, mice from Groups 1, 3, 4, 6, and 7 underwent intracranial implantation of 1E4 TU-2449 cells. Group 8 mice were not implanted with tumor. On Day 4, mice were injected (IC; 5 µL/mouse) with vehicle (Group 1); IC with AC3-yCD2(V) at 1.7E5 TU/g (Groups 6, 7); IC with AC3-yCD2(V) at 1.7E6 TU/g (Groups 3, 4); Group 8 mice were not treated. Starting on Day 10, mice were treated IP BID for 4 consecutive days with PBS (Groups 1, 3, 7) or 5-FC (500 mg/kg/dose, Groups 4, 6, 8). Cycles of 4 days BID treatment with PBS or 5-FC followed by 10 days of viral spread were repeated. Survival analysis to Day 180 was performed on 10 mice each from Groups 3-7.

| Group Assignments | | | |
|---|---|---|---|
| | | N per analysis category | |
| Group | Treatment | Survival | Scheduled Sacrifice |
| 1 | Control (vehicle injection) + PBS | | 1 at day 10 |
| 3 | AC3-yCD2(V) E6 + PBS | 10 | |
| 4 | AC3-yCD2(V) E6 + 5-FC | 10 | 3 at day 10, 24, 38, and 52 |
| 6 | AC3-yCD2(V) E5 + 5-FC | 10 | 3 at day 10, 24, 38, and 52. |
| 7 | AC3-yCD2(V) E5 + PBS | 10 | |
| 8 (no tumor) | 5-FC | | 1 at day 10, 24, 38, and 52 |
| TOTAL | | 40 | 29 |

AC3-yCD2(V) (5 µL) was infused at 0.33 µL per minute (15 minutes, followed by a hold of 5 minutes) intracranially through an injection cannula with a 3.5 mm projection inserted through the guide cannula. 5-FC (500 mg/kg/dose) or PBS (800 µL) was administered IP BID for 4 consecutive days starting at days 10, 24, 38, and 52.

Short Term Experiments to Determine the Level of Viral Genome and Super-Infection in Tu2449 Tumors In Vivo.

The study consisted of 6 groups of female mice (see Table below). All groups underwent intracranial administration into the right striatum of 1E4 TU-2449 cells administered/mouse on Day 0. At Day 4, all groups received intracranial/intratumoral administration of AC3-YCD2(V) vector at 2.4E6 TU/5 ul (Lot#T511019) or PBS buffer control. Two days of BID 5-FC administration began when the mice started losing weight (approximately 15 days post-tumor implantation). Group 5 had 5-FC delivered by oral gavage (OG) and all other groups IP. One more dose of 5-FC was given 1 hour before sacrifice the following day. From each brain, the tumor was isolated and processed directly into RIPA buffer for analysis of 5-FC and 5-FU by HPLC. A small portion of the tumor was retained for western blot analysis.

| Group Assignments and Dose Levels | | | | | |
|---|---|---|---|---|---|
| Group | Treatment | Route | TX | Route | Dosing | N |
| 1 | AC3-YCD2(V) | IC | NONE | N/A | N/A | 3 |
| 2 | PBS | IC | 5FC | IP | 250 mg/kg | 4 |
| 3 | PBS | IC | 5FC | IP | 500 mg/kg | 2 |
| 4 | AC3-YCD2(V) | IC | 5FC | IP | 250 mg/kg | 3 |
| 5 | AC3-YCD2(V) | IC | 5FC | OG | 250 mg/kg | 2 |
| 6 | AC3-YCD2(V) | IC | 5FC | IP | 500 mg/kg | 2 |
| | Total animals | | | | | 16 |

IC—intracranial;
IP—intraperitoneal;
OG—oral gavage

AC3-yCD2(V) (5 µL) was infused at 0.33 µL per minute (15 minutes, followed by a hold of 5 minutes) intracranially at the same coordinates as TU-2449 cells were injected. 5-FC or PBS was administered IP or OG BID for 2consecutive days and 1 hour before sacrifice.

Tissue Processing Procedures.

From each brain, tumors were isolated and trimmed if large enough for multiple analyses (more than 0.05 g). Tumors sections for HPLC analysis were crushed in a 1.5 mL centrifuge tube using a plunger from a 1 mL syringe. Crushed samples were mixed with 150 uL RIPA buffer and vortexed vigorously for 10 minutes. Samples were spun at 4° C. at 20000 rcf for 10 minutes. Supernatants were removed and mixed thoroughly with 150 uL of 10% trichloroacetic acid and spun as above. Supernatants were removed for analysis by the Agilent HPLC unit with a Hypersil BDS C18 column run isocratically at 1 mL/min with 95% Buffer A containing 50 mM ammonium phosphate and 0.1% tetra-n-butylammoniumperchlorate with pH adjustment of the buffer to 2.1 with phosphoric acid and 5% Solvent B which is 100% methanol (see WI RD-053). The run time is 5 minutes with each sample run twice. The photodiode detector array scans from 190 to 350 nm with chromatograms selected to display at 285 nm for 5-fluorocytosine and 264 nm for 5-fluorouracil. Data was expressed in relative milli absorbance units (mAU) of peak area from the chromatograms.

Protein Gels and Western Blots.

When sufficient tumor was available, tumor fragments for protein gels and Western blots were mixed with a separate aliquot of RIPA lysis buffer, and 20 ug of total protein from each sample was electrophoresed on polyacrylamide gels, Western blotted and the blot developed with sheep anti-yeast CD antibody as in Example 30. Western blot data was scanned and quantified using BioRad Quantity One software (version 4.6.7).

QPCR on Tumor Fragments.

Remaining pellets, after supernatants were removed for HPLC analysis, were extracted for genomic DNA. Samples were analyzed by qPCR for proviral integration copy number using primers and probe for MLV LTR as in example 30. Samples were also analyzed in parallel using previously characterized primers and probes for the amphotropic env gene (Env2) and the CD gene (yCD2).

yCD2 Primer and Probe Set:

5' AC3-YCD2(V) yCD2 Primer:
(SEQ ID NO: 67)
ATCATCATGTACGGCATCCCTAG

3' AC3-YCD2(V) yCD2 Primer:
(SEQ ID NO: 68)
TGAACTGCTTCATCAGCTTCTTAC yCD2 Probe:
(SEQ ID NO: 69)
/5FAM/TCATCGTCAACAACCACCACCTCGT/3BHQ_1/

These primers and probe target and amplify the CD gene exclusively.

Env2 Primer and Probe Set:

Env2-Forward:
(SEQ ID NO: 70)
AACCTCAACCTCCCCTACAAGT

Env2-Reverse:
(SEQ ID NO: 71)
GTTAAGCGCCTGATAGGCTC

Env2-Probe:
(SEQ ID NO: 72)
/5TEX615/AGCCACCCCCAGGAACTGGAGATAGA/3IAbRQSp/

These primers and probe target and amplify the envelope (Env) gene exclusively.

Results. Survival Analysis.

The Kaplan Meyer survival plot is shown in FIG. 32. The median survival of AC3-yCD2(V) control groups treated with PBS (Group 3 and 7) was approximately 33-38 days. The survival medians of mid and high dose AC3-yCD2(V) in combination with 5-FC (Group 6 and 4) were not reached before sacrifice at 189 days. Log-Rank (Mantel-Cox) pairwise comparison showed no difference in survival between the two control groups; AC3-yCD2(V) E5 dose plus PBS (Group 7) and AC3-yCD2(V) E6 dose plus PBS (Group 3).

AC3-yCD2(V) treatment at both dose levels in combination with 5-FC resulted in prolonged survival. A statistically significant survival advantage was observed for AC3-yCD2(V) E5 plus 5-FC (Group 6) treated mice compared to vector plus PBS control (Group 7) mice (p<0.0354, hazard ratio 0.2605, 95% CI 0.07439 to 0.9119). A statistically significant survival advantage was observed for AC3-yCD2(V) E6 plus 5-FC (Group 4) treated mice compared to vector plus PBS control (Group 3) mice (p<0.0036, hazard ratio 0.1130, 95% CI 0.02598 to 0.4911).

Short Term Experiments to Determine the Level of Viral Genome and Super-Infection in Tu2449 Tumors In Vivo HPLC Analysis.

In vivo conversion of 5-FC to 5-FU was detected by HPLC in all groups dosed with Toca511 and 5-FC (FIG. 33). Group 1 that was given AC3-yCD2(V) but no 5-FC had neither 5-FC nor 5-FU detectable signals as expected (FIG. 33). The small counts observed (47-84) for 5-FC is attributable to background from nearby peaks on the chromatography trace. Groups 2 and 3 that were not dosed with AC3-yCD2(V) but dosed with varying levels of 5-FC had detectable 5-FC signals but no signal for 5-FU. Group 4 mice dosed with AC3-yCD2 (V) and 5-FC IP and Group 5 mice dosed with AC3-yCD2(V) and 5-FC OG had comparable signal levels of 5-FU and very low or background levels of 5-FC. Group 6 mice dosed with Toca-511 and high levels of 5-FC showed readily detectable levels of 5-FU and low signal for 5-FC.

CD Western Blot Analysis.

Tissue samples from isolated TU-2449 tumors were processed for western blot analysis of CD expression. All groups (1, 4, and 5) treated with AC3-yCD2(V) had readily observable CD expression while Group 2 that was not given AC3-yCD2(V) did not have detectable CD expression (FIG. 34).

PCR Analysis of Genomic DNA Isolated from Tumors.

The remaining pellets, after supernatants were removed for HPLC analysis, were extracted for genomic DNA. Samples were analyzed by quantitative PCR for proviral integration using the standardized assay and MLV-LTR primers and probe. Parallel assays using the envelope and CD gene primers and probes analyses gave similar C(t) values showing that the viral genome appeared quite stable. An in vitro transduced cell line served as positive control. The negative control was genomic tumor DNA from Group 2 that was not dosed with AC3-yCD2(V) and did not have detectable signal for any of the qPCR protocols.

Summary Table of relative CD protein levels, viral vector copy #, and relative levels of 5-FU production

| Group | Mouse # | Relative CD protein levels | Copies#/ diploid genome | 5-FU (relative peak area units) |
|---|---|---|---|---|
| Group 1 | 194 | 21,746 | 1.4 | 0 |
|  | 199 | No Data | 14.6 | 0 |
| Group 2 | 191 | 162 | 0 | 0 |
|  | 187 | 75 | 0 | 0 |
|  | 188 | −453 | 0 | 0 |
| Group 4 | 185 | 17,349 | 1.8 | 1642 |
|  | 200 | 45,446 | 7.3 | 1576 |
| Group 5 | 189 | 25,417 | 3.7 | 942 |
|  | 198 | 23,660 | 6.6 | 1371 |

For samples with enough starting material for all three analyses to be done, the relationship between integrated MLV copy number, expression of CD, and the amount of 5-FC to 5-FU conversion is summarized in the above table (199 did not have material for Western analysis). The relative CD protein levels (estimated from Western blots) vary over a three-fold range and the DNA copy number over a 5-fold range. There is some correlation between DNA copy number and relative level of CD expression. All of the tumors have vector copy numbers/genome above 1, showing that even at this early time-point after vector administration (13-14 days) superinfection of tumor cells is a usual occurrence, and may contribute to observed therapeutic effects (FIG. 32). The CD values displayed represent the values after average background correction, and the Group 2 numbers represent the variability in that background.

This study supports the proposed mechanism of action and shows that this efficacy can be attributed to the conversion of the 5-FC prodrug into the anticancer drug 5-FU after delivery of the CD gene by AC3-yCD2(V). Using the TU-2449 mouse glioma model, AC3-yCD2(V) treatment in combination with 5-FC resulted in efficient in vivo conversion of 5-FC into 5-FU. 5-FC was converted efficiently into 5-FU at two dose levels (500 and 250 mg/kg) as 5-FC levels were at least ten fold lower than the controls, and 5-FU levels were readily detectable in AC3-yCD2(V) treated but not in the untreated controls. IP or OG delivery of 5-FC did not affect the efficiency of conversion. Tumors isolated from mice given AC3-yCD2(V) had observable expression of CD protein that had some correlation with the numbers of copies of the vector genome. The number of integrated vector genomes ranged from 1.4 to 15 copies/diploid genome (mean: 5.9). The infection here was the result of about 12 days infection and previous experiments with GFP vectors in other models suggest that this corresponds to infection of approximately 50% of the cells in the tumor, giving an adjusted vector copy number/cell of 11.8 copies/diploid genome. Typical tumors are not diploid but are triploid or further polyploid with a genome larger than the diploid genome. This would further increase the actual vector copy number per cell. The experiments described here also provide a method of testing a recombinant replication competent retrovirus for the property of multiple infections of a target cell population. These observations support the conclusion that AC3-yCD2(V) is efficiently delivering a functional CD gene for expression in glioma cells. In the efficacy study with this model, almost no spread of vector from the site of injection (tumor in the right cerebrum) was observed in the first 24 days. The observations in this study show that over the same initial period of time there is extensive viral vector infection of the tumor, showing that infection is quite tumor specific, and that already at this early time-point there is extensive super-infection of the tumor cells by the viral vector.

Example 32

Clonal Analyses of HT1080 Cell Line Infected with AC3-yCD2(V) Shows That the Majority of the Clones Have Multiple Copies of the Viral Vector Genome and were Susceptible to Super-Infection The human sarcoma line HT1080 (ATCC: CCL 121) was grown in tissue culture under standard culture conditions. 2E7 cells were infected with AC3-yCD2(V) made by transient transfection on 293 cells, at a multiplicity of 0.1, allowed to grow for 14 days, and frozen down as a pool. About 1 month later cells were thawed and clonal cell lines from this culture were isolated by limiting dilution in 96 well dishes at 0.3 cells/well. The clones that grew out were expanded and analyzed by qPCR with the MLV LTR primers for vector genome copy number per microgram DNA in triplicate. This was converted to copy number/diploid genome by dividing by 150,000, as described in example 30. The Table below lists the clones that were analyzed and the corresponding copy number for the viral vector genome. Only 1 of 10 clones (13-5) has approximately 1 copy of the viral genome per diploid genome. The range was 0.9 to 20.4 copies/cell and the mean copy number was 10.6 copies/cell. Typical tumors are not diploid but are triploid or further polyploid with a genome larger than the diploid genome. This would further increase the actual vector copy number per cell. It is well known that normally a viral infection of this nature leads to a single or few copies of viral genome/cell, due to resistance to superinfection through receptor masking or down regulation (see, for example, Ch3 p104 of "Retroviruses" J M Coffin, S H Hughes & H E Varmus, 1997 Cold Spring Harbor Laboratory Press, Cold Spring Harbor N.Y.).

Listing of viral vector copy number in infected HT1080 clones infected with AC3-yCD2 and expanded.

| Sample # | Test article | Average copy number/genome |
|---|---|---|
| 1 | Negative control (HT1080) | 0 |
| 2 | Positive control (recently transduced HT1080 pool) | 1.89 |
| 3 | Clone# 3-5 | 18.26 |
| 4 | Clone# 4-1 | 5.28 |
| 5 | Clone# 7-1 | 18.87 |
| 6 | Clone# 8-3 | 14.04 |
| 7 | Clone# 9-1 | 15.29 |
| 8 | Clone# 10-1 | 9.73 |
| 9 | Clone# 11-1 | 20.44 |
| 10 | Clone# 12-6 | 6.08 |
| 11 | Clone# 13-5 | 0.93 |
| 12 | Clone# 19-2 | 5.24 |

Therefore this is an unexpected and surprising result that confirms the in vivo tumor model data of Examples 30 and 31. More particularly, the data demonstrate that this virus allows multiple super-infections in the great majority of the cells it infects, unlike normal MLV infection. The experiments described here also provide a method of testing a recombinant replication competent retrovirus for the property of multiple infections of a target cell population.

Example 33 miRNA Knockdown Experiments

Plasmid Construction.

Figure 11A:
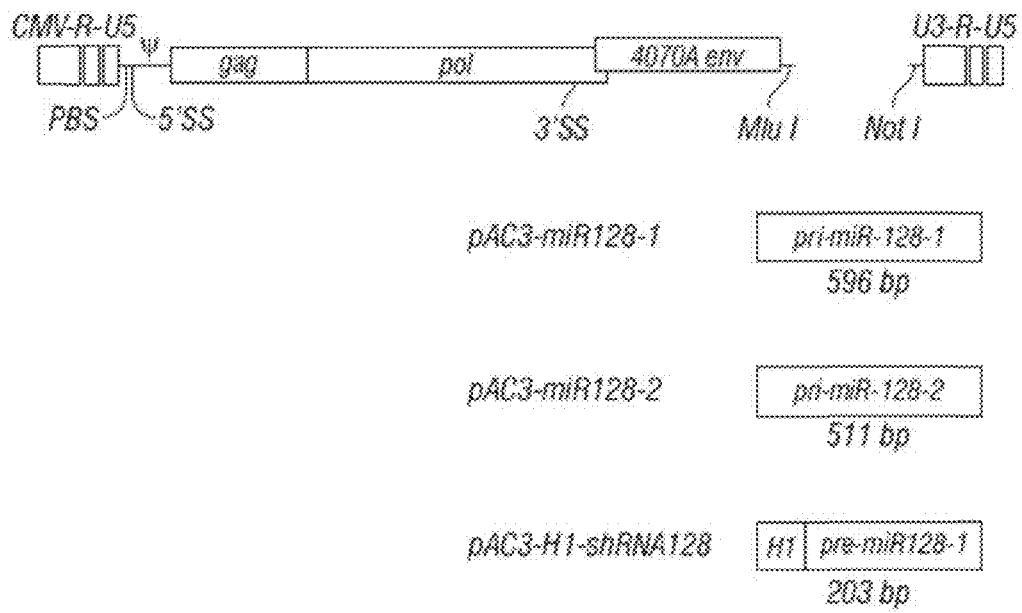
FIG. 11A-E shows vector maps and miRNA results. A. is a schematic vector map of the MLV retroviral vector pAC3 backbone containing polynucleotide sequences of human primary precursor miR-128-1, human primary precursor miR-128-2 and human precursor miR-128 linked to a human H1 promoter, designated pAC3-miR128-1, pAC3-miR-128-2, and pAC3-H1-shRNAmiR128, respectively. B. is a schematic vector map of the MLV retroviral vector pAC3-yCD2 backbone containing polynucleotide sequences of a human precursor miR-128 linked to a human H1 promoter, designated pAC3-yCD2-H1-shRNAmiR128. C. shows a schematic vector map of the MLV retroviral vector pAC3 backbone containing polynucleotide sequences of human primary precursor miR-142-3pT. D. shows sequences for 142-3p (SEQ ID NOs: 35 and 36) and primers (SEQ ID NO:41 and 42). E. shows results from transformation with a vector containing miR-142-3pT.
Figure 11B:
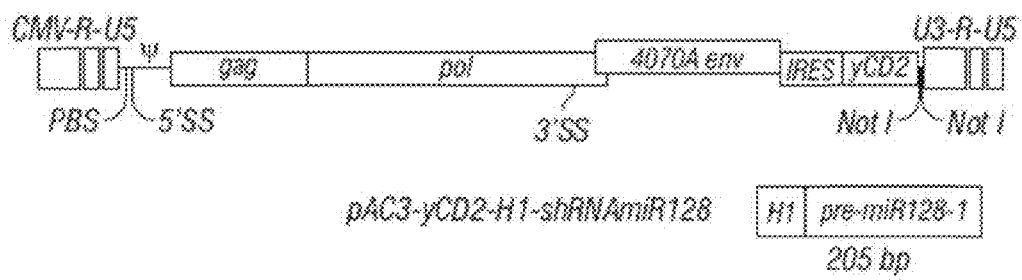
Figures 11C, 11D:
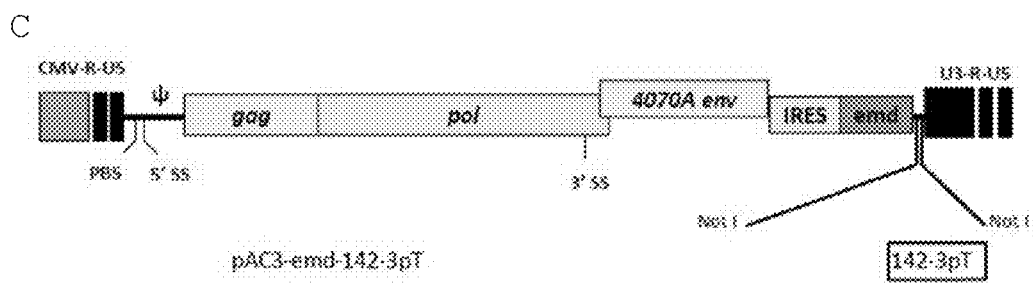
Figure 11E:
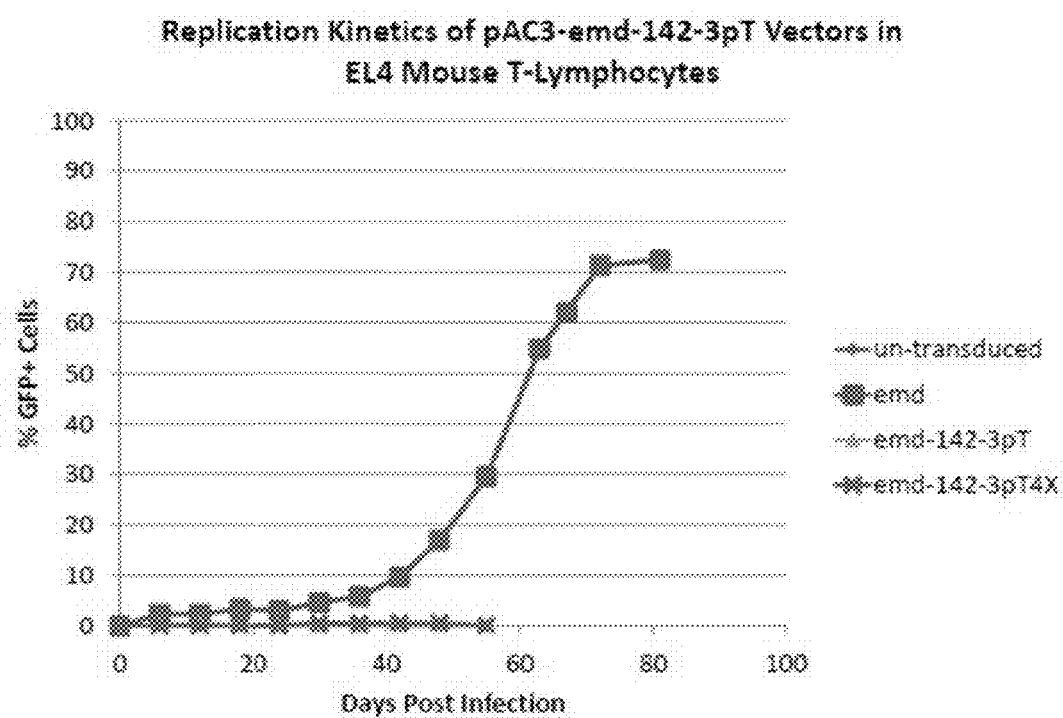

Single or four tandem repeats of 142-3pT completely complementary to the sequence of miR 142-3p were synthesized with an endonuclease restriction site Not I at both ends and cloned into the corresponding Not I site downstream of the IRES-GFP cassette in the RCR vector (FIG. 11C-D). The sequence of the single 142-3pT: gcggccgcGTCGAC TCCATAAAGTAGGAAACACTACAgcggccgc (SEQ ID NO:35) and the sequence of four tandem repeats of 142-3pT henceforth 142-3pT4X: gcggccgcGTCGAC TCCATAAAGTAGGAAACACTACACGAT TCCATAAAGTAGGAAACACTACAaccg gt TCCATAAAGTAGGAAACACTACATCAC TCCATAAAGTAGGAAACACTACAgcggccgc (SEQ ID NO:36) were synthesized by BioBasic Inc. The underlined sequences are sequence complementary to miR-142-3p in both mouse and human. The sequence of the synthesized DNA fragments were confirmed before and after cloning into the pAC3-emd vector using the primers: 5'-CTGATCT-TACTCTTTGGACCTTG-3' (SEQ ID NO:62), and 5'-CCCCTTTTTCTGGAGACTAAATAA-3' (SEQ ID NO:63).

Cell Culture.

Human astrocytoma cells U-87MG, human prostate adenocarcinoma cells PC3, human lymphoblastic leukemia cells Sup-T1, human histocytic lymphoma cells U-937 and mouse T lymphoblastic cells were obtained from ATCC. 293T, U-87MG, PC3 and EL-4 cells were cultured in complete DMEM medium containing 10% FBS (Hyclone), sodium pyruvate, glutamax, and penicillin/streptomycin (Cellgro). Sup-T1 and U-937 cells were cultured in complete RPMI medium containing 10% FBS, glutamx and penicillin/ streptomycin.

Virus Production.

Virus stock was produced by transient transfection of 293T cells using calcium phosphate precipitation method. Cells were seeded at 2e6 cells per 10 cm petri dish the day before transfection. Cells were transfected with 20 µg of pAC3-emd, pAC3-emd-142-3pT or pAC3-emd-142-3pT4X the next day. Eighteen hours post transfection, cells were washed with PBS twice and incubated with fresh complete culture medium. Viral supernatant was collected approximately 42 hours post transfection and filtered through a 0.45 µm. Viral supernatant were stored in aliquots at −80° C.

Viral infection was performed by adding viral stock at 1:50 dilution in 1mL total volume in each well. AZT at 40 µm was added to prevent further viral replication and cells were harvested 48 h post infection for gDNA isolation. Viral titer was determined by quantitative real time PCR (qPCR) using the following primer set and probe which will bind to all proviral DNA derived from the vectors as well as proviral DNA containing deleted IRES-GFP cassette: 5'-AGCCCACAAC-CCCTCACTC-3' (SEQ ID NO:64), 5'-TCTCCCGAT CCCGGACGA-3' (SEQ ID NO:65), and 5'-FAM-CCC CAA ATG AAA GAC CCC CGC TGA CG-BHQ-3' (SEQ ID NO:66). The reaction was performed in a total volume of 20 µL containing 2× iQ SuperMix (BioRad); 0.3 µM of each primer and 0.1 µM of the probe. PCR reaction was performed in triplicates using CFX-96 (BioRad) thermo cycler with the following parameters: 95° C. 10 min; and 40 cycles of 95° C. 15 s; 60° C. 1 min. Viral titer reported in transduction unit per milliliter (TU/mL) was determined by calculation of Ct values derived from a standard curve ranging from 1e7 copies to 10 copies of plasmid DNA and from known amount of gDNA input, number of cells, and dilution factor of viral stock per reaction used in each reaction.

Viral Replication Kinetics.

To monitor viral replication in infected cells, 2e5 U-87MG cells, or 1e6 EL4, Sup-T1, and U-937 cells were infected with pAC3-emd, pAC3-emd-142-3pT, or pAC3-emd-142-3p4X at an MOI of 0.1 (U-87MG cells) or an MOI of 2 (EL4, Sup-T1, and U-937 cells). Every 3-4 days, a portion of cells were passaged for continuing monitoring of viral replication, and a portion of cells were harvested for GFP expression by flow cytometric analysis. Cells harvested for flow cytometric analysis were washed with PBS and centrifuged at 1000 rpm for 5 minutes. Cell pellets were resuspended in PBS containing 1% PFA. Percentage of GFP % cells were measured by Becton Dickison Canton II using FL1 channel. Viral replication kinetics were obtained by plotting % GFP positive cells over time.

Vector Stability Assay and Amplification of IRES-GFP cassette.

U-87MG cells at 5e4 cells per well in 6-well plate were infected with tock virus at an MOI of 0.1. At d4 post infection viral supernatant from ~70% infected cells were collected and filtered through a 0.45 µm filter unit. A 1:10 dilution of the viral supernatant was then used to infected fresh U-87MG cells seeded the night before. Four-day infected U-87 cells were harvested for gDNA isolation for IRES-GFP PCR. This virus infection cycle was repeated at least 12 times.

gDNA extraction was carried out using the Maxwell 16 DNA purification kit (Promega). DNA concentration and quality was determined by spectrophotometer using Nanodrop 1000 (Thermo Scientific). To assess the integrity of the IRES-GFP cassette in proviral DNA, standard PCR was performed using the following primer set: 5'-CTGATCT-TACTCTTTGGACCTTG-3' (SEQ ID NO:62), and 5'-CCCC TTTTT CTGGAGACTAAATAA-3' (SEQ ID NO:63). The reaction was performed in total volume of 25 µL containing 0.4 µM of each primer, 0.4 mM dNTP and 2.5 unit of Super-Taq (Ambion), and the PCR reaction was performed with the following parameters: 95° C. 10 min; and 40 cycles of 95° C. 15 s; 60° C. 1 min. 95° C. 2 min and 40 cycles of 95° C., 15 s; 55° C., 30 s; 72° C., 1 min, followed by 72° C., 5 min. One fifth of the PCR reaction was loaded on 1% agarose gel to resolve PCR products. The expected PCR product of an intact IRES-GFP cassette is ~1.2 kb. PCR products less than 1.2 kb indicates partial or complete deletion in the IRES-GFP region.

For experiment in which the PCR products were excised from the gel for sequencing, gel extraction kit (Qiagen) was used to obtained PCR product. The same set of primers used for PCR reaction was used for PCR product sequencing.

miRNA Expression Assay.

miRNA-enriched RNA was extracted from U-87MG, 293T, Sup-T1, U-937 and Sup-T1 cells by using the mirVana miRNA isolation kit followed by DNase treatment (Ambion) according to manufacturer's protocols. Taqman microRNA reverse transcription kit was used with RT primer for miR-142-3p (assay ID #000464) and RNU6 (assay ID#001093)

and sno135 (assay #001230) as endogenous controls for human and mouse cell lines, respectively, to produce cDNA for TaqMan microRNA assay (assay ID#TM000464), (Ambion). Reverse transcription and quantitative PCR reactions were set up and carried out according to manufacturer's protocols. $2^{-\Delta Ct}$ was calculated to obtain miR-142-3p expression relative to endogenous control.

Having confirmed the expression of miR142-3p in hematopoietic-lineage derived cells, cells were then infected with pAC3-emd, pAC3-emd-142-3pT and pAC3-emd-142-3pT4X vectors, respectively, at MOI 2. The data showed that in EL4 cells viral replication of parental vector pAC3-emd was extremely slow in early time with a lag phase that lasted up to 30 days and reached to maximal infectivity (~70% infectivity) by day 80 post infection. In contrast, GFP expression and viral replication of pAC3-emd-142-3pT and pAC3-emd-142-3pT4X vectors were completely abrogated in early time during infection (FIG. 11D).

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A recombinant replication competent retrovirus comprising:
    a retroviral GAG protein;
    a retroviral POL protein;
    a retroviral envelope;
    a retroviral polynucleotide sequence comprising a Long-Terminal Repeat (LTR) sequence at the 3' end of the retroviral polynucleotide sequence, wherein the 3' LTR comprises a sequence that is at least 98% identical to the sequence from about nucleotide 9405 to about 9998 of SEQ ID NO:19 or 22, a promoter sequence at the 5' end of the retroviral polynucleotide sequence, said promoter being suitable for expression in a mammalian cell, a gag nucleic acid domain, a pol nucleic acid domain and an env nucleic acid domain, wherein the promoter, gag, pol and env domains comprise a sequence that is at least 98% identical to the sequence from about 1 to about 8323 of SEQ ID NO:19 or 22 and wherein the retroviral polynucleotide sequence lacks 70 base pairs of MLV sequence downstream from the 3'LTR compared to a pACE vector of SEQ ID NO:21;
    a cassette comprising an internal ribosome entry site (IRES) comprising a sequence that is at least 98% identical to the sequence from about 8327 to 8876 of SEQ ID NO:19 or 22, operably linked to a heterologous polynucleotide, wherein the cassette is positioned 5' to the 3' LTR and 3' to the env nucleic acid domain encoding the retroviral envelope and wherein SEQ ID NO: 19 and 22 lack small repeats on either side of the cassette compared to the pACE vector of SEQ ID NO:21; and
    cis-acting sequences necessary for reverse transcription, packaging and integration in a target cell,
    wherein the RCR maintains higher replication competency after 6 passages compared to a pACE vector comprising SEQ ID NO:21.

2. The recombinant replication competent retrovirus of claim 1, wherein the virus is capable of infecting a target cell multiple times resulting in an average number of copies/diploid genome of 5 or greater.

3. The retrovirus of claim 1, wherein the retroviral polynucleotide sequence is derived from a virus selected from the group consisting of murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus(XMRV), avian reticuloendotheliosis virus (REV), or Gibbon ape leukemia virus (GALV).

4. The retrovirus of claim 1, wherein the retroviral envelope is an amphotropic MLV envelope.

5. The retrovirus of claim 1, wherein the retrovirus is a gammaretrovirus.

6. The retrovirus of claim 1, wherein the promoter comprises a CMV promoter having a sequence as set forth in SEQ ID NO:19, 20 or 22 from nucleotide 1 to about nucleotide 582.

7. The retrovirus of claim 1, wherein the promoter comprises a CMV-R-U5 domain polynucleotide.

8. The retrovirus of claim 7, wherein the CMV-R-U5 domain comprises the immediately early promoter from human cytomegalovirus linked to an MLV R-U5 region.

9. The retrovirus of claim 8, wherein the CMV-R-U5 domain polynucleotide comprises a sequence as set forth in SEQ ID NO:19, 20 or 22 from about nucleotide 1 to about nucleotide 1202 or sequences that are at least 99% identical to a sequence as set forth in SEQ ID NO:19, 20 or 22, wherein the polynucleotide promotes transcription of a nucleic acid molecule operably linked thereto.

10. The retrovirus of claim 1, wherein the gag polynucleotide is derived from a gammaretrovirus.

11. The retrovirus of claim 10, wherein the gag nucleic acid domain comprises a sequence from about nucleotide number 1203 to about nucleotide 2819 of SEQ ID NO: 19 or 22 or a sequence having at least 99% or 99.8% identity thereto.

12. The retrovirus of claim 1, wherein the pol domain of the polynucleotide is derived from a gammaretrovirus.

13. The retrovirus of claim 12, wherein the pol domain comprises a sequence from about nucleotide number 2820 to about nucleotide 6358 of SEQ ID NO:19 or 22 or a sequence having at least 99% or 99.9% identity thereto.

14. The retrovirus of claim 1, wherein the env domain comprises a sequence from about nucleotide number 6359 to about nucleotide 8323 of SEQ ID NO:19 or 22 or a sequence having at least 99% or 99.8% identity thereto.

15. The retrovirus of claim 1, wherein the IRES is derived from an encephalomyocarditis virus.

16. The retrovirus of claim 15, wherein the IRES comprises a sequence from about nucleotide number 8327 to about nucleotide 8876 of SEQ ID NO:19 or 22 or a sequence having at least 99% identity thereto.

17. The retrovirus of claim 1, wherein the heterologous polynucleotide comprises a polynucleotide having a sequence as set forth in SEQ ID NO:3, 5, 11, 13, 15 or 17.

18. The retrovirus of claim 1, wherein the heterologous polynucleotide encodes a polypeptide comprising a sequence as set forth in SEQ ID NO:4.

19. The retrovirus of claim 1, wherein the heterologous polynucleotide is human codon optimized and encodes a polypeptide as set forth in SEQ ID NO:4.

20. The retrovirus of claim 1, wherein the heterologous polynucleotide comprises a sequence as set forth in SEQ ID NO: 19 or 22 from about nucleotide number 8877 to about 9353.

21. The retrovirus of claim 1, wherein the 3' LTR is derived from a gammaretrovirus.

22. The retrovirus of claim 1, wherein the retroviral polynucleotide comprises a sequence as set forth in SEQ ID NO:19, 20 or 22.

23. The retrovirus of claim 22, wherein the 3' LTR comprises a U3-R-U5 domain.

24. The retrovirus of claim 23, wherein the 3' LTR comprises a sequence as set forth in SEQ ID NO:19 or 22 from about nucleotide 9405 to about 9998 or a sequence that is at least 99.5% identical thereto.

25. The retrovirus of claim 1, wherein the heterologous polynucleotide encodes an immunopotentiating cytokine.

26. The retrovirus according to claim 25, wherein the immunopotentiating cytokine is selected from the group consisting of interleukins 1 through 15, interferon, tumor necrosis factor (TNF), and granulocyte-macrophage-colony stimulating factor (GM-CSF).

27. The retrovirus according to claim 1, wherein the heterologous polynucleotide encodes a polypeptide that converts a nontoxic prodrug into a toxic drug.

28. The retrovirus according to claim 27, wherein the polypeptide that converts a nontoxic prodrug into a toxic drug is thymidine kinase, purine nucleoside phosphorylase (PNP), or cytosine deaminase.

29. The retrovirus according to claim 1, wherein the heterologous polynucleotide encodes a receptor domain, an antibody, or antibody fragment.

30. The retrovirus according to claim 1, wherein the heterologous polynucleotide comprises an inhibitory polynucleotide.

31. The retrovirus according to claim 30, wherein the inhibitory polynucleotide comprises an miRNA, RNAi or siRNA sequence.

32. The retrovirus of claim 1, wherein the heterologous polynucleotide has been human codon optimized.

33. The retrovirus of claim 1, wherein said retrovirus further comprises an miRNA, RNAi or siRNA sequence.

* * * * *

SEQUENCE LISTING

```
<160> NUMBER OF SEQ ID NOS: 72

<210> SEQ ID NO 1
<211> LENGTH: 477
<212> TYPE: DNA
<213> ORGANISM: Saccharomyces cerevisiae
<220> FEATURE:
<221> NAME/KEY: CDS
<222> LOCATION: (1)..(477)

<400> SEQUENCE: 1 atg gtg aca ggg gga atg gca agc aag tgg gat cag aag ggt atg gac        48
Met Val Thr Gly Gly Met Ala Ser Lys Trp Asp Gln Lys Gly Met Asp
1               5                   10                  15 att gcc tat gag gag gcg gcc tta ggt tac aaa gag ggt ggt gtt cct        96
Ile Ala Tyr Glu Glu Ala Ala Leu Gly Tyr Lys Glu Gly Gly Val Pro
            20                  25                  30 att ggc gga tgt ctt atc aat aac aaa gac gga agt gtt ctc ggt cgt       144
Ile Gly Gly Cys Leu Ile Asn Asn Lys Asp Gly Ser Val Leu Gly Arg
        35                  40                  45 ggt cac aac atg aga ttt caa aag gga tcc gcc aca cta cat ggt gag       192
Gly His Asn Met Arg Phe Gln Lys Gly Ser Ala Thr Leu His Gly Glu
    50                  55                  60 atc tcc act ttg gaa aac tgt ggg aga tta gag ggc aaa gtg tac aaa       240
Ile Ser Thr Leu Glu Asn Cys Gly Arg Leu Glu Gly Lys Val Tyr Lys
65                  70                  75                  80 gat acc act ttg tat acg acg ctg tct cca tgc gac atg tgt aca ggt       288
Asp Thr Thr Leu Tyr Thr Thr Leu Ser Pro Cys Asp Met Cys Thr Gly
                85                  90                  95 gcc atc atc atg tat ggt att cca cgc tgt gtt gtc ggt gag aac gtt       336
Ala Ile Ile Met Tyr Gly Ile Pro Arg Cys Val Val Gly Glu Asn Val
            100                 105                 110 aat ttc aaa agt aag ggc gag aaa tat tta caa act aga ggt cac gag       384
Asn Phe Lys Ser Lys Gly Glu Lys Tyr Leu Gln Thr Arg Gly His Glu
        115                 120                 125 gtt gtt gtt gtt gac gat gag agg tgt aaa aag atc atg aaa caa ttt       432
Val Val Val Val Asp Asp Glu Arg Cys Lys Lys Ile Met Lys Gln Phe
    130                 135                 140 atc gat gaa aga cct cag gat tgg ttt gaa gat att ggt gag tag           477
Ile Asp Glu Arg Pro Gln Asp Trp Phe Glu Asp Ile Gly Glu
145                 150                 155

<210> SEQ ID NO 2
<211> LENGTH: 158
<212> TYPE: PRT
<213> ORGANISM: Saccharomyces cerevisiae

<400> SEQUENCE: 2

Met Val Thr Gly Gly Met Ala Ser Lys Trp Asp Gln Lys Gly Met Asp
1               5                   10                  15
```

```
Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155
```

<210> SEQ ID NO 3
<211> LENGTH: 477
<212> TYPE: DNA
<213> ORGANISM: Artificial Sequence
<220> FEATURE:
<223> OTHER INFORMATION: Engineered cytosine deaminase
<220> FEATURE:
<221> NAME/KEY: CDS
<222> LOCATION: (1)..(477)

<400> SEQUENCE: 3

```
atg gtg aca ggg gga atg gca agc aag tgg gat cag aag ggt atg gac      48
Met Val Thr Gly Gly Met Ala Ser Lys Trp Asp Gln Lys Gly Met Asp
1               5                   10                  15 att gcc tat gag gag gcg tta tta ggt tac aaa gag ggt ggt gtt cct      96
Ile Ala Tyr Glu Glu Ala Leu Leu Gly Tyr Lys Glu Gly Gly Val Pro
            20                  25                  30 att ggc gga tgt ctt atc aat aac aaa gac gga agt gtt ctc ggt cgt     144
Ile Gly Gly Cys Leu Ile Asn Asn Lys Asp Gly Ser Val Leu Gly Arg
        35                  40                  45 ggt cac aac atg aga ttt caa aag gga tcc gcc aca cta cat ggt gag     192
Gly His Asn Met Arg Phe Gln Lys Gly Ser Ala Thr Leu His Gly Glu
    50                  55                  60 atc tcc act ttg gaa aac tgt ggg aga tta gag ggc aaa gtg tac aaa     240
Ile Ser Thr Leu Glu Asn Cys Gly Arg Leu Glu Gly Lys Val Tyr Lys
65                  70                  75                  80 gat acc act ttg tat acg acg ctg tct cca tgc gac atg tgt aca ggt     288
Asp Thr Thr Leu Tyr Thr Thr Leu Ser Pro Cys Asp Met Cys Thr Gly
                85                  90                  95 gcc atc atc atg tat ggt att cca cgc tgt gtc atc ggt gag aac gtt     336
Ala Ile Ile Met Tyr Gly Ile Pro Arg Cys Val Ile Gly Glu Asn Val
            100                 105                 110 aat ttc aaa agt aag ggc gag aaa tat tta caa act aga ggt cac gag     384
Asn Phe Lys Ser Lys Gly Glu Lys Tyr Leu Gln Thr Arg Gly His Glu
        115                 120                 125 gtt gtt gtt gtt gac gat gag agg tgt aaa aag tta atg aaa caa ttt     432
Val Val Val Val Asp Asp Glu Arg Cys Lys Lys Leu Met Lys Gln Phe
    130                 135                 140 atc gat gaa aga cct cag gat tgg ttt gaa gat att ggt gag tag         477
Ile Asp Glu Arg Pro Gln Asp Trp Phe Glu Asp Ile Gly Glu
```

<210> SEQ ID NO 4
<211> LENGTH: 158
<212> TYPE: PRT
<213> ORGANISM: Artificial Sequence
<220> FEATURE:
<223> OTHER INFORMATION: Synthetic Construct

<400> SEQUENCE: 4

```
Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu
145                 150                 155
```

<210> SEQ ID NO 5
<211> LENGTH: 480
<212> TYPE: DNA
<213> ORGANISM: Artificial Sequence
<220> FEATURE:
<223> OTHER INFORMATION: Human codon optimized cytosine deaminase
<220> FEATURE:
<221> NAME/KEY: CDS
<222> LOCATION: (1)..(480)

<400> SEQUENCE: 5

```
atg gtg acc ggc ggc atg gcc tcc aag tgg gat caa aag ggc atg gat      48
Met Val Thr Gly Gly Met Ala Ser Lys Trp Asp Gln Lys Gly Met Asp
1               5                   10                  15 atc gct tac gag gag gcc gca ctg ggc tac aag gag ggc ggc gtg cct      96
Ile Ala Tyr Glu Glu Ala Ala Leu Gly Tyr Lys Glu Gly Gly Val Pro
            20                  25                  30 atc ggc ggc tgt ctg atc aac aac aag gac ggc agt gtg ctg ggc agg     144
Ile Gly Gly Cys Leu Ile Asn Asn Lys Asp Gly Ser Val Leu Gly Arg
        35                  40                  45 ggc cac aac atg agg ttc cag aag ggc tcc gcc acc ctg cac ggc gag     192
Gly His Asn Met Arg Phe Gln Lys Gly Ser Ala Thr Leu His Gly Glu
    50                  55                  60 atc tcc acc ctg gag aac tgt ggc agg ctg gag ggc aag gtg tac aag     240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc     288
Asp Thr Thr Leu Tyr Thr Thr Leu Ser Pro Cys Asp Met Cys Thr Gly
                85                  90                  95
```

```
gct atc atc atg tac ggc atc cct agg tgt gtg gtc ggc gag aac gtg    336
Ala Ile Ile Met Tyr Gly Ile Pro Arg Cys Val Val Gly Glu Asn Val
            100                 105                 110 aac ttc aag tcc aag ggc gag aag tac ctg caa acc agg ggc cac gag    384
Asn Phe Lys Ser Lys Gly Glu Lys Tyr Leu Gln Thr Arg Gly His Glu
        115                 120                 125 gtg gtg gtt gtt gac gat gag agg tgt aag aag atc atg aag cag ttc    432
Val Val Val Val Asp Asp Glu Arg Cys Lys Lys Ile Met Lys Gln Phe
130                 135                 140 atc gac gag agg cct cag gac tgg ttc gag gat atc ggc gag tga taa    480
Ile Asp Glu Arg Pro Gln Asp Trp Phe Glu Asp Ile Gly Glu
145                 150                 155
```

<210> SEQ ID NO 6
<211> LENGTH: 158
<212> TYPE: PRT
<213> ORGANISM: Artificial Sequence
<220> FEATURE:
<223> OTHER INFORMATION: Synthetic Construct

<400> SEQUENCE: 6

```
Met Val Thr Gly Gly Met Ala Ser Lys Trp Asp Gln Lys Gly Met Asp
1               5                   10                  15

Ile Ala Tyr Glu Glu Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155
```

<210> SEQ ID NO 7
<211> LENGTH: 756
<212> TYPE: DNA
<213> ORGANISM: Saccharomyces cerevisiae
<220> FEATURE:
<221> NAME/KEY: CDS
<222> LOCATION: (1)..(756)

<400> SEQUENCE: 7

```
atg aac ccg tta ttc ttt ttg gct tct cca ttc ttg tac ctt aca tat    48
Met Asn Pro Leu Phe Phe Leu Ala Ser Pro Phe Leu Tyr Leu Thr Tyr
1               5                   10                  15 ctt ata tat tat cca aac aaa ggg tct ttc gtt agc aaa cct aga aat    96
Leu Ile Tyr Tyr Pro Asn Lys Gly Ser Phe Val Ser Lys Pro Arg Asn
            20                  25                  30 ctg caa aaa atg tct tcg gaa cca ttt aag aac gtc tac ttg cta cct    144
Leu Gln Lys Met Ser Ser Glu Pro Phe Lys Asn Val Tyr Leu Leu Pro
        35                  40                  45
```

```
caa aca aac caa ttg ctg ggt ttg tac acc atc atc aga aat aag aat    192
Gln Thr Asn Gln Leu Leu Gly Leu Tyr Thr Ile Ile Arg Asn Lys Asn
    50                  55                  60 aca act aga cct gat ttc att ttc tac tcc gat aga atc atc aga ttg    240
Thr Thr Arg Pro Asp Phe Ile Phe Tyr Ser Asp Arg Ile Ile Arg Leu
65                  70                  75                  80 ttg gtt gaa gaa ggt ttg aac cat cta cct gtg caa aag caa att gtg    288
Leu Val Glu Glu Gly Leu Asn His Leu Pro Val Gln Lys Gln Ile Val
                85                  90                  95 gaa act gac acc aac gaa aac ttc gaa ggt gtc tca ttc atg ggt aaa    336
Glu Thr Asp Thr Asn Glu Asn Phe Glu Gly Val Ser Phe Met Gly Lys
            100                 105                 110 atc tgt ggt gtt tcc att gtc aga gct ggt gaa tcg atg gag caa gga    384
Ile Cys Gly Val Ser Ile Val Arg Ala Gly Glu Ser Met Glu Gln Gly
        115                 120                 125 tta aga gac tgt tgt agg tct gtg cgt atc ggt aaa att tta att caa    432
Leu Arg Asp Cys Cys Arg Ser Val Arg Ile Gly Lys Ile Leu Ile Gln
    130                 135                 140 agg gac gag gag act gct tta cca aag tta ttc tac gaa aaa tta cca    480
Arg Asp Glu Glu Thr Ala Leu Pro Lys Leu Phe Tyr Glu Lys Leu Pro
145                 150                 155                 160 gag gat ata tct gaa agg tat gtc ttc cta tta gac cca atg ctg gcc    528
Glu Asp Ile Ser Glu Arg Tyr Val Phe Leu Leu Asp Pro Met Leu Ala
                165                 170                 175 acc ggt ggt agt gct atc atg gct aca gaa gtc ttg att aag aga ggt    576
Thr Gly Gly Ser Ala Ile Met Ala Thr Glu Val Leu Ile Lys Arg Gly
            180                 185                 190 gtt aag cca gag aga att tac ttc tta aac cta atc tgt agt aag gaa    624
Val Lys Pro Glu Arg Ile Tyr Phe Leu Asn Leu Ile Cys Ser Lys Glu
        195                 200                 205 ggg att gaa aaa tac cat gcc gcc ttc cca gag gtc aga att gtt act    672
Gly Ile Glu Lys Tyr His Ala Ala Phe Pro Glu Val Arg Ile Val Thr
    210                 215                 220 ggt gcc ctc gac aga ggt cta gat gaa aac aag tat cta gtt cca ggg    720
Gly Ala Leu Asp Arg Gly Leu Asp Glu Asn Lys Tyr Leu Val Pro Gly
225                 230                 235                 240 ttg ggt gac ttt ggt gac aga tac tac tgt gtt taa                    756
Leu Gly Asp Phe Gly Asp Arg Tyr Tyr Cys Val
                245                 250

<210> SEQ ID NO 8
<211> LENGTH: 251
<212> TYPE: PRT
<213> ORGANISM: Saccharomyces cerevisiae

<400> SEQUENCE: 8

Met Asn Pro Leu Phe Phe Leu Ala Ser Pro Phe Leu Tyr Leu Thr Tyr
1               5                   10                  15

Leu Ile Tyr Tyr Pro Asn Lys Gly Ser Phe Val Ser Lys Pro Arg Asn
            20                  25                  30

Leu Gln Lys Met Ser Ser Glu Pro Phe Lys Asn Val Tyr Leu Leu Pro
        35                  40                  45

Gln Thr Asn Gln Leu Leu Gly Leu Tyr Thr Ile Ile Arg Asn Lys Asn
    50                  55                  60

Thr Thr Arg Pro Asp Phe Ile Phe Tyr Ser Asp Arg Ile Ile Arg Leu
65                  70                  75                  80

Leu Val Glu Glu Gly Leu Asn His Leu Pro Val Gln Lys Gln Ile Val
                85                  90                  95

Glu Thr Asp Thr Asn Glu Asn Phe Glu Gly Val Ser Phe Met Gly Lys
```

```
                100             105             110
        Ile Cys Gly Val Ser Ile Val Arg Ala Gly Glu Ser Met Glu Gln Gly
                    115                 120                 125

Leu Arg Asp Cys Cys Arg Ser Val Arg Ile Gly Lys Ile Leu Ile Gln
                130                 135                 140

Arg Asp Glu Glu Thr Ala Leu Pro Lys Leu Phe Tyr Glu Lys Leu Pro
        145                 150                 155                 160

Glu Asp Ile Ser Glu Arg Tyr Val Phe Leu Leu Asp Pro Met Leu Ala
                        165                 170                 175

Thr Gly Gly Ser Ala Ile Met Ala Thr Glu Val Leu Ile Lys Arg Gly
                    180                 185                 190

Val Lys Pro Glu Arg Ile Tyr Phe Leu Asn Leu Ile Cys Ser Lys Glu
                195                 200                 205

Gly Ile Glu Lys Tyr His Ala Ala Phe Pro Glu Val Arg Ile Val Thr
            210                 215                 220

Gly Ala Leu Asp Arg Gly Leu Asp Glu Asn Lys Tyr Leu Val Pro Gly
        225                 230                 235                 240

Leu Gly Asp Phe Gly Asp Arg Tyr Tyr Cys Val
                        245                 250

<210> SEQ ID NO 9
<211> LENGTH: 1443
<212> TYPE: DNA
<213> ORGANISM: homo sapiens
<220> FEATURE:
<221> NAME/KEY: CDS
<222> LOCATION: (1)..(1443)

<400> SEQUENCE: 9 atg gct gtt gct cgt gct gct ctt ggt cct ctt gtt act ggt ctt tat    48
Met Ala Val Ala Arg Ala Ala Leu Gly Pro Leu Val Thr Gly Leu Tyr
1               5                   10                  15 gat gtt caa gct ttt aaa ttt ggt gat ttt gtt ctt aaa tct ggt ctt    96
Asp Val Gln Ala Phe Lys Phe Gly Asp Phe Val Leu Lys Ser Gly Leu
                20                  25                  30 tct tct cct att tat att gat ctt cgt ggt att gtt tct cgt cct cgt   144
Ser Ser Pro Ile Tyr Ile Asp Leu Arg Gly Ile Val Ser Arg Pro Arg
            35                  40                  45 ctt ctt tct caa gtt gct gat att ctt ttt caa act gct caa aat gct   192
Leu Leu Ser Gln Val Ala Asp Ile Leu Phe Gln Thr Ala Gln Asn Ala
        50                  55                  60 ggt att tct ttt gat act gtt tgt ggt gtt cct tat act gct ctt cct   240
Gly Ile Ser Phe Asp Thr Val Cys Gly Val Pro Tyr Thr Ala Leu Pro
65                  70                  75                  80 ctt gct act gtt att tgt tct act aat caa att cct atg ctt att cgt   288
Leu Ala Thr Val Ile Cys Ser Thr Asn Gln Ile Pro Met Leu Ile Arg
                85                  90                  95 cgt aaa gaa act aaa gat tat ggt act aaa cgt ctt gtt gaa ggt act   336
Arg Lys Glu Thr Lys Asp Tyr Gly Thr Lys Arg Leu Val Glu Gly Thr
                100                 105                 110 att aat cct ggt gaa act tgt ctt att att gaa gat gtt gtt act tct   384
Ile Asn Pro Gly Glu Thr Cys Leu Ile Ile Glu Asp Val Val Thr Ser
            115                 120                 125 ggt tct tct gtt ctt gaa act gtt gaa gtt ctt caa aaa gaa ggt ctt   432
Gly Ser Ser Val Leu Glu Thr Val Glu Val Leu Gln Lys Glu Gly Leu
        130                 135                 140 aaa gtt act gat gct att gtt ctt ctt gat cgt gaa caa ggt ggt aaa   480
Lys Val Thr Asp Ala Ile Val Leu Leu Asp Arg Glu Gln Gly Gly Lys
145                 150                 155                 160
```

| | | |
|---|---|---|
| gat aaa ctt caa gct cat ggt att cgt ctt cat tct gtt tgt act ctt<br>Asp Lys Leu Gln Ala His Gly Ile Arg Leu His Ser Val Cys Thr Leu<br>165 170 175 | 528 | |
| tct aaa atg ctt gaa att ctt gaa caa caa aaa aaa gtt gat gct gaa<br>Ser Lys Met Leu Glu Ile Leu Glu Gln Gln Lys Lys Val Asp Ala Glu<br>180 185 190 | 576 | |
| act gtt ggt cgt gtt aaa cgt ttt att caa gaa aat gtt ttt gtt gct<br>Thr Val Gly Arg Val Lys Arg Phe Ile Gln Glu Asn Val Phe Val Ala<br>195 200 205 | 624 | |
| gct aat cat aat ggt tct cct ctt tct att aaa gaa gct cct aaa gaa<br>Ala Asn His Asn Gly Ser Pro Leu Ser Ile Lys Glu Ala Pro Lys Glu<br>210 215 220 | 672 | |
| ctt tct ttt ggt gct cgt gct gaa ctt cct cgt att cat cct gtt gct<br>Leu Ser Phe Gly Ala Arg Ala Glu Leu Pro Arg Ile His Pro Val Ala<br>225 230 235 240 | 720 | |
| tct aaa ctt ctt cgt ctt atg caa aaa aaa gaa act aat ctt tgt ctt<br>Ser Lys Leu Leu Arg Leu Met Gln Lys Lys Glu Thr Asn Leu Cys Leu<br>245 250 255 | 768 | |
| tct gct gat gtt tct ctt gct cgt gaa ctt ctt caa ctt gct gat gct<br>Ser Ala Asp Val Ser Leu Ala Arg Glu Leu Leu Gln Leu Ala Asp Ala<br>260 265 270 | 816 | |
| ctt ggt cct tct att tgt atg ctt aaa act cat gtt gat att ctt aat<br>Leu Gly Pro Ser Ile Cys Met Leu Lys Thr His Val Asp Ile Leu Asn<br>275 280 285 | 864 | |
| gat ttt act ctt gat gtt atg aaa gaa ctt att act ctt gct aaa tgt<br>Asp Phe Thr Leu Asp Val Met Lys Glu Leu Ile Thr Leu Ala Lys Cys<br>290 295 300 | 912 | |
| cat gaa ttt ctt att ttt gaa gat cgt aaa ttt gct gat att ggt aat<br>His Glu Phe Leu Ile Phe Glu Asp Arg Lys Phe Ala Asp Ile Gly Asn<br>305 310 315 320 | 960 | |
| act gtt aaa aaa caa tat gaa ggt ggt att ttt aaa att gct tct tgg<br>Thr Val Lys Lys Gln Tyr Glu Gly Gly Ile Phe Lys Ile Ala Ser Trp<br>325 330 335 | 1008 | |
| gct gat ctt gtt aat gct cat gtt gtt cct ggt tct ggt gtt gtt aaa<br>Ala Asp Leu Val Asn Ala His Val Val Pro Gly Ser Gly Val Val Lys<br>340 345 350 | 1056 | |
| ggt ctt caa gaa gtt ggt ctt cct ctt cat cgt ggt tgt ctt ctt att<br>Gly Leu Gln Glu Val Gly Leu Pro Leu His Arg Gly Cys Leu Leu Ile<br>355 360 365 | 1104 | |
| gct gaa atg tct tct act ggt tct ctt gct act ggt gat tat act cgt<br>Ala Glu Met Ser Ser Thr Gly Ser Leu Ala Thr Gly Asp Tyr Thr Arg<br>370 375 380 | 1152 | |
| gct gct gtt cgt atg gct gaa gaa cat tct gaa ttt gtt gtt ggt ttt<br>Ala Ala Val Arg Met Ala Glu Glu His Ser Glu Phe Val Val Gly Phe<br>385 390 395 400 | 1200 | |
| att tct ggt tct cgt gtt tct atg aaa cct gaa ttt ctt cat ctt act<br>Ile Ser Gly Ser Arg Val Ser Met Lys Pro Glu Phe Leu His Leu Thr<br>405 410 415 | 1248 | |
| cct ggt gtt caa ctt gaa gct ggt ggt gat aat ctt ggt caa caa tat<br>Pro Gly Val Gln Leu Glu Ala Gly Gly Asp Asn Leu Gly Gln Gln Tyr<br>420 425 430 | 1296 | |
| aat tct cct caa gaa gtt att ggt aaa cgt ggt tct gat att att att<br>Asn Ser Pro Gln Glu Val Ile Gly Lys Arg Gly Ser Asp Ile Ile Ile<br>435 440 445 | 1344 | |
| gtt ggt cgt ggt att att tct gct gct gat cgt ctt gaa gct gct gaa<br>Val Gly Arg Gly Ile Ile Ser Ala Ala Asp Arg Leu Glu Ala Ala Glu<br>450 455 460 | 1392 | |
| atg tat cgt aaa gct gct tgg gaa gct tat ctt tct cgt ctt ggt gtt<br>Met Tyr Arg Lys Ala Ala Trp Glu Ala Tyr Leu Ser Arg Leu Gly Val | 1440 | |

-continued

```
taa                                                         1443

<210> SEQ ID NO 10
<211> LENGTH: 480
<212> TYPE: PRT
<213> ORGANISM: homo sapiens

<400> SEQUENCE: 10

Met Ala Val Ala Arg Ala Leu Gly Pro Leu Val Thr Gly Leu Tyr
1               5                   10                  15

Asp Val Gln Ala Phe Lys Phe Gly Asp Phe Val Leu Lys Ser Gly Leu
                20                  25                  30

Ser Ser Pro Ile Tyr Ile Asp Leu Arg Gly Ile Val Ser Arg Pro Arg
            35                  40                  45

Leu Leu Ser Gln Val Ala Asp Ile Leu Phe Gln Thr Ala Gln Asn Ala
        50                  55                  60

Gly Ile Ser Phe Asp Thr Val Cys Gly Val Pro Tyr Thr Ala Leu Pro
65                  70                  75                  80

Leu Ala Thr Val Ile Cys Ser Thr Asn Gln Ile Pro Met Leu Ile Arg
                85                  90                  95

Arg Lys Glu Thr Lys Asp Tyr Gly Thr Lys Arg Leu Val Glu Gly Thr
                100                 105                 110

Ile Asn Pro Gly Glu Thr Cys Leu Ile Ile Glu Asp Val Val Thr Ser
            115                 120                 125

Gly Ser Ser Val Leu Glu Thr Val Glu Val Leu Gln Lys Glu Gly Leu
        130                 135                 140

Lys Val Thr Asp Ala Ile Val Leu Leu Asp Arg Glu Gln Gly Gly Lys
145                 150                 155                 160

Asp Lys Leu Gln Ala His Gly Ile Arg Leu His Ser Val Cys Thr Leu
                165                 170                 175

Ser Lys Met Leu Glu Ile Leu Glu Gln Gln Lys Lys Val Asp Ala Glu
                180                 185                 190

Thr Val Gly Arg Val Lys Arg Phe Ile Gln Glu Asn Val Phe Val Ala
            195                 200                 205

Ala Asn His Asn Gly Ser Pro Leu Ser Ile Lys Glu Ala Pro Lys Glu
        210                 215                 220

Leu Ser Phe Gly Ala Arg Ala Glu Leu Pro Arg Ile His Pro Val Ala
225                 230                 235                 240

Ser Lys Leu Leu Arg Leu Met Gln Lys Lys Glu Thr Asn Leu Cys Leu
                245                 250                 255

Ser Ala Asp Val Ser Leu Ala Arg Glu Leu Leu Gln Leu Ala Asp Ala
                260                 265                 270

Leu Gly Pro Ser Ile Cys Met Leu Lys Thr His Val Asp Ile Leu Asn
            275                 280                 285

Asp Phe Thr Leu Asp Val Met Lys Glu Leu Ile Thr Leu Ala Lys Cys
        290                 295                 300

His Glu Phe Leu Ile Phe Glu Asp Arg Lys Phe Ala Asp Ile Gly Asn
305                 310                 315                 320

Thr Val Lys Lys Gln Tyr Glu Gly Gly Ile Phe Lys Ile Ala Ser Trp
                325                 330                 335

Ala Asp Leu Val Asn Ala His Val Val Pro Gly Ser Gly Val Val Lys
                340                 345                 350

Gly Leu Gln Glu Val Gly Leu Pro Leu His Arg Gly Cys Leu Leu Ile
```

-continued

```
            355                 360                 365
Ala Glu Met Ser Ser Thr Gly Ser Leu Ala Thr Gly Asp Tyr Thr Arg
        370                 375                 380

Ala Ala Val Arg Met Ala Glu His Ser Glu Phe Val Val Gly Phe
385                 390                 395                 400

Ile Ser Gly Ser Arg Val Ser Met Lys Pro Glu Phe Leu His Leu Thr
                405                 410                 415

Pro Gly Val Gln Leu Glu Ala Gly Asp Asn Leu Gly Gln Gln Tyr
            420                 425                 430

Asn Ser Pro Gln Glu Val Ile Gly Lys Arg Gly Ser Asp Ile Ile Ile
            435                 440                 445

Val Gly Arg Gly Ile Ile Ser Ala Ala Asp Arg Leu Glu Ala Ala Glu
            450                 455                 460

Met Tyr Arg Lys Ala Ala Trp Glu Ala Tyr Leu Ser Arg Leu Gly Val
465                 470                 475                 480

<210> SEQ ID NO 11
<211> LENGTH: 1227
<212> TYPE: DNA
<213> ORGANISM: Artificial Sequence
<220> FEATURE:
<223> OTHER INFORMATION: Fusion construct CDopt-UPRT
<220> FEATURE:
<221> NAME/KEY: CDS
<222> LOCATION: (1)..(1227)

<400> SEQUENCE: 11 atg gtg acc ggc ggc atg gcc tcc aag tgg gat caa aag ggc atg gat     48
Met Val Thr Gly Gly Met Ala Ser Lys Trp Asp Gln Lys Gly Met Asp
1               5                   10                  15 atc gct tac gag gag gcc ctg ctg ggc tac aag gag ggc ggc gtg cct     96
Ile Ala Tyr Glu Glu Ala Leu Leu Gly Tyr Lys Glu Gly Gly Val Pro
                20                  25                  30 atc ggc ggc tgt ctg atc aac aac aag gac ggc agt gtg ctg ggc agg    144
Ile Gly Gly Cys Leu Ile Asn Asn Lys Asp Gly Ser Val Leu Gly Arg
            35                  40                  45 ggc cac aac atg agg ttc cag aag ggc tcc gcc acc ctg cac ggc gag    192
Gly His Asn Met Arg Phe Gln Lys Gly Ser Ala Thr Leu His Gly Glu
        50                  55                  60 atc tcc acc ctg gag aac tgt ggc agg ctg gag ggc aag gtg tac aag    240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc    288
Asp Thr Thr Leu Tyr Thr Thr Leu Ser Pro Cys Asp Met Cys Thr Gly
                85                  90                  95 gct atc atc atg tac ggc atc cct agg tgt gtg atc ggc gag aac gtg    336
Ala Ile Ile Met Tyr Gly Ile Pro Arg Cys Val Ile Gly Glu Asn Val
                100                 105                 110 aac ttc aag tcc aag ggc gag aag tac ctg caa acc agg ggc cac gag    384
Asn Phe Lys Ser Lys Gly Glu Lys Tyr Leu Gln Thr Arg Gly His Glu
            115                 120                 125 gtg gtg gtt gtt gac gat gag agg tgt aag aag ctg atg aag cag ttc    432
Val Val Val Val Asp Asp Glu Arg Cys Lys Lys Leu Met Lys Gln Phe
        130                 135                 140 atc gac gag agg cct cag gac tgg ttc gag gat atc ggc gag aac ccg    480
Ile Asp Glu Arg Pro Gln Asp Trp Phe Glu Asp Ile Gly Glu Asn Pro
145                 150                 155                 160 tta ttc ttt ttg gct tct cca ttc ttg tac ctt aca tat ctt ata tat    528
Leu Phe Phe Leu Ala Ser Pro Phe Leu Tyr Leu Thr Tyr Leu Ile Tyr
                165                 170                 175
```

| | | | | | | | | | | | | | | | |
|---|---|---|---|---|---|---|---|---|---|---|---|---|---|---|---|
| tat | cca | aac | aaa | ggg | tct | ttc | gtt | agc | aaa | cct | aga | aat | ctg | caa | aaa | 576 |
| Tyr | Pro | Asn | Lys | Gly | Ser | Phe | Val | Ser | Lys | Pro | Arg | Asn | Leu | Gln | Lys |
| | | | 180 | | | | | 185 | | | | | 190 | | | atg tct tcg gaa cca ttt aag aac gtc tac ttg cta cct caa aca aac    624
Met Ser Ser Glu Pro Phe Lys Asn Val Tyr Leu Leu Pro Gln Thr Asn
        195                 200                 205 caa ttg ctg ggt ttg tac acc atc atc aga aat aag aat aca act aga    672
Gln Leu Leu Gly Leu Tyr Thr Ile Ile Arg Asn Lys Asn Thr Thr Arg
    210                 215                 220 cct gat ttc att ttc tac tcc gat aga atc atc aga ttg ttg gtt gaa    720
Pro Asp Phe Ile Phe Tyr Ser Asp Arg Ile Ile Arg Leu Leu Val Glu
225                 230                 235                 240 gaa ggt ttg aac cat cta cct gtg caa aag caa att gtg gaa act gac    768
Glu Gly Leu Asn His Leu Pro Val Gln Lys Gln Ile Val Glu Thr Asp
                245                 250                 255 acc aac gaa aac ttc gaa ggt gtc tca ttc atg ggt aaa atc tgt ggt    816
Thr Asn Glu Asn Phe Glu Gly Val Ser Phe Met Gly Lys Ile Cys Gly
            260                 265                 270 gtt tcc att gtc aga gct ggt gaa tcg atg gag caa gga tta aga gac    864
Val Ser Ile Val Arg Ala Gly Glu Ser Met Glu Gln Gly Leu Arg Asp
        275                 280                 285 tgt tgt agg tct gtg cgt atc ggt aaa att tta att caa agg gac gag    912
Cys Cys Arg Ser Val Arg Ile Gly Lys Ile Leu Ile Gln Arg Asp Glu
    290                 295                 300 gag act gct tta cca aag tta ttc tac gaa aaa tta cca gag gat ata    960
Glu Thr Ala Leu Pro Lys Leu Phe Tyr Glu Lys Leu Pro Glu Asp Ile
305                 310                 315                 320 tct gaa agg tat gtc ttc cta tta gac cca atg ctg gcc acc ggt ggt    1008
Ser Glu Arg Tyr Val Phe Leu Leu Asp Pro Met Leu Ala Thr Gly Gly
                325                 330                 335 agt gct atc atg gct aca gaa gtc ttg att aag aga ggt gtt aag cca    1056
Ser Ala Ile Met Ala Thr Glu Val Leu Ile Lys Arg Gly Val Lys Pro
            340                 345                 350 gag aga att tac ttc tta aac cta atc tgt agt aag gaa ggg att gaa    1104
Glu Arg Ile Tyr Phe Leu Asn Leu Ile Cys Ser Lys Glu Gly Ile Glu
        355                 360                 365 aaa tac cat gcc gcc ttc cca gag gtc aga att gtt act ggt gcc ctc    1152
Lys Tyr His Ala Ala Phe Pro Glu Val Arg Ile Val Thr Gly Ala Leu
    370                 375                 380 gac aga ggt cta gat gaa aac aag tat cta gtt cca ggg ttg ggt gac    1200
Asp Arg Gly Leu Asp Glu Asn Lys Tyr Leu Val Pro Gly Leu Gly Asp
385                 390                 395                 400 ttt ggt gac aga tac tac tgt gtt taa                                1227
Phe Gly Asp Arg Tyr Tyr Cys Val
                405

<210> SEQ ID NO 12
<211> LENGTH: 408
<212> TYPE: PRT
<213> ORGANISM: Artificial Sequence
<220> FEATURE:
<223> OTHER INFORMATION: Synthetic Construct

<400> SEQUENCE: 12

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
            50                  55                  60

Ile Ser Thr Leu Glu Asn Cys Gly Arg Leu Glu Gly Lys Val Tyr Lys
 65                  70                  75                  80

Asp Thr Thr Leu Tyr Thr Thr Leu Ser Pro Cys Asp Met Cys Thr Gly
                    85                  90                  95

Ala Ile Ile Met Tyr Gly Ile Pro Arg Cys Val Ile Gly Glu Asn Val
                100                 105                 110

Asn Phe Lys Ser Lys Gly Glu Lys Tyr Leu Gln Thr Arg Gly His Glu
                115                 120                 125

Val Val Val Asp Asp Glu Arg Cys Lys Lys Leu Met Lys Gln Phe
            130                 135                 140

Ile Asp Glu Arg Pro Gln Asp Trp Phe Glu Asp Ile Gly Glu Asn Pro
145                 150                 155                 160

Leu Phe Phe Leu Ala Ser Pro Phe Leu Tyr Leu Thr Tyr Leu Ile Tyr
                    165                 170                 175

Tyr Pro Asn Lys Gly Ser Phe Val Ser Lys Pro Arg Asn Leu Gln Lys
                180                 185                 190

Met Ser Ser Glu Pro Phe Lys Asn Val Tyr Leu Leu Pro Gln Thr Asn
                195                 200                 205

Gln Leu Leu Gly Leu Tyr Thr Ile Ile Arg Asn Lys Asn Thr Thr Arg
210                 215                 220

Pro Asp Phe Ile Phe Tyr Ser Asp Arg Ile Ile Arg Leu Leu Val Glu
225                 230                 235                 240

Glu Gly Leu Asn His Leu Pro Val Gln Lys Gln Ile Val Glu Thr Asp
                    245                 250                 255

Thr Asn Glu Asn Phe Glu Gly Val Ser Phe Met Gly Lys Ile Cys Gly
                260                 265                 270

Val Ser Ile Val Arg Ala Gly Glu Ser Met Glu Gln Gly Leu Arg Asp
            275                 280                 285

Cys Cys Arg Ser Val Arg Ile Gly Lys Ile Leu Ile Gln Arg Asp Glu
            290                 295                 300

Glu Thr Ala Leu Pro Lys Leu Phe Tyr Glu Lys Leu Pro Glu Asp Ile
305                 310                 315                 320

Ser Glu Arg Tyr Val Phe Leu Leu Asp Pro Met Leu Ala Thr Gly Gly
                    325                 330                 335

Ser Ala Ile Met Ala Thr Glu Val Leu Ile Lys Arg Gly Val Lys Pro
                340                 345                 350

Glu Arg Ile Tyr Phe Leu Asn Leu Ile Cys Ser Lys Glu Gly Ile Glu
            355                 360                 365

Lys Tyr His Ala Ala Phe Pro Glu Val Arg Ile Val Thr Gly Ala Leu
370                 375                 380

Asp Arg Gly Leu Asp Glu Asn Lys Tyr Leu Val Pro Gly Leu Gly Asp
385                 390                 395                 400

Phe Gly Asp Arg Tyr Tyr Cys Val
                405

<210> SEQ ID NO 13
<211> LENGTH: 1287
<212> TYPE: DNA
<213> ORGANISM: Artificial Sequence
<220> FEATURE:
<223> OTHER INFORMATION: Fusion construction - CDopt - linker - UPRT
<220> FEATURE:
<221> NAME/KEY: CDS

<222> LOCATION: (1)..(1287)

<400> SEQUENCE: 13

| | | | | | | | | | | | | | | | | |
|---|---|---|---|---|---|---|---|---|---|---|---|---|---|---|---|---|
| atg | gtg | acc | ggc | ggc | atg | gcc | tcc | aag | tgg | gat | caa | aag | ggc | atg | gat | 48 |
| Met | Val | Thr | Gly | Gly | Met | Ala | Ser | Lys | Trp | Asp | Gln | Lys | Gly | Met | Asp | |
| 1 | | | | 5 | | | | | 10 | | | | | 15 | | |
| atc | gct | tac | gag | gag | gcc | ctg | ctg | ggc | tac | aag | gag | ggc | ggc | gtg | cct | 96 |
| Ile | Ala | Tyr | Glu | Glu | Ala | Leu | Leu | Gly | Tyr | Lys | Glu | Gly | Gly | Val | Pro | |
| | | | 20 | | | | | 25 | | | | | 30 | | | |
| atc | ggc | ggc | tgt | ctg | atc | aac | aac | aag | gac | ggc | agt | gtg | ctg | ggc | agg | 144 |
| Ile | Gly | Gly | Cys | Leu | Ile | Asn | Asn | Lys | Asp | Gly | Ser | Val | Leu | Gly | Arg | |
| | | 35 | | | | | 40 | | | | | 45 | | | | |
| ggc | cac | aac | atg | agg | ttc | cag | aag | ggc | tcc | gcc | acc | ctg | cac | ggc | gag | 192 |
| Gly | His | Asn | Met | Arg | Phe | Gln | Lys | Gly | Ser | Ala | Thr | Leu | His | Gly | Glu | |
| | 50 | | | | | 55 | | | | | 60 | | | | | |
| atc | tcc | acc | ctg | gag | aac | tgt | ggc | agg | ctg | gag | ggc | aag | gtg | tac | aag | 240 |
| Ile | Ser | Thr | Leu | Glu | Asn | Cys | Gly | Arg | Leu | Glu | Gly | Lys | Val | Tyr | Lys | |
| 65 | | | | | 70 | | | | | 75 | | | | | 80 | |
| gac | acc | acc | ctg | tac | acc | acc | ctg | tcc | cct | tgt | gac | atg | tgt | acc | ggc | 288 |
| Asp | Thr | Thr | Leu | Tyr | Thr | Thr | Leu | Ser | Pro | Cys | Asp | Met | Cys | Thr | Gly | |
| | | | | 85 | | | | | 90 | | | | | 95 | | |
| gct | atc | atc | atg | tac | ggc | atc | cct | agg | tgt | gtg | atc | ggc | gag | aac | gtg | 336 |
| Ala | Ile | Ile | Met | Tyr | Gly | Ile | Pro | Arg | Cys | Val | Ile | Gly | Glu | Asn | Val | |
| | | | 100 | | | | | 105 | | | | | 110 | | | |
| aac | ttc | aag | tcc | aag | ggc | gag | aag | tac | ctg | caa | acc | agg | ggc | cac | gag | 384 |
| Asn | Phe | Lys | Ser | Lys | Gly | Glu | Lys | Tyr | Leu | Gln | Thr | Arg | Gly | His | Glu | |
| | | 115 | | | | | 120 | | | | | 125 | | | | |
| gtg | gtg | gtt | gtt | gac | gat | gag | agg | tgt | aag | aag | ctg | atg | aag | cag | ttc | 432 |
| Val | Val | Val | Val | Asp | Asp | Glu | Arg | Cys | Lys | Lys | Leu | Met | Lys | Gln | Phe | |
| | 130 | | | | | 135 | | | | | 140 | | | | | |
| atc | gac | gag | agg | cct | cag | gac | tgg | ttc | gag | gat | atc | ggc | gag | tcc | ggc | 480 |
| Ile | Asp | Glu | Arg | Pro | Gln | Asp | Trp | Phe | Glu | Asp | Ile | Gly | Glu | Ser | Gly | |
| 145 | | | | | 150 | | | | | 155 | | | | | 160 | |
| ggc | ggc | gcc | tcc | ggc | ggc | ggc | gcc | tcc | ggc | ggc | ggc | gcc | tcc | ggc | ggc | 528 |
| Gly | Gly | Ala | Ser | Gly | Gly | Gly | Ala | Ser | Gly | Gly | Gly | Ala | Ser | Gly | Gly | |
| | | | | 165 | | | | | 170 | | | | | 175 | | |
| ggc | gcc | aac | ccg | tta | ttc | ttt | ttg | gct | tct | cca | ttc | ttg | tac | ctt | aca | 576 |
| Gly | Ala | Asn | Pro | Leu | Phe | Phe | Leu | Ala | Ser | Pro | Phe | Leu | Tyr | Leu | Thr | |
| | | | 180 | | | | | 185 | | | | | 190 | | | |
| tat | ctt | ata | tat | tat | cca | aac | aaa | ggg | tct | ttc | gtt | agc | aaa | cct | aga | 624 |
| Tyr | Leu | Ile | Tyr | Tyr | Pro | Asn | Lys | Gly | Ser | Phe | Val | Ser | Lys | Pro | Arg | |
| | | 195 | | | | | 200 | | | | | 205 | | | | |
| aat | ctg | caa | aaa | atg | tct | tcg | gaa | cca | ttt | aag | aac | gtc | tac | ttg | cta | 672 |
| Asn | Leu | Gln | Lys | Met | Ser | Ser | Glu | Pro | Phe | Lys | Asn | Val | Tyr | Leu | Leu | |
| | 210 | | | | | 215 | | | | | 220 | | | | | |
| cct | caa | aca | aac | caa | ttg | ctg | ggt | ttg | tac | acc | atc | atc | aga | aat | aag | 720 |
| Pro | Gln | Thr | Asn | Gln | Leu | Leu | Gly | Leu | Tyr | Thr | Ile | Ile | Arg | Asn | Lys | |
| 225 | | | | | 230 | | | | | 235 | | | | | 240 | |
| aat | aca | act | aga | cct | gat | ttc | att | ttc | tac | tcc | gat | aga | atc | atc | aga | 768 |
| Asn | Thr | Thr | Arg | Pro | Asp | Phe | Ile | Phe | Tyr | Ser | Asp | Arg | Ile | Ile | Arg | |
| | | | | 245 | | | | | 250 | | | | | 255 | | |
| ttg | ttg | gtt | gaa | gaa | ggt | ttg | aac | cat | cta | cct | gtg | caa | aag | caa | att | 816 |
| Leu | Leu | Val | Glu | Glu | Gly | Leu | Asn | His | Leu | Pro | Val | Gln | Lys | Gln | Ile | |
| | | | 260 | | | | | 265 | | | | | 270 | | | |
| gtg | gaa | act | gac | acc | aac | gaa | aac | ttc | gaa | ggt | gtc | tca | ttc | atg | ggt | 864 |
| Val | Glu | Thr | Asp | Thr | Asn | Glu | Asn | Phe | Glu | Gly | Val | Ser | Phe | Met | Gly | |
| | | 275 | | | | | 280 | | | | | 285 | | | | |
| aaa | atc | tgt | ggt | gtt | tcc | att | gtc | aga | gct | ggt | gaa | tcg | atg | gag | caa | 912 |
| Lys | Ile | Cys | Gly | Val | Ser | Ile | Val | Arg | Ala | Gly | Glu | Ser | Met | Glu | Gln | |
| | 290 | | | | | 295 | | | | | 300 | | | | | |

```
gga tta aga gac tgt tgt agg tct gtg cgt atc ggt aaa att tta att        960
Gly Leu Arg Asp Cys Cys Arg Ser Val Arg Ile Gly Lys Ile Leu Ile
305                 310                 315                 320 caa agg gac gag gag act gct tta cca aag tta ttc tac gaa aaa tta       1008
Gln Arg Asp Glu Glu Thr Ala Leu Pro Lys Leu Phe Tyr Glu Lys Leu
                325                 330                 335 cca gag gat ata tct gaa agg tat gtc ttc cta tta gac cca atg ctg       1056
Pro Glu Asp Ile Ser Glu Arg Tyr Val Phe Leu Leu Asp Pro Met Leu
            340                 345                 350 gcc acc ggt ggt agt gct atc atg gct aca gaa gtc ttg att aag aga       1104
Ala Thr Gly Gly Ser Ala Ile Met Ala Thr Glu Val Leu Ile Lys Arg
        355                 360                 365 ggt gtt aag cca gag aga att tac ttc tta aac cta atc tgt agt aag       1152
Gly Val Lys Pro Glu Arg Ile Tyr Phe Leu Asn Leu Ile Cys Ser Lys
    370                 375                 380 gaa ggg att gaa aaa tac cat gcc gcc ttc cca gag gtc aga att gtt       1200
Glu Gly Ile Glu Lys Tyr His Ala Ala Phe Pro Glu Val Arg Ile Val
385                 390                 395                 400 act ggt gcc ctc gac aga ggt cta gat gaa aac aag tat cta gtt cca       1248
Thr Gly Ala Leu Asp Arg Gly Leu Asp Glu Asn Lys Tyr Leu Val Pro
                405                 410                 415 ggg ttg ggt gac ttt ggt gac aga tac tac tgt gtt taa                   1287
Gly Leu Gly Asp Phe Gly Asp Arg Tyr Tyr Cys Val
            420                 425

<210> SEQ ID NO 14
<211> LENGTH: 428
<212> TYPE: PRT
<213> ORGANISM: Artificial Sequence
<220> FEATURE:
<223> OTHER INFORMATION: Synthetic Construct

<400> SEQUENCE: 14

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ser Gly
145                 150                 155                 160

Gly Gly Ala Ser Gly Gly Ala Ser Gly Gly Ala Ser Gly Gly
                165                 170                 175

Gly Ala Asn Pro Leu Phe Phe Leu Ala Ser Pro Phe Tyr Leu Thr
        180                 185                 190
```

```
Tyr Leu Ile Tyr Tyr Pro Asn Lys Gly Ser Phe Val Ser Lys Pro Arg
            195                 200                 205

Asn Leu Gln Lys Met Ser Ser Glu Pro Phe Lys Asn Val Tyr Leu Leu
    210                 215                 220

Pro Gln Thr Asn Gln Leu Leu Gly Leu Tyr Thr Ile Ile Arg Asn Lys
225                 230                 235                 240

Asn Thr Thr Arg Pro Asp Phe Ile Phe Tyr Ser Asp Arg Ile Ile Arg
                245                 250                 255

Leu Leu Val Glu Gly Leu Asn His Leu Pro Val Gln Lys Gln Ile
            260                 265                 270

Val Glu Thr Asp Thr Asn Glu Asn Phe Glu Gly Val Ser Phe Met Gly
        275                 280                 285

Lys Ile Cys Gly Val Ser Ile Val Arg Ala Gly Glu Ser Met Glu Gln
    290                 295                 300

Gly Leu Arg Asp Cys Cys Arg Ser Val Arg Ile Gly Lys Ile Leu Ile
305                 310                 315                 320

Gln Arg Asp Glu Glu Thr Ala Leu Pro Lys Leu Phe Tyr Glu Lys Leu
                325                 330                 335

Pro Glu Asp Ile Ser Glu Arg Tyr Val Phe Leu Leu Asp Pro Met Leu
            340                 345                 350

Ala Thr Gly Gly Ser Ala Ile Met Ala Thr Glu Val Leu Ile Lys Arg
        355                 360                 365

Gly Val Lys Pro Glu Arg Ile Tyr Phe Leu Asn Leu Ile Cys Ser Lys
    370                 375                 380

Glu Gly Ile Glu Lys Tyr His Ala Ala Phe Pro Glu Val Arg Ile Val
385                 390                 395                 400

Thr Gly Ala Leu Asp Arg Gly Leu Asp Glu Asn Lys Tyr Leu Val Pro
                405                 410                 415

Gly Leu Gly Asp Phe Gly Asp Arg Tyr Tyr Cys Val
            420                 425

<210> SEQ ID NO 15
<211> LENGTH: 1200
<212> TYPE: DNA
<213> ORGANISM: Artificial Sequence
<220> FEATURE:
<223> OTHER INFORMATION: Fusion Construct - CDopt3 - OPRT
<220> FEATURE:
<221> NAME/KEY: CDS
<222> LOCATION: (1)..(1200)

<400> SEQUENCE: 15 atg gtg acc ggc ggc atg gcc tcc aag tgg gat caa aag ggc atg gat      48
Met Val Thr Gly Gly Met Ala Ser Lys Trp Asp Gln Lys Gly Met Asp
1               5                   10                  15 atc gct tac gag gag gcc ctg ctg ggc tac aag gag ggc ggc gtg cct      96
Ile Ala Tyr Glu Glu Ala Leu Leu Gly Tyr Lys Glu Gly Gly Val Pro
            20                  25                  30 atc ggc ggc tgt ctg atc aac aac aag gac ggc agt gtg ctg ggc agg     144
Ile Gly Gly Cys Leu Ile Asn Asn Lys Asp Gly Ser Val Leu Gly Arg
        35                  40                  45 ggc cac aac atg agg ttc cag aag ggc tcc gcc acc ctg cac ggc gag     192
Gly His Asn Met Arg Phe Gln Lys Gly Ser Ala Thr Leu His Gly Glu
    50                  55                  60 atc tcc acc ctg gag aac tgt ggc agg ctg gag ggc aag gtg tac aag     240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc     288
```

-continued

```
                Asp Thr Thr Leu Tyr Thr Thr Leu Ser Pro Cys Asp Met Cys Thr Gly
                             85                  90                  95 gct atc atc atg tac ggc atc cct agg tgt gtg atc ggc gag aac gtg       336
Ala Ile Ile Met Tyr Gly Ile Pro Arg Cys Val Ile Gly Glu Asn Val
            100                 105                 110 aac ttc aag tcc aag ggc gag aag tac ctg caa acc agg ggc cac gag       384
Asn Phe Lys Ser Lys Gly Glu Lys Tyr Leu Gln Thr Arg Gly His Glu
        115                 120                 125 gtg gtg gtt gtt gac gat gag agg tgt aag aag ctg atg aag cag ttc       432
Val Val Val Val Asp Asp Glu Arg Cys Lys Lys Leu Met Lys Gln Phe
    130                 135                 140 atc gac gag agg cct cag gac tgg ttc gag gat atc ggc gag gcg gtc       480
Ile Asp Glu Arg Pro Gln Asp Trp Phe Glu Asp Ile Gly Glu Ala Val
145                 150                 155                 160 gct cgt gca gct ttg ggg cca ttg gtg acg ggt ctg tac gac gtg cag       528
Ala Arg Ala Ala Leu Gly Pro Leu Val Thr Gly Leu Tyr Asp Val Gln
                165                 170                 175 gct ttc aag ttt ggg gac ttc gtg ctg aag agc ggg ctt tcc tcc ccc       576
Ala Phe Lys Phe Gly Asp Phe Val Leu Lys Ser Gly Leu Ser Ser Pro
            180                 185                 190 atc tac atc gat ctg cgg ggc atc gtg tct cga ccg cgt ctt ctg agt       624
Ile Tyr Ile Asp Leu Arg Gly Ile Val Ser Arg Pro Arg Leu Leu Ser
        195                 200                 205 cag gtt gca gat att tta ttc caa act gcc caa aat gca ggc atc agt       672
Gln Val Ala Asp Ile Leu Phe Gln Thr Ala Gln Asn Ala Gly Ile Ser
    210                 215                 220 ttt gac acc gtg tgt gga gtg cct tat aca gct ttg cca ttg gct aca       720
Phe Asp Thr Val Cys Gly Val Pro Tyr Thr Ala Leu Pro Leu Ala Thr
225                 230                 235                 240 gtt atc tgt tca acc aat caa att cca atg ctt att aga agg aaa gaa       768
Val Ile Cys Ser Thr Asn Gln Ile Pro Met Leu Ile Arg Arg Lys Glu
                245                 250                 255 aca aag gat tat gga act aag cgt ctt gta gaa gga act att aat cca       816
Thr Lys Asp Tyr Gly Thr Lys Arg Leu Val Glu Gly Thr Ile Asn Pro
            260                 265                 270 gga gaa acc tgt tta atc att gaa gat gtt gtc acc agt gga tct agt       864
Gly Glu Thr Cys Leu Ile Ile Glu Asp Val Val Thr Ser Gly Ser Ser
        275                 280                 285 gtt ttg gaa act gtt gag gtt ctt cag aag gag ggc ttg aag gtc act       912
Val Leu Glu Thr Val Glu Val Leu Gln Lys Glu Gly Leu Lys Val Thr
    290                 295                 300 gat gcc ata gtg ctg ttg gac aga gag cag gga ggc aag gac aag ttg       960
Asp Ala Ile Val Leu Leu Asp Arg Glu Gln Gly Gly Lys Asp Lys Leu
305                 310                 315                 320 cag gcg cac ggg atc cgc ctc cac tca gtg tgt aca ttg tcc aaa atg      1008
Gln Ala His Gly Ile Arg Leu His Ser Val Cys Thr Leu Ser Lys Met
                325                 330                 335 ctg gag att ctc gag cag cag aaa aaa gtt gat gct gag aca gtt ggg      1056
Leu Glu Ile Leu Glu Gln Gln Lys Lys Val Asp Ala Glu Thr Val Gly
            340                 345                 350 aga gtg aag agg ttt att cag gag aat gtc ttt gtg gca gcg aat cat      1104
Arg Val Lys Arg Phe Ile Gln Glu Asn Val Phe Val Ala Ala Asn His
        355                 360                 365 aat ggt tct ccc ctt tct ata aag gaa gca ccc aaa gaa ctc agc ttc      1152
Asn Gly Ser Pro Leu Ser Ile Lys Glu Ala Pro Lys Glu Leu Ser Phe
    370                 375                 380 ggt gca cgt gca gag ctg ccc agg atc cac cca gtt gca tcg aag taa      1200
Gly Ala Arg Ala Glu Leu Pro Arg Ile His Pro Val Ala Ser Lys
385                 390                 395
```

<210> SEQ ID NO 16
<211> LENGTH: 399
<212> TYPE: PRT
<213> ORGANISM: Artificial Sequence
<220> FEATURE:
<223> OTHER INFORMATION: Synthetic Construct

<400> SEQUENCE: 16

```
Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ala Val
145                 150                 155                 160

Ala Arg Ala Ala Leu Gly Pro Leu Val Thr Gly Leu Tyr Asp Val Gln
                165                 170                 175

Ala Phe Lys Phe Gly Asp Phe Val Leu Lys Ser Gly Leu Ser Ser Pro
            180                 185                 190

Ile Tyr Ile Asp Leu Arg Gly Ile Val Ser Arg Pro Arg Leu Leu Ser
        195                 200                 205

Gln Val Ala Asp Ile Leu Phe Gln Thr Ala Gln Asn Ala Gly Ile Ser
    210                 215                 220

Phe Asp Thr Val Cys Gly Val Pro Tyr Thr Ala Leu Pro Leu Ala Thr
225                 230                 235                 240

Val Ile Cys Ser Thr Asn Gln Ile Pro Met Leu Ile Arg Arg Lys Glu
                245                 250                 255

Thr Lys Asp Tyr Gly Thr Lys Arg Leu Val Glu Gly Thr Ile Asn Pro
            260                 265                 270

Gly Glu Thr Cys Leu Ile Ile Glu Asp Val Val Thr Ser Gly Ser Ser
        275                 280                 285

Val Leu Glu Thr Val Glu Val Leu Gln Lys Glu Gly Leu Lys Val Thr
    290                 295                 300

Asp Ala Ile Val Leu Leu Asp Arg Glu Gln Gly Gly Lys Asp Lys Leu
305                 310                 315                 320

Gln Ala His Gly Ile Arg Leu His Ser Val Cys Thr Leu Ser Lys Met
                325                 330                 335

Leu Glu Ile Leu Glu Gln Gln Lys Lys Val Asp Ala Glu Thr Val Gly
            340                 345                 350

Arg Val Lys Arg Phe Ile Gln Glu Asn Val Phe Val Ala Ala Asn His
        355                 360                 365
```

```
        Asn Gly Ser Pro Leu Ser Ile Lys Glu Ala Pro Lys Glu Leu Ser Phe
            370                 375                 380

Gly Ala Arg Ala Glu Leu Pro Arg Ile His Pro Val Ala Ser Lys
        385                 390                 395

<210> SEQ ID NO 17
<211> LENGTH: 1260
<212> TYPE: DNA
<213> ORGANISM: Artificial Sequence
<220> FEATURE:
<223> OTHER INFORMATION: Fusion Construct - CDopt3 - linker - OPRT
<220> FEATURE:
<221> NAME/KEY: CDS
<222> LOCATION: (1)..(1260)

<400> SEQUENCE: 17 atg gtg acc ggc ggc atg gcc tcc aag tgg gat caa aag ggc atg gat      48
Met Val Thr Gly Gly Met Ala Ser Lys Trp Asp Gln Lys Gly Met Asp
1               5                   10                  15 atc gct tac gag gag gcc ctg ctg ggc tac aag gag ggc ggc gtg cct      96
Ile Ala Tyr Glu Glu Ala Leu Leu Gly Tyr Lys Glu Gly Gly Val Pro
                20                  25                  30 atc ggc ggc tgt ctg atc aac aac aag gac ggc agt gtg ctg ggc agg     144
Ile Gly Gly Cys Leu Ile Asn Asn Lys Asp Gly Ser Val Leu Gly Arg
            35                  40                  45 ggc cac aac atg agg ttc cag aag ggc tcc gcc acc ctg cac ggc gag     192
Gly His Asn Met Arg Phe Gln Lys Gly Ser Ala Thr Leu His Gly Glu
        50                  55                  60 atc tcc acc ctg gag aac tgt ggc agg ctg gag ggc aag gtg tac aag     240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc     288
Asp Thr Thr Leu Tyr Thr Thr Leu Ser Pro Cys Asp Met Cys Thr Gly
                85                  90                  95 gct atc atc atg tac ggc atc cct agg tgt gtg atc ggc gag aac gtg     336
Ala Ile Ile Met Tyr Gly Ile Pro Arg Cys Val Ile Gly Glu Asn Val
            100                 105                 110 aac ttc aag tcc aag ggc gag aag tac ctg caa acc agg ggc cac gag     384
Asn Phe Lys Ser Lys Gly Glu Lys Tyr Leu Gln Thr Arg Gly His Glu
        115                 120                 125 gtg gtg gtt gtt gac gat gag agg tgt aag aag ctg atg aag cag ttc     432
Val Val Val Val Asp Asp Glu Arg Cys Lys Lys Leu Met Lys Gln Phe
    130                 135                 140 atc gac gag agg cct cag gac tgg ttc gag gat atc ggc gag tcc ggc     480
Ile Asp Glu Arg Pro Gln Asp Trp Phe Glu Asp Ile Gly Glu Ser Gly
145                 150                 155                 160 ggc ggc gcc tcc ggc ggc ggc gcc tcc ggc ggc ggc gcc tcc ggc ggc     528
Gly Gly Ala Ser Gly Gly Gly Ala Ser Gly Gly Gly Ala Ser Gly Gly
                165                 170                 175 ggc gcc gcg gtc gct cgt gca gct ttg ggg cca ttg gtg acg ggt ctg     576
Gly Ala Ala Val Ala Arg Ala Ala Leu Gly Pro Leu Val Thr Gly Leu
            180                 185                 190 tac gac gtg cag gct ttc aag ttt ggg gac ttc gtg ctg aag agc ggg     624
Tyr Asp Val Gln Ala Phe Lys Phe Gly Asp Phe Val Leu Lys Ser Gly
        195                 200                 205 ctt tcc tcc ccc atc tac atc gat ctg cgg ggc atc gtg tct cga ccg     672
Leu Ser Ser Pro Ile Tyr Ile Asp Leu Arg Gly Ile Val Ser Arg Pro
    210                 215                 220 cgt ctt ctg agt cag gtt gca gat att tta ttc caa act gcc caa aat     720
Arg Leu Leu Ser Gln Val Ala Asp Ile Leu Phe Gln Thr Ala Gln Asn
225                 230                 235                 240
```

```
gca ggc atc agt ttt gac acc gtg tgt gga gtg cct tat aca gct ttg    768
Ala Gly Ile Ser Phe Asp Thr Val Cys Gly Val Pro Tyr Thr Ala Leu
            245                 250                 255 cca ttg gct aca gtt atc tgt tca acc aat caa att cca atg ctt att    816
Pro Leu Ala Thr Val Ile Cys Ser Thr Asn Gln Ile Pro Met Leu Ile
        260                 265                 270 aga agg aaa gaa aca aag gat tat gga act aag cgt ctt gta gaa gga    864
Arg Arg Lys Glu Thr Lys Asp Tyr Gly Thr Lys Arg Leu Val Glu Gly
    275                 280                 285 act att aat cca gga gaa acc tgt tta atc att gaa gat gtt gtc acc    912
Thr Ile Asn Pro Gly Glu Thr Cys Leu Ile Ile Glu Asp Val Val Thr
290                 295                 300 agt gga tct agt gtt ttg gaa act gtt gag gtt ctt cag aag gag ggc    960
Ser Gly Ser Ser Val Leu Glu Thr Val Glu Val Leu Gln Lys Glu Gly
305                 310                 315                 320 ttg aag gtc act gat gcc ata gtg ctg ttg gac aga gag cag gga ggc   1008
Leu Lys Val Thr Asp Ala Ile Val Leu Leu Asp Arg Glu Gln Gly Gly
                325                 330                 335 aag gac aag ttg cag gcg cac ggg atc cgc ctc cac tca gtg tgt aca   1056
Lys Asp Lys Leu Gln Ala His Gly Ile Arg Leu His Ser Val Cys Thr
            340                 345                 350 ttg tcc aaa atg ctg gag att ctc gag cag cag aaa aaa gtt gat gct   1104
Leu Ser Lys Met Leu Glu Ile Leu Glu Gln Gln Lys Lys Val Asp Ala
        355                 360                 365 gag aca gtt ggg aga gtg aag agg ttt att cag gag aat gtc ttt gtg   1152
Glu Thr Val Gly Arg Val Lys Arg Phe Ile Gln Glu Asn Val Phe Val
    370                 375                 380 gca gcg aat cat aat ggt tct ccc ctt tct ata aag gaa gca ccc aaa   1200
Ala Ala Asn His Asn Gly Ser Pro Leu Ser Ile Lys Glu Ala Pro Lys
385                 390                 395                 400 gaa ctc agc ttc ggt gca cgt gca gag ctg ccc agg atc cac cca gtt   1248
Glu Leu Ser Phe Gly Ala Arg Ala Glu Leu Pro Arg Ile His Pro Val
                405                 410                 415 gca tcg aag taa                                                   1260
Ala Ser Lys <210> SEQ ID NO 18
<211> LENGTH: 419
<212> TYPE: PRT
<213> ORGANISM: Artificial Sequence
<220> FEATURE:
<223> OTHER INFORMATION: Synthetic Construct

<400> SEQUENCE: 18

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
```

|  |  |  | 115 |  |  |  | 120 |  |  |  | 125 |  |  |
|---|---|---|---|---|---|---|---|---|---|---|---|---|---|
| Val | Val | Val | Asp | Asp | Glu | Arg | Cys | Lys | Lys | Leu | Met | Lys | Gln | Phe |
|  |  | 130 |  |  |  |  | 135 |  |  |  |  | 140 |  |  |

Ile Asp Glu Arg Pro Gln Asp Trp Phe Glu Asp Ile Gly Glu Ser Gly
145                 150                 155                 160

Gly Gly Ala Ser Gly Gly Ala Ser Gly Gly Ala Ser Gly Gly
                165                 170                 175

Gly Ala Ala Val Ala Arg Ala Ala Leu Gly Pro Leu Val Thr Gly Leu
            180                 185                 190

Tyr Asp Val Gln Ala Phe Lys Phe Gly Asp Phe Val Leu Lys Ser Gly
                195                 200                 205

Leu Ser Ser Pro Ile Tyr Ile Asp Leu Arg Gly Ile Val Ser Arg Pro
            210                 215                 220

Arg Leu Leu Ser Gln Val Ala Asp Ile Leu Phe Gln Thr Ala Gln Asn
225                 230                 235                 240

Ala Gly Ile Ser Phe Asp Thr Val Cys Gly Val Pro Tyr Thr Ala Leu
                245                 250                 255

Pro Leu Ala Thr Val Ile Cys Ser Thr Asn Gln Ile Pro Met Leu Ile
            260                 265                 270

Arg Arg Lys Glu Thr Lys Asp Tyr Gly Thr Lys Arg Leu Val Glu Gly
275                 280                 285

Thr Ile Asn Pro Gly Glu Thr Cys Leu Ile Glu Asp Val Val Thr
            290                 295                 300

Ser Gly Ser Ser Val Leu Glu Thr Val Glu Val Leu Gln Lys Glu Gly
305                 310                 315                 320

Leu Lys Val Thr Asp Ala Ile Val Leu Leu Asp Arg Glu Gln Gly Gly
                325                 330                 335

Lys Asp Lys Leu Gln Ala His Gly Ile Arg Leu His Ser Val Cys Thr
            340                 345                 350

Leu Ser Lys Met Leu Glu Ile Leu Glu Gln Gln Lys Lys Val Asp Ala
            355                 360                 365

Glu Thr Val Gly Arg Val Lys Arg Phe Ile Gln Glu Asn Val Phe Val
            370                 375                 380

Ala Ala Asn His Asn Gly Ser Pro Leu Ser Ile Lys Glu Ala Pro Lys
385                 390                 395                 400

Glu Leu Ser Phe Gly Ala Arg Ala Glu Leu Pro Arg Ile His Pro Val
                405                 410                 415

Ala Ser Lys

<210> SEQ ID NO 19
<211> LENGTH: 11892
<212> TYPE: DNA
<213> ORGANISM: Artificial Sequence
<220> FEATURE:
<223> OTHER INFORMATION: RCR Vector - pAC3-yCD2

<400> SEQUENCE: 19

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
```

```
catggtgatg cggttttggc agtacatcaa tgggcgtgga tagcggtttg actcacgggg      420
atttccaagt ctccacccca ttgacgtcaa tgggagtttg ttttggcacc aaaatcaacg      480
ggactttcca aaatgtcgta acaactccgc cccattgacg caaatgggcg gtaggcgtgt      540
acggtgggag gtctatataa gcagagctgg tttagtgaac cggcgccagt cctccgattg      600
actgagtcgc ccgggtaccc gtgtatccaa taaaccctct tgcagttgca tccgacttgt      660
ggtctcgctg ttccttggga gggtctcctc tgagtgattg actacccgtc agcggggtc       720 tttcatttgg ggctcgtcc gggatcggga gacccctgcc cagggaccac cgacccacca      780
ccgggaggta agctggccag caacttatct gtgtctgtcc gattgtctag tgtctatgac      840
tgattttatg cgcctgcgtc ggtactagtt agctaactag ctctgtatct ggcggacccg      900
tggtggaact gacgagttcg gaacaccgg ccgcaaccct gggagacgtc ccagggactt       960
cgggggccgt ttttgtggcc cgacctgagt ccaaaaatcc cgatcgtttt ggactctttg     1020
gtgcaccccc cttagaggag ggatatgtgg ttctggtagg agacgagaac ctaaaacagt     1080
tcccgcctcc gtctgaattt tgctttcgg tttgggaccg aagccgcgcc gcgcgtcttg      1140
tctgctgcag catcgttctg tgttgtctct gtctgactgt gtttctgtat ttgtctgaga     1200
atatgggcca gactgttacc actcccttaa gtttgacctt aggtcactgg aaagatgtcg     1260
agcggatcgc tcacaaccag tcggtagatg tcaagaagag acgttgggtt accttctgct     1320
ctgcagaatg gccaaccttt aacgtcggat ggccgcgaga cggcacctt aaccgagacc      1380 tcatcaccca ggttaagatc aaggtctttt cacctggccc gcatggacac ccagaccagg     1440
tcccctacat cgtgacctgg gaagccttgg cttttgaccc ccctccctgg gtcaagccct     1500
ttgtacaccc taagcctccg cctcctcttc tccatccgc cccgtctctc cccctgaac      1560 ctcctcgttc gaccccgcct cgatcctccc tttatccagc cctcactcct tctctaggcg     1620
ccaaacctaa acctcaagtt ctttctgaca gtggggggcc gctcatcgac ctacttacag     1680 aagaccccc gccttatagg gacccaagac cacccccttc cgacagggac ggaaatggtg      1740
gagaagcgac ccctgcggga gaggcaccgg acccctcccc aatggcatct cgcctacgtg     1800
ggagacggga gcccctgtg gccgactcca ctacctcgca ggcattcccc ctccgcgcag     1860
gaggaaacgg acagcttcaa tactggccgt tctcctcttc tgacctttac aactggaaaa     1920
ataataaccc ttcttttttct gaagatccag gtaaactgac agctctgatc gagtctgttc     1980
tcatcaccca tcagcccacc tggacgact gtcagcagct gttggggact ctgctgaccg      2040
gagaagaaaa acaacgggtg ctcttagagg ctagaaaggc ggtgcggggc gatgatgggc     2100
gccccactca actgcccaat gaagtcgatg ccgcttttcc cctcgagcgc ccagactggg     2160
attacaccac ccaggcaggt aggaaccacc tagtccacta cgccagttg ctcctagcgg      2220 gtctccaaaa cgcgggcaga agccccacca atttggccaa ggtaaaagga ataacacaag     2280
ggcccaatga gtctccctcg gccttcctag agagacttaa ggaagcctat cgcaggtaca     2340
ctccttatga ccctgaggac ccagggcaag aaactaatgt gtctatgtct ttcatttggc     2400
agtctgcccc agacattggg agaaagttag agaggttaga gatttaaaa aacaagacgc      2460 ttggagattt ggttagagag gcagaaaaga tctttaataa cgagaaacc ccggaagaaa      2520 gagaggaacg tatcaggaga gaaacagagg aaaaagaaga acgccgtagg acagaggatg     2580
agcagaaaga gaaagaaaga gatcgtagga gacatagaga gatgagcaag ctattggcca     2640
ctgtcgttag tggacagaaa caggatagac agggaggaga acgaaggagg tcccaactcg     2700
```

```
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc cccctgaac ccaggataac cctcaaagtc gggggcaac     2880 ccgtcacctt cctggtagat actggggccc aacactccgt gctgacccaa aatcctggac    2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg gcatgggac    3300 tggcagttcg ccaagctcct ctgatcatac ctctgaaagc aacctctacc ccgtgtcca    3360 taaaacaata ccccatgtca caagaagcca gactggggat caagcccac atacagagac    3420 tgttggacca gggaatactg gtaccctgcc agtcccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctccac    3600 cgtcccacca gtggtacact gtgcttgatt taaaggatgc ctttttctgc ctgagactcc    3660
accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900 gggcctgtt acaaacccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattgggc ccagaccaac    4200 aaaaggccta tcaagaaatc aagcaagctc ttctaactgc cccagccctg gggttgccag    4260
atttgactaa gcccttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aaccccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cggacatcc gctcagcggg    4860 ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct cttctctgccc aaaagactta gcataatcca ttgtccagga catcaaaagg    5100
```

```
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagttttat agatacctt tctggctgga   5640 tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttgggat tgattggaaa ttacattgtg   5820
catacagacc ccaaagctca ggccaggtag aaagaatgaa tagaaccatc aaggagactt   5880
taactaaatt aacgcttgca actggctcta gagactgggg ctcctactc cccttagccc   5940 tgtaccgagc ccgcaacacg ccgggccccc atggcctcac cccatatgag atcttatatg   6000
gggcaccccc gcccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc accccaccg ccctcaaagt agacggcatc gcagcttgga   6300
tacacgccgc ccacgtgaag gctgccgacc ccggggggtgg accatcctct agactgacat   6360
ggcgcgttca acgctctcaa aacccctca agataagatt aacccgtgga agcccttaat   6420
agtcatggga gtcctgttag gagtagggat ggcagagagc ccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggactttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca cccccctggga   6840 cacgggatgc tctaaagttg cctgtggccc ctgctacgac ctctccaaag tatccaattc   6900
cttccaaggg gctactcgag ggggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg accccgagt   7080 ccccataggg cccaacccag tattacccga ccaaagactc ccttcctcac caatagagat   7140
tgtaccggct ccacagccac ctagcccct caataccagt tacccccctt ccactaccag   7200
tacaccctca acctccccta caagtccaag tgtcccacag ccaccccag gaactggaga   7260 tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
```

```
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
gagagacagc atggccaaat taagagaaag gcttaatcag acacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca tgaacgcgtt actggccgaa    8340
gccgcttgga ataaggccgg tgtgcgtttg tctatatgtt atttttccacc atattgccgt    8400 cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca cccccagtgc cacgttgtga gttggatagt tgtggaaaga gtcaaatggc    8700
tctcctcaag cgtattcaac aagggctga aggatgccca aaggtaccc cattgtatgg    8760
```

```
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcgggggt ctttcattac atgtgagcaa aaggccagca   10020
aaaggccagg aaccgtaaaa aggccgcgtt gctggcgttt ttccataggc tccgcccccc   10080
tgacgagcat cacaaaaatc gacgctcaag tcagaggtgg cgaaacccga caggactata   10140
aagataccag gcgtttcccc ctggaagctc cctcgtgcgc tctcctgttc cgaccctgcc   10200
gcttaccgga tacctgtccg cctttctccc ttcgggaagc gtggcgcttt ctcaatgctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
cgctcagtgg aacgaaaact cacgttaagg gattttggtc atgagattat caaaaaggat   10740
cttcacctag atccttttaa attaaaaatg aagttttaaa tcaatctaaa gtatatatga   10800
gtaaacttgg tctgacagtt accaatgctt aatcagtgag gcacctatct cagcgatctg   10860
tctatttcgt tcatccatag ttgcctgact ccccgtcgtg tagataacta cgatacggga   10920
gggcttacca tctggcccca gtgctgcaat gataccgcga cccacgct caccggctcc   10980
agatttatca gcaataaacc agccagccgg aagggccgag cgcagaagtg gtcctgcaac   11040
tttatccgcc tccatccagt ctattaattg ttgccgggaa gctagagtaa gtagttcgcc   11100
agttaatagt ttgcgcaacg ttgttgccat tgctgcaggc atcgtggtgt cacgctcgtc   11160
gtttggtatg gcttcattca gctccggttc ccaacgatca aggcgagtta catgatcccc   11220
catgttgtgc aaaaaagcgg ttagctcctt cggtcctccg atcgttgtca gaagtaagtt   11280
ggccgcagtg ttatcactca tggttatggc agcactgcat aattctctta ctgtcatgcc   11340
atccgtaaga tgcttttctg tgactggtga gtactcaacc aagtcattct gagaatagtg   11400
tatgcggcga ccgagttgct cttgcccggc gtcaacacgg gataataccg cgccacatag   11460
cagaacttta aaagtgctca tcattggaaa acgttcttcg gggcgaaaac tctcaaggat   11520
cttaccgctg ttgagatcca gttcgatgta acccactcgt gcacccaact gatcttcagc   11580
atcttttact ttcaccagcg tttctgggtg agcaaaaaca ggaaggcaaa atgccgcaaa   11640
aaagggaata agggcgacac ggaaatgttg aatactcata ctcttccttt ttcaatatta   11700
ttgaagcatt tatcagggtt attgtctcat gagcggatac atatttgaat gtatttagaa   11760
aaataaacaa ataggggttc cgcgcacatt ccccgaaaa gtgccacctg acgtctaaga   11820
aaccattatt atcatgacat taacctataa aaataggcgt atcacgaggc cctttcgtct   11880
tcaagaattc at                                                      11892

<210> SEQ ID NO 20
<211> LENGTH: 11892
<212> TYPE: DNA
<213> ORGANISM: Artificial Sequence
<220> FEATURE:
<223> OTHER INFORMATION: RCR Vector - pAC3-yCD
```

```
<400> SEQUENCE: 20
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcggggggtc     720 tttcatttgg ggctcgtcc gggatcggga acccctgcc cagggaccac cgacccacca     780
ccgggaggta agctggccag caacttatct gtgtctgtcc gattgtctag tgtctatgac     840
tgattttatg cgcctgcgtc ggtactagtt agctaactag ctctgtatct ggcggacccg     900
tggtggaact gacgagttcg gaacaccogg ccgcaaccct gggagacgtc ccagggactt     960
cgggggccgt ttttgtggcc cgacctgagt ccaaaaatcc cgatcgtttt ggactctttg    1020
gtgcaccccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcacctt aaccgagacc    1380 tcatcaccca ggttaagatc aaggtctttt cacctggccc gcatggacac ccagaccagg    1440
tcccctacat cgtgacctgg gaagccttgg cttttgaccc ccctccctgg gtcaagccct    1500
ttgtacaccc taagcctccg cctcctcttc tccatccgc cccgtctctc cccttgaac     1560 ctcctcgttc gaccccgcct cgatcctccc tttatccagc cctcactcct tctctaggcg    1620
ccaaacctaa acctcaagtt cttttctgaca gtggggggcc gctcatcgac ctacttacag    1680
aagacccccc gccttatagg gacccaagac caccccttc cgacagggac ggaaatggtg    1740
gagaagcgac ccctgcggga gaggcaccgg acccctcccc aatggcatct cgcctacgtg    1800
ggagacggga gcccctgtg ccgactcca ctacctcgca ggcattcccc ctccgcgcag    1860
gaggaaacgg acagcttcaa tactggccgt tctcctcttc tgacctttac aactggaaaa    1920
ataataaccc ttcttttct gaagatccag gtaaactgac agctctgatc gagtctgttc    1980
tcatcaccca tcagcccacc tgggacgact gtcagcagct gttgggact ctgctgaccg    2040 gagaagaaaa acaacgggtg ctcttagagg ctagaaaggc ggtgcgggc gatgatgggc    2100 gcccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
```

```
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg gctaaagat tgtcccaaga    2760 aaccacgagg acctcgggga ccaagacccc agacctccct cctgacccta gatgactagg   2820
gaggtcaggg tcaggagccc cccctgaac ccaggataac cctcaaagtc gggggcaac     2880 ccgtcacctt cctggtagat actggggccc aacactccgt gctgacccaa aatcctggac   2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag catcggctac atgagacctc aaaagagcca gatgtttctc    3240
tagggtccac atggctgtct gattttcctc aggcctgggc ggaaaccggg ggcatgggac   3300
tggcagttcg ccaagctcct ctgatcatac ctctgaaagc aacctctacc ccgtgtcca    3360 taaaacaata ccccatgtca caagaagcca gactggggat caagcccac atacagagac    3420 tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc cttttttctgc ctgagactcc   3660 accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg gggttgccag   4260
atttgactaa gcccttgaa ctctttgtcg acgagaagca gggctacgcc aaaggtgtcc    4320
taacgcaaaa actgggacct ggcgtcggc cggtggccta cctgtccaaa aagctagacc    4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgcccttgat atcctggccg   4680
```

```
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacacgcg cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacctttt tctggctgga    5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccaccg ccctcaaagt agacggcatc gcagcttgga    6300
tacacgccgc ccacgtgaag gctgccgacc ccggggtgg accatcctct agactgacat    6360
ggcgcgttca acgctctcaa aaccccctca agataagatt aacccgtgga agcccttaat    6420
agtcatggga gtcctgttag gagtagggat ggcagagagc cccatcagg tctttaatgt    6480 aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggacttttg acttttacgt gtgccctggg catacgtaa agtcggggtg    6720 tgggggacca ggagagggct actgtggtaa atgggggtgt gaaaccaccg acaggctta    6780 ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caacccctcta gtcctagaat tcactgatgc    6960
aggaaaaaag gctaactggg acgggcccaa atcgtgggga ctgagactgt accgacagg    7020 aacagatcct attaccatgt tctccctgac ccggcaggtc cttaatgtgg gaccccgagt    7080
```

```
ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga     7260
tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa agaagaatg ttgtttttat gcagaccaca cggggctagt     8040
gagagacagc atggccaaat taagagaaag gcttaatcag agacaaaaac tatttgagac    8100
aggccaagga tggttcgaag ggctgtttaa tagatcccc tggttaccca ccttaatctc      8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca tgaacgcgtt actggccgaa    8340
gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgacaggggg aatggcaagc aagtgggatc agaagggtat ggacattgcc tatgaggagg    8940
cggccttagg ttacaaagag ggtggtgttc ctattggcgg atgtcttatc aataacaaag    9000
acggaagtgt tctcggtcgt ggtcacaaca tgagatttca aaagggatcc gccacactac    9060
atggtgagat ctccactttg gaaaactgtg ggagattaga gggcaaagtg tacaaagata    9120
ccactttgta tacgacgctg tctccatgcg acatgtgtac aggtgccatc atcatgtatg    9180
gtattccacg ctgtgttgtc ggtgagaacg ttaatttcaa aagtaagggc gagaaatatt    9240
tacaaactag aggtcacgag gttgttgttg ttgacgatga gaggtgtaaa aagatcatga    9300
aacaatttat cgatgaaaga cctcaggatt ggtttgaaga tattggtgag taggcggccg    9360
cagataaaat aaaagatttt atttagtctc cagaaaaagg ggggaatgaa agaccccacc    9420
```

```
tgtaggtttg gcaagctagc ttaagtaacg ccattttgca aggcatggaa aaatacataa    9480
ctgagaatag agaagttcag atcaaggtca ggaacagatg gaacagctga atatgggcca    9540
aacaggatat ctgtggtaag cagttcctgc cccggctcag ggccaagaac agatggaaca    9600
gctgaatatg gccaaacag gatatctgtg gtaagcagtt cctgcccgg ctcagggcca     9660
agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcggggt ctttcattac atgtgagcaa aaggccagca    10020
aaaggccagg aaccgtaaaa aggccgcgtt gctggcgttt tccataggc tccgccccc    10080
tgacgagcat cacaaaaatc gacgctcaag tcagaggtgg cgaaacccga caggactata    10140
aagataccag gcgtttcccc ctggaagctc cctcgtgcgc tctcctgttc cgaccctgcc    10200
gcttaccgga tacctgtccg cctttctccc ttcgggaagc gtggcgcttt ctcaatgctc    10260
acgctgtagg tatctcagtt cggtgtaggt cgttcgctcc aagctgggct gtgtgcacga    10320
acccccgtt cagcccgacc gctgcgcctt atccggtaac tatcgtcttg agtccaaccc    10380
ggtaagacac gacttatcgc cactggcagc agccactggt aacaggatta gcagagcgag    10440
gtatgtaggc ggtgctacag agttcttgaa gtggtggcct aactacggct acactagaag    10500
gacagtattt ggtatctgcg ctctgctgaa gccagttacc ttcggaaaaa gagttggtag    10560
ctcttgatcc ggcaaacaaa ccaccgctgg tagcggtggt ttttttgttt gcaagcagca    10620
gattacgcgc agaaaaaaag gatctcaaga agatcctttg atcttttcta cggggtctga    10680
cgctcagtgg aacgaaaact cacgttaagg gattttggtc atgagattat caaaaaggat    10740
cttcacctag atcctttta attaaaaatg aagttttaaa tcaatctaaa gtatatatga    10800
gtaaacttgg tctgacagtt accaatgctt aatcagtgag gcacctatct cagcgatctg    10860
tctatttcgt tcatccatag ttgcctgact ccccgtcgtg tagataacta cgatacggga    10920
gggcttacca tctggcccca gtgctgcaat gataccgcga gacccacgct caccggctcc    10980
agatttatca gcaataaacc agccagccgg aagggccgag cgcagaagtg gtcctgcaac    11040
tttatccgcc tccatccagt ctattaattg ttgccgggaa gctagagtaa gtagttcgcc    11100
agttaatagt ttgcgcaacg ttgttgccat tgctgcaggc atcgtggtgt cacgctcgtc    11160
gtttggtatg gcttcattca gctccggttc ccaacgatca aggcgagtta catgatcccc    11220
catgttgtgc aaaaaagcgg ttagctcctt cggtcctccg atcgttgtca gaagtaagtt    11280
ggccgcagtg ttatcactca tggttatggc agcactgcat aattctctta ctgtcatgcc    11340
atccgtaaga tgcttttctg tgactggtga gtactcaacc aagtcattct gagaatagtg    11400
tatgcggcga ccgagttgct cttgcccggc gtcaacacgg gataataccg cgccacatag    11460
cagaacttta aaagtgctca tcattggaaa acgttcttcg ggcgaaaac tctcaaggat     11520
cttaccgctg ttgagatcca gttcgatgta acccactcgt gcacccaact gatcttcagc    11580
atcttttact ttcaccagcg tttctgggtg agcaaaaaca ggaaggcaaa atgccgcaaa    11640
aaagggaata agggcgacac ggaaatgttg aatactcata ctcttccttt ttcaatatta    11700
ttgaagcatt tatcagggtt attgtctcat gagcggatac atatttgaat gtatttagaa    11760
aaataaacaa ataggggttc cgcgcacatt tccccgaaaa gtgccacctg acgtctaaga    11820
```

| | |
|---|---|
| aaccattatt atcatgacat taacctataa aaataggcgt atcacgaggc cctttcgtct | 11880 |
| tcaagaattc at | 11892 |

<210> SEQ ID NO 21
<211> LENGTH: 12007
<212> TYPE: DNA
<213> ORGANISM: Artificial Sequence
<220> FEATURE:
<223> OTHER INFORMATION: RCR Vector - pACE-CD

<400> SEQUENCE: 21

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta caactccgcc ccattgacg caaatgggcg gtaggcgtgt | 540 |
| acggtgggag gtctatataa gcagagctgg tttagtgaac cggcgccagt cctccgattg | 600 |
| actgagtcgc ccgggtaccc gtgtatccaa taaaccctct tgcagttgca tccgacttgt | 660 |
| ggtctcgctg ttccttggga gggtctcctc tgagtgattg actacccgtc agcggggtc | 720 |
| tttcatttgg gggctcgtcc gggatcggga gacccctgcc cagggaccac cgacccacca | 780 |
| ccgggaggta agctggccag caacttatct gtgtctgtcc gattgtctag tgtctatgac | 840 |
| tgatttatg cgcctgcgtc ggtactagtt agctaactag ctctgtatct ggcggacccg | 900 |
| tggtggaact gacgagttcg gaacacccgg ccgcaaccct gggagacgtc ccagggactt | 960 |
| cgggggccgt ttttgtggcc cgacctgagt ccaaaaatcc cgatcgtttt ggactctttg | 1020 |
| gtgcacccc cttagaggag ggatatgtgg ttctggtagg agacgagaac ctaaaacagt | 1080 |
| tcccgcctcc gtctgaattt ttgctttcgg tttgggaccg aagccgcgcc gcgcgtcttg | 1140 |
| tctgctgcag catcgttctg tgttgtctct gtctgactgt gtttctgtat ttgtctgaga | 1200 |
| atatgggcca gactgttacc actcccttaa gtttgacctt aggtcactgg aaagatgtcg | 1260 |
| agcggatcgc tcacaaccag tcggtagatg tcaagaagag acgttgggtt accttctgct | 1320 |
| ctgcagaatg gccaaccttt aacgtcggat ggccgcgaga cggcaccttt aaccgagacc | 1380 |
| tcatcaccca ggttaagatc aaggtctttt cacctggccc gcatggacac ccagaccagg | 1440 |
| tcccctacat cgtgacctgg gaagccttgg cttttgaccc ccctccctgg gtcaagccct | 1500 |
| ttgtacaccc taagcctccg cctcctcttc tccatccgc ccgtctctc ccccttgaac | 1560 |
| ctcctcgttc gaccccgcct cgatcctccc tttatccagc cctcactcct tctctaggcg | 1620 |
| ccaaacctaa acctcaagtt ctttctgaca gtggggggcc gctcatcgac ctacttacag | 1680 |
| aagaccccc gccttatagg gacccaagac cacccccttc cgacagggac ggaaatggtg | 1740 |
| gagaagcgac ccctgcggga gaggcaccgg accctcccc aatggcatct cgcctacgtg | 1800 |
| ggagacggga gccccctgtg gccgactcca tacctcgca ggcattcccc ctccgcgcag | 1860 |
| gaggaaacgg acagcttcaa tactggccgt tctcctcttc tgacctttac aactggaaaa | 1920 |

```
ataataaccc ttcttttcct gaagatccag gtaaactgac agctctgatc gagtctgttc    1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaagaaga acgccgtagg acagaggatg    2580
agcagaaaga gaaagaaaga gatcgtagga gacatagaga gatgagcaag ctattggcca    2640
ctgtcgttag tggacagaaa caggatcgac agggaggaga acgaaggagg tcccaactcg    2700
atcgcgacca gtgtgcctac tgcaaagaaa agggcactg gctaaagat tgtcccaaga    2760
aaccacgagg acctcgggga ccaagacccc agacctccct cctgaccca gatgactagg    2820
gaggtcaggg tcaggagccc ccccctgaac ccaggataac cctcaaagtc gggggcaac    2880
ccgtcacctt cctggtagat actggggccc aacactccgt gctgacccaa atcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg gcatgggac    3300
tggcagttcg ccaagctcct ctgatcatac ctctgaaagc aacctctacc ccgtgtcca    3360
taaaacaata ccccatgtca caagaagcca gactggggat caagcccac atacagagac    3420
tgttggacca gggaatactg gtaccctgcc agtccccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc ctttttctgc ctgagactcc    3660
accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagcctg ggttgccag    4260
atttgactaa gcccttgaa ctctttgtcg acgagaagca gggctacgcc aaaggtgtcc    4320
```

```
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacctttt ctggctgga    5640
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttgggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcacccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccaccg ccctcaaagt agacggcatc gcagcttgga    6300
tacacgccgc ccacgtgaag gctgccgacc ccggggggtgg accatcctct agactgacat    6360
ggcgcgttca acgctctcaa aaccccctca agataagatt aacccgtgga agcccttaat    6420
agtcatggga gtcctgttag gagtagggat ggcagagagc cccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
```

```
acagcggacc cggactttig acttttacgt gtgccctggg cataccgtaa agtcggggtg    6720
tgggggacca ggagagggct actgtggtaa atggggggtgt gaaaccaccg gacaggctta    6780
ctggaagccc acatcatcgt gggacctaat ctcccttaag cgcggtaaca cccctgggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accgacagg    7020 aacagatcct attaccatgt tctccctgac ccggcaggtc cttaatgtgg gaccccgagt    7080
ccccataggg cccaacccag tattaccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atggggggcag tacctaaaac    7500 tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680 ctccccccgat tatatgtatg gtcagcttga acagcgtacc aaatataaaa gagagccagt    7740
atcattgacc ctggcccttc tactaggagg attaaccatg ggaggattg cagctggaat    7800 agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
gagagacagc atggccaaat taagagaaag gcttaatcag agacaaaaac tatttgagac    8100
aggccaagga tggttcgaag gctgttttaa tagatccccc tggtttacca ccttaatctc    8160
caccatcatg ggacctctaa tagtactctt actgatctta ctctttggac cttgcattct    8220
caatcgatta gtccaatttg ttaaagacag gatatcagtg gtccaggctc tagttttgac    8280
tcaacaatat caccagctga agcctataga gtacgagcca tgacgtacgt tactggccga    8340
agccgcttgg aataaggccg gtgtgcgttt gtctatatgt tattttccac catattgccg    8400
tcttttggca atgtgagggc ccggaaacct ggccctgtct tcttgacgag cattcctagg    8460
ggtctttccc ctctcgccaa aggaatgcaa ggtctgttga atgtcgtgaa ggaagcagtt    8520
cctctggaag cttcttgaag acaaacaacg tctgtagcga ccctttgcag gcagcggaac    8580
cccccacctg gcgacaggtg cctctgcggc caaaagccac gtgtataaga tacacctgca    8640
aaggcggcac aaccccagtg ccacgttgtg agttggatag ttgtggaaag agtcaaatgg    8700
ctctcctcaa gcgtattcaa caaggggctg aaggatgccc agaaggtacc ccattgtatg    8760
ggatctgatc tggggcctcg gtgcacatgc tttacatgtg tttagtcgag gttaaaaaaa    8820
cgtctaggcc ccccgaacca cggggacgtg ttttcctttg aaaacacg ataataccat    8880 ggtgacaggg ggaatggcaa gcaagtggga tcagaagggt atggacattg cctatgagga    8940
ggcggcctta ggttacaaag agggtggtgt tcctattggc ggatgtctta tcaataacaa    9000
agacggaagt gttctcggtc gtggtcacaa catgagattt caaaagggat ccgccacact    9060
```

```
acatggtgag atctccactt tggaaaactg tgggagatta gagggcaaag tgtacaaaga    9120
taccactttg tatacgacgc tgtctccatg cgacatgtgt acaggtgcca tcatcatgta    9180
tggtattcca cgctgtgttg tcggtgagaa cgttaatttc aaaagtaagg gcgagaaata    9240
tttacaaact agaggtcacg aggttgttgt tgttgacgat gagaggtgta aaagatcat    9300 gaaacaattt atcgatgaaa gacctcagga ttggtttgaa gatattggtg agtaggcggc    9360
cgcgccatag ataaaataaa agattttatt tagtctccag aaaaagggg gaatgaaaga    9420 ccccacctgt aggtttggca agctagctta agtaacgcca ttttgcaagg catggaaaaa    9480
tacataactg agaatagaga agttcagatc aaggtcagga acagatggaa cagctgaata    9540
tgggccaaac aggatatctg tggtaagcag ttcctgcccc ggctcagggc caagaacaga    9600
tggaacagct gaatatgggc caaacaggat atctgtggta agcagttcct gcccggctc    9660 agggccaaga acagatggtc cccagatgcg gtccagccct cagcagtttc tagagaacca    9720
tcagatgttt ccagggtgcc ccaaggacct gaaatgaccc tgtgccttgt ttaaactaac    9780
caatcagttc gcttctcgct tctgttcgcg cgcttctgct ccccgagctc aataaaagag    9840
cccacaaccc ctcactcggg gcgccagtcc tccgattgac tgagtcgccc gggtacccgt    9900
gtatccaata aaccctcttg cagttgcatc cgacttgtgg tctcgctgtt ccttgggagg    9960
gtctcctctg agtgattgac tacccgtcag cgggggtctt tcatttgggg gctcgtccgg   10020
gatcgggaga cccctgccca ggaccaccg acccaccacc gggaggtaag ctggctgcct   10080
cgcgcgtttc ggtgatgacg gtgaaaacct ctgacatgtg agcaaaaggc cagcaaaagg   10140
ccaggaaccg taaaaaggcc gcgttgctgg cgttttttcca taggctccgc cccctgacg   10200 agcatcacaa aaatcgacgc tcaagtcaga ggtggcgaaa cccgacagga ctataaagat   10260
accaggcgtt ccccctgga agctccctcg tgcgctctcc tgttccgacc ctgccgctta   10320
ccggatacct gtccgccttt ctcccttcgg gaagcgtggc gctttctcaa tgctcacgct   10380
gtaggtatct cagttcggtg taggtcgttc gctccaagct gggctgtgtg cacgaacccc   10440
ccgttcagcc cgaccgctgc gccttatccg gtaactatcg tcttgagtcc aacccggtaa   10500
gacacgactt atcgccactg gcagcagcca ctggtaacag gattagcaga gcgaggtatg   10560
taggcggtgc tacagagttc ttgaagtggt ggcctaacta cggctacact agaaggacag   10620
tatttggtat ctgcgctctg ctgaagccag ttaccttcgg aaaaagagtt ggtagctctt   10680
gatccggcaa acaaaccacc gctggtagcg gtggtttttt tgtttgcaag cagcagatta   10740
cgcgcagaaa aaaaggatct caagaagatc ctttgatctt ttctacgggg tctgacgctc   10800
agtggaacga aaactcacgt taagggattt tggtcatgag attatcaaaa aggatcttca   10860
cctagatcct ttttaaattaa aaatgaagtt ttaaatcaat ctaaagtata tatgagtaaa   10920
cttggtctga cagttaccaa tgcttaatca gtgaggcacc tatctcagcg atctgtctat   10980
ttcgttcatc catagttgcc tgactccccg tcgtgtagat aactacgata cgggagggct   11040
taccatctgg ccccagtgct gcaatgatac cgcgagaccc acgctcaccg gctccagatt   11100
tatcagcaat aaaccagcca gccggaaggg ccgagcgcag aagtggtcct gcaactttat   11160
ccgcctccat ccagtctatt aattgttgcc gggaagctag agtaagtagt tcgccagtta   11220
atagtttgcg caacgttgtt gccattgctg caggcatcgt ggtgtcacgc tcgtcgtttg   11280
gtatggcttc attcagctcc ggttcccaac gatcaaggcg agttacatga tcccccatgt   11340
tgtgcaaaaa agcggttagc tccttcggtc ctccgatcgt tgtcagaagt aagttggccg   11400
```

| | |
|---|---|
| cagtgttatc actcatggtt atggcagcac tgcataattc tcttactgtc atgccatccg | 11460 |
| taagatgctt ttctgtgact ggtgagtact caaccaagtc attctgagaa tagtgtatgc | 11520 |
| ggcgaccgag ttgctcttgc ccggcgtcaa cacgggataa taccgcgcca catagcagaa | 11580 |
| ctttaaaagt gctcatcatt ggaaaacgtt cttcggggcg aaaactctca aggatcttac | 11640 |
| cgctgttgag atccagttcg atgtaaccca ctcgtgcacc caactgatct tcagcatctt | 11700 |
| ttactttcac cagcgtttct gggtgagcaa aacaggaag gcaaaatgcc gcaaaaaagg | 11760 |
| gaataagggc gacacggaaa tgttgaatac tcatactctt ccttttcaa tattattgaa | 11820 |
| gcatttatca gggttattgt ctcatgagcg gatacatatt tgaatgtatt tagaaaaata | 11880 |
| aacaaatagg ggttccgcgc acatttcccc gaaaagtgcc acctgacgtc taagaaacca | 11940 |
| ttattatcat gacattaacc tataaaaata ggcgtatcac gaggccctt cgtcttcaag | 12000 |
| aattcat | 12007 |

<210> SEQ ID NO 22
<211> LENGTH: 11893
<212> TYPE: DNA
<213> ORGANISM: Artificial Sequence
<220> FEATURE:
<223> OTHER INFORMATION: RCR Vector - pAC3-yCD2

<400> SEQUENCE: 22

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta caactccgcc ccattgacg caaatgggcg gtaggcgtgt | 540 |
| acggtgggag gtctatataa gcagagctgg tttagtgaac cggcgccagt cctccgattg | 600 |
| actgagtcgc ccgggtaccc gtgtatccaa taaaccctct tgcagttgca tccgacttgt | 660 |
| ggtctcgctg ttccttggga gggtctcctc tgagtgattg actaccgtc agcggggtc | 720 |
| tttcatttgg gggctcgtcc gggatcggga gaccctgcc cagggaccac cgacccacca | 780 |
| ccgggaggta agctggccag caacttatct gtgtctgtcc gattgtctag tgtctatgac | 840 |
| tgattttatg cgcctgcgtc ggtactagtt agctaactag ctctgtatct ggcggacccg | 900 |
| tggtggaact gacgagttcg gaacacccgg ccgcaaccct gggagacgtc ccagggactt | 960 |
| cgggggccgt ttttgtggcc cgacctgagt ccaaaaatcc cgatcgtttt ggactctttg | 1020 |
| gtgcacccc cttagaggag ggatatgtgg ttctggtagg agacgagaac ctaaaacagt | 1080 |
| tcccgcctcc gtctgaattt ttgctttcgg tttgggaccg aagccgcgcc gcgcgtcttg | 1140 |
| tctgctgcag catcgttctg tgttgtctct gtctgactgt gtttctgtat ttgtctgaaa | 1200 |
| atatgggcca gactgttacc actcccttaa gtttgacctt aggtcactgg aaagatgtcg | 1260 |
| agcggatcgc tcacaaccag tcggtagatg tcaagaagag acgttgggtt accttctgct | 1320 |
| ctgcagaatg gccaaccttt aacgtcggat ggccgcgaga cggcaccttt aaccgagacc | 1380 |
| tcatcaccca ggttaagatc aaggtctttt cacctggccc gcatggacac ccagaccagg | 1440 |

```
tcccctacat cgtgacctgg gaagccttgg cttttgaccc ccctccctgg gtcaagccct    1500
ttgtacaccc taagcctccg cctcctcttc ctccatccgc cccgtctctc cccttgaac    1560
ctcctcgttc gaccccgcct cgatcctccc tttatccagc cctcactcct tctctaggcg    1620
ccaaacctaa acctcaagtt ctttctgaca gtggggggcc gctcatcgac ctacttacag    1680
aagacccccc gccttatagg acccaagac caccccttc cgacagggac ggaaatggtg       1740
gagaagcgac ccctgcggga gaggcaccgg accccctccc aatggcatct cgcctacgtg    1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttttct gaagatccag gtaaactgac agctctgatc gagtctgtcc   1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc gggggggcaac   2880
ccgtcacctt cctggtagat actggggccc aacactccgt gctgacccaa aatcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag tatcggctac atgagacctc aaaagagcca gatgtttctc    3240
tagggtccac atggctgtct gattttcctc aggcctgggc ggaaaccggg gcatgggac    3300
tggcagttcg ccaagctcct ctgatcatac ctctgaaagc aacctctacc cccgtgtcca    3360
taaaacaata ccccatgtca caagaagcca gactggggat caagcccac atacagagac    3420
tgttggacca gggaatactg gtaccctgcc agtccccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttttctgc ctgagactcc    3660
accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
```

```
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg ggttgccag     4260 atttgactaa gcccttgaa ctctttgtcg acgagaagca gggctacgcc aaaggtgtcc     4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca gcggcccga aaggcagcca     5160 tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacctt tctggctgga     5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttgggat tgattggaaa ttacattgtg      5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000 ggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
```

```
gcgacacagt gtgggtccgc cgacaccaga ctaagaacct agaacctcgc tggaaaggac    6240
cttacacagt cctgctgacc accccaccg ccctcaaagt agacggcatc gcagcttgga    6300
tacacgccgc ccacgtgaag gctgccgacc ccgggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcaggag    6660 acagcggacc cggacttttg acttttacgt gtgccctggg cataccgtaa agtcggggtg    6720
tgggggacca ggagagggct actgtggtaa atggggtgt gaaaccaccg gacaggctta    6780
ctggaagccc acatcatcgt gggacctaat ctcccttaag cgcggtaaca cccctggga    6840 cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt taccccccctt ccactaccag    7200 tacaccctca acctcccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacgt    7620 gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
gagagacagc atggccaaat aagagaaag gcttaatcag agacaaaaac tatttgagac    8100
aggccaagga tggttcgaag gctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca tgaacgcgtt actggccgaa    8340
gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
```

```
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgaccggcgg catggcctcc aagtgggatc aaaagggcat ggatatcgct tacgaggagg    8940
ccctgctggg ctacaaggag ggcggcgtgc ctatcggcgg ctgtctgatc aacaacaagg    9000
acggcagtgt gctgggcagg ggccacaaca tgaggttcca gaagggctcc gccaccctgc    9060
acggcgagat ctccaccctg gagaactgtg gcaggctgga gggcaaggtg tacaaggaca    9120
ccaccctgta caccaccctg tccccttgtg acatgtgtac cggcgctatc atcatgtacg    9180
gcatccctag gtgtgtgatc ggcgagaacg tgaacttcaa gtccaagggc gagaagtacc    9240
tgcaaaccag gggccacgag gtggtggttg ttgacgatga gaggtgtaag aagctgatga    9300
agcagttcat cgacgagagg cctcaggact ggttcgagga tatcggcgag taagcggccg    9360
cagataaaat aaaagatttt atttagtctc cagaaaaagg ggggaatgaa agaccccacc    9420
tgtaggtttg gcaagctagc ttaagtaacg ccattttgca aggcatggaa aatacataa    9480
ctgagaatag agaagttcag atcaaggtca ggaacagatg aacagctga atatgggcca    9540
aacaggatat ctgtggtaag cagttcctgc cccggctcag gccaagaac agatggaaca    9600
gctgaatatg ggccaaacag gatatctgtg gtaagcagtt cctgccccgg ctcagggcca    9660
agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcgggggt ctttcattac atgtgagcaa aaggccagca    10020
aaaggccagg aaccgtaaaa aggccgcgtt gctggcgttt ttccataggc tccgcccccc    10080
tgacgagcat cacaaaaatc gacgctcaag tcagaggtgg cgaaacccga caggactata    10140
aagataccag gcgtttcccc ctggaagctc cctcgtgcgc tctcctgttc cgaccctgcc    10200
gcttaccgga tacctgtccg cctttctccc ttcgggaagc gtggcgcttt ctcatagctc    10260
acgctgtagg tatctcagtt cggtgtaggt cgttcgctcc aagctgggct gtgtgcacga    10320
accccccgtt cagcccgacc gctgcgcctt atccggtaac tatcgtcttg agtccaaccc    10380
ggtaagacac gacttatcgc cactggcagc agccactggt aacaggatta gcagagcgag    10440
gtatgtaggc ggtgctacag agttcttgaa gtggtggcct aactacggct acactagaag    10500
gacagtattt ggtatctgcg ctctgctgaa gccagttacc ttcggaaaaa gagttggtag    10560
ctcttgatcc ggcaaacaaa ccaccgctgg tagcggtggt ttttttgttt gcaagcagca    10620
gattacgcgc agaaaaaaag gatctcaaga agatcctttg atcttttcta cggggtctga    10680
cgctcagtgg aacgaaaact cacgttaagg gattttggtc atgagattat caaaaaggat    10740
cttcacctag atccttttaa attaaaaatg aagttttaaa tcaatctaaa gtatatatga    10800
gtaaacttgg tctgacagtt accaatgctt aatcagtgag gcacctatct cagcgatctg    10860
tctatttcgt tcatccatag ttgcctgact ccccgtcgtg tagataacta cgatacggga    10920
```

-continued

```
gggcttacca tctggcccca gtgctgcaat gataccgcga gacccacgct caccggctcc    10980
agatttatca gcaataaacc agccagccgg aagggccgag cgcagaagtg gtcctgcaac    11040
tttatccgcc tccatccagt ctattaattg ttgccgggaa gctagagtaa gtagttcgcc    11100
agttaatagt ttgcgcaacg ttgttgccat tgctgcaggc atcgtggtgt cacgctcgtc    11160
gtttggtatg gcttcattca gctccggttc ccaacgatca aggcgagtta catgatcccc    11220
catgttgtgc aaaaaagcgg ttagctcctt cggtcctccg atcgttgtca gaagtaagtt    11280
ggccgcagtg ttatcactca tggttatggc agcactgcat aattctctta ctgtcatgcc    11340
atccgtaaga tgcttttctg tgactggtga gtactcaacc aagtcattct gagaatagtg    11400
tatgcggcga ccgagttgct cttgcccggc gtcaacacgg gataataccg cgccacatag    11460
cagaacttta aaagtgctca tcattggaaa acgttcttcg gggcgaaaac tctcaaggat    11520
cttaccgctg ttgagatcca gttcgatgta acccactcgt gcacccaact gatcttcagc    11580
atcttttact ttcaccagcg tttctgggtg agcaaaaaca ggaaggcaaa atgccgcaaa    11640
aaagggaata agggcgacac ggaaatgttg aatactcata ctcttccttt tcaatatta    11700 ttgaagcatt tatcagggtt attgtctcat gagcggatac atatttgaat gtatttagaa    11760
aaataaacaa atagggggttc gcgcacatt tccccgaaaa gtgccacctg acgtctaaga    11820
aaccattatt atcatgacat taacctataa aaataggcgt atcacgaggc cctttcgtct    11880
tcaagaattc cat                                                       11893

<210> SEQ ID NO 23
<211> LENGTH: 4473
<212> TYPE: DNA
<213> ORGANISM: Homo sapiens
<220> FEATURE:
<221> NAME/KEY: CDS
<222> LOCATION: (175)..(3942)

<400> SEQUENCE: 23
aaggggaggt aaccctggcc cctttggtcg ggccccggg cagccgcgcg ccccttccca    60 cggggcccctt tactgcgccg cgcgcccggc ccccaccct cgcagcaccc cgcgccccgc    120
gccctcccag ccgggtccag ccggagccat ggggccggag ccgcagtgag cacc atg     177
                                                              Met
                                                                1 gag ctg gcg gcc ttg tgc cgc tgg ggg ctc ctc ctc gcc ctc ttg ccc     225
Glu Leu Ala Ala Leu Cys Arg Trp Gly Leu Leu Leu Ala Leu Leu Pro
            5                  10                  15 ccc gga gcc gcg agc acc caa gtg tgc acc ggc aca gac atg aag ctg     273
Pro Gly Ala Ala Ser Thr Gln Val Cys Thr Gly Thr Asp Met Lys Leu
       20                  25                  30 cgg ctc cct gcc agt ccc gag acc cac ctg gac atg ctc cgc cac ctc     321
Arg Leu Pro Ala Ser Pro Glu Thr His Leu Asp Met Leu Arg His Leu
    35                  40                  45 tac cag ggc tgc cag gtg gtg cag gga aac ctg gaa ctc acc tac ctg     369
Tyr Gln Gly Cys Gln Val Val Gln Gly Asn Leu Glu Leu Thr Tyr Leu
 50                  55                  60                  65 ccc acc aat gcc agc ctg tcc ttc ctg cag gat atc cag gag gtg cag     417
Pro Thr Asn Ala Ser Leu Ser Phe Leu Gln Asp Ile Gln Glu Val Gln
                 70                  75                  80 ggc tac gtg ctc atc gct cac aac caa gtg agg cag gtc cca ctg cag     465
Gly Tyr Val Leu Ile Ala His Asn Gln Val Arg Gln Val Pro Leu Gln
             85                  90                  95 agg ctg cgg att gtg cga ggc acc cag ctc ttt gag gac aac tat gcc     513
```

```
                Arg Leu Arg Ile Val Arg Gly Thr Gln Leu Phe Glu Asp Asn Tyr Ala
                            100                 105                 110 ctg gcc gtg cta gac aat gga gac ccg ctg aac aat acc acc cct gtc        561
Leu Ala Val Leu Asp Asn Gly Asp Pro Leu Asn Asn Thr Thr Pro Val
115                 120                 125 aca ggg gcc tcc cca gga ggc ctg cgg gag ctg cag ctt cga agc ctc        609
Thr Gly Ala Ser Pro Gly Gly Leu Arg Glu Leu Gln Leu Arg Ser Leu
130                 135                 140                 145 aca gag atc ttg aaa gga ggg gtc ttg atc cag cgg aac ccc cag ctc        657
Thr Glu Ile Leu Lys Gly Gly Val Leu Ile Gln Arg Asn Pro Gln Leu
                150                 155                 160 tgc tac cag gac acg att ttg tgg aag gac atc ttc cac aag aac aac        705
Cys Tyr Gln Asp Thr Ile Leu Trp Lys Asp Ile Phe His Lys Asn Asn
                165                 170                 175 cag ctg gct ctc aca ctg ata gac acc aac cgc tct cgg gcc tgc cac        753
Gln Leu Ala Leu Thr Leu Ile Asp Thr Asn Arg Ser Arg Ala Cys His
                180                 185                 190 ccc tgt tct ccg atg tgt aag ggc tcc cgc tgc tgg gga gag agt tct        801
Pro Cys Ser Pro Met Cys Lys Gly Ser Arg Cys Trp Gly Glu Ser Ser
            195                 200                 205 gag gat tgt cag agc ctg acg cgc act gtc tgt gcc ggt ggc tgt gcc        849
Glu Asp Cys Gln Ser Leu Thr Arg Thr Val Cys Ala Gly Gly Cys Ala
210                 215                 220                 225 cgc tgc aag ggg cca ctg ccc act gac tgc tgc cat gag cag tgt gct        897
Arg Cys Lys Gly Pro Leu Pro Thr Asp Cys Cys His Glu Gln Cys Ala
                230                 235                 240 gcc ggc tgc acg ggc ccc aag cac tct gac tgc ctg gcc tgc ctc cac        945
Ala Gly Cys Thr Gly Pro Lys His Ser Asp Cys Leu Ala Cys Leu His
                245                 250                 255 ttc aac cac agt ggc atc tgt gag ctg cac tgc cca gcc ctg gtc acc        993
Phe Asn His Ser Gly Ile Cys Glu Leu His Cys Pro Ala Leu Val Thr
                260                 265                 270 tac aac aca gac acg ttt gag tcc atg ccc aat ccc gag ggc cgg tat       1041
Tyr Asn Thr Asp Thr Phe Glu Ser Met Pro Asn Pro Glu Gly Arg Tyr
275                 280                 285 aca ttc ggc gcc agc tgt gtg act gcc tgt ccc tac aac tac ctt tct       1089
Thr Phe Gly Ala Ser Cys Val Thr Ala Cys Pro Tyr Asn Tyr Leu Ser
290                 295                 300                 305 acg gac gtg gga tcc tgc acc ctc gtc tgc ccc ctg cac aac caa gag       1137
Thr Asp Val Gly Ser Cys Thr Leu Val Cys Pro Leu His Asn Gln Glu
                310                 315                 320 gtg aca gca gag gat gga aca cag cgg tgt gag aag tgc agc aag ccc       1185
Val Thr Ala Glu Asp Gly Thr Gln Arg Cys Glu Lys Cys Ser Lys Pro
                325                 330                 335 tgt gcc cga gtg tgc tat ggt ctg ggc atg gag cac ttg cga gag gtg       1233
Cys Ala Arg Val Cys Tyr Gly Leu Gly Met Glu His Leu Arg Glu Val
                340                 345                 350 agg gca gtt acc agt gcc aat atc cag gag ttt gct ggc tgc aag aag       1281
Arg Ala Val Thr Ser Ala Asn Ile Gln Glu Phe Ala Gly Cys Lys Lys
355                 360                 365 atc ttt ggg agc ctg gca ttt ctg ccg gag agc ttt gat ggg gac cca       1329
Ile Phe Gly Ser Leu Ala Phe Leu Pro Glu Ser Phe Asp Gly Asp Pro
370                 375                 380                 385 gcc tcc aac act gcc ccg ctc cag cca gag cag ctc caa gtg ttt gag       1377
Ala Ser Asn Thr Ala Pro Leu Gln Pro Glu Gln Leu Gln Val Phe Glu
                390                 395                 400 act ctg gaa gag atc aca ggt tac cta tac atc tca gca tgg ccg gac       1425
Thr Leu Glu Glu Ile Thr Gly Tyr Leu Tyr Ile Ser Ala Trp Pro Asp
                405                 410                 415
```

-continued

| | | |
|---|---|---|
| agc ctg cct gac ctc agc gtc ttc cag aac ctg caa gta atc cgg gga<br>Ser Leu Pro Asp Leu Ser Val Phe Gln Asn Leu Gln Val Ile Arg Gly<br>420                        425                           430 | | 1473 |
| cga att ctg cac aat ggc gcc tac tcg ctg acc ctg caa ggg ctg ggc<br>Arg Ile Leu His Asn Gly Ala Tyr Ser Leu Thr Leu Gln Gly Leu Gly<br>    435                    440                    445 | | 1521 |
| atc agc tgg ctg ggg ctg cgc tca ctg agg gaa ctg ggc agt gga ctg<br>Ile Ser Trp Leu Gly Leu Arg Ser Leu Arg Glu Leu Gly Ser Gly Leu<br>450                       455                    460                465 | | 1569 |
| gcc ctc atc cac cat aac acc cac ctc tgc ttc gtg cac acg gtg ccc<br>Ala Leu Ile His His Asn Thr His Leu Cys Phe Val His Thr Val Pro<br>                 470                    475                    480 | | 1617 |
| tgg gac cag ctc ttt cgg aac ccg cac caa gct ctg ctc cac act gcc<br>Trp Asp Gln Leu Phe Arg Asn Pro His Gln Ala Leu Leu His Thr Ala<br>                      485                    490                    495 | | 1665 |
| aac cgg cca gag gac gag tgt gtg ggc gag ggc ctg gcc tgc cac cag<br>Asn Arg Pro Glu Asp Glu Cys Val Gly Glu Gly Leu Ala Cys His Gln<br>500                       505                    510 | | 1713 |
| ctg tgc gcc cga ggg cac tgc tgg ggt cca ggg ccc acc cag tgt gtc<br>Leu Cys Ala Arg Gly His Cys Trp Gly Pro Gly Pro Thr Gln Cys Val<br>    515                    520                    525 | | 1761 |
| aac tgc agc cag ttc ctt cgg ggc cag gag tgc gtg gag gaa tgc cga<br>Asn Cys Ser Gln Phe Leu Arg Gly Gln Glu Cys Val Glu Glu Cys Arg<br>530                       535                    540                545 | | 1809 |
| gta ctg cag ggg ctc ccc agg gag tat gtg aat gcc agg cac tgt ttg<br>Val Leu Gln Gly Leu Pro Arg Glu Tyr Val Asn Ala Arg His Cys Leu<br>                 550                    555                    560 | | 1857 |
| ccg tgc cac cct gag tgt cag ccc cag aat ggc tca gtg acc tgt ttt<br>Pro Cys His Pro Glu Cys Gln Pro Gln Asn Gly Ser Val Thr Cys Phe<br>                      565                    570                    575 | | 1905 |
| gga ccg gag gct gac cag tgt gtg gcc tgt gcc cac tat aag gac cct<br>Gly Pro Glu Ala Asp Gln Cys Val Ala Cys Ala His Tyr Lys Asp Pro<br>580                       585                    590 | | 1953 |
| ccc ttc tgc gtg gcc cgc tgc ccc agc ggt gtg aaa cct gac ctc tcc<br>Pro Phe Cys Val Ala Arg Cys Pro Ser Gly Val Lys Pro Asp Leu Ser<br>    595                    600                    605 | | 2001 |
| tac atg ccc atc tgg aag ttt cca gat gag gag ggc gca tgc cag cct<br>Tyr Met Pro Ile Trp Lys Phe Pro Asp Glu Glu Gly Ala Cys Gln Pro<br>610                       615                    620                625 | | 2049 |
| tgc ccc atc aac tgc acc cac tcc tgt gtg gac ctg gat gac aag ggc<br>Cys Pro Ile Asn Cys Thr His Ser Cys Val Asp Leu Asp Asp Lys Gly<br>                 630                    635                    640 | | 2097 |
| tgc ccc gcc gag cag aga gcc agc cct ctg acg tcc atc atc tct gcg<br>Cys Pro Ala Glu Gln Arg Ala Ser Pro Leu Thr Ser Ile Ile Ser Ala<br>                      645                    650                655 | | 2145 |
| gtg gtt ggc att ctg ctg gtc gtg gtc ttg ggg gtg gtc ttt ggg atc<br>Val Val Gly Ile Leu Leu Val Val Val Leu Gly Val Val Phe Gly Ile<br>660                       665                    670 | | 2193 |
| ctc atc aag cga cgg cag cag aag atc cgg aag tac acg atg cgg aga<br>Leu Ile Lys Arg Arg Gln Gln Lys Ile Arg Lys Tyr Thr Met Arg Arg<br>    675                    680                    685 | | 2241 |
| ctg ctg cag gaa acg gag ctg gtg gag ccg ctg aca cct agc gga gcg<br>Leu Leu Gln Glu Thr Glu Leu Val Glu Pro Leu Thr Pro Ser Gly Ala<br>690                       695                    700                705 | | 2289 |
| atg ccc aac cag gcg cag atg cgg atc ctg aaa gag acg gag ctg agg<br>Met Pro Asn Gln Ala Gln Met Arg Ile Leu Lys Glu Thr Glu Leu Arg<br>                         710                    715                720 | | 2337 |
| aag gtg aag gtg ctt gga tct ggc gct ttt ggc aca gtc tac aag ggc<br>Lys Val Lys Val Leu Gly Ser Gly Ala Phe Gly Thr Val Tyr Lys Gly<br>725                       730                    735 | | 2385 |

-continued

```
atc tgg atc cct gat ggg gag aat gtg aaa att cca gtg gcc atc aaa    2433
Ile Trp Ile Pro Asp Gly Glu Asn Val Lys Ile Pro Val Ala Ile Lys
        740                 745                 750 gtg ttg agg gaa aac aca tcc ccc aaa gcc aac aaa gaa atc tta gac    2481
Val Leu Arg Glu Asn Thr Ser Pro Lys Ala Asn Lys Glu Ile Leu Asp
755                 760                 765 gaa gca tac gtg atg gct ggt gtg ggc tcc cca tat gtc tcc cgc ctt    2529
Glu Ala Tyr Val Met Ala Gly Val Gly Ser Pro Tyr Val Ser Arg Leu
770                 775                 780                 785 ctg ggc atc tgc ctg aca tcc acg gtg cag ctg gta aca cag ctt atg    2577
Leu Gly Ile Cys Leu Thr Ser Thr Val Gln Leu Val Thr Gln Leu Met
                790                 795                 800 ccc tat ggc tgc ctc tta gac cat gtc cgg gaa aac cgc gga cgc ctg    2625
Pro Tyr Gly Cys Leu Leu Asp His Val Arg Glu Asn Arg Gly Arg Leu
            805                 810                 815 ggc tcc cag gac ctg ctg aac tgg tgt atg cag att gcc aag ggg atg    2673
Gly Ser Gln Asp Leu Leu Asn Trp Cys Met Gln Ile Ala Lys Gly Met
        820                 825                 830 agc tac ctg gag gat gtg cgg ctc gta cac agg gac ttg gcc gct cgg    2721
Ser Tyr Leu Glu Asp Val Arg Leu Val His Arg Asp Leu Ala Ala Arg
835                 840                 845 aac gtg ctg gtc aag agt ccc aac cat gtc aaa att aca gac ttc ggg    2769
Asn Val Leu Val Lys Ser Pro Asn His Val Lys Ile Thr Asp Phe Gly
850                 855                 860                 865 ctg gct cgg ctg ctg gac att gac gag aca gag tac cat gca gat ggg    2817
Leu Ala Arg Leu Leu Asp Ile Asp Glu Thr Glu Tyr His Ala Asp Gly
                870                 875                 880 ggc aag gtg ccc atc aag tgg atg gcg ctg gag tcc att ctc cgc cgg    2865
Gly Lys Val Pro Ile Lys Trp Met Ala Leu Glu Ser Ile Leu Arg Arg
            885                 890                 895 cgg ttc acc cac cag agt gat gtg tgg agt tat ggt gtg act gtg tgg    2913
Arg Phe Thr His Gln Ser Asp Val Trp Ser Tyr Gly Val Thr Val Trp
        900                 905                 910 gag ctg atg act ttt ggg gcc aaa cct tac gat ggg atc cca gcc cgg    2961
Glu Leu Met Thr Phe Gly Ala Lys Pro Tyr Asp Gly Ile Pro Ala Arg
915                 920                 925 gag atc cct gac ctg ctg gaa aag ggg gag cgg ctg ccc cag ccc ccc    3009
Glu Ile Pro Asp Leu Leu Glu Lys Gly Glu Arg Leu Pro Gln Pro Pro
930                 935                 940                 945 atc tgc acc att gat gtc tac atg atc atg gtc aaa tgt tgg atg att    3057
Ile Cys Thr Ile Asp Val Tyr Met Ile Met Val Lys Cys Trp Met Ile
                950                 955                 960 gac tct gaa tgt cgg cca aga ttc cgg gag ttg gtg tct gaa ttc tcc    3105
Asp Ser Glu Cys Arg Pro Arg Phe Arg Glu Leu Val Ser Glu Phe Ser
            965                 970                 975 cgc atg gcc agg gac ccc cag cgc ttt gtg gtc atc cag aat gag gac    3153
Arg Met Ala Arg Asp Pro Gln Arg Phe Val Val Ile Gln Asn Glu Asp
        980                 985                 990 ttg ggc cca gcc agt ccc ttg gac agc acc ttc tac cgc tca ctg ctg    3201
Leu Gly Pro Ala Ser Pro Leu Asp Ser Thr Phe Tyr Arg Ser Leu Leu
    995                 1000                1005 gag gac gat gac atg ggg gac ctg gtg gat gct gag gag tat ctg       3246
Glu Asp Asp Asp Met Gly Asp Leu Val Asp Ala Glu Glu Tyr Leu
1010                1015                1020 gta ccc cag cag ggc ttc ttc tgt cca gac cct gcc ccg ggc gct       3291
Val Pro Gln Gln Gly Phe Phe Cys Pro Asp Pro Ala Pro Gly Ala
1025                1030                1035 ggg ggc atg gtc cac cac agg cac cgc agc tca tct acc agg agt       3336
Gly Gly Met Val His His Arg His Arg Ser Ser Ser Thr Arg Ser
```

| | | |
|---|---|---|
| ggc ggt ggg gac ctg aca cta ggg ctg gag ccc tct gaa gag gag<br>Gly Gly Gly Asp Leu Thr Leu Gly Leu Glu Pro Ser Glu Glu Glu<br>1055      1060      1065 | | 3381 |
| gcc ccc agg tct cca ctg gca ccc tcc gaa ggg gct ggc tcc gat<br>Ala Pro Arg Ser Pro Leu Ala Pro Ser Glu Gly Ala Gly Ser Asp<br>1070      1075      1080 | | 3426 |
| gta ttt gat ggt gac ctg gga atg ggg gca gcc aag ggg ctg caa<br>Val Phe Asp Gly Asp Leu Gly Met Gly Ala Ala Lys Gly Leu Gln<br>1085      1090      1095 | | 3471 |
| agc ctc ccc aca cat gac ccc agc cct cta cag cgg tac agt gag<br>Ser Leu Pro Thr His Asp Pro Ser Pro Leu Gln Arg Tyr Ser Glu<br>1100      1105      1110 | | 3516 |
| gac ccc aca gta ccc ctg ccc tct gag act gat ggc tac gtt gcc<br>Asp Pro Thr Val Pro Leu Pro Ser Glu Thr Asp Gly Tyr Val Ala<br>1115      1120      1125 | | 3561 |
| ccc ctg acc tgc agc ccc cag cct gaa tat gtg aac cag cca gat<br>Pro Leu Thr Cys Ser Pro Gln Pro Glu Tyr Val Asn Gln Pro Asp<br>1130      1135      1140 | | 3606 |
| gtt cgg ccc cag ccc cct tcg ccc cga gag ggc cct ctg cct gct<br>Val Arg Pro Gln Pro Pro Ser Pro Arg Glu Gly Pro Leu Pro Ala<br>1145      1150      1155 | | 3651 |
| gcc cga cct gct ggt gcc act ctg gaa agg ccc aag act ctc tcc<br>Ala Arg Pro Ala Gly Ala Thr Leu Glu Arg Pro Lys Thr Leu Ser<br>1160      1165      1170 | | 3696 |
| cca ggg aag aat ggg gtc gtc aaa gac gtt ttt gcc ttt ggg ggt<br>Pro Gly Lys Asn Gly Val Val Lys Asp Val Phe Ala Phe Gly Gly<br>1175      1180      1185 | | 3741 |
| gcc gtg gag aac ccc gag tac ttg aca ccc cag gga gga gct gcc<br>Ala Val Glu Asn Pro Glu Tyr Leu Thr Pro Gln Gly Gly Ala Ala<br>1190      1195      1200 | | 3786 |
| cct cag ccc cac cct cct cct gcc ttc agc cca gcc ttc gac aac<br>Pro Gln Pro His Pro Pro Pro Ala Phe Ser Pro Ala Phe Asp Asn<br>1205      1210      1215 | | 3831 |
| ctc tat tac tgg gac cag gac cca cca gag cgg ggg gct cca ccc<br>Leu Tyr Tyr Trp Asp Gln Asp Pro Pro Glu Arg Gly Ala Pro Pro<br>1220      1225      1230 | | 3876 |
| agc acc ttc aaa ggg aca cct acg gca gag aac cca gag tac ctg<br>Ser Thr Phe Lys Gly Thr Pro Thr Ala Glu Asn Pro Glu Tyr Leu<br>1235      1240      1245 | | 3921 |
| ggt ctg gac gtg cca gtg tga accagaaggc caagtccgca gaagccctga<br>Gly Leu Asp Val Pro Val<br>1250      1255 | | 3972 |
| tgtgtcctca gggagcaggg aaggcctgac ttctgctggc atcaagaggt gggagggccc | | 4032 |
| tccgaccact tccaggggaa cctgccatgc caggaacctg tcctaaggaa ccttccttcc | | 4092 |
| tgcttgagtt cccagatggc tggaaggggt ccagcctcgt tggaagagga acagcactgg | | 4152 |
| ggagtctttg tggattctga ggccctgccc aatgagactc tagggtccag tggatgccac | | 4212 |
| agcccagctt ggccctttcc ttccagatcc tgggtactga aagccttagg gaagctggcc | | 4272 |
| tgagaggga agcggcccta agggagtgtc taagaacaaa agcgacccat tcagagactg | | 4332 |
| tccctgaaac ctagtactgc cccccatgag gaaggaacag caatggtgtc agtatccagg | | 4392 |
| ctttgtacag agtgcttttc tgtttagttt ttactttttt tgttttgttt tttttaaagat | | 4452 |
| gaaataaaga cccaggggga g | | 4473 |

<210> SEQ ID NO 24
<211> LENGTH: 1255

<212> TYPE: PRT
<213> ORGANISM: Homo sapiens

<400> SEQUENCE: 24

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400
```

```
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
```

```
Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
```

<210> SEQ ID NO 25
<211> LENGTH: 1212
<212> TYPE: DNA
<213> ORGANISM: Homo sapiens
<220> FEATURE:
<221> NAME/KEY: CDS
<222> LOCATION: (1)..(1212)

<400> SEQUENCE: 25

| | | | | | | | | | | | | | | | | |
|---|---|---|---|---|---|---|---|---|---|---|---|---|---|---|---|---|
| atg | aca | gcc | atc | atc | aaa | gag | atc | gtt | agc | aga | aac | aaa | agg | aga | tat | 48 |
| Met | Thr | Ala | Ile | Ile | Lys | Glu | Ile | Val | Ser | Arg | Asn | Lys | Arg | Arg | Tyr | |
| 1 | | | | 5 | | | | | 10 | | | | | 15 | | |
| caa | gag | gat | gga | ttc | gac | tta | gac | ttg | acc | tat | att | tat | cca | aac | att | 96 |
| Gln | Glu | Asp | Gly | Phe | Asp | Leu | Asp | Leu | Thr | Tyr | Ile | Tyr | Pro | Asn | Ile | |
| | | | 20 | | | | | 25 | | | | | 30 | | | |
| att | gct | atg | gga | ttt | cct | gca | gaa | aga | ctt | gaa | ggc | gta | tac | agg | aac | 144 |
| Ile | Ala | Met | Gly | Phe | Pro | Ala | Glu | Arg | Leu | Glu | Gly | Val | Tyr | Arg | Asn | |
| | | 35 | | | | | 40 | | | | | 45 | | | | |
| aat | att | gat | gat | gta | gta | agg | ttt | ttg | gat | tca | aag | cat | aaa | aac | cat | 192 |
| Asn | Ile | Asp | Asp | Val | Val | Arg | Phe | Leu | Asp | Ser | Lys | His | Lys | Asn | His | |
| 50 | | | | | 55 | | | | | 60 | | | | | | |
| tac | aag | ata | tac | aat | ctt | tgt | gct | gaa | aga | cat | tat | gac | acc | gcc | aaa | 240 |
| Tyr | Lys | Ile | Tyr | Asn | Leu | Cys | Ala | Glu | Arg | His | Tyr | Asp | Thr | Ala | Lys | |
| 65 | | | | 70 | | | | | 75 | | | | | 80 | | |
| ttt | aat | tgc | aga | gtt | gca | caa | tat | cct | ttt | gaa | gac | cat | aac | cca | cca | 288 |
| Phe | Asn | Cys | Arg | Val | Ala | Gln | Tyr | Pro | Phe | Glu | Asp | His | Asn | Pro | Pro | |
| | | | 85 | | | | | 90 | | | | | 95 | | | |
| cag | cta | gaa | ctt | atc | aaa | ccc | ttt | tgt | gaa | gat | ctt | gac | caa | tgg | cta | 336 |
| Gln | Leu | Glu | Leu | Ile | Lys | Pro | Phe | Cys | Glu | Asp | Leu | Asp | Gln | Trp | Leu | |
| | | | 100 | | | | | 105 | | | | | 110 | | | |
| agt | gaa | gat | gac | aat | cat | gtt | gca | gca | att | cac | tgt | aaa | gct | gga | aag | 384 |
| Ser | Glu | Asp | Asp | Asn | His | Val | Ala | Ala | Ile | His | Cys | Lys | Ala | Gly | Lys | |
| | | 115 | | | | | 120 | | | | | 125 | | | | |
| gga | cga | act | ggt | gta | atg | ata | tgt | gca | tat | tta | tta | cat | cgg | ggc | aaa | 432 |
| Gly | Arg | Thr | Gly | Val | Met | Ile | Cys | Ala | Tyr | Leu | Leu | His | Arg | Gly | Lys | |
| | 130 | | | | | 135 | | | | | 140 | | | | | |
| ttt | tta | aag | gca | caa | gag | gcc | cta | gat | ttc | tat | ggg | gaa | gta | agg | acc | 480 |
| Phe | Leu | Lys | Ala | Gln | Glu | Ala | Leu | Asp | Phe | Tyr | Gly | Glu | Val | Arg | Thr | |
| 145 | | | | | 150 | | | | | 155 | | | | | 160 | |
| aga | gac | aaa | aag | gga | gta | act | att | ccc | agt | cag | agg | cgc | tat | gtg | tat | 528 |
| Arg | Asp | Lys | Lys | Gly | Val | Thr | Ile | Pro | Ser | Gln | Arg | Arg | Tyr | Val | Tyr | |
| | | | | 165 | | | | | 170 | | | | | 175 | | |
| tat | tat | agc | tac | ctg | tta | aag | aat | cat | ctg | gat | tat | aga | cca | gtg | gca | 576 |
| Tyr | Tyr | Ser | Tyr | Leu | Leu | Lys | Asn | His | Leu | Asp | Tyr | Arg | Pro | Val | Ala | |
| | | | 180 | | | | | 185 | | | | | 190 | | | |
| ctg | ttg | ttt | cac | aag | atg | atg | ttt | gaa | act | att | cca | atg | ttc | agt | ggc | 624 |
| Leu | Leu | Phe | His | Lys | Met | Met | Phe | Glu | Thr | Ile | Pro | Met | Phe | Ser | Gly | |
| | | | 195 | | | | | 200 | | | | | 205 | | | |
| gga | act | tgc | aat | cct | cag | ttt | gtg | gtc | tgc | cag | cta | aag | gtg | aag | ata | 672 |
| Gly | Thr | Cys | Asn | Pro | Gln | Phe | Val | Val | Cys | Gln | Leu | Lys | Val | Lys | Ile | |
| | | 210 | | | | | 215 | | | | | 220 | | | | |
| tat | tcc | tcc | aat | tca | gga | ccc | aca | cga | cgg | gaa | gac | aag | ttc | atg | tac | 720 |
| Tyr | Ser | Ser | Asn | Ser | Gly | Pro | Thr | Arg | Arg | Glu | Asp | Lys | Phe | Met | Tyr | |
| 225 | | | | | 230 | | | | | 235 | | | | | 240 | |

Pro Ser Thr Phe Lys Gly Thr Pro Thr Ala Glu Asn Pro Glu Tyr
        1235                    1240                1245

Leu Gly Leu Asp Val Pro Val
        1250            1255

| | | | | | | | | | | | | | | | | |
|---|---|---|---|---|---|---|---|---|---|---|---|---|---|---|---|---|
| ttt | gag | ttc | cct | cag | ccg | tta | cct | gtg | tgt | ggt | gat | atc | aaa | gta | gag | 768 |
| Phe | Glu | Phe | Pro | Gln | Pro | Leu | Pro | Val | Cys | Gly | Asp | Ile | Lys | Val | Glu | |
| | | | | 245 | | | | 250 | | | | | 255 | | | |
| ttc | ttc | cac | aaa | cag | aac | aag | atg | cta | aaa | aag | gac | aaa | atg | ttt | cac | 816 |
| Phe | Phe | His | Lys | Gln | Asn | Lys | Met | Leu | Lys | Lys | Asp | Lys | Met | Phe | His | |
| | | | 260 | | | | | 265 | | | | | 270 | | | |
| ttt | tgg | gta | aat | aca | ttc | ttc | ata | cca | gga | cca | gag | gaa | acc | tca | gaa | 864 |
| Phe | Trp | Val | Asn | Thr | Phe | Phe | Ile | Pro | Gly | Pro | Glu | Glu | Thr | Ser | Glu | |
| | | | 275 | | | | | 280 | | | | | 285 | | | |
| aaa | gta | gaa | aat | gga | agt | cta | tgt | gat | caa | gaa | atc | gat | agc | att | tgc | 912 |
| Lys | Val | Glu | Asn | Gly | Ser | Leu | Cys | Asp | Gln | Glu | Ile | Asp | Ser | Ile | Cys | |
| | | 290 | | | | | 295 | | | | | 300 | | | | |
| agt | ata | gag | cgt | gca | gat | aat | gac | aag | gaa | tat | cta | gta | ctt | act | tta | 960 |
| Ser | Ile | Glu | Arg | Ala | Asp | Asn | Asp | Lys | Glu | Tyr | Leu | Val | Leu | Thr | Leu | |
| 305 | | | | | 310 | | | | | 315 | | | | | 320 | |
| aca | aaa | aat | gat | ctt | gac | aaa | gca | aat | aaa | gac | aaa | gcc | aac | cga | tac | 1008 |
| Thr | Lys | Asn | Asp | Leu | Asp | Lys | Ala | Asn | Lys | Asp | Lys | Ala | Asn | Arg | Tyr | |
| | | | | 325 | | | | | 330 | | | | | 335 | | |
| ttt | tct | cca | aat | ttt | aag | gtg | aag | ctg | tac | ttc | aca | aaa | aca | gta | gag | 1056 |
| Phe | Ser | Pro | Asn | Phe | Lys | Val | Lys | Leu | Tyr | Phe | Thr | Lys | Thr | Val | Glu | |
| | | | 340 | | | | | 345 | | | | | 350 | | | |
| gag | ccg | tca | aat | cca | gag | gct | agc | agt | tca | act | tct | gta | aca | cca | gat | 1104 |
| Glu | Pro | Ser | Asn | Pro | Glu | Ala | Ser | Ser | Ser | Thr | Ser | Val | Thr | Pro | Asp | |
| | | 355 | | | | | 360 | | | | | 365 | | | | |
| gtt | agt | gac | aat | gaa | cct | gat | cat | tat | aga | tat | tct | gac | acc | act | gac | 1152 |
| Val | Ser | Asp | Asn | Glu | Pro | Asp | His | Tyr | Arg | Tyr | Ser | Asp | Thr | Thr | Asp | |
| 370 | | | | | 375 | | | | | 380 | | | | | | |
| tct | gat | cca | gag | aat | gaa | cct | ttt | gat | gaa | gat | cag | cat | aca | caa | att | 1200 |
| Ser | Asp | Pro | Glu | Asn | Glu | Pro | Phe | Asp | Glu | Asp | Gln | His | Thr | Gln | Ile | |
| 385 | | | | | 390 | | | | | 395 | | | | | 400 | |
| aca | aaa | gtc | tga | | | | | | | | | | | | | 1212 |
| Thr | Lys | Val | | | | | | | | | | | | | | |

<210> SEQ ID NO 26
<211> LENGTH: 403
<212> TYPE: PRT
<213> ORGANISM: Homo sapiens

<400> SEQUENCE: 26

Met Thr Ala Ile Ile Lys Glu Ile Val Ser Arg Asn Lys Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ile His Cys Lys Ala Gly Lys
            115                 120                 125

Gly Arg Thr Gly Val Met Ile Cys Ala Tyr Leu Leu His Arg Gly Lys
        130                 135                 140

Phe Leu Lys Ala Gln Glu Ala Leu Asp Phe Tyr Gly Glu Val Arg Thr

```
                  145                 150                 155                 160
            Arg Asp Lys Lys Gly Val Thr Ile Pro Ser Gln Arg Arg Tyr Val Tyr
                            165                 170                 175

Tyr Tyr Ser Tyr Leu Leu Lys Asn His Leu Asp Tyr Arg Pro Val Ala
                            180                 185                 190

Leu Leu Phe His Lys Met Met Phe Glu Thr Ile Pro Met Phe Ser Gly
                            195                 200                 205

Gly Thr Cys Asn Pro Gln Phe Val Val Cys Gln Leu Lys Val Lys Ile
                            210                 215                 220

Tyr Ser Ser Asn Ser Gly Pro Thr Arg Arg Glu Asp Lys Phe Met Tyr
            225                 230                 235                 240

Phe Glu Phe Pro Gln Pro Leu Pro Val Cys Gly Asp Ile Lys Val Glu
                            245                 250                 255

Phe Phe His Lys Gln Asn Lys Met Leu Lys Lys Asp Lys Met Phe His
                            260                 265                 270

Phe Trp Val Asn Thr Phe Phe Ile Pro Gly Pro Glu Glu Thr Ser Glu
                            275                 280                 285

Lys Val Glu Asn Gly Ser Leu Cys Asp Gln Glu Ile Asp Ser Ile Cys
                            290                 295                 300

Ser Ile Glu Arg Ala Asp Asn Asp Lys Glu Tyr Leu Val Leu Thr Leu
            305                 310                 315                 320

Thr Lys Asn Asp Leu Asp Lys Ala Asn Lys Asp Lys Ala Asn Arg Tyr
                            325                 330                 335

Phe Ser Pro Asn Phe Lys Val Lys Leu Tyr Phe Thr Lys Thr Val Glu
                            340                 345                 350

Glu Pro Ser Asn Pro Glu Ala Ser Ser Thr Ser Val Thr Pro Asp
                            355                 360                 365

Val Ser Asp Asn Glu Pro Asp His Tyr Arg Tyr Ser Asp Thr Thr Asp
                            370                 375                 380

Ser Asp Pro Glu Asn Glu Pro Phe Asp Glu Asp Gln His Thr Gln Ile
            385                 390                 395                 400

Thr Lys Val

<210> SEQ ID NO 27
<211> LENGTH: 597
<212> TYPE: DNA
<213> ORGANISM: Homo sapiens
<220> FEATURE:
<221> NAME/KEY: CDS
<222> LOCATION: (1)..(597)

<400> SEQUENCE: 27 atg tca aac gtg cga gtg tct aac ggg agc cct agc ctg gag cgg atg        48
Met Ser Asn Val Arg Val Ser Asn Gly Ser Pro Ser Leu Glu Arg Met
1               5                   10                  15 gac gcc agg cag gcg gag cac ccc aag ccc tcg gcc tgc agg aac ctc        96
Asp Ala Arg Gln Ala Glu His Pro Lys Pro Ser Ala Cys Arg Asn Leu
                20                  25                  30 ttc ggc ccg gtg gac cac gaa gag tta acc cgg gac ttg gag aag cac       144
Phe Gly Pro Val Asp His Glu Glu Leu Thr Arg Asp Leu Glu Lys His
            35                  40                  45 tgc aga gac atg gaa gag gcg agc cag cgc aag tgg aat ttc gat ttt       192
Cys Arg Asp Met Glu Glu Ala Ser Gln Arg Lys Trp Asn Phe Asp Phe
        50                  55                  60 cag aat cac aaa ccc cta gag ggc aag tac gag tgg caa gag gtg gag       240
Gln Asn His Lys Pro Leu Glu Gly Lys Tyr Glu Trp Gln Glu Val Glu
65                  70                  75                  80
```

```
aag ggc agc ttg ccc gag ttc tac tac aga ccc ccg cgg ccc ccc aaa      288
Lys Gly Ser Leu Pro Glu Phe Tyr Tyr Arg Pro Pro Arg Pro Pro Lys
            85                  90                  95 ggt gcc tgc aag gtg ccg gcg cag gag agc cag gat gtc agc ggg agc      336
Gly Ala Cys Lys Val Pro Ala Gln Glu Ser Gln Asp Val Ser Gly Ser
        100                 105                 110 cgc ccg gcg gcg cct tta att ggg gct ccg gct aac tct gag gac acg      384
Arg Pro Ala Ala Pro Leu Ile Gly Ala Pro Ala Asn Ser Glu Asp Thr
    115                 120                 125 cat ttg gtg gac cca aag act gat ccg tcg gac agc cag acg ggg tta      432
His Leu Val Asp Pro Lys Thr Asp Pro Ser Asp Ser Gln Thr Gly Leu
130                 135                 140 gcg gag caa tgc gca gga ata agg aag cga cct gca acc gac gat tct      480
Ala Glu Gln Cys Ala Gly Ile Arg Lys Arg Pro Ala Thr Asp Asp Ser
145                 150                 155                 160 tct act caa aac aaa aga gcc aac aga aca gaa gaa aat gtt tca gac      528
Ser Thr Gln Asn Lys Arg Ala Asn Arg Thr Glu Glu Asn Val Ser Asp
                165                 170                 175 ggt tcc cca aat gcc ggt tct gtg gag cag acg ccc aag aag cct ggc      576
Gly Ser Pro Asn Ala Gly Ser Val Glu Gln Thr Pro Lys Lys Pro Gly
            180                 185                 190 ctc aga aga cgt caa acg taa                                          597
Leu Arg Arg Arg Gln Thr
            195
```

<210> SEQ ID NO 28
<211> LENGTH: 198
<212> TYPE: PRT
<213> ORGANISM: Homo sapiens

<400> SEQUENCE: 28

```
Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
            85                  90                  95

Gly Ala Cys Lys Val Pro Ala Gln Glu Ser Gln Asp Val Ser Gly Ser
        100                 105                 110

Arg Pro Ala Ala Pro Leu Ile Gly Ala Pro Ala Asn Ser Glu Asp Thr
    115                 120                 125

His Leu Val Asp Pro Lys Thr Asp Pro Ser Asp Ser Gln Thr Gly Leu
130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
            195
```

<210> SEQ ID NO 29
<211> LENGTH: 894
<212> TYPE: DNA
<213> ORGANISM: Homo sapiens
<220> FEATURE:
<221> NAME/KEY: CDS
<222> LOCATION: (1)..(894)

<400> SEQUENCE: 29

| | | | | | | | | | | | | | | | | |
|---|---|---|---|---|---|---|---|---|---|---|---|---|---|---|---|---|
| atg | aca | aca | ccc | aga | aat | tca | gta | aat | ggg | act | ttc | ccg | gca | gag | cca | 48 |
| Met | Thr | Thr | Pro | Arg | Asn | Ser | Val | Asn | Gly | Thr | Phe | Pro | Ala | Glu | Pro | |
| 1 | | | | 5 | | | | | 10 | | | | | 15 | | |
| atg | aaa | ggc | cct | att | gct | atg | caa | tct | ggt | cca | aaa | cca | ctc | ttc | agg | 96 |
| Met | Lys | Gly | Pro | Ile | Ala | Met | Gln | Ser | Gly | Pro | Lys | Pro | Leu | Phe | Arg | |
| | | | 20 | | | | | 25 | | | | | 30 | | | |
| agg | atg | tct | tca | ctg | gtg | ggc | ccc | acg | caa | agc | ttc | ttc | atg | agg | gaa | 144 |
| Arg | Met | Ser | Ser | Leu | Val | Gly | Pro | Thr | Gln | Ser | Phe | Phe | Met | Arg | Glu | |
| | 35 | | | | | 40 | | | | | 45 | | | | | |
| tct | aag | act | ttg | ggg | gct | gtc | cag | att | atg | aat | ggg | ctc | ttc | cac | att | 192 |
| Ser | Lys | Thr | Leu | Gly | Ala | Val | Gln | Ile | Met | Asn | Gly | Leu | Phe | His | Ile | |
| 50 | | | | | 55 | | | | | 60 | | | | | | |
| gcc | ctg | ggg | ggt | ctt | ctg | atg | atc | cca | gca | ggg | atc | tat | gca | ccc | atc | 240 |
| Ala | Leu | Gly | Gly | Leu | Leu | Met | Ile | Pro | Ala | Gly | Ile | Tyr | Ala | Pro | Ile | |
| 65 | | | | | 70 | | | | | 75 | | | | | 80 | |
| tgt | gtg | act | gtg | tgg | tac | cct | ctc | tgg | gga | ggc | att | atg | tat | att | att | 288 |
| Cys | Val | Thr | Val | Trp | Tyr | Pro | Leu | Trp | Gly | Gly | Ile | Met | Tyr | Ile | Ile | |
| | | | | 85 | | | | | 90 | | | | | 95 | | |
| tcc | gga | tca | ctc | ttg | gca | gca | acg | gag | aaa | aac | tct | agg | aag | tgt | ttg | 336 |
| Ser | Gly | Ser | Leu | Leu | Ala | Ala | Thr | Glu | Lys | Asn | Ser | Arg | Lys | Cys | Leu | |
| | | | 100 | | | | | 105 | | | | | 110 | | | |
| gtc | aaa | gga | aaa | atg | ata | atg | aat | tca | ttg | agc | ctc | ttt | gct | gcc | att | 384 |
| Val | Lys | Gly | Lys | Met | Ile | Met | Asn | Ser | Leu | Ser | Leu | Phe | Ala | Ala | Ile | |
| | | 115 | | | | | 120 | | | | | 125 | | | | |
| tct | gga | atg | att | ctt | tca | atc | atg | gac | ata | ctt | aat | att | aaa | att | tcc | 432 |
| Ser | Gly | Met | Ile | Leu | Ser | Ile | Met | Asp | Ile | Leu | Asn | Ile | Lys | Ile | Ser | |
| 130 | | | | | 135 | | | | | 140 | | | | | | |
| cat | ttt | tta | aaa | atg | gag | agt | ctg | aat | ttt | att | aga | gct | cac | aca | cca | 480 |
| His | Phe | Leu | Lys | Met | Glu | Ser | Leu | Asn | Phe | Ile | Arg | Ala | His | Thr | Pro | |
| 145 | | | | | 150 | | | | | 155 | | | | | 160 | |
| tat | att | aac | ata | tac | aac | tgt | gaa | cca | gct | aat | ccc | tct | gag | aaa | aac | 528 |
| Tyr | Ile | Asn | Ile | Tyr | Asn | Cys | Glu | Pro | Ala | Asn | Pro | Ser | Glu | Lys | Asn | |
| | | | | 165 | | | | | 170 | | | | | 175 | | |
| tcc | cca | tct | acc | caa | tac | tgt | tac | agc | ata | caa | tct | ctg | ttc | ttg | ggc | 576 |
| Ser | Pro | Ser | Thr | Gln | Tyr | Cys | Tyr | Ser | Ile | Gln | Ser | Leu | Phe | Leu | Gly | |
| | | | 180 | | | | | 185 | | | | | 190 | | | |
| att | ttg | tca | gtg | atg | ctg | atc | ttt | gcc | ttc | ttc | cag | gaa | ctt | gta | ata | 624 |
| Ile | Leu | Ser | Val | Met | Leu | Ile | Phe | Ala | Phe | Phe | Gln | Glu | Leu | Val | Ile | |
| | | 195 | | | | | 200 | | | | | 205 | | | | |
| gct | ggc | atc | gtt | gag | aat | gaa | tgg | aaa | aga | acg | tgc | tcc | aga | ccc | aaa | 672 |
| Ala | Gly | Ile | Val | Glu | Asn | Glu | Trp | Lys | Arg | Thr | Cys | Ser | Arg | Pro | Lys | |
| | 210 | | | | | 215 | | | | | 220 | | | | | |
| tct | aac | ata | gtt | ctc | ctg | tca | gca | gaa | gaa | aaa | aaa | gaa | cag | act | att | 720 |
| Ser | Asn | Ile | Val | Leu | Leu | Ser | Ala | Glu | Glu | Lys | Lys | Glu | Gln | Thr | Ile | |
| 225 | | | | | 230 | | | | | 235 | | | | | 240 | |
| gaa | ata | aaa | gaa | gaa | gtg | gtt | ggg | cta | act | gaa | aca | tct | tcc | caa | cca | 768 |
| Glu | Ile | Lys | Glu | Glu | Val | Val | Gly | Leu | Thr | Glu | Thr | Ser | Ser | Gln | Pro | |
| | | | | 245 | | | | | 250 | | | | | 255 | | |
| aag | aat | gaa | gaa | gac | att | gaa | att | att | cca | atc | caa | gaa | gag | gaa | gaa | 816 |
| Lys | Asn | Glu | Glu | Asp | Ile | Glu | Ile | Ile | Pro | Ile | Gln | Glu | Glu | Glu | Glu | |
| | | | 260 | | | | | 265 | | | | | 270 | | | |

```
gaa gaa aca gag acg aac ttt cca gaa cct ccc caa gat cag gaa tcc    864
Glu Glu Thr Glu Thr Asn Phe Pro Glu Pro Pro Gln Asp Gln Glu Ser
        275                 280                 285 tca cca ata gaa aat gac agc tct cct taa                            894
Ser Pro Ile Glu Asn Asp Ser Ser Pro
        290                 295

<210> SEQ ID NO 30
<211> LENGTH: 297
<212> TYPE: PRT
<213> ORGANISM: Homo sapiens

<400> SEQUENCE: 30

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 31
<211> LENGTH: 596
<212> TYPE: DNA
<213> ORGANISM: homo sapiens
```

<400> SEQUENCE: 31

```
acgcgtactg gagtcaatga aagcaactat ttcaaaagat cagattactt accagtttca      60
ctaataaaga tttattactt taaacccttta tcataaaatg tatgctttga atactgtgaa    120
gtacactgca tataaggagt gtggtatagt ataaagaaac tttctgcagg tagtaattat    180
agtgaagatt ttaggtttac aaagccctag ctgttttctg tgtagctttt attattctta    240
tgactcttga caagtttgta gcttcaccat atacatttaa tattttgcaa taattggcct    300
tgttcctgag ctgttggatt cggggccgta gcactgtctg agaggtttac atttctcaca    360
gtgaaccggt ctcttttca gctgcttcct ggcttctttt tactcaggtt tccactgctt     420
ttttgctttt tttaatgctg tatgaaggtg ttaacatttg tttatatttt tcattaattg    480
taatacccttt aaatcatgca tcatactcag aaatagggat tagaatttaa gtgacatctt    540
tggcctaata taatttacct gttaaaaatt tgtgaaagct attgcttagc ggccgc         596
```

<210> SEQ ID NO 32
<211> LENGTH: 511
<212> TYPE: DNA
<213> ORGANISM: Homo sapiens

<400> SEQUENCE: 32

```
acgcgtccat gtccgtacct ttctagttca taccttcttt taatttttt tttcttttca      60
atttgaagag agtgcttcct ctgttcttaa ggctagggaa ccaaattagg ttgtttcaat    120
atcgtgctaa aagatactgc ctttagaaga aggctattga caatccagcg tgtctcggtg    180
gaactctgac tccatggttc actttcatga tggccacatg cctcctgccc agagcccggc    240
agccactgtg cagtgggaag gggggccgat acactgtacg agagtgagta gcaggtctca    300
cagtgaaccg gtctctttcc ctactgtgtc acactcctaa tggaatgccg ttatccaaag    360
agcagcacga acccgacagg gctgagtggc ttgtgctagg gagaggtttg tgtcattcct    420
gctgaccaaa ctgcaggaaa aactgctaat tgtcatgctg aagactgcct gacggggaga    480
ctctgccttc tgtaagtagg tcagcggccg c                                   511
```

<210> SEQ ID NO 33
<211> LENGTH: 203
<212> TYPE: DNA
<213> ORGANISM: Homo sapiens

<400> SEQUENCE: 33

```
acgcgtaatt catatttgca tgtcgctatg tgttctggga aatcaccata aacgtgaaat      60
gtctttggat ttgggaatct tataagttct gtatgagacc actcggatga gctgttggat    120
tcggggccgt agcactgtct gagaggttta catttctcac agtgaaccgg tctctttttc    180
agctgcttct tttttgcggc cgc                                            203
```

<210> SEQ ID NO 34
<211> LENGTH: 205
<212> TYPE: DNA
<213> ORGANISM: Homo sapiens

<400> SEQUENCE: 34

```
gcggccgcaa ttcatatttg catgtcgcta tgtgttctgg gaaatcacca taaacgtgaa      60
atgtctttgg atttgggaat cttataagtt ctgtatgaga ccactcggat gagctgttgg    120
attcggggcc gtagcactgt ctgagaggtt tacatttctc acagtgaacc ggtctctttt    180
```
tcagctgctt cttttttgcg gccgc                                               205

<210> SEQ ID NO 35
<211> LENGTH: 45
<212> TYPE: DNA
<213> ORGANISM: Artificial Sequence
<220> FEATURE:
<223> OTHER INFORMATION: DNA target sequence of the miR-142-3p

<400> SEQUENCE: 35
gcggccgcgt cgactccata aagtaggaaa cactacagcg gccgc                         45

<210> SEQ ID NO 36
<211> LENGTH: 128
<212> TYPE: DNA
<213> ORGANISM: Artificial Sequence
<220> FEATURE:
<223> OTHER INFORMATION: DNA target sequence four time repeat
      miR-142-3pT4X

<400> SEQUENCE: 36
gcggccgcgt cgactccata aagtaggaaa cactacacga ttccataaag taggaaacac         60
tacaaccggt tccataaagt aggaaacact acatcactcc ataaagtagg aaacactaca        120
gcggccgc                                                                 128

<210> SEQ ID NO 37
<211> LENGTH: 1131
<212> TYPE: DNA
<213> ORGANISM: herpes simplex virus 1

<400> SEQUENCE: 37
atggcttcgt accccggcca tcagcacgcg tctgcgttcg accaggctgc gcgttctcgc         60
ggccatagca accgacgtac ggcgttgcgc cctcgccggc agcaagaagc cacggaagtc        120
cgcccggagc agaaaatgcc cacgctactg cgggtttata tagacggtcc ccacgggatg        180
gggaaaacca ccaccacgca actgctggtg gccctgggtt cgcgcgacga tatcgtctac        240
gtacccgagc cgatgactta ctggcaggtg ctgggggctt ccgagacaat cgcgaacatc        300
tacaccacac aacaccgcct cgaccagggt gagatatcgg ccggggacgc ggcggtggta        360
atgacaagcg cccagataac aatgggcatg ccttatgccg tgaccgacgc cgttctggct        420
cctcatatcg ggggggaggc tgggagctca catgcccccgc ccccgccct caccctcatc        480 ttcgaccgcc atcccatcgc cgccctcctg tgttacccgg ccgcgcgata ccttatgggc        540
agcatgaccc ccaggccgt gctggcgttc gtggccctca tcccgccgac cttgcccggc        600
acaaacatcg tgttgggggc ccttccggag acagacaca tcgaccgcct ggccaaacgc        660
cagcgccccg cgagcggct tgacctggct atgctggccg cgattcgccg cgtttacgag        720
ctgcttgcca atacggtgcg gtatctgcag ggcggcgggt cgtggcggga ggattgggga        780
cagctttcgg gacggccgt gccgcccag ggtgccgagc cccagagcaa cgcgggccca        840
cgaccccata tcggggacac gttatttacc ctgtttcggg ccccgagtt gctggccccc        900 aacggcgacc tgtataacgt gtttgcctgg gccttggacg tcttggccaa acgcctccgt        960
cccatgcacg tctttatcct ggattacgac caatcgcccg ccggctaccg ggacgccctg       1020
ctgcaactta cctccgggat ggtccagacc cacgtcacca cccccggctc cataccgacg       1080
atctgcgacc tggcgcgcac gtttgcccgg gagatggggg aggctaacta a               1131

<210> SEQ ID NO 38

<211> LENGTH: 499
<212> TYPE: DNA
<213> ORGANISM: Homo sapiens

<400> SEQUENCE: 38

```
atgaaatata caagttatat cttggctttt cagctctgca tcgttttggg ttctcttggc     60
tgttactgcc aggaccatat gtaaaagaag cagaaaacct aagaaatat  tttaatgcag    120
gtcattcaga tgtagcggat aatggaactc ttttcttagg cattttgaag aattggaaag    180
aggagagtga cagaaaaata atgcagagcc aaattgtctc cttttacttc aaactttta     240
aaaactttaa agatgaccag agcatccaaa agagtgtgga gaccatcaag aagacatga    300
atgtaagttt ttcaatagca acaaaagaa acgagatgac ttcgaaaagc tgactaatta    360
ttcggtaact gacttgaatg tccaacgcaa agcaatacat gaactcatcc aagtgatggc    420
tgaactgtcg ccagcagcta aacagggaa gcgaaaaagg agtcagatgc tgtttcgagg     480
tcgaagagca tcccagtaa                                                  499
```

<210> SEQ ID NO 39
<211> LENGTH: 468
<212> TYPE: DNA
<213> ORGANISM: Mus musculus

<400> SEQUENCE: 39

```
atgaacgcta cacactgcat cttggctttg cagctcttcc tcatggctgt ttctggctgt     60
tactgccacg gcacagtcat tgaaagccta gaaagtctga ataactattt taactcaagt    120
ggcatagatg tggaagaaaa gagtctcttc ttggatatct ggaggaactg gcaaaaggat    180
ggtgacatga aaatcctgca gagccagatt atctctttct acctcagact ctttgaagtc    240
ttgaaagaca atcaggccat cagcaacaac ataagcgtca ttgaatcaca cctgattact    300
accttcttca gcaacagcaa ggcgaaaaag gatgcattca tgagtattgc caagtttgag    360
gtcaacaacc cacaggtcca gcgccaagca ttcaatgagc tcatccgagt ggtccaccag    420
ctgttgccgg aatccagcct caggaagcgg aaaaggagtc gctgctga                 468
```

<210> SEQ ID NO 40
<211> LENGTH: 462
<212> TYPE: DNA
<213> ORGANISM: Homo sapiens

<400> SEQUENCE: 40

```
atgtacagga tgcaactcct gtcttgcatt gcactaagtc ttgcacttgt cacaaacagt     60
gcacctactt caagttctac aaagaaaaca cagctacaac tggagcattt actgctggat    120
ttacagatga ttttgaatgg aattaataat acaagaatc  ccaaactcac caggatgctc    180
acatttaagt tttacatgcc caagaaggcc acagaactga acatcttca  gtgtctagaa    240
gaagaactca aacctctgga ggaagtgcta aatttagctc aaagcaaaaa ctttcactta    300
agacccaggg acttaatcag caatatcaac gtaaagtttc tggaactaaa gggatctgaa    360
acaacattca tgtgtgaata tgctgatgag acagcaacca ttgtagaatt tctgaacaga    420
tggattacct tttgtcaaag catcatctca acactgactt ga                       462
```

<210> SEQ ID NO 41
<211> LENGTH: 23
<212> TYPE: RNA
<213> ORGANISM: Artificial Sequence
<220> FEATURE:
<223> OTHER INFORMATION: Oligonucleotide primer

<400> SEQUENCE: 41
uguaguguuu ccuacuuuau gga                                    23

<210> SEQ ID NO 42
<211> LENGTH: 23
<212> TYPE: RNA
<213> ORGANISM: Artificial Sequence
<220> FEATURE:
<223> OTHER INFORMATION: Oligonucleotide primer

<400> SEQUENCE: 42
uguaguguuu ccuacuuuau gga                                    23

<210> SEQ ID NO 43
<211> LENGTH: 546
<212> TYPE: DNA
<213> ORGANISM: Artificial Sequence
<220> FEATURE:
<223> OTHER INFORMATION: Yeast cytosine deaminase with cloning sites

<400> SEQUENCE: 43
aacacgatta taaatggtga caggggaat ggcaagcaag tgggatcaga agggtatgga     60
cattgcctat gaggaggcgg ccttaggtta caaagagggt ggtgttccta ttggcggatg    120
tcttatcaat aacaaagacg gaagtgttct cggtcgtggt cacaacatga gatttcaaaa    180
gggatccgcc acactacatg gtgagatctc cactttggaa aactgtggga gattagaggg    240
caaagtgtac aaagatacca ctttgtatac gacgctgtct ccatgcgaca tgtgtacagg    300
tgccatcatc atgtatggta ttccacgctg tgttgtcggt gagaacgtta atttcaaaag    360
taagggcgag aaatatttac aaactagagg tcacgaggtt gttgttgttg acgatgagag    420
gtgtaaaaag atcatgaaac aatttatcga tgaaagacct caggattggt ttgaagatat    480
tggtgagtag gcggccgcgc catagataaa ataaaagatt ttatttagtc tccagaaaaa    540
gggggg                                                              546

<210> SEQ ID NO 44
<211> LENGTH: 537
<212> TYPE: DNA
<213> ORGANISM: Artificial Sequence
<220> FEATURE:
<223> OTHER INFORMATION: CD codon optimized with cloning sites

<400> SEQUENCE: 44
ttataaatgg tgaccggcgg catggcctcc aagtgggatc aaaagggcat ggatatcgct     60
tacgaggagg ccgccctggg ctacaaggag ggcggcgtgc ctatcggcgg ctgtctgatc    120
aacaacaagg acggcagtgt gctgggcagg ggccacaaca tgaggttcca gaagggctcc    180
gccaccctgc acggcgagat ctccacccctg gagaactgtg gcaggctgga gggcaaggtg    240
tacaaggaca ccaccctgta caccaccctg tcccccttgtg acatgtgtac cggcgctatc    300
atcatgtacg gcatccctag gtgtgtggtg ggcgagaacg tgaacttcaa gtccaagggc    360
gagaagtacc tgcaaaccag gggccacgag gtggtggttg ttgacgatga gaggtgtaag    420
aagatcatga agcagttcat cgacgagagg cctcaggact ggttcgagga tatcggcgag    480
tgataagcgg ccgcagataa aataaaagat tttatttagt ctccagaaaa agggggg      537

<210> SEQ ID NO 45
<211> LENGTH: 40
<212> TYPE: DNA

```
<213> ORGANISM: Artificial Sequence
<220> FEATURE:
<223> OTHER INFORMATION: Oligonucleotide primer

<400> SEQUENCE: 45
tcgaggatat cggcgagtga aacccgttat tcttttttggc                                40

<210> SEQ ID NO 46
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 46
gccaaaaaga taacgggtt tcactcgccg atatcctcga                                 40

<210> SEQ ID NO 47
<211> LENGTH: 82
<212> TYPE: DNA
<213> ORGANISM: Artificial Sequence
<220> FEATURE:
<223> OTHER INFORMATION: Oligonucleotide primer

<400> SEQUENCE: 47
tcggcgagtg atccggcggc ggcgcctccg gcggcggcgc ctccggcggc ggcgcctccg          60
gcggcggcgc caacccgtta tt                                                   82

<210> SEQ ID NO 48
<211> LENGTH: 82
<212> TYPE: DNA
<213> ORGANISM: Artificial Sequence
<220> FEATURE:
<223> OTHER INFORMATION: Oligonucleotide Primer

<400> SEQUENCE: 48
aataacgggt tggcgccgcc gccggaggcg ccgccgccgg aggcgccgcc gccggaggcg          60
ccgccgccgg atcactcgcc ga                                                   82

<210> SEQ ID NO 49
<211> LENGTH: 480
<212> TYPE: DNA
<213> ORGANISM: Artificial Sequence
<220> FEATURE:
<223> OTHER INFORMATION: Cytosine deaminase codon optimized heat
      stabilized

<400> SEQUENCE: 49
atggtgaccg gcggcatggc ctccaagtgg gatcaaaagg gcatggatat cgcttacgag          60
gaggccctgc tgggctacaa ggagggcggc gtgcctatcg cggctgtct gatcaacaac         120 aaggacggca gtgtgctggg caggggccac aacatgaggt tccagaaggg ctccgccacc        180
ctgcacggcg agatctccac cctggagaac tgtggcaggc tggagggcaa ggtgtacaag        240
gacaccaccc tgtacaccac cctgtcccct tgtgacatgt gtaccggcgc tatcatcatg        300
tacggcatcc ctaggtgtgt gatcggcgag aacgtgaact tcaagtccaa gggcgagaag        360
tacctgcaaa ccaggggcca cgaggtggtg gttgttgacg atgagaggtg taagaagctg        420
atgaagcagt tcatcgacga gaggcctcag gactggttcg aggatatcgg cgagtgataa        480

<210> SEQ ID NO 50
<211> LENGTH: 546
<212> TYPE: DNA
```

<213> ORGANISM: Artificial Sequence
<220> FEATURE:
<223> OTHER INFORMATION: Cytosine deaminase codon optimized heat stabilized

<400> SEQUENCE: 50

```
aacacgatta taaatggtga ccggcggcat ggcctccaag tgggatcaaa agggcatgga      60
tatcgcttac gaggaggccc tgctgggcta caaggagggc ggcgtgccta tcggcggctg     120
tctgatcaac aacaaggacg gcagtgtgct gggcaggggc cacaacatga ggttccagaa     180
gggctccgcc accctgcacg gcgagatctc caccctggag aactgtggca ggctggaggg     240
caaggtgtac aaggacacca ccctgtacac caccctgtcc ccttgtgaca tgtgtaccgg     300
cgctatcatc atgtacggca tccctaggtg tgtgatcggc gagaacgtga acttcaagtc     360
caagggcgag aagtacctgc aaaccagggg ccacgaggtg gtggttgttg acgatgagag     420
gtgtaagaag ctgatgaagc agttcatcga cgagaggcct caggactggt tcgaggatat     480
cggcgagtaa gcggccgcgc catagataaa ataaaagatt ttatttagtc tccagaaaaa     540
gggggg                                                                546
```

<210> SEQ ID NO 51
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 51

```
tcgaggatat cggcgagtga aacccgttat cttttttggc                            40
```

<210> SEQ ID NO 52
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 52

```
gccaaaaaga taacgggttt cactcgccga tatcctcga                             40
```

<210> SEQ ID NO 53
<211> LENGTH: 52
<212> TYPE: DNA
<213> ORGANISM: Artificial Sequence
<220> FEATURE:
<223> OTHER INFORMATION: Oligonucleotide primer complement

<400> SEQUENCE: 53

```
ccaagctcct atagccgctc actatctact tgggcaataa gaaaaaccga ag              52
```

<210> SEQ ID NO 54
<211> LENGTH: 52
<212> TYPE: DNA
<213> ORGANISM: Artificial Sequence
<220> FEATURE:
<223> OTHER INFORMATION: Oligonucleotide primer complement

<400> SEQUENCE: 54

```
ggttcgagga tatcggcgag tgatagatga acccgttatt cttttttggct tc             52
```

<210> SEQ ID NO 55
<211> LENGTH: 1296
<212> TYPE: DNA

<213> ORGANISM: Artificial Sequence
<220> FEATURE:
<223> OTHER INFORMATION: CD-UPRT cloning sequence

<400> SEQUENCE: 55

```
aacacgatta taaatggtga ccggcggcat ggcctccaag tgggatcaaa agggcatgga      60
tatcgcttac gaggaggccc tgctgggcta caaggagggc ggcgtgccta tcggcggctg     120
tctgatcaac aacaaggacg gcagtgtgct gggcaggggc cacaacatga ggttccagaa     180
gggctccgcc accctgcacg gcgagatctc caccctggag aactgtggca ggctggaggg     240
caaggtgtac aaggacacca ccctgtacac caccctgtcc ccttgtgaca tgtgtaccgg     300
cgctatcatc atgtacggca tccctaggtg tgtgatcggc gagaacgtga acttcaagtc     360
caagggcgag aagtacctgc aaaccagggg ccacgaggtg gtggttgttg acgatgagag     420
gtgtaagaag ctgatgaagc agttcatcga cgagaggcct caggactggt tcgaggatat     480
cggcgagaac ccgttattct ttttggcttc tccattcttg taccttacat atcttatata     540
ttatccaaac aaagggtctt tcgttagcaa acctagaaat ctgcaaaaaa tgtcttcgga     600
accatttaag aacgtctact tgctacctca aacaaaccaa ttgctgggtt tgtacaccat     660
catcagaaat aagaatacaa ctagacctga tttcattttc tactccgata gaatcatcag     720
attgttggtt gaagaaggtt tgaaccatct acctgtgcaa agcaaattg tggaaactga     780
caccaacgaa aacttcgaag gtgtctcatt catgggtaaa atctgtgtg tttccattgt     840
cagagctggt gaatcgatgg agcaaggatt aagagactgt tgtaggtctg tgcgtatcgg     900
taaaatttta attcaaaggg acgaggagac tgctttacca aagttattct acgaaaaatt     960
accagaggat atatctgaaa ggtatgtctt cctattagac ccaatgctgg ccaccggtgg    1020
tagtgctatc atggctacag aagtcttgat taagagaggt gttaagccag agagaattta    1080
cttcttaaac ctaatctgta gtaaggaagg gattgaaaaa taccatgccg ccttcccaga    1140
ggtcagaatt gttactggtg ccctcgacag aggtctagat gaaaacaagt atctagttcc    1200
agggttgggt gactttggtg acagatacta ctgtgtttaa gcggccgcgc catagataaa    1260
ataaaagatt ttatttagtc tccagaaaaa gggggg                              1296
```

<210> SEQ ID NO 56
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 56

Ser Gly Gly Gly Gly
1               5

<210> SEQ ID NO 57
<211> LENGTH: 82
<212> TYPE: DNA
<213> ORGANISM: Artificial Sequence
<220> FEATURE:
<223> OTHER INFORMATION: Oligonucleotide primer

<400> SEQUENCE: 57

```
tcggcgagtg atccggcggc ggcgcctccg gcggcggcgc ctccggcggc ggcgcctccg      60
gcggcggcgc caacccgtta tt                                              82
```

<210> SEQ ID NO 58

<211> LENGTH: 82
<212> TYPE: DNA
<213> ORGANISM: Artificial Sequence
<220> FEATURE:
<223> OTHER INFORMATION: Oligonucleotide primer

<400> SEQUENCE: 58

```
aataacgggt tggcgccgcc gccggaggcg ccgccgccgg aggcgccgcc gccggaggcg      60
ccgccgccgg atcactcgcc ga                                              82
```

<210> SEQ ID NO 59
<211> LENGTH: 1356
<212> TYPE: DNA
<213> ORGANISM: Artificial Sequence
<220> FEATURE:
<223> OTHER INFORMATION: CD codon optimized heat stabilized linker UPRT

<400> SEQUENCE: 59

```
aacacgatta taaatggtga ccggcggcat ggcctccaag tgggatcaaa agggcatgga      60
tatcgcttac gaggaggccc tgctgggcta caaggagggc ggcgtgccta tcggcggctg     120
tctgatcaac aacaaggacg cagtgtgct gggcaggggc cacaacatga ggttccagaa     180
gggctccgcc accctgcacg cgagatctc caccctggaa actgtggca ggctggaggg      240
caaggtgtac aaggacacca ccctgtacac caccctgtcc ccttgtgaca tgtgtaccgg      300
cgctatcatc atgtacggca tccctaggtg tgtgatcggc gagaacgtga acttcaagtc      360
caagggcgag aagtacctgc aaaccagggg ccacgaggtg gtggttgttg acgatgagag      420
gtgtaagaag ctgatgaagc agttcatcga cgagaggcct caggactggt tcaggatat      480
cggcgagtcc ggcggcggcg cctccggcgg cggcgcctcc ggcggcggcg cctccggcgg      540
cggcgccaac ccgttattct ttttggcttc tccattcttg taccttacat atcttatata      600
ttatccaaac aaagggtctt tcgttagcaa acctagaaat ctgcaaaaaa tgtcttcgga      660
accatttaag aacgtctact tgctacctca acaaaccaa ttgctgggtt tgtacaccat      720
catcagaaat aagaatacaa ctagacctga tttcatttc tactccgata gaatcatcag      780
attgttggtt gaagaaggtt tgaaccatct acctgtgcaa aagcaaattg tggaaactga      840
caccaacgaa aacttcgaag gtgtctcatt catgggtaaa atctgtggtg tttccattgt      900
cagagctggt gaatcgatgg agcaaggatt aagagactgt tgtaggtctg tgcgtatcgg      960
taaaatttta attcaaaggg acgaggagac tgctttacca aagttattct acgaaaaatt     1020
accagaggat atatctgaaa ggtatgtctt cctattagac ccaatgctgg ccaccggtgg     1080
tagtgctatc atggctacag aagtcttgat taagagaggt gttaagccag agagaattta     1140
cttcttaaac ctaatctgta gtaaggaagg gattgaaaaa taccatgccg ccttcccaga     1200
ggtcagaatt gttactggtg ccctcgacag aggtctagat gaaaacaagt atctagttcc     1260
agggttgggt gactttggtg acagatacta ctgtgtttaa gcggccgcgc catagataaa     1320
ataaaagatt ttatttagtc tccagaaaaa gggggg                               1356
```

<210> SEQ ID NO 60
<211> LENGTH: 1269
<212> TYPE: DNA
<213> ORGANISM: Artificial Sequence
<220> FEATURE:
<223> OTHER INFORMATION: CD codon optimized heat stabilized OPRT

<400> SEQUENCE: 60

```
aacacgatta taaatggtga ccggcggcat ggcctccaag tgggatcaaa agggcatgga      60
```

```
tatcgcttac gaggaggccc tgctgggcta caaggagggc ggcgtgccta tcggcggctg      120
tctgatcaac aacaaggacg gcagtgtgct gggcaggggc cacaacatga ggttccagaa      180
gggctccgcc accctgcacg gcgagatctc caccctggag aactgtggca ggctggaggg      240
caaggtgtac aaggacacca ccctgtacac caccctgtcc ccttgtgaca tgtgtaccgg      300
cgctatcatc atgtacggca tccctaggtg tgtgatcggc gagaacgtga acttcaagtc      360
caagggcgag aagtacctgc aaaccagggg ccacgaggtg gtggttgttg acgatgagag      420
gtgtaagaag ctgatgaagc agttcatcga cgagaggcct caggactggt tcgaggatat      480
cggcgaggcg gtcgctcgtg cagctttggg gccattggtg acgggtctgt acgacgtgca      540 ggcttt caag tttggggact tcgtgctgaa gagcgggctt tcctcccca tctacatcga      600 tctgcggggc atcgtgtctc gaccgcgtct tctgagtcag gttgcagata ttttattcca      660
aactgcccaa aatgcaggca tcagttttga caccgtgtgt ggagtgcctt atacagcttt      720
gccattggct acagttatct gttcaaccaa tcaaattcca atgcttatta gaaggaaaga      780
aacaaaggat tatggaacta gcgtcttgt agaaggaact attaatccag gagaaacctg      840
tttaatcatt gaagatgttg tcaccagtgg atctagtgtt ttggaaactg ttgaggttct      900
tcagaaggag ggcttgaagg tcactgatgc catagtgctg ttggacagag agcagggagg      960
caaggacaag ttgcaggcgc acgggatccg cctccactca gtgtgtacat tgtccaaaat     1020
gctggagatt ctcgagcagc agaaaaaagt tgatgctgag acagttggga gagtgaagag     1080
gtttattcag gagaatgtct ttgtggcagc gaatcataat ggttctcccc tttctataaa     1140
ggaagcaccc aaagaactca gcttcggtgc acgtgcagag ctgccagga tccacccagt      1200 tgcatcgaag taagcggccg cgccatagat aaaataaaag attttattta gtctccagaa     1260
aaaggggggg                                                             1269

<210> SEQ ID NO 61
<211> LENGTH: 1329
<212> TYPE: DNA
<213> ORGANISM: Artificial Sequence
<220> FEATURE:
<223> OTHER INFORMATION: CD codon optimized heat stabilized linker OPRT

<400> SEQUENCE: 61
aacacgatta taaatggtga ccggcggcat ggcctccaag tgggatcaaa agggcatgga       60
tatcgcttac gaggaggccc tgctgggcta caaggagggc ggcgtgccta tcggcggctg      120
tctgatcaac aacaaggacg gcagtgtgct gggcaggggc cacaacatga ggttccagaa      180
gggctccgcc accctgcacg gcgagatctc caccctggag aactgtggca ggctggaggg      240
caaggtgtac aaggacacca ccctgtacac caccctgtcc ccttgtgaca tgtgtaccgg      300
cgctatcatc atgtacggca tccctaggtg tgtgatcggc gagaacgtga acttcaagtc      360
caagggcgag aagtacctgc aaaccagggg ccacgaggtg gtggttgttg acgatgagag      420
gtgtaagaag ctgatgaagc agttcatcga cgagaggcct caggactggt tcgaggatat      480
cggcgagtcc ggcggcggcg cctcggcgg cggcgcctcc ggcggcggcg cctccggcgg      540
cggcgccgcg gtcgctcgtg cagctttggg gccattggtg acgggtctgt acgacgtgca      600 ggcttt caag tttggggact tcgtgctgaa gagcgggctt tcctcccca tctacatcga      660 tctgcggggc atcgtgtctc gaccgcgtct tctgagtcag gttgcagata ttttattcca      720
aactgcccaa aatgcaggca tcagttttga caccgtgtgt ggagtgcctt atacagcttt      780
```

-continued

```
gccattggct acagttatct gttcaaccaa tcaaattcca atgcttatta gaaggaaaga        840
aacaaaggat tatggaacta agcgtcttgt agaaggaact attaatccag gagaaacctg        900
tttaatcatt gaagatgttg tcaccagtgg atctagtgtt ttggaaactg ttgaggttct        960
tcagaaggag ggcttgaagg tcactgatgc catagtgctg ttggacagag agcagggagg       1020
caaggacaag ttgcaggcgc acgggatccg cctccactca gtgtgtacat tgtccaaaat       1080
gctggagatt ctcgagcagc agaaaaaagt tgatgctgag acagttggga gagtgaagag       1140
gtttattcag gagaatgtct tgtggcagc gaatcataat ggttctcccc tttctataaa        1200
ggaagcaccc aaagaactca gcttcggtgc acgtgcagag ctgccaggga tccacccagt       1260
tgcatcgaag taagcggccg cgccatagat aaaataaaag attttattta gtctccagaa       1320
aaaggggggg                                                              1329
```

<210> SEQ ID NO 62
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 62
ctgatcttac tctttggacc ttg        23

<210> SEQ ID NO 63
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 63
cccctttttc tggagactaa ataa        24

<210> SEQ ID NO 64
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 64
agcccacaac ccctcactc        19

<210> SEQ ID NO 65
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 65
tctcccgatc ccggacga        18

<210> SEQ ID NO 66
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 66
cccaaaatga agaccccccg ctgacg        26

<210> SEQ ID NO 67
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 67
atcatcatgt acggcatccc tag                                       23

<210> SEQ ID NO 68
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 68
tgaactgctt catcagcttc ttac                                      24

<210> SEQ ID NO 69
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 69
tcatcgtcaa caaccaccac ctcgt                                     25

<210> SEQ ID NO 70
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 70
aacctcaacc tcccctacaa gt                                        22

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 71
gttaagcgcc tgataggctc                                           20

<210> SEQ ID NO 72
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 72
agccaccccc aggaactgga gataga                                    26